(12) United States Patent
Revell et al.

(10) Patent No.: US 10,414,811 B2
(45) Date of Patent: Sep. 17, 2019

(54) PROTEASE-RESISTANT LIPIDATED GLP-1 ANALOGS

(71) Applicant: MEDIMMUNE LIMITED, Cambridge (GB)

(72) Inventors: Jefferson Revell, Cambridge (GB); Maria Bednarek, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 15/579,774

(22) PCT Filed: Jun. 9, 2016

(86) PCT No.: PCT/EP2016/063206
§ 371 (c)(1),
(2) Date: Dec. 5, 2017

(87) PCT Pub. No.: WO2016/198544
PCT Pub. Date: Dec. 15, 2016

(65) Prior Publication Data
US 2018/0162920 A1  Jun. 14, 2018

Related U.S. Application Data

(60) Provisional application No. 62/173,631, filed on Jun. 10, 2015, provisional application No. 62/343,390, filed on May 31, 2016.

(51) Int. Cl.
| | |
|---|---|
| C07K 7/00 | (2006.01) |
| C07K 14/605 | (2006.01) |
| A61K 38/28 | (2006.01) |
| A61K 45/06 | (2006.01) |
| A61K 47/60 | (2017.01) |
| A61K 38/26 | (2006.01) |

(52) U.S. Cl.
CPC ........... *C07K 14/605* (2013.01); *A61K 38/26* (2013.01); *A61K 38/28* (2013.01); *A61K 45/06* (2013.01); *A61K 47/60* (2017.08)

(58) Field of Classification Search
None
See application file for complete search history.

(56) References Cited

U.S. PATENT DOCUMENTS

| | | | |
|---|---|---|---|
| 9,714,277 B2 * | 7/2017 | Bednarek | ............. C07K 14/605 |
| 2008/0045461 A1 | 2/2008 | Ewing et al. | |
| 2013/0143800 A1 | 6/2013 | Montminy et al. | |
| 2013/0303436 A1 | 11/2013 | Wilson et al. | |

FOREIGN PATENT DOCUMENTS

| EP | 0154316 | | 9/1985 |
|---|---|---|---|
| EP | 0401384 | A1 | 12/1990 |
| EP | 2173890 | | 3/2011 |
| WO | WO 2004/022004 | A2 | 3/2004 |
| WO | WO 2008/023050 | A1 | 2/2008 |
| WO | WO 2009/125424 | A2 | 10/2009 |
| WO | WO 2011/143209 | A1 | 11/2010 |
| WO | WO 2010/148089 | A1 | 12/2010 |
| WO | WO 2011/048614 | A2 | 4/2011 |
| WO | WO2014049610 | A2 | 3/2014 |
| WO | WO2015086686 | A2 | 10/2014 |
| WO | WO2014088631 | A1 | 12/2014 |

OTHER PUBLICATIONS

Hui, Diabetes Metab Res Rev 2005; 21: 313-331 (Year: 2005).*
Hongxiang, H., et al., "Structure and function studies of glucagon-like peptide-1 (GLP-1): the designing of a novel pharmacological agent for the treatment of diabetes," Diabetes/Metabolism Research and Reviews, Wiley, vol. 21, No. 4, Jul. 1, 2005, pp. 313-331.
Green, B., et al., "Degradation, Receptor Binding, Insulin Secreting and Antihyperglycaemic Actions of Palmitate-Derivatised Native and ALA8-Substituted GLP-1 Analogues," Biological Chemistry, Walter De Gruyter GMBH & Co., vol. 385, No. 2, Feb. 1, 2004, pp. 169-177.
Youn, et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability", Biochemical Pharmacology, vol. 73, No. 1, Dec. 6, 2006, pp. 84-93.
Kim, S., et al., "Synthesis, bioactivity and specificity of glucagon-like peptide-1 (7-37)/polymer conjugate to isolated rat islets," Biomaterials, Elsevier Science Publishers BV., vol. 26, No. 17, Jun. 1, 2005, pp. 3597-3606.
Chae, S.Y., et al., "The fatty acid conjugated exendin-4 analogs for type 2 antidiabetic therapeutics", Journal of Controlled Release, Elsevier, Amsterdam, NL, 144, pp. 10-16, May 21, 2010.
Merrifield, R.B., et al., "Solid Phase Peptide Synthesis. I. The Synthesis of a Tetrapeptide," Journal of the American Chemical Society, vol. 85 (14), pp. 2149-2154, Jul. 1963.
Baggio, L.L., et al., "A Recombinant Human Glucagon-Like Peptide (GLP)-1—Albumin Proteing (Albugon) Mimics Peptidergic Activation of GLP-1 Receptor-Dependent Pathways Coupled with Satiety, Gastrointestinal Motility, and Glucose Homeostasis", Diabetes, vol. 53, pp. 2492-2500, Sep. 2004.
Barrington, P. et al., "LY2189265, a long-acting glucagon-like peptide-1 analogue, showed a dose-dependent effect on insulin secretion in healthy subjects," Diabetes, Obesity and Metabolism, 13, pp. 434-438, 2011.

(Continued)

*Primary Examiner* — Satyanarayana R Gudibande

(57) ABSTRACT

The present invention provides protease-resistant peptides, methods of making such peptides, as well as compositions comprising protease-resistant peptides and method of treatment utilizing such peptides. A combination of lipidation of certain amino acid residues and substitution of alpha-methyl functionalized amino acids for natural amino acids has been determined to produce protease-resistant peptides.

15 Claims, 16 Drawing Sheets

Specification includes a Sequence Listing.

(56) References Cited

OTHER PUBLICATIONS

Paulik, P., et al., Poster 1946, "Long-Acting PYY and GLP-1 Agonism in Combination Synergistically Normalizes Weight, Glucose, Metabolic and Metabolomic Parameters in Diet Induced Obese Mice," American Diabetes Association, 2012.

Schellenberger, V., et al., "A recombinant polypeptide extends the in vivo half-life of peptides and proteins in a tunable manner," Nature Biotechnology, 27, pp. 1186-1190, Nov. 15, 2009.

Dennis, M.S., et al., "Albumin Binding as a General Strategy for Improving the Pharmacokinetics of Proteins," The Journal of Biology Chemistry, vol. 277, No. 38, pp. 35035-35043, 2002.

Walker, A. et al., "Anti-serum albumin domain antibodies in the development of highly potent, efficacious and long-acting interferon," Protein Engineering, Design & Selection, vol. 23, No. 4, pp. 271-278, 2010.

Hjorth, S.A., et al., "Glucagon and Glucagon-Like Peptide 1: Selective Receptor Recognition via Distinct Peptide Epitopes", Journal of Biological Chemistry, American Society of Biochemistry and molecular Biology, US., vol. 269, No. 48, pp. 30121-30124, Jan. 1, 1994.

Karlin, S., et al., "Applications and statistics for multiple high-scorng segments in molecular sequences," Proc. Natl. Acad. Sci. USA, 90, 5873-5877, Jun. 1993.

Underwood, C.R., et al., "Crystal Structure of Glucagon-like Peptide-1 in Complex with the Extracellular Domain of the Glucagon-like Peptide-1 Receptor," The Journal of Biological Chemistry, vol. 285, No. 1, pp. 723-730, Jan. 1, 2010.

Runge, S., et al., "Crystal Structure of the Ligand-bound Glucagon-like Peptide-1 Receptor Extracellular Domain," The Journal of Biological Chemistry, vol. 283, No. 17, pp. 11340-11347, Apr. 25, 2008.

Francis, G.E., "Protein modification and fusion proteins," Focus on Growth Factors, 1992;3:4-10, Mediscript.

Gallwitz Baptist et al., "GLP-1-analogues resistant to degradation by dipeptidyl-peptidase IV in vitro," Regulatory Peptides, Elsevier Science BV, NL, vol. 86, No. 1-3, Jan. 29, 2000, pp. 103-111.

\* cited by examiner

SEQ ID NO: 3
Chemical Formula: $C_{183}H_{286}N_{38}O_{57}$
Molecular Weight: 3930.51

SEQ ID NO: 17
Chemical Formula: $C_{149}H_{227}N_{35}O_{45}$
Molecular Weight: 3228.66

SEQ ID NO: 48
Chemical Formula: $C_{182}H_{284}N_{38}O_{57}$
Molecular Weight: 3916.48

SEQ ID NO: 60
Chemical Formula: $C_{183}H_{284}N_{38}O_{59}$
Molecular Weight: 3960.49

SEQ ID NO: 68
Chemical Formula: $C_{185}H_{285}N_{39}O_{59}$
Molecular Weight: 3999.53

SEQ ID NO: 252
Chemical Formula: $C_{201}H_{324}N_{42}O_{67}$
Molecular Weight: 4401.03

SEQ ID NO: 263
Chemical Formula: $C_{196}H_{322}N_{42}O_{67}$
Molecular Weight: 4338.96

SEQ ID NO: 269
Chemical Formula: $C_{199}H_{320}N_{42}O_{68}$
Molecular Weight: 4388.98

SEQ ID NO: 405
Chemical Formula: $C_{197}H_{324}N_{42}O_{67}$
Molecular Weight: 4352.99

SEQ ID NO: 406
Chemical Formula: $C_{197}H_{324}N_{42}O_{68}$
Molecular Weight: 4368.99

SEQ ID NO: 407
Chemical Formula: $C_{193}H_{324}N_{42}O_{67}$
Molecular Weight: 4304.94

SEQ ID NO: 408
Chemical Formula: $C_{201}H_{332}N_{42}O_{67}$
Molecular Weight: 4409.09

SEQ ID NO: 409
Chemical Formula: $C_{205}H_{340}N_{42}O_{67}$
Molecular Weight: 4465.20

SEQ ID NO: 410
Chemical Formula: $C_{209}H_{348}N_{42}O_{67}$
Molecular Weight: 4521.31

SEQ ID NO: 488
Chemical Formula: $C_{150}H_{228}N_{40}O_{45}$
Molecular Weight: 3311.71

SEQ ID NO: 489
Chemical Formula: $C_{170}H_{268}N_{38}O_{46}$
Molecular Weight: 3580.23

SEQ ID NO: 490 (Liraglutide)
Chemical Formula: $C_{172}H_{265}N_{43}O_{51}$
Molecular Weight: 3751.26

SEQ ID NO: 491 (Semaglutide)
Chemical Formula: $C_{187}H_{291}N_{45}O_{59}$
Molecular Weight: 4113.64

PROTEASE-RESISTANT LIPIDATED GLP-1 ANALOGS

CROSS-REFERENCE TO RELATED APPLICATIONS

This application is a U.S. National Stage application of International Application No. PCT/EP2016/063206 filed 056973, filed Jun. 9, 2016, said International Application No. PCT/EP2016/063206 claims priority under 35 U.S.C. § 119 to U.S. Provisional Application Ser. No. 62/173,631, filed Jun. 10, 2015 and U.S. Provisional Application Ser. No. 62/343,390, filed May 31, 2016 each of which are incorporated herein by reference in their entirety.

REFERENCE TO SEQUENCE LISTING SUBMITTED ELECTRONICALLY

The content of the electronically submitted sequence listing in ASCII text file (Name: ORPEP-101WO1_SL.txt; Size: 424,418 bytes; and Date of Creation: Jun. 7, 2016) filed with the application is incorporated herein by reference in its entirety.

BACKGROUND

The present disclosure provides protease-resistant peptides, methods of making such peptides, as well as compositions comprising protease-resistant peptides and methods of treatment utilizing such peptides. Lipid modification of amino acids at certain positions in the peptide sequence is described herein.

The development of long-acting peptide therapeutics is hampered by factors such as short plasma half-life and poor oral bioavailability, largely a result of the natural susceptibility of peptides to enzymatic degradation. The majority of proteolytic functions are necessary, including regulating essential biomolecular processes such as turning off peptide signaling events at cell surfaces, or the gastric breakdown of proteins and peptides during digestion. Thus, the activity of the responsible proteases cannot simply be inhibited without, in many cases, causing other metabolic disturbances.

In order to overcome degradation, increasing the enzymatic resistance of a peptide of interest is therefore desirable. Generally, two methods are utilized to increase enzymatic resistance: sequence specific modifications, e.g., those affecting the primary structure of the peptide itself; and globally effective modifications, e.g., those which alter certain overall physicochemical characteristics of the peptide. Introduced strategically, such modifications can reduce the effects of natural physiological processes which would otherwise eliminate or inactivate a peptide whose action is desired, e.g. enzymatic degradation and/or clearance by renal ultrafiltration.

Sequence specific modifications include incorporation of proteolysis-resistant unusual amino acids, or more involved modifications including cyclization between naturally occurring side-chain functions, e.g. disulfide formation (Cys-Cys), or lactamization (Lys-Glu or Lys-Asp). Additional modifications include cyclization between unnatural amino acid surrogates within the peptide backbone e.g. olefin metathesis stapling.

Global modifications include processes such as peptide lipidation e.g. palmitoylation and/or PEGylation. Palmitoylation has the effect of creating a circulating reservoir of peptide which reversibly associates with naturally abundant albumin in blood serum. Peptide associated with albumin effectively escapes renal ultrafiltration since the size of the associated complex is above the glomerular filtration cutoff. As the peptide dissociates from the surface of the albumin it is again free to interact with endogenous receptors. PEGylation has the effect of physically shielding the peptide from proteolysis and imparts significant hydrophilicity which upon hydration greatly increases the hydrodynamic radius of the therapeutic molecule to overcome renal clearance.

While these technologies can be broadly applicable to therapeutic peptides in general, and to an extent are able to extend circulatory half-life, a need still exists for methods of increasing stability of peptides and proteins to enzymatic degradation, particularly in light of the desire to produce peptides suitable for oral administration.

SUMMARY

The present disclosure provides for an isolated polypeptide comprising the amino acid sequence: H X2 E G S X6 T S D V X11 X12 X13 L E G E A A X20 E X22 I X24 X25 V V X28 G G (SEQ ID NO: 2) wherein X2 is A or Aib, X6 is F or an alpha-methyl functionalized amino acid, X11 is S or an alpha-methyl functionalized amino acid, X12 is S or a lipid modified K, X13 is Y or an alpha-methyl functionalized amino acid, X20 is a lipid modified K, K, or an alpha-methyl functionalized amino acid, X22 is F or an alpha-methyl functionalized amino acid, X24 is A or a lipid modified K; X25 is W or an alpha-methyl functionalized amino acid, and X28 is K, E, or an alpha-methyl functionalized amino acid, wherein the polypeptide is lipidated on only one of X12, X20, or X24.

In certain embodiments, a peptide comprising the amino acid sequence of SEQ ID NO: 2 comprises a C-terminal amide. In certain embodiments, a peptide comprising the amino acid sequence of SEQ ID NO: 2 comprises a C-terminal acid.

In certain embodiments of a peptide comprising the amino acid sequence of SEQ ID NO: 2, X2 is Aib. In certain embodiments of a peptide comprising the amino acid sequence of SEQ ID NO: 2, the lipid modified K is selected from the group consisting of: K(ε-(PEG)$_2$-(PEG)$_2$-γE-Stearate), K(ε-γE-Palmitoyl), K(ε-(PEG)$_2$-(PEG)$_2$-(PEG)$_2$-Stearoyl), K(ε-γE-Lauroyl), K(ε-γE-γE-Lauroyl), K(ε-γE-γE-γE-Lauroyl), K(ε-Ahx-Lauroyl), K(ε-Ahx-Ahx-Lauroyl), K(ε-Ahx-Ahx-Ahx-Lauroyl), K(ε-(PEG)$_2$-Lauroyl), K(ε-(PEG)$_2$-(PEG)$_2$-Lauroyl), K(ε-(PEG)$_2$-(PEG)$_2$-(PEG)$_2$-Lauroyl), K(ε-γE-12-(4-carboxyphenoxy)dodecanoyl), K(ε-γE-γE-12-(4-carboxyphenoxy)dodecanoyl), K(ε-γE-γE-γE-12-(4-carboxyphenoxy)dodecanoyl), K(ε-Ahx-12-(4-carboxyphenoxy)dodecanoyl), K(ε-Ahx-Ahx-12-(4-carboxyphenoxy)dodecanoyl), K(ε-Ahx-Ahx-Ahx-12-(4-carboxyphenoxy)dodecanoyl), K(ε-(PEG)$_2$-12-(4-carboxyphenoxy)dodecanoyl), K(ε-(PEG)$_2$-(PEG)$_2$-12-(4-carboxyphenoxy)dodecanoyl), K(ε-(PEG)$_2$-(PEG)$_2$-(PEG)$_2$-12-(4-carboxyphenoxy)dodecanoyl), K(ε-γE-Stearoyl), K(ε-γE-γE-Stearoyl), K(ε-γE-γE-γE-Stearoyl), K(ε-Ahx-Stearoyl), K(ε-Ahx-Ahx-Stearoyl), K(ε-Ahx-Ahx-Ahx-Stearoyl), K(ε-(PEG)$_2$-Stearoyl), K(ε-(PEG)$_2$-(PEG)$_2$-Stearoyl), K(ε-(PEG)$_2$-(PEG)$_2$-(PEG)$_2$-Stearoyl), K(ε-γE-Stearate), K(ε-γE-γE-Stearate), K(ε-γE-γE-γE-Stearate), K(ε-Ahx-Stearate), K(ε-Ahx-Ahx-Stearate), K(ε-Ahx-Ahx-Ahx-Stearate), K(ε-(PEG)$_2$-Stearate), K(ε-(PEG)$_2$-(PEG)$_2$-Stearate), K(ε-(PEG)$_2$-(PEG)$_2$-(PEG)$_2$-Stearate), and any combination thereof. In certain embodiments, the lipid modified K is K(ε-(PEG)$_2$-(PEG)$_2$-γE-Stearate).

In certain embodiments of a peptide comprising the amino acid sequence of SEQ ID NO: 2, X6 is α-MeF, X11 is α-MeS, X13 is α-MeF, X22 is α-MeF, X25 is α-MeF, X28 is α-MeK, or any combination thereof. In certain embodiments, X2 is Aib, X6 is α-MeF, X11 is α-MeS, X13 is α-MeF, X20 is K(ε-(PEG)$_2$-(PEG)$_2$-γE-Stearate), X22 is α-MeF, X25 is α-MeF, and X28 is α-MeK (SEQ ID NO: 3). In certain embodiments, the peptide comprises the amino acid sequence of SEQ ID NO: 48, SEQ ID NO: 60, or SEQ ID NO: 68.

In certain embodiments of a peptide comprising the amino acid sequence of SEQ ID NO: 2, the polypeptide is substantially resistant to proteolytic degradation. In certain embodiments, the polypeptide is substantially resistant to DPP-IV, neprilysin, α-chymotrypsin, plasmin, thrombin, kallikrein, trypsin, elastase and/or pepsin degradation. In certain embodiments, the polypeptide at least maintains substantially the same receptor potency as a corresponding non-lipidated polypeptide. In certain embodiments, the polypeptide at least maintains substantially the same receptor selectivity as a corresponding non-lipidated polypeptide. In certain embodiments, the polypeptide exhibits increased receptor potency over a corresponding non-lipidated polypeptide.

The present disclosure also provides for an isolated polypeptide comprising the amino acid sequence: H X2 E G X5 X6 T S D X10 X11 X12 X13 X14 E G X17 A A X20 E X22 I X24 X25 X26 V X28 G X30 (SEQ ID NO: 4); wherein X2 is A or Aib, X5 is T or S, X6 is F or an alpha-methyl functionalized amino acid, X10 is V or a lipid modified K, X11 is S or an alpha-methyl functionalized amino acid, X12 is S or a lipid modified K, X13 is Y, F, or a lipid modified K, X14 is L or a lipid modified K, X17 is Q or E, X20 is K, E, or an alpha-methyl functionalized amino acid, X22 is F, norleucine, tyrosine methyl ester, or an alpha-methyl functionalized amino acid, X24 is A or a lipid modified K, X25 is W, F, or a lipid modified K, X26 is L, V, or a lipid modified K, X28 is K or E, and X30 is R or G, wherein the polypeptide comprises two lipid modified K residues, and wherein one of X10, X12, X13, or X14 is a lipid modified K residue and one of X24, X25, or X26 is a lipid modified K residue. In certain embodiments: X6 is F, α-MeF, α-MeS, or α-MeK; X11 is S α-MeF, α-MeS, or α-MeK; and X20 is K, E, α-MeF, α-MeS, or α-MeK.

In certain embodiments, a peptide comprising the amino acid sequence of SEQ ID NO: 4 comprises a C-terminal amide. In certain embodiments, a peptide comprising the amino acid sequence of SEQ ID NO: 4 comprises a C-terminal acid.

In certain embodiments of a peptide comprising the amino acid sequence of SEQ ID NO: 4, X2 is Aib. In certain embodiments, the two lipid modified K residues are the same or are different, and are selected from the group consisting of: K(ε-(PEG)$_2$-(PEG)$_2$-γE-Lauroyl), K(ε-(PEG)$_2$-(PEG)$_2$-γE-Palmitate), K(ε-(PEG)$_2$-(PEG)$_2$-γE-Myristoyl), K(ε-(PEG)$_2$-(PEG)$_2$-γE-Palmitoyl), K(ε-(PEG)$_2$-(PEG)$_2$-γE-Stearoyl), K(ε-(PEG)$_2$-(PEG)$_2$-γE-Stearate), and any combination thereof. In certain embodiments, the two lipid modified K residues are both K(ε-(PEG)$_2$-(PEG)$_2$-γE-Lauroyl), both K(ε-(PEG)$_2$-(PEG)$_2$-γE-Palmitate), both K(ε-(PEG)$_2$-(PEG)$_2$-γE-Myristoyl), both K(ε-(PEG)$_2$-(PEG)$_2$-γE-Palmitoyl), both K(ε-(PEG)$_2$-(PEG)$_2$-γE-Stearoyl), or both K(ε-(PEG)$_2$-(PEG)$_2$-γE-Stearate).

In certain embodiments of a peptide comprising the amino acid sequence of SEQ ID NO: 4, X10 is a lipid modified K and one of X24, X25, or X26 is a lipid modified K. In certain embodiments, X12 is a lipid modified K and one of X24, X25, or X26 is a lipid modified K. In certain embodiments, X13 is a lipid modified K and one of X24, X25, or X26 is a lipid modified K. In certain embodiments, X14 is a lipid modified K and one of X24, X25, or X26 is a lipid modified K. In certain embodiments, X24 is a lipid modified K and one of X10, X12, X13, or X14 is a lipid modified K. In certain embodiments, X25 is a lipid modified K and one of X10, X12, X13, or X14 is a lipid modified K. In certain embodiments, X26 is a lipid modified K and one of X10, X12, X13, or X14 is a lipid modified K.

In certain embodiments of a peptide comprising the amino acid sequence of SEQ ID NO: 4: X6 is α-MeF, X11 is α-MeS, X20 is α-MeK, X6 is α-MeF and X11 is α-MeS, X6 is α-MeF and X20 is α-MeK, X11 is α-MeS, and X20 is α-MeK or X6 is α-MeF, X11 is α-MeS, and X20 is α-MeK. In certain embodiments, X13 is a lipid modified K and one of X24, X25, or X26 is a lipid modified K. In certain embodiments, X14 is a lipid modified K and one of X24, X25, or X26 is a lipid modified K. In certain embodiments, X5 is S. In certain embodiments, X17 is E, X28 is E, and X30 is G. In certain embodiments, the polypeptide comprises the amino acid sequence of SEQ ID NO: 252; SEQ ID NO: 263; SEQ ID NO: 269; SEQ ID NO: 405; SEQ ID NO: 408; SEQ ID NO: 409; or SEQ ID NO: 410.

The present disclosure also provides for an isolated polypeptide comprising the amino acid sequence: H (Aib) E G S (α-MeF) T S D X10 X11 X12 X13 X14 E X16 X17 X18 A (α-MeK) X21 F I X24 X25 X26 V E G G (SEQ ID NO: 487), wherein X10 is V or a lipid modified K; X11 is S or an alpha-methyl functionalized amino acid; X12 is S or a lipid modified K; X13 is Y or a lipid modified K; X14 is L or a lipid modified K; X16 is G or a lipid modified K; X17 is E or a lipid modified K; X18 is A or a lipid modified K; X21 is E or a lipid modified K; X24 is A or a lipid modified K; X25 is F or a lipid modified K; X26 is V or a lipid modified K; and wherein the polypeptide comprises three lipid modified K residues, and wherein one of X10, X12, X13, or X14 is a lipid modified K residue and one of X16, X17, X18, or X21 is a lipid modified K residue and one of X24, X25, or X26 is a lipid modified K residue.

In certain embodiments, a peptide comprising the amino acid sequence of SEQ ID NO: 487 comprises a C-terminal amide. In certain embodiments, a peptide comprising the amino acid sequence of SEQ ID NO: 487 comprises a C-terminal acid.

In certain embodiments, the lipid modified K residues can be attached to a variety of lipids or lipid moieties such as any of those described herein. In certain embodiments, examples include those selected from the group consisting of: K(ε-(PEG)$_2$-(PEG)$_2$-γE-Lauroyl); K(ε-(PEG)$_2$-(PEG)$_2$-γE-Palmitate); K(ε-(PEG)$_2$-(PEG)$_2$-γE-Myristoyl); K(ε-(PEG)$_2$-(PEG)$_2$-γE-Palmitoyl); K(ε-(PEG)$_2$-(PEG)$_2$-γE-Stearoyl); K(ε-(PEG)$_2$-(PEG)$_2$-γE-Stearate); and any combination thereof. In other embodiments, the lipid modification of the K residues can be the same or different. In certain embodiments, they are the same. Thus, in certain embodiments, at least three lipid modified K residues can all be K(ε-(PEG)$_2$-(PEG)$_2$-γE-Lauroyl); all be K(ε-(PEG)$_2$-(PEG)$_2$-γE-Palmitate); all be K(ε-(PEG)$_2$-(PEG)$_2$-γE-Myristoyl); all be K(ε-(PEG)$_2$-(PEG)$_2$-γE-Palmitoyl); all be K(ε-(PEG)$_2$-(PEG)$_2$-γE-Stearoyl); or all be K(ε-(PEG)$_2$-(PEG)$_2$-γE-Stearate). In certain embodiments of a peptide comprising the amino acid sequence of SEQ ID NO: 487: all modified residues can be K(ε-(PEG)$_2$-(PEG)$_2$-γE-Lauroyl); all can be K(ε-(PEG)$_2$-(PEG)$_2$-γE-Palmitate); all can be K(ε-(PEG)$_2$-(PEG)$_2$-γE-Myristoyl); all can be K(ε-(PEG)$_2$-(PEG)$_2$-γE-Palmitoyl); all can be K(ε-(PEG)$_2$-(PEG)$_2$-γE-Stearoyl); or all can be K(ε-(PEG)$_2$-(PEG)$_2$-γE-Stearate).

In certain embodiments of a peptide comprising the amino acid sequence of SEQ ID NO: 4 or 487, the polypeptide is substantially resistant to proteolytic degradation. In certain embodiments, the synthetic peptide is substantially resistant to DPP-IV, neprilysin, α-chymotrypsin, plasmin, thrombin, kallikrein, trypsin, elastase and/or pepsin degradation. In certain embodiments, the polypeptide, which comprises two lipid modified K residues, at least maintains substantially the same receptor potency as a corresponding non-lipidated peptide. In certain embodiments, the polypeptide, which comprises two lipid modified K residues, at least maintains substantially the same receptor selectivity as a corresponding non-lipidated peptide. In certain embodiments, the polypeptide, which comprises two lipid modified K residues, exhibits increased receptor potency over a corresponding non-lipidated polypeptide.

Provided herein are lipidated peptidse that can bind to a human GLP-1 receptor with an EC50 in the cAMP assay less than 5000 pM, less than 2500 pM, less than 1000 pM, less than 900 pM, less than 800 pM, less than 700 pM, less than 600 pM, less than 500 pM, less than 400 pM, less than 300 pM, less than 200 pM, less than 100 pM, less than 50 pM, less than 25 pM, less than 20 pM, less than 15 pM, less than 10 pM, less than 5 pM, less than 4 pM, less than 3 pM, or less than 2 pM.

The disclosure also provides for isolated polynucleotides encoding any of the lipidted polypeptide described herein. Certain embodiments provide for vectors comprising such polynucleotides. Certain embodiments provide for host cells comprising such nucleotides or vectors.

Certain embodiments provide for methods of making a lipidated polypeptide described herein. In certain embodiments, the method comprises culturing a host cell under conditions allowing expression of the peptide, and recovering the peptide.

Certain embodiments provide for pharmaceutical compositions comprising a lipidated polypeptide described in detail elsewhere herein. In certain embodiments, a kit comprises such composition.

Certain embodiments provide for methods of treating or preventing a disease or condition caused or characterized by hypoglycemia or impaired insulin release. Such methods comprise administering to a subject in need of treatment an effective amount of a lipidated polypeptide described in detail elsewhere herein or as pharmaceutical composition comprising such polypeptide. In certain embodiments, the disease or condition is diabetes. In certain embodiments, the disease or condition is type-2 diabetes. In certain embodiments, the administration further improves glycemic control, provides body weight control, improves β-cell function and mass, reduces the rate of gastric acid secretion and gastric emptying, or any combination thereof. In certain embodiments, the polypeptide or the pharmaceutical composition is administered orally or by injection. In certain embodiments, the polypeptide or the pharmaceutical composition is administered orally. In certain embodiments, the injection is administered subcutaneously or intravenously. In certain embodiments, the peptide or the pharmaceutical composition is administered once per day. In certain embodiments, methods of treating or preventing a disease or condition further comprise administering one or more additional therapies. In certain embodiments, the additional therapy comprises blood sugar monitoring, diet modifications, exercise, insulin, a thiazolidinedione, a sulfonylurea, an incretin, metformin, a glyburide, a dipeptidyl peptidase 4 inhibitor, a bile acid sequestrant, or any combination thereof. In certain embodiments, the subject treated is a human.

BRIEF DESCRIPTIONS OF THE DRAWINGS

DETAILED DESCRIPTION

Figure 1:
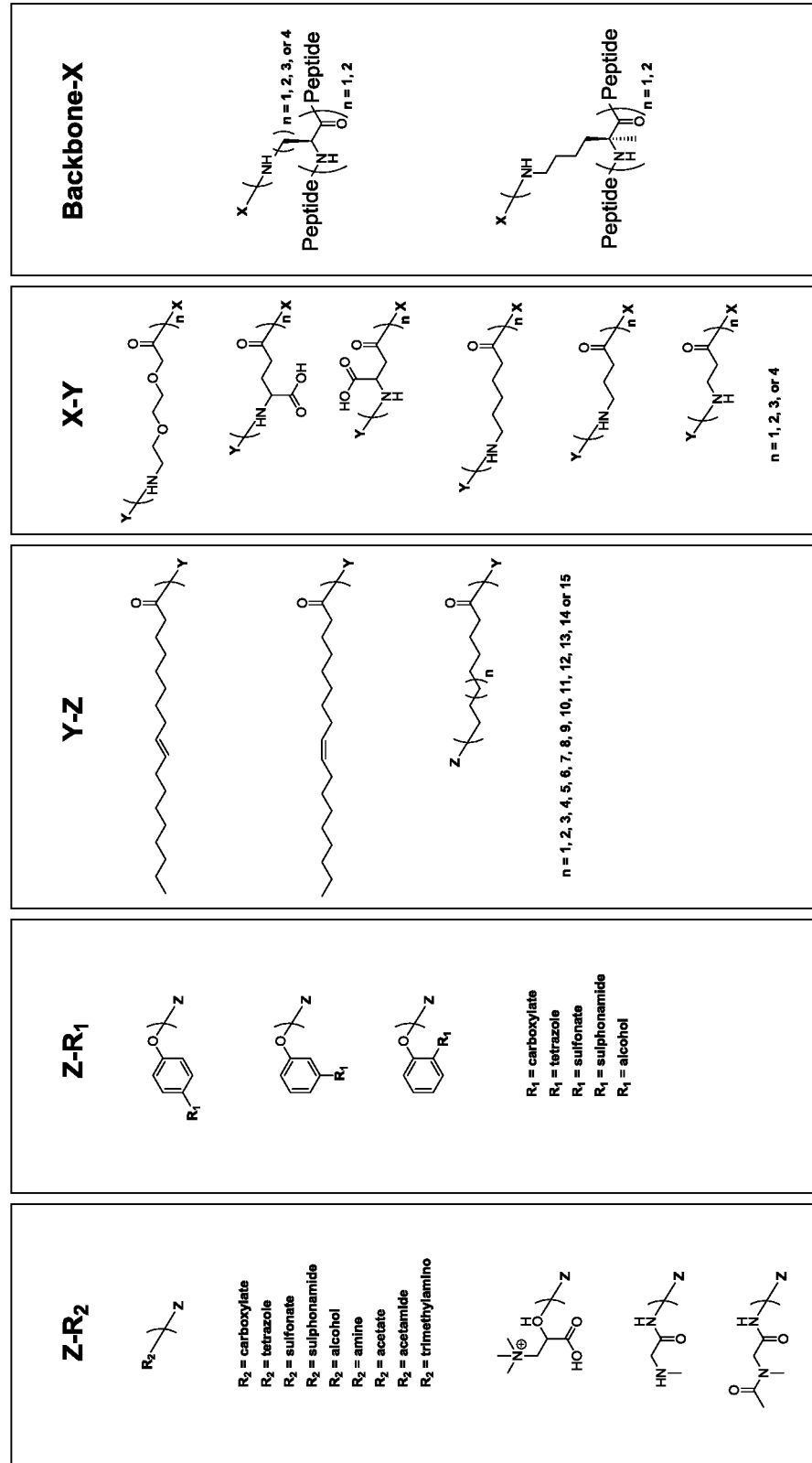
FIG. 1 shows representative lipid, lipid moieties, and linkers for forming lipidated polypeptides disclosed herein.
Figure 2:
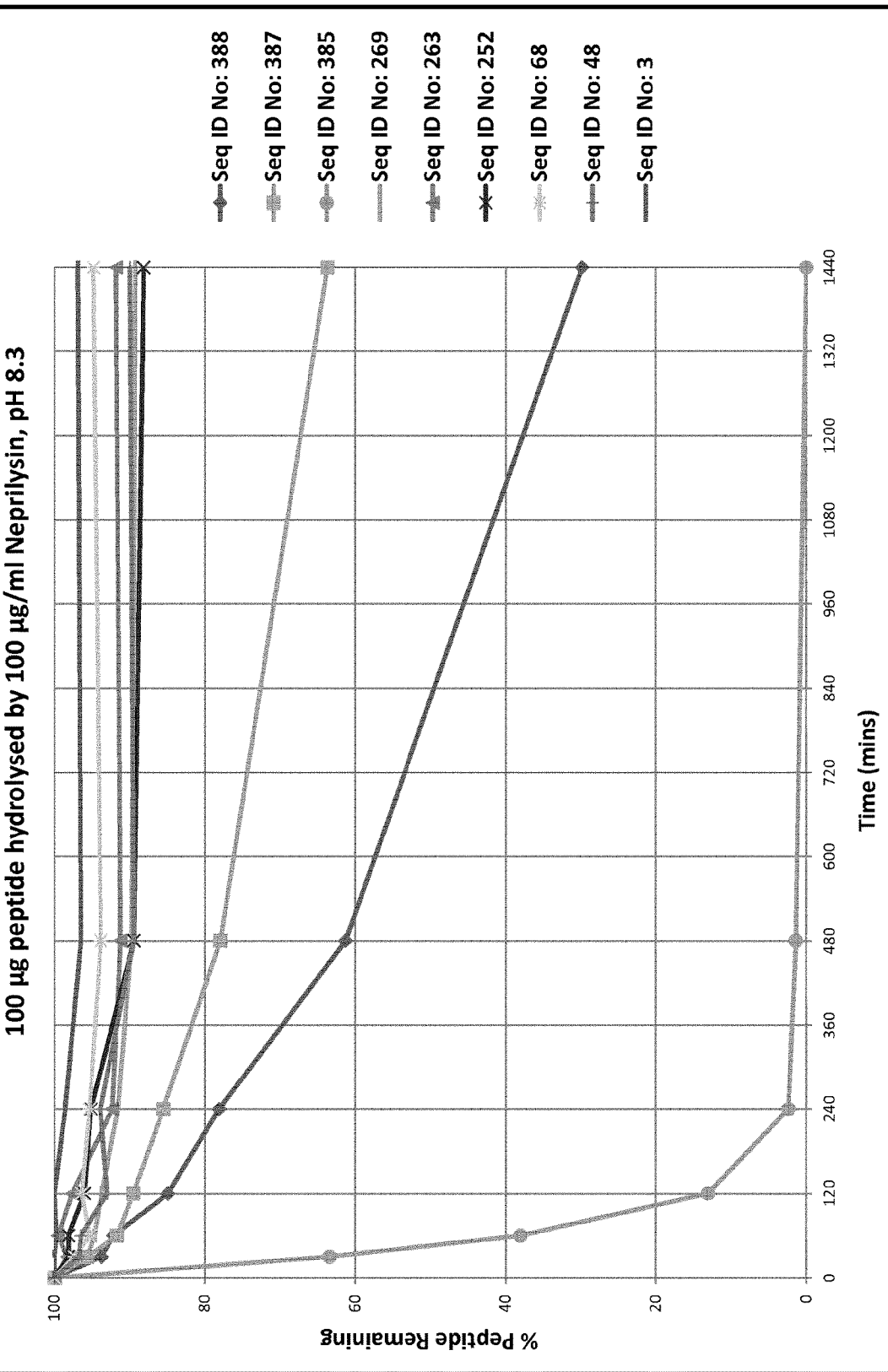
FIG. 2 shows the percent peptide remaining of 100 μg of peptide hydrolysed by 100 μg/mL Neprilysin at pH 8.3.
Figure 3:
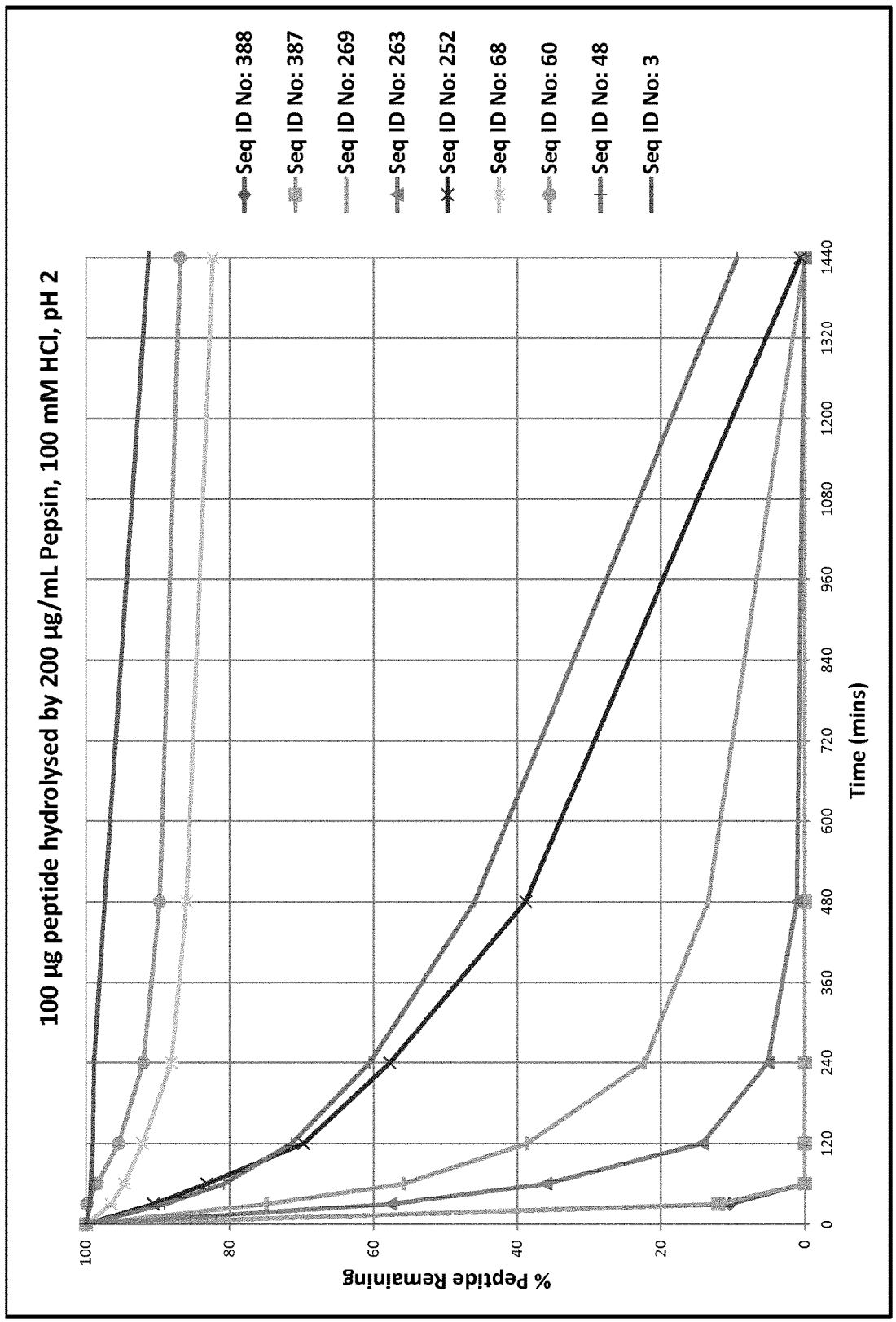
FIG. 3 shows the percent peptide remaining of 100 μg of peptide hydrolysed by 200 μg/mL Pepsin, 100 mM HCl at pH 2.
Figure 4:
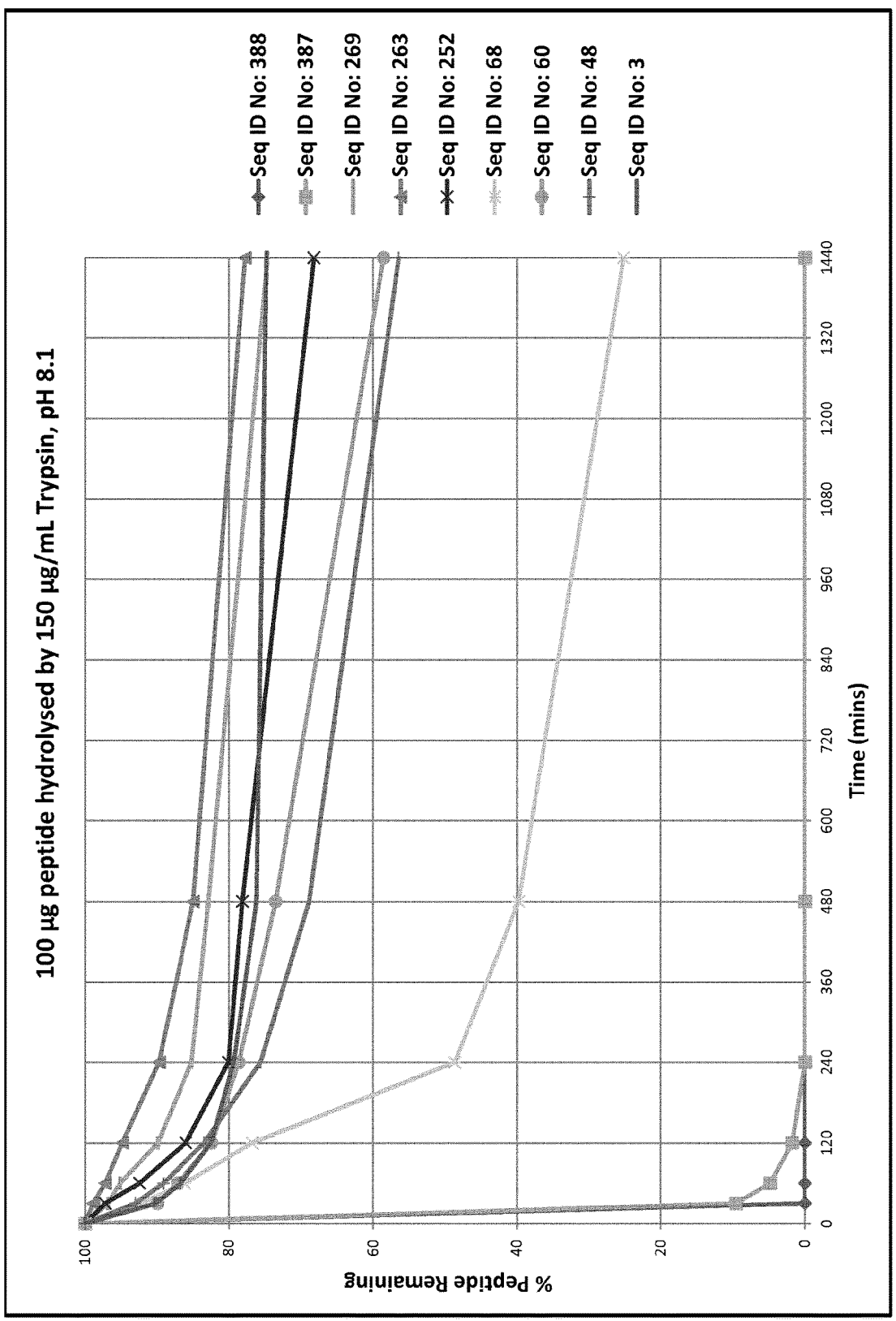
FIG. 4 shows the percent peptide remaining of 100 μg of peptide hydrolysed by 150 μg/mL Trypsin at pH 8.1.
Figure 5:
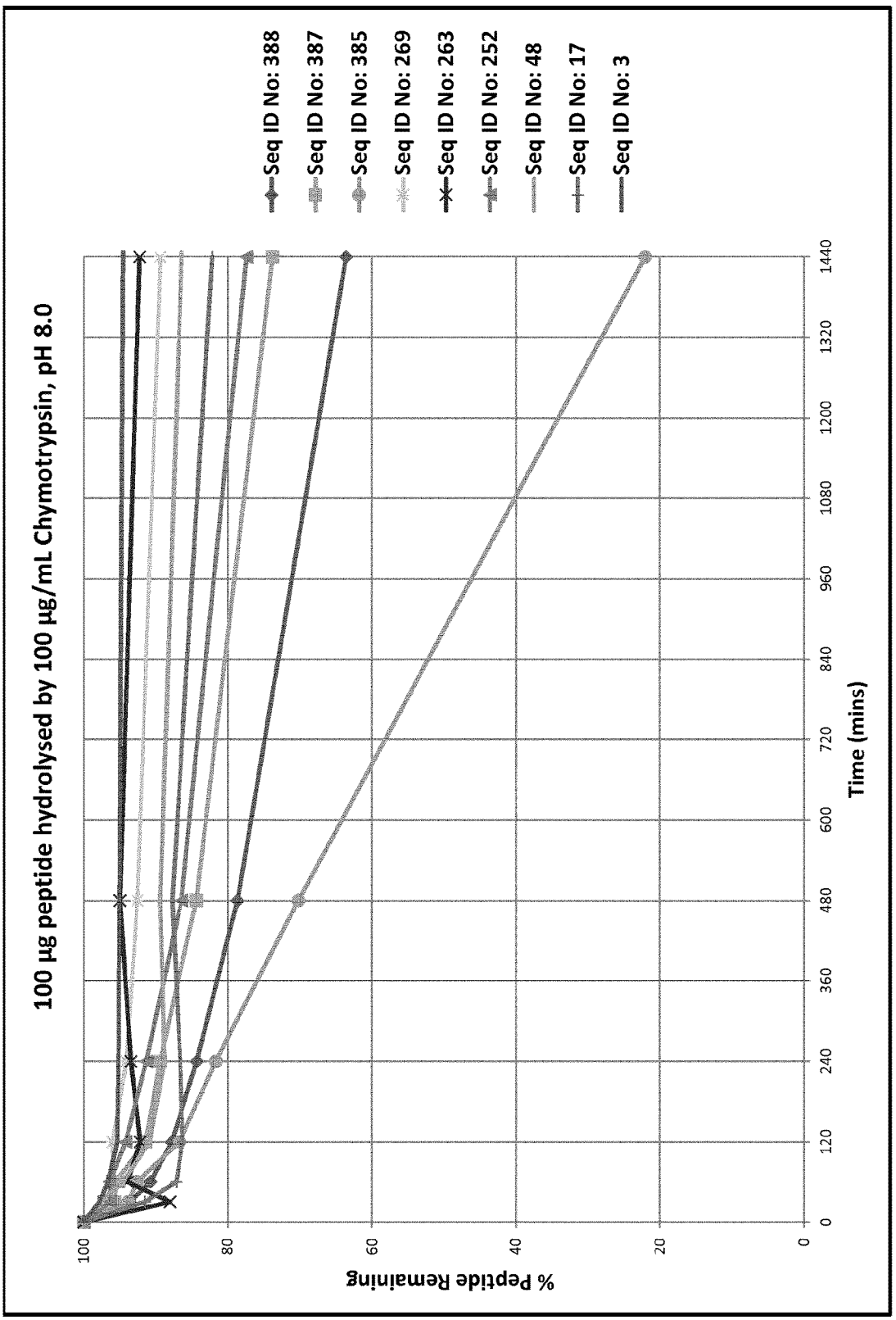
FIG. 5 shows the percent peptide remaining of 100 μg of peptide hydrolysed by 100 μg/mL Chymotrypsin at pH 8.
Figure 6:
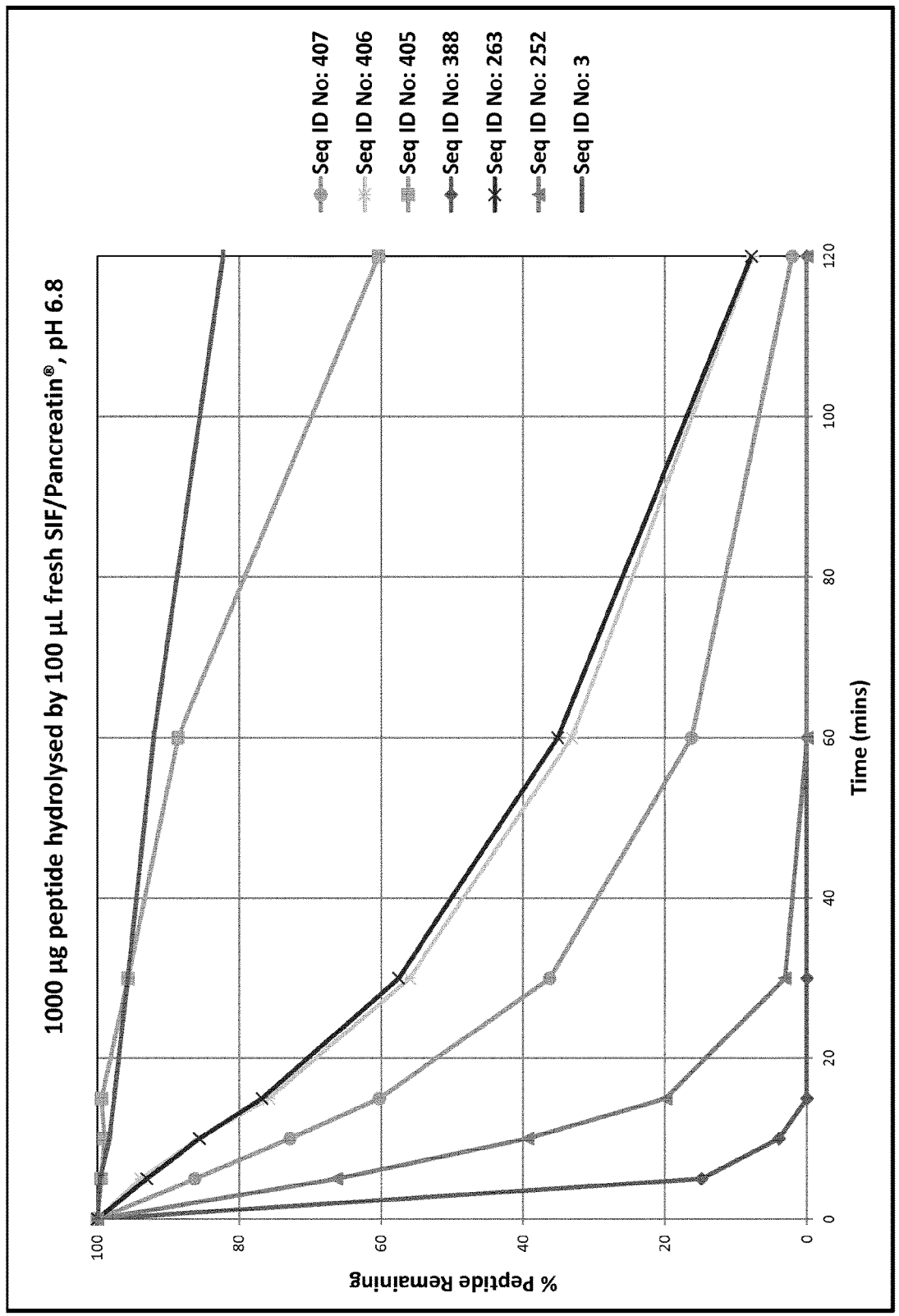
FIG. 6 shows the percent peptide remaining of 1000 μg of peptide hydrolysed by 100 μg/mL fresh SIF/Pancreatin® at pH 6.8.
Figure 7:
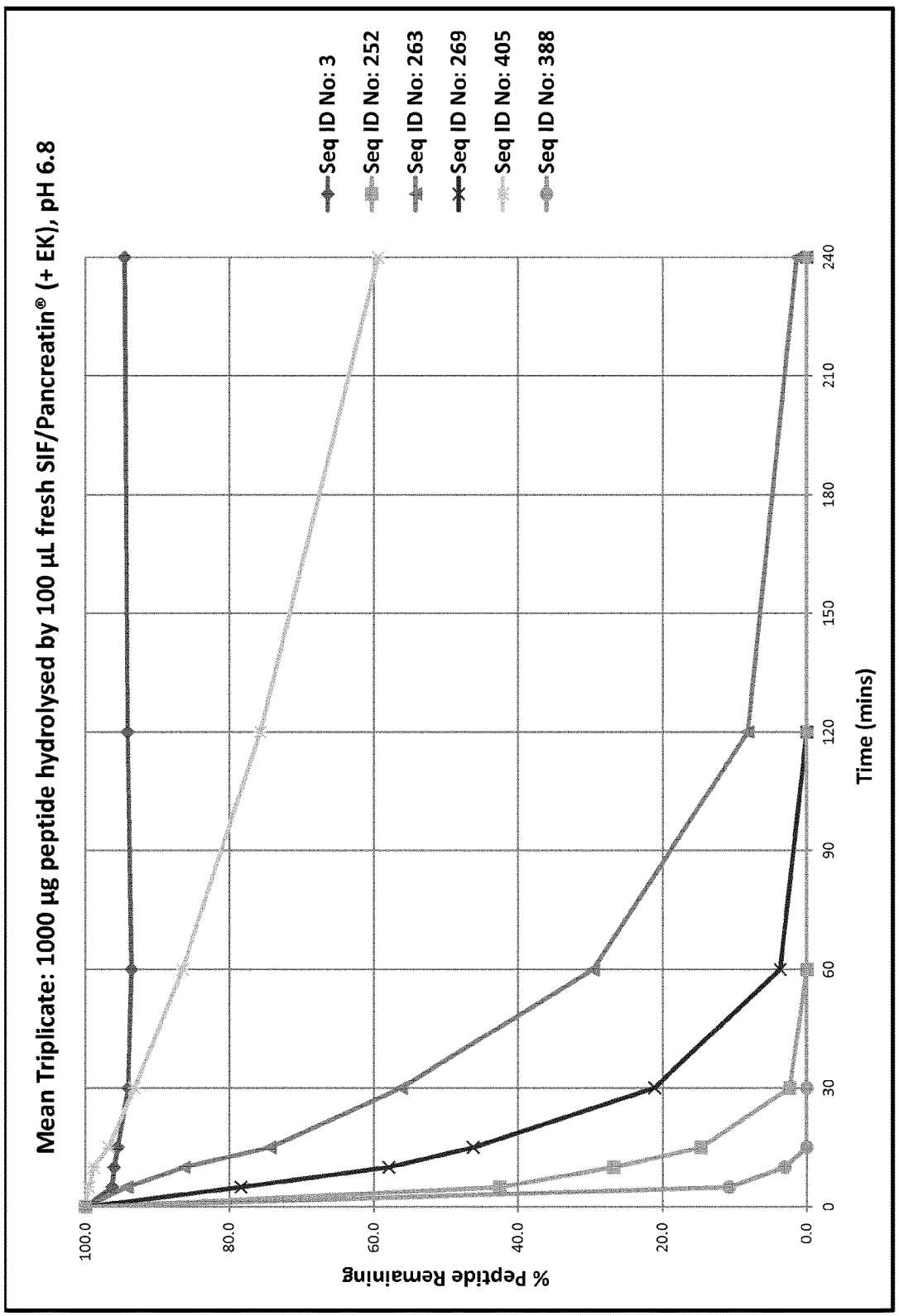
FIG. 7 shows the mean values from a triplicate run of the percent peptide remaining of 1000 μg of peptide hydrolysed by 100 μg/mL fresh SIF/Pancreatin® (with Enterokinase) at pH 6.8.
Figure 8:
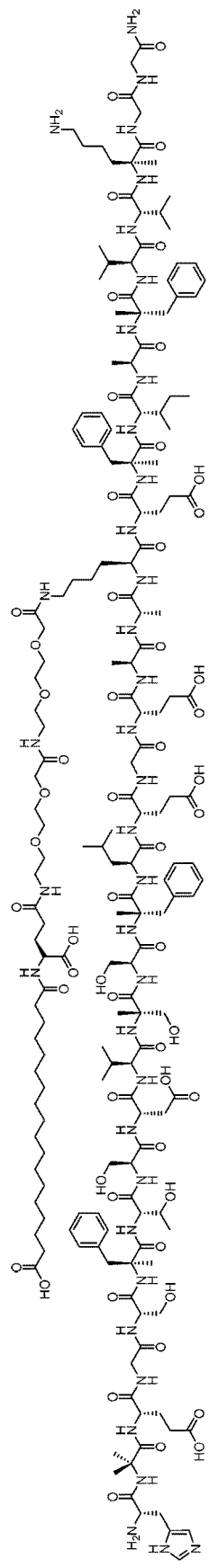
FIG. 8 shows the chemical structure, chemical formula and molecular weight for SEQ ID NO:3 and SEQ ID NO:17.
Figure 8:
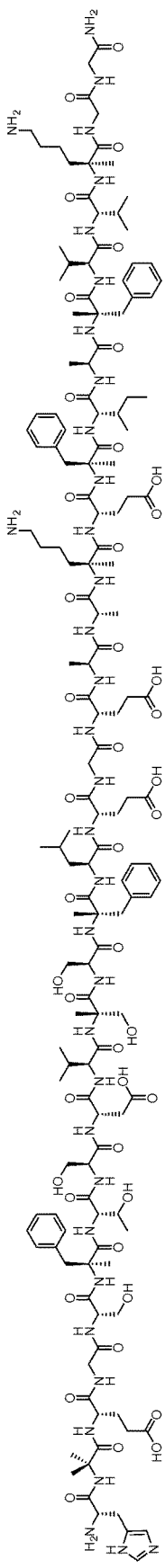
Figure 9:
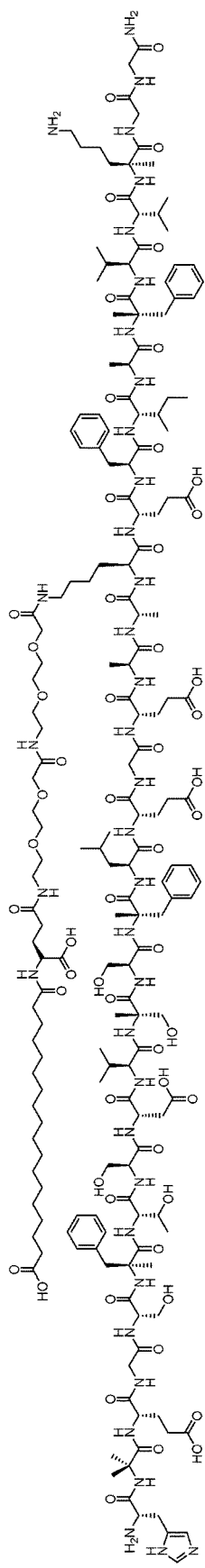
FIG. 9 shows the FIG. 9 shows the chemical structure, chemical formula and molecular weight for SEQ ID NO:48 and SEQ ID NO:60.
Figure 9:
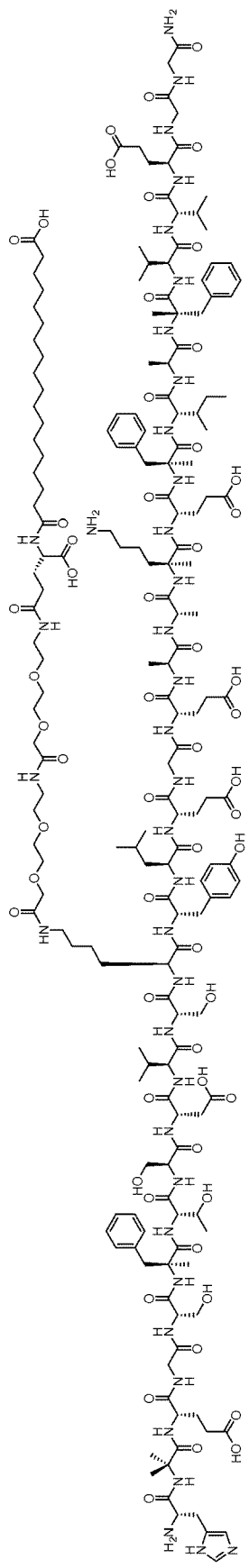
Figure 10:
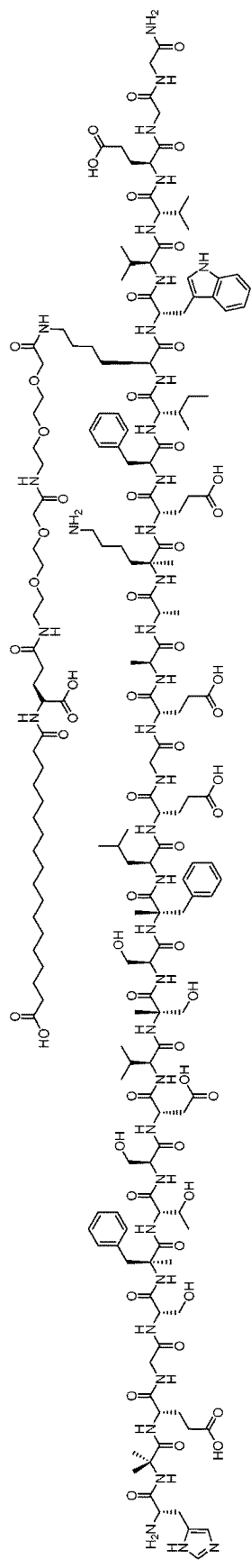
FIG. 10 shows the chemical structure, chemical formula and molecular weight for SEQ ID NO:68 and SEQ ID NO:252.
Figure 10:
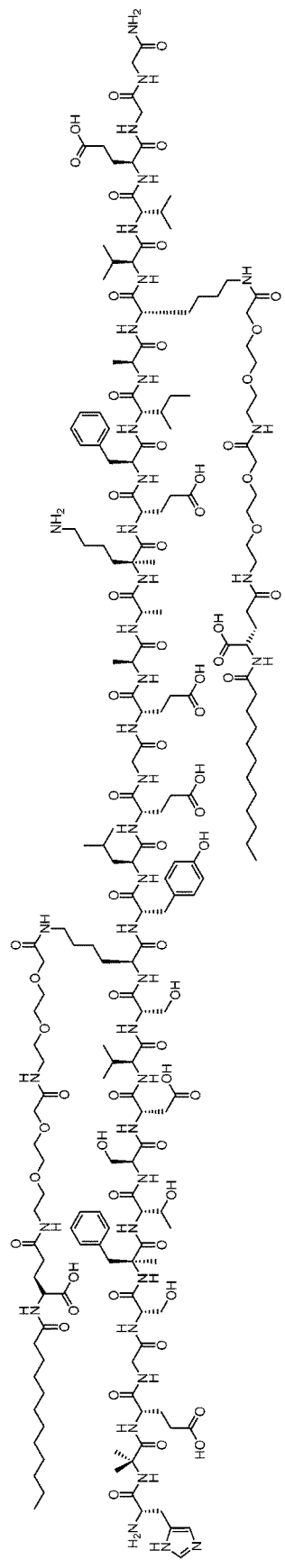
Figure 11:
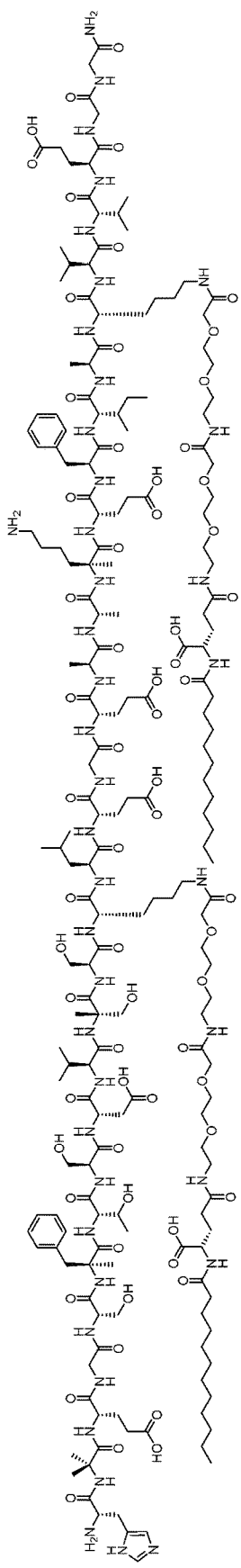
FIG. 11 shows the chemical structure, chemical formula and molecular weight for SEQ ID NO:263 and SEQ ID NO:269.
Figure 11:
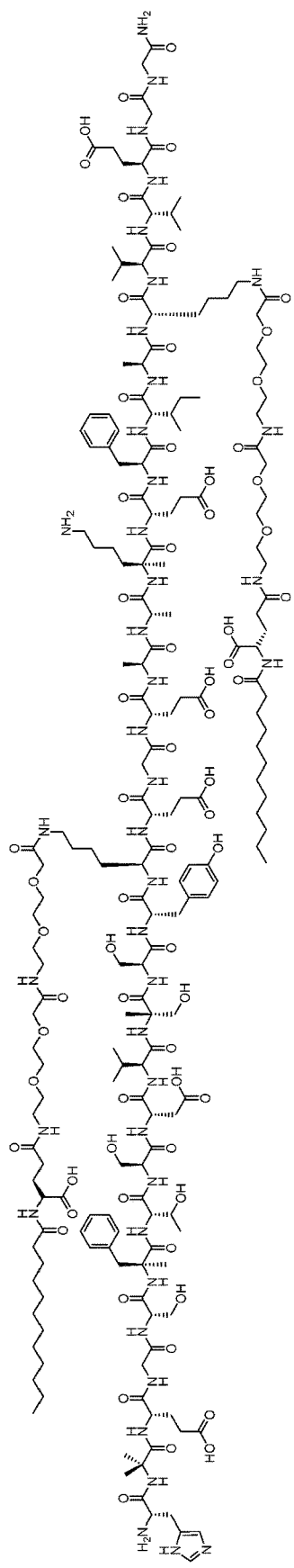
Figure 12:
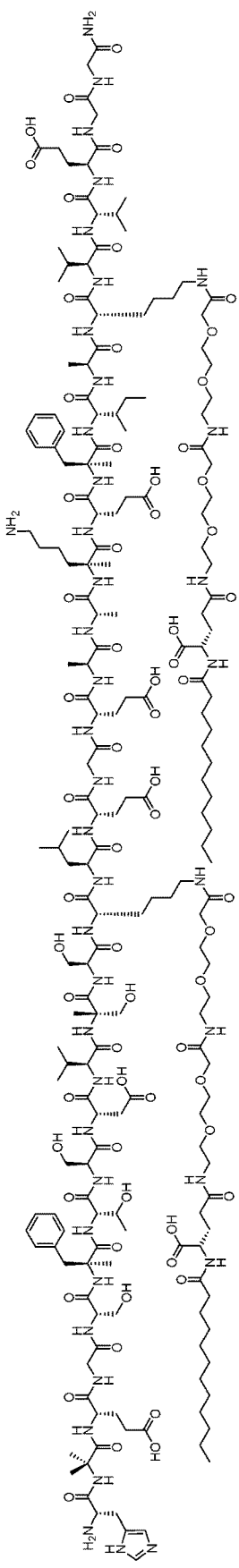
FIG. 12 shows the chemical structure, chemical formula and molecular weight for SEQ ID NO:405 and SEQ ID NO:406.
Figure 12:
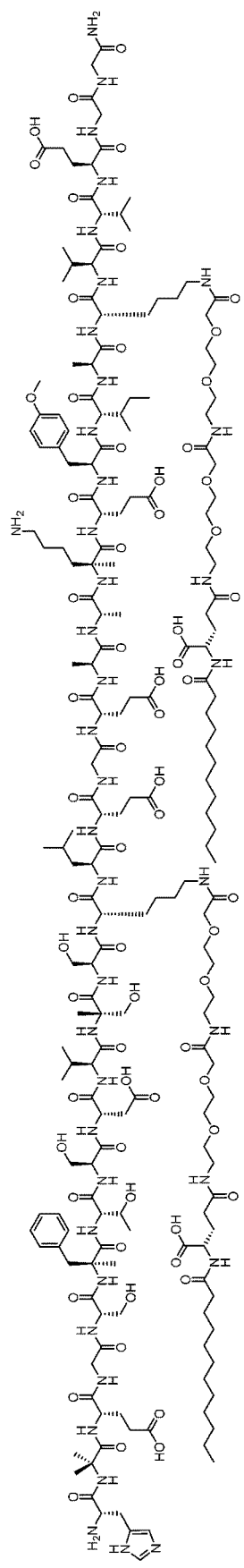
Figure 13:
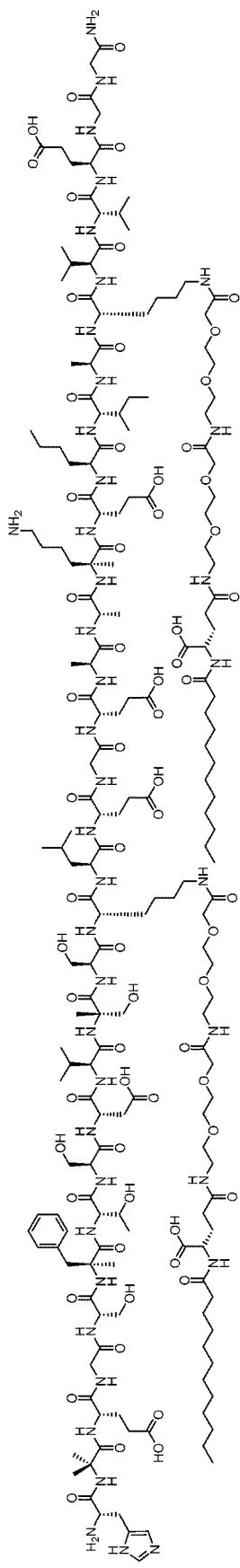
FIG. 13 shows the chemical structure, chemical formula and molecular weight for SEQ ID NO:407 and SEQ ID NO:408.
Figure 13:
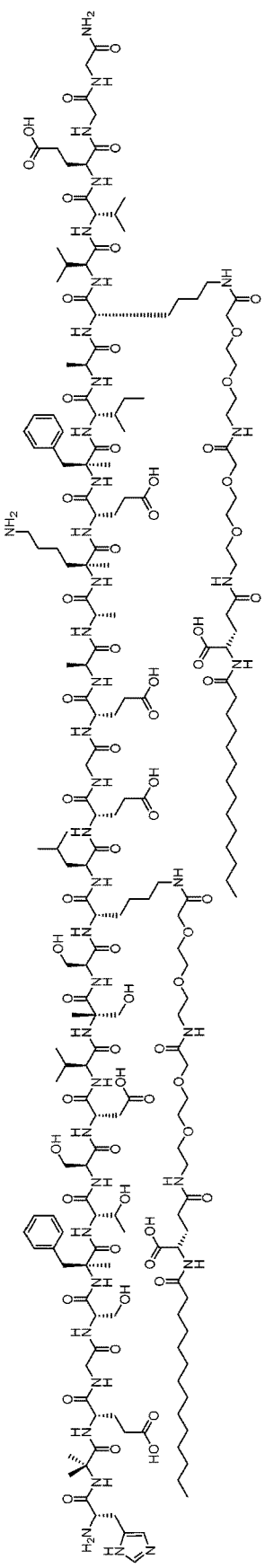
Figure 14:
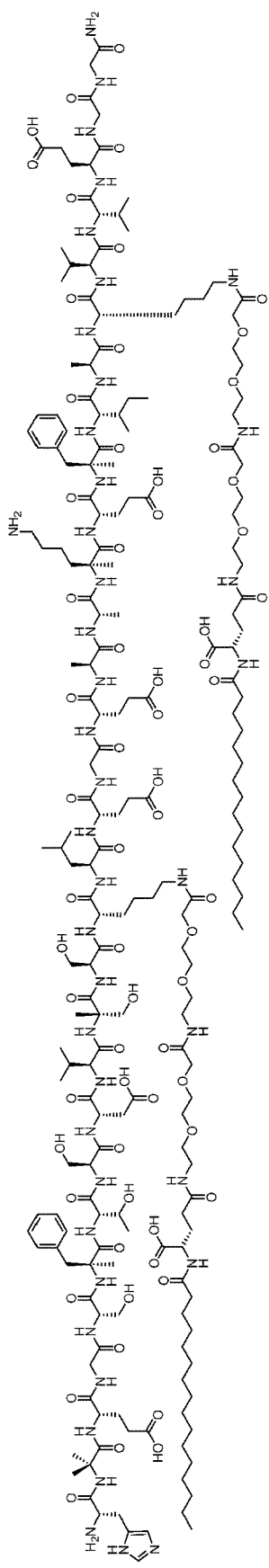
FIG. 14 shows the chemical structure, chemical formula and molecular weight for SEQ ID NO:409 and SEQ ID NO:410.
Figure 14:
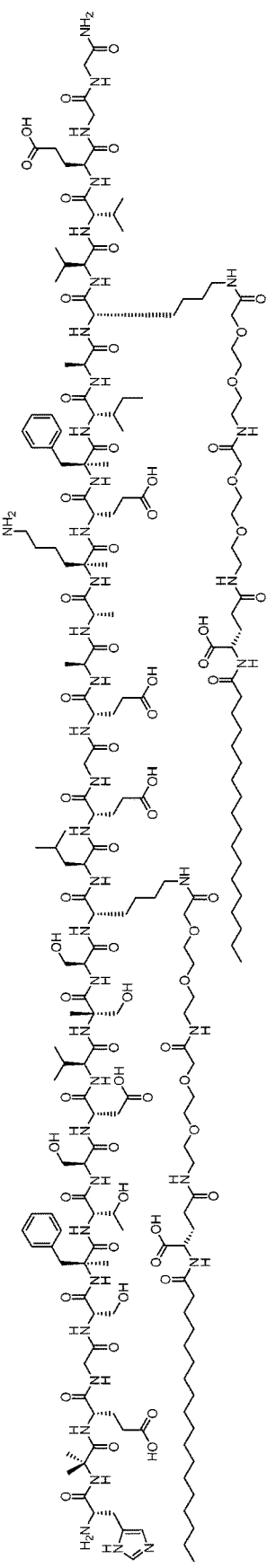
Figure 15:
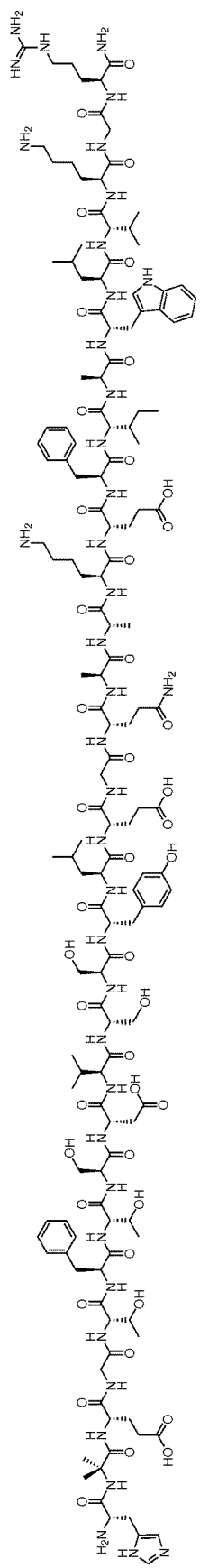
FIG. 15 shows the chemical structure, chemical formula and molecular weight for SEQ ID NO:488 and SEQ ID NO:489.
Figure 15:
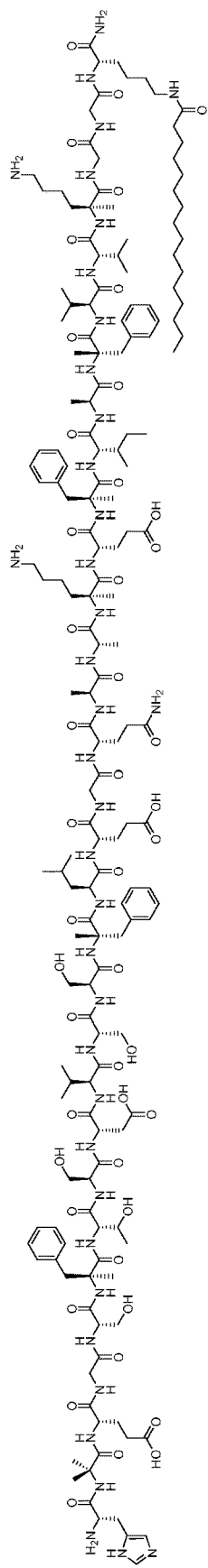
Figure 16:
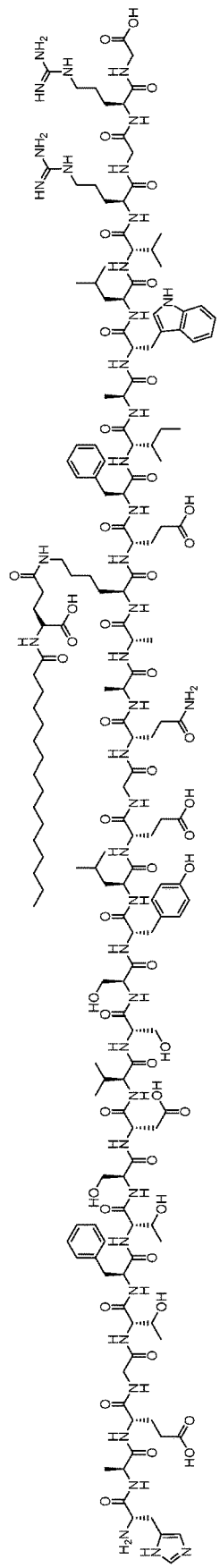
FIG. 16 shows the chemical structure, chemical formula and molecular weight for SEQ ID NO:490 (Liraglutide) and SEQ ID NO:491 (Semaglutide)
Figure 16:
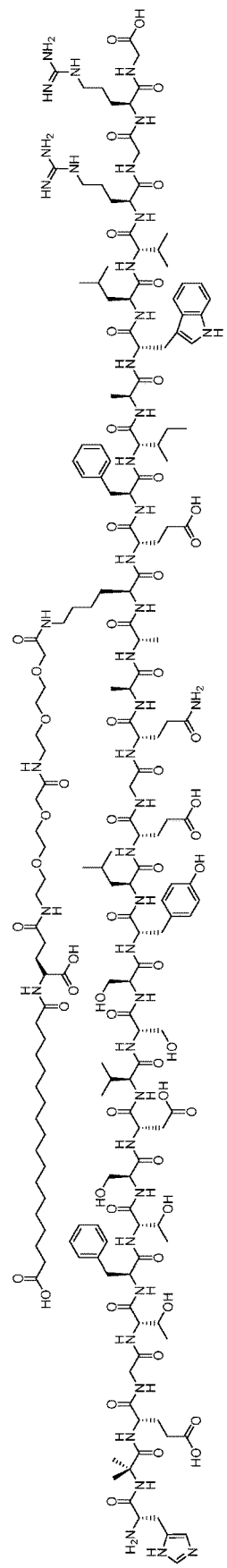

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Technical and scientific terms used herein have the meaning commonly understood by one of ordinary skill in the art to which the present application pertains, unless otherwise defined. Reference is made herein to various methodologies and materials known to those of skill in the art. Standard reference works setting forth the general principles of peptide synthesis include W. C. Chan and P. D. White, "Fmoc Solid Phase Peptide Synthesis: A Practical Approach", Oxford University Press, Oxford (2004).

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function similarly to a naturally occurring amino acid. The terms "amino acid" and "amino acid residue" are used interchangeably throughout.

The terms "fragment," "analog," "derivative," or "variant" when referring to a lipidated peptide as provided herein includes any peptide that retains at least some activity of a corresponding native peptide, e.g., GLP-1. As used herein, the term "lipidated GLP-1 peptide analog" refers to, e.g., a synthetic peptide comprising one or more lipidated amino acids, e.g., to render the peptide protease resistant, while still maintaining at least some of the GLP-1 activities of a native GLP-1 peptide. Chemical modifications intended to improve metabolic stability of peptides can involve additional chemical manipulation following synthesis of the main peptide chain. Examples of manipulation include lactamization, disulfide bridge closure, lipidation and/or PEGylation.

The terms "lipid modified amino acid" and "lipidated amino acid" are used interchangeably herein, and refer to an amino acid, typically a lysine or cysteine, which has a lipid moiety attached. The terms "lipidated polypeptide," "lipoprotein," and the like refer to a peptide or polypeptide that includes one or more lipid modified amino acids. FIG. 1 illustrates various representative examples of lipids, lipid moieties, and linkers.

The terms "composition" or "pharmaceutical composition" refer to compositions containing a peptide or polypeptide provided herein, along with e.g., pharmaceutically acceptable carriers, excipients, or diluents for administration to a subject in need of treatment.

The term "pharmaceutically acceptable" refers to compositions that are, within the scope of sound medical judgment, suitable for contact with the tissues of human beings and animals without excessive toxicity or other complications commensurate with a reasonable benefit/risk ratio.

An "effective amount" is that amount of a peptide or polypeptide provided herein, the administration of which to a subject, either in a single dose or as part of a series, is effective for treatment.

The term "subject" is meant any subject, particularly a mammalian subject, in need of treatment with a peptide or polypeptide provided herein. Mammalian subjects include, but are not limited to, humans, dogs, cats, guinea pigs, rabbits, rats, mice, horses, cattle, bears, cows, apes, monkeys, orangutans, and chimpanzees, and so on. In one aspect, the subject is a human subject.

Provided herein are compositions and methods that address the natural enzymatic liabilities of peptides. By lipidating selected amino acid residues, peptides are provided that demonstrate increased resistance to enzymatic degradation, while still maintaining substantially the same or exhibiting increased receptor potency and selectivity as a wild-type peptide.

Peptides Demonstrating Protease Resistance

This disclosure provides lipidated peptides with improved protease resistance and increased potency. Improvements in protease resistance and potency can be associated with the position of the lipidation on the peptide. Lipidation can include carboxyl- or amino-terminal lipidation, or main-chain lipidation. In certain embodiments, the modification is of a main-chain amino acid residue. In certain embodiments, improvements in protease resistance and increased potency are associated with the selective and strategic position of the lipidation of one or more main-chain amino acid residues. Methods of preparing peptides with lipid modified amino acids are known in the art.

In certain embodiments, a lipidated peptide comprising at least one lipidated amino acid residue is provided. In certain embodiments, the lipidated peptide comprises at least two lipidated amino acid residues. In certain embodiments, the lipidated peptide contains only one lipidated amino acid residue. As used herein, a peptide with one lipid or lipid moiety attached is referred to as a mono-lipidated peptide. In other embodiments, the lipidated peptide contains two lipidated amino acid residues. As used herein, a peptide with two lipids or lipid moieties attached is referred to as a bis-lipidated peptide.

In certain embodiments, the lipidated peptide is a synthetic peptide. See International Patent Application No. PCT/EP2014/077240, published as WO2015/086686A2, which is incorporated by reference herein in its entirety. In certain embodiments, the lipidated synthetic peptide comprises at least one substitution of an alpha-methyl functionalized amino acid for a native amino acid residue. In other embodiments, a lipidated synthetic peptide comprises at least two, three, four, five, six, or more substitutions of alpha-methyl functionalized amino acids for native amino acid residues.

As described herein, "synthetic peptide" refers to a polymer of amino acid residues that has been generated by chemically coupling a carboxyl group or C-terminus of one amino acid to an amino group or N-terminus of another. Chemical peptide synthesis typically starts at the C-terminus of the peptide and ends at the N-terminus. Various methods for generating synthetic peptides are well known in the art.

As described herein "alpha-methyl functionalized amino acids" refer to amino acids in which the first (alpha) carbon atom of the amino acid includes a methyl group ($CH_3$) substituent bound to the alpha carbon. Alpha-methyl functionalized amino acids include any of the naturally occurring twenty amino acids that include such a functionalization.

As described throughout, alpha-methyl functionalized amino acids can replace any native amino acid in a peptide. The term "native" amino acid refers to one of the standard 20 amino acids that exist in biologically generated proteins.

Substitution refers to the replacement of a native amino acid with, e.g., an alpha-functionalized amino acid. During chemical synthesis of a synthetic peptide, the native amino acid can be readily replaced by an alpha functionalized amino acid.

The synthetic peptides described herein can be of any length, e.g., any number of amino acids in length, e.g., about 5 amino acids to about 200 amino acids in length, about 10 amino acids to about 150 amino acids in length, about 20 amino acids to about 100 amino acids in length, about 30 amino acids to about 75 amino acids in length, or about 20 amino acids, about 30 amino acids, about 40 amino acids, about 50 amino acids, about 60 amino acids, about 70 amino acids, about 80 amino acids, about 90 amino acids, or about 100 amino acids in length.

Certain lipidated synthetic peptides described herein contain one or more alpha-functionalized amino acids substituted for native amino acids, while at least maintaining substantially the same or exhibiting increased receptor potency as a corresponding synthetic peptide that does not comprise the substitutions.

Improvements in protease resistance and potency can be associated with the selective and strategic position of the lipidation and alpha-functionalized amino acids substituted amino acids on the peptide. In certain embodiments, synthetic peptides that at least maintain substantially the same or exhibit increased receptor potency and selectivity contain two or more alpha-functionalized amino acids substituted for native amino acids. In some embodiments, synthetic peptides that at least maintain substantially the same or exhibiting increased receptor potency and selectivity contain three four, five, six or more alpha-functionalized amino acids substituted for the native amino acids.

The term receptor "potency" refers to the inverse of the half maximum (50%) effective concentration ($EC_{50}$) of the peptide. The $EC_{50}$ refers to the concentration of peptide that induces a biological response halfway between the baseline response and maximum response, after a specified exposure time, for a selected target of the peptide. Thus, peptides exhibiting a small value for $EC_{50}$ have a corresponding high receptor potency, while peptides exhibiting a large value for $EC_{50}$ have a corresponding low receptor potency—the more peptide required to induce a response related to a receptor, the less potent the peptide is for that receptor.

Methods for determining the receptor potency and $EC_{50}$ are known in the art and suitably involve determining stimulation of one or more cellular receptor responses. For example, suitable cell lines expressing GLP-1 receptor (GLP-1R), glucagon receptor (GCGR) or glucose-dependent insulinotropic peptide (gastric inhibitory polypeptide) receptor (GIPR) are generated by standard methods. Peptide activation of these various receptors results in downstream production of a cAMP second messenger which can be measured in a functional activity assay. From these measurements, $EC_{50}$ values are readily determined.

As described throughout, lipidated peptides comprising one or more, e.g., one or two, attached lipids or lipid moieties and and substituition of alpha-methyl functionalized amino acids for the native amino acids can maintain "substantially the same" or exhibit increased receptor potency as compared to a corresponding peptide that does not comprise the lipids or lipid moieties or the non-natural amino acids. As used herein, "substantially the same" when referring to receptor potency, means that the lipidated peptide can exhibit, e.g., at least about 75% of the receptor potency, when the lipidated peptide is compared to the receptor potency of a corresponding peptide that is unlipidated or unlipidated and having different and/or fewer amino acid modifications, or other suitable comparator sequence (e.g., a control). In further embodiments, a lipidated peptide as provided herein can exhibit, e.g., about 80% of the receptor potency, about 85% of the receptor potency, about 90% of the receptor potency, about 91% of the receptor potency, about 92% of the receptor potency, about 93% of the receptor potency, about 94% of the receptor potency, about 95% of the receptor potency, about 96% of the receptor potency, about 97% of the receptor potency, about 98% of the receptor potency, about 99% of the receptor potency, about 99.1% of the receptor potency, about 99.2% of the receptor potency, about 99.3% of the receptor potency, about 99.4% of the receptor potency, about 99.5% of the receptor potency, about 99.6% of the receptor potency, about 99.7% of the receptor potency, about 99.8% of the receptor potency, about 99.9% of the receptor potency, or about 100% of the receptor potency, when the lipidated peptide is compared to the receptor potency of a corresponding peptide that is unlipidated or unlipidated and having different and/or fewer amino acid modification, or other suitable comparator sequence (e.g., a control). As used herein, "increased" when referring to receptor potency, means that the lipidated peptide exhibits greater receptor potency greater than the receptor potency of a corresponding peptide that is unlipidated or unlipidated and having different and/or fewer amino acid modifications, or other suitable comparator sequence (e.g., a control). In certain embodiments, increased receptor potency refers to, for example, 1% greater receptor potency, 2% percent greater receptor potency, 3% percent greater receptor potency, 4% percent greater receptor potency, 5% percent greater receptor potency, 6% percent greater receptor potency, 7% percent greater receptor potency, 8% percent greater receptor potency, 9% percent greater receptor potency, 10% percent greater receptor potency. In certain embodiments, increased receptor potency refers to for example, 1% to 10% greater receptor potency, 1% to 20% percent greater receptor potency, 1% to 30% percent greater receptor potency, 1% to 40% percent greater receptor potency, 1% to 50% percent greater receptor potency, 5% to 10% greater receptor potency, 5% to 20% percent greater receptor potency, 5% to 30% percent greater receptor potency, 5% to 40% percent greater receptor potency, 5% to 50% percent greater receptor potency, 10 to 50% percent greater receptor potency, 20 to 50% percent greater receptor potency, 30 to 50% percent greater receptor potency, 40% to 50% percent greater receptor potency, or 50% to 100% percent greater receptor potency.

As described throughout, a lipidated peptide as provided herein comprising one or more, e.g., one or two, attached lipids or lipid moieties and substituition of alpha-methyl functionalized amino acids for native amino acids can also at least maintain "substantially the same selectivity" as a corresponding peptide that does not comprise the lipid or lipid moiety or non-natural amino acids, or other suitable comparator sequence (e.g., a control), as described herein. As used herein, "selectivity," refers to the ability of a peptide to bind its target (e.g., the agonist to which it is designed to bind) while not binding to other non-target proteins. A lipidated peptide as provided herein can exhibit "substantially the same selectivity" and thus exhibit, e.g., at least about 75% of the selectivity when the lipidated peptides are compared to the selectivity of peptides that do not comprise the lipid or lipid moiety, or other suitable comparator sequence (e.g., a control), as described herein. For example, a lipidated peptide as provided herein can exhibit about 80% of the selectivity, about 85% of the selectivity, about 90% of the selectivity, about 91% of the selectivity, about 92% of the selectivity, about 93% of the selectivity, about 94% of the selectivity, about 95% of the selectivity, about 96% of the selectivity, about 97% of the selectivity, about 98% the selectivity, about 99% of the selectivity, about 99.1% of the selectivity, about 99.2% of the selectivity, about 99.3% of the selectivity, about 99.4% of the selectivity, about 99.5% of the selectivity, about 99.6% of the selectivity, about 99.7% of the selectivity, about 99.8% of the selectivity, about 99.9% of the selectivity, or about 100% of the selectivity, when the lipidated peptide is compared to the selectivity of a corresponding peptide that does not comprise the lipid or lipid moiety, or other suitable comparator sequence (e.g., a control), as described herein. In certain embodiments, the selective and strategic incorporation of lipidation and/or alpha-methyl amino acids in GLP-1 analogues both increases GLP-1 receptor potency and accordingly, increases selectivity for this receptor.

In certain embodiments, a lipidated peptide as provided herein can also comprise one or more alpha-methyl functionalized amino acids corresponding to the substituted native amino acids in a corresponding wild-type protein. For example, the amino acid in the original, wild-type peptide sequence can be substituted with an alpha-methyl functionalized amino acid that has the same side chain, e.g., Phe, Trp, Tyr, Ser, Arg, Ala, Val, Leu, His, or Lys, can be substituted with α-MePhe, α-MeTrp, α-MeTyr, α-MeSer, α-MeArg, α-MeAla (Aib), α-MeVal, α-MeLeu, α-MeHis, or α-MeLys, respectively.

In certain embodiments, an alpha-methyl functionalized amino acid in a lipidated peptide as provided herein can correspond to the same class as the substituted native amino acids. For example, aliphatic alpha-methyl functionalized amino acids can be substituted for aliphatic native amino acids; hydroxyl alpha-methyl functionalized amino acids can be substituted for hydroxyl native amino acids; sulfur-containing alpha-methyl functionalized amino acids can be substituted for sulfur-containing native amino acids; cyclic alpha-methyl functionalized amino acids can be substituted for cyclic native amino acids; aromatic alpha-methyl functionalized amino acids can be substituted for aromatic native amino acids; basic alpha-methyl functionalized amino acids can be substituted for basic native amino acids; and/or acidic alpha-methyl functionalized amino acids can be substituted for acidic native amino acids.

In additional embodiments, an alpha-methyl functionalized amino acid in a lipidated peptide as provided herein does not correspond to the substituted native amino acids.

Commercial sources of alpha-methyl functionalized amino acids include, for example, Bachem AG, Switzerland.

In certain embodiments, at least one alpha-methyl functionalized amino acid in a lipidated synthetic peptide described herein is alpha-methyl phenylalanine.

In certain embodiments, at least one alpha-methyl functionalized amino acid in a synthetic lipidated peptide described herein is selected from alpha-methyl functionalized Histidine, alpha-methyl functionalized Alanine, alpha-methyl functionalized Isoleucine, alpha-methyl functionalized Arginine, alpha-methyl functionalized Leucine, alpha-methyl functionalized Asparagine, alpha-methyl functionalized Lysine, alpha-methyl functionalized Aspartic acid, alpha-methyl functionalized Methionine, alpha-methyl functionalized Cysteine, alpha-methyl functionalized Phenylalanine, alpha-methyl functionalized Glutamic acid, alpha-methyl functionalized Threonine, alpha-methyl functionalized Glutamine, alpha-methyl functionalized Tryptophan, alpha-methyl functionalized Glycine, alpha-methyl functionalized Valine, alpha-methyl functionalized Ornithine, alpha-methyl functionalized Proline, alpha-methyl functionalized Selenocysteine, alpha-methyl functionalized Serine and alpha-methyl functionalized Tyrosine.

In certain embodiments, the lipidated peptides described herein can be substantially resistant to proteolytic degradation.

As used herein, "proteolytic degradation" means the breakdown of peptides into smaller peptides or even amino acids, generally caused by the hydrolysis of a peptide bond by enzymes.

Lipidated peptides that are "substantially resistant" to proteolytic degradation can, for example, remain at least about 50% intact following exposure to an enzyme in conditions that the enzyme is generally active (e.g., suitable pH, temperature, other environmental conditions) for a defined period of time. Lipidated peptides provided herein can be substantially resistant to proteolytic degradation for a period of at least 4 hours, at least 8 hours, at least 12 hours, at least 24 hours, at least 36 hours, at least 48 hours, at least 72 hours, at least 96 hours, at least 120 hours, at least 144 hours, at least 168 hours, at least 192 hours, at least 216 hours, at least 240 hours, or about 36 hours to about 240 hours, about 48 hours to 240 hours, about 72 hours to about 240 hours, about 96 hours to about 240 hours, about 120 hours to about 240 hours, about 144 hours to about 240 hours, about 168 hours to about 240 hours, about 192 hours to about 240 hours, or about 216 hours to about 240 hours. In certain embodiments, at least about 60% of the lipidated peptide remains intact following exposure to an enzyme in conditions that the enzyme is generally active for a defined period of time, for example, at least about 70%, at least about 80%, at least about 85%, at least about 90%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, or at least about 100% of the lipidated peptide remains intact following exposure to an enzyme in conditions that the enzyme is generally active for a defined period of time.

Lipidated peptides provided herein can be substantially resistant to proteolytic degradation by one or more enzymes found in a mammalian body, e.g., the human body. For example, the lipidated peptides can be substantially resistant to proteolytic degradation by one or more of dipeptidyl peptidase-IV (DPP-IV), neprilysin, α-chymotrypsin, plasmin, thrombin, kallikrein, trypsin, elastase and pepsin. In certain embodiments, the lipidated peptides can be resistant to proteolytic degradation by to two or more, three or more, four or more, five or more, six or more, seven or more, or suitably all of the recited enzymes. The lipidated peptides described herein can also be substantially resistant to proteolytic degradation by other enzymes known in the art. In certain embodiments, the lipidated peptides described herein can be substantially resistant to proteolytic degradation by digestive (gastric) enzymes and/or enzymes in the blood/serum.

In certain embodiments, the lipidated peptides described herein can be substantially resistant to proteolytic degradation by DPP-IV and neprilysin. In certain embodiments, the lipidated peptides described herein can be substantially resistant to proteolytic degradation by pepsin, trypsin, α-chymotrypsin, and elastase. In certain embodiments, the lipidated peptides described herein can be substantially resistant to proteolytic degradation by plasmin, thrombin, and kallikrein. In certain embodiments, the lipidated peptides described herein can be substantially resistant to proteolytic degradation by pepsin, trypsin and α-chymotrypsin. In certain embodiments, the lipidated peptides described herein can be substantially resistant to proteolytic degradation by pepsin and trypsin, etc.

As described herein, including in various embodiments provided throughout, lipidation of amino acid residues and/or substitution of alpha-functionalized amino acids for native amino acids can occur at native amino acid residues that are sites susceptible to proteolytic cleavage. That is, the amino acid residues that are substituted are determined to be sites where proteolytic enzymes are active in cleaving peptide bonds in the native peptides. Methods for determining sites of proteolytic cleavage are well known in the art and described herein.

Any class of peptide can be prepared according to the methods provided herein to yield lipidated peptides having the recited characteristics.

In exemplary embodiments, the lipidated peptides can be incretin class peptides. Exemplary synthetic incretin class peptides that can be prepared as described herein include, but are not limited to, glucagon-like peptide 1 (GLP-1), a glucose-dependent insulinotropic peptide (GIP), an exenatide peptide, plus glucagon, secretins, tenomodulin, oxyntomodulin, insulin, or vasoactive intestinal peptide (VIP).

Additional classes of peptides can be prepared as described herein.

In certain embodiments, the lipidated peptide described herein is derived from the sequence of GLP-1 and referred to herein as a lipidated GLP-1 peptide analog.

Sequences for the native (wild type) peptides of the various peptides and classes of peptides described herein that can be prepared to yield synthetic peptides having the recited characteristics are well known in the art.

The native amino acid sequence for GLP-1 (7-36) is known in the art as set forth below:

(SEQ ID NO: 1)
HAEGTFTSDVSSYLEGQAAKEFIAWLVKGR.

In certain embodiments, lipidated GLP-1 peptide analogs are provided comprising at least one lipid modified amino acid residue, such as those shown in Table 1. In certain embodiments, the lipidated GLP-1 peptide analog contains only one lipid modified amino acid residue. Mono-lipidated GLP-1 peptide analogs disclosed herein can be substantially resistant to proteolytic degradation. For example, in certain embodiments the mono-lipidated peptide is substantially resistant to DPP-IV, neprilysin, α-chymotrypsin, plasmin, thrombin, kallikrein, trypsin, elastase, and/or pepsin degradation. Mono-lipidated GLP-1 peptide analogs disclosed herein can maintain substantially the same or exhibit increased receptor potency and selectivity as a corresponding non-lipidated GLP-1 peptide or GLP-1 peptide analog.

In certain embodiments, a mono-lipidated peptide is lipidated on only one K (lysine) or only one C (cysteine) residue. Thus, certain embodiments provide for an isolated polypeptide comprising the amino acid sequence:

(SEQ ID NO: 2)
H X2 E G S X6 T S D V X11 X12 X13 L E G E A A X20
E X22 I X24 X25 V V X28 G G;

wherein X2 is A or Aib;
X6 is F or an alpha-methyl functionalized amino acid;
X11 is S or an alpha-methyl functionalized amino acid;
X12 is S, a lipid modified K, or a lipid modified C;
X13 is Y or an alpha-methyl functionalized amino acid;
X20 is a lipid modified K, a lipid modified C, K, or an alpha-methyl functionalized amino acid;
X22 is F or an alpha-methyl functionalized amino acid;
X24 is A, a lipid modified K, or a lipid modified C;
X25 is W or an alpha-methyl functionalized amino acid; and
X28 is K, E, or an alpha-methyl functionalized amino acid,
wherein the polypeptide is lipidated on only one of X12, X20, or X24.

In certain embodiments, a mono-lipidated peptide comprises one or more aminoisobutyric acid (Aib) substitutions. In certain embodiments of a peptide comprising the amino acid sequence of SEQ ID NO: 2: X2 is Aib.

The lipidated K or lipidated C can be attached to a variety of lipids or lipid moieties such as any of those described herein. Examples include those selected from the group consisting of: K(ε-(PEG)$_2$-(PEG)$_2$-γE-Stearate); K(ε-γE-Palmitoyl); K(ε-(PEG)$_2$-(PEG)$_2$-γE-Stearate); K(γE-Palmitoyl); K(ε-(PEG)$_2$-(PEG)$_2$-(PEG)$_2$-Stearoyl); K(ε-γE-Lauroyl); K(ε-γE-γE-Lauroyl); K(ε-γE-γE-γE-Lauroyl); K(ε-Ahx-Lauroyl); K(ε-Ahx-Ahx-Lauroyl); K(ε-Ahx-Ahx-Ahx-Lauroyl); K(ε-(PEG)$_2$-Lauroyl); K(ε-(PEG)$_2$-(PEG)$_2$-Lauroyl); K(ε-(PEG)$_2$-(PEG)$_2$-(PEG)$_2$-Lauroyl); K(ε-γE-12-(4-carboxyphenoxy)dodecanoyl); K(ε-γE-12-(4-carboxyphenoxy)dodecanoyl); K(ε-γE-γE-12-(4-carboxyphenoxy)dodecanoyl); K(ε-Ahx-12-(4-carboxyphenoxy)dodecanoyl); K(ε-Ahx-Ahx-12-(4- carboxyphenoxy)dodecanoyl); K(ε-Ahx-Ahx-Ahx-12-(4-carboxyphenoxy)dodecanoyl); K(ε-(PEG)$_2$-12-(4-carboxyphenoxy)dodecanoyl); K(ε-(PEG)$_2$-(PEG)$_2$-12-(4-carboxyphenoxy)dodecanoyl); K(ε-(PEG)$_2$-(PEG)$_2$-(PEG)$_2$-12-(4-carboxyphenoxy)dodecanoyl); K(ε-γE-Stearoyl); K(ε-γE-γE-Stearoyl); K(ε-γE-γE-γE-Stearoyl); K(ε-Ahx-Stearoyl); K(ε-Ahx-Ahx-Stearoyl); K(ε-Ahx-Ahx-Ahx-Stearoyl); K(ε-(PEG)$_2$-Stearoyl); K(ε-(PEG)$_2$-(PEG)$_2$-Stearoyl); K(ε-(PEG)$_2$-(PEG)$_2$-(PEG)$_2$-Stearoyl); K(ε-γE-Stearate); K(ε-γE-γE-Stearate); K(ε-γE-γE-γE-Stearate); K(ε-Ahx-Stearate); K(ε-Ahx-Ahx-Stearate); K(ε-Ahx-Ahx-Ahx-Stearate); K(ε-(PEG)$_2$-Stearate); K(ε-(PEG)$_2$-(PEG)$_2$-Stearate); K(ε-(PEG)$_2$-(PEG)$_2$-(PEG)$_2$-Stearate), and any combination thereof. For example, in certain embodiments of a peptide comprising the amino acid sequence of SEQ ID NO: 2: X20 is K(ε-(PEG)$_2$-(PEG)$_2$-γE-Stearate).

In certain embodiments, the alpha-methyl functionalized amino acid is α-MeF, α-MeS, or α-MeK. In certain embodiments of a peptide comprising the amino acid sequence of SEQ ID NO: 2: X6 is α-MeF; X11 is α-MeS; X13 is α-MeF; X22 is α-MeF; X25 is α-MeF; and/or X28 is α-MeK. In certain embodiments of a peptide comprising the amino acid sequence of SEQ ID NO: 2: X6 is α-MeF; X11 is α-MeS; X13 is α-MeF; X22 is α-MeF; X25 is α-MeF; and X28 is α-MeK. In certain embodiments of a peptide comprising the amino acid sequence of SEQ ID NO: 2: X2 is Aib; X6 is α-MeF; X11 is α-MeS; X13 is α-MeF; X20 is K(ε-(PEG)$_2$-(PEG)$_2$-γE-Stearate); X22 is α-MeF; X25 is α-MeF; and X28 is α-MeK (SEQ ID NO: 3; Table 1).

In certain embodiments, the peptide comprises the amino acid sequence of SEQ ID NO: 48 (Table 1), SEQ ID NO: 60 (Table 1), or SEQ ID NO: 68 (Table 1).

In certain embodiments, a peptide comprising the amino acid sequence of SEQ ID NO: 2, 3, 48, 60, or 68 is substantially resistant to proteolytic degradation. For example, in certain embodiments the peptide is substantially resistant to DPP-IV, neprilysin, α-chymotrypsin, plasmin, thrombin, kallikrein, trypsin, elastase, and/or pepsin degradation. In certain embodiments, a peptide comprising the amino acid sequence of SEQ ID NO: 2, 3, 48, 60, or 68 at least maintains substantially the same receptor potency or exhibits increased receptor potency as compared to a corresponding non-lipidated peptide. In certain embodiments, a peptide comprising the amino acid sequence of SEQ ID NO: 2, 3, 48, 60, or 68 at least maintains substantially the same receptor or exhibits increased receptor potency and selectivity as compared to a corresponding non-lipidated peptide.

TABLE 1

Substituted and Mono-lipidated Peptide Sequences

| ID | SEQ ID NO | Peptide |
|---|---|---|
| GLP-1 (7-36) | 1 | HAEGT$^5$ FTSDV$^{10}$ SSYLE$^{15}$ GQAAK$^{20}$ EFIAW$^{25}$ LVKGR$^{30}$-amide |
| mono- | 2 | H X2 E G S X6 T S D V X11 X12 X13 L E G E A A X20 E X22 I X24 X25 V V X28 G G |
| | 3 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| | 5 | H-(Aib)$^2$-EGT$^5$ FTSDV$^{10}$ SSYLE$^{15}$ GQAAK$^{20}$ EFIAW$^{25}$ LVKGR$^{30}$-K(ε-γE-Palmitoyl) |
| | 6 | H-(Aib)$^2$-EGT$^5$ FTSDV$^{10}$ SSYLE$^{15}$ GQAAK$^{20}$ EFIAW$^{25}$ LVKGR$^{30}$-K(ε-(PEG)$_2$-(PEG)$_2$-γE-Stearate) |
| | 7 | H-(Aib)$^2$-EG-(S)$^5$-(α-MeF)-TS-(E)$^9$-V$^{10}$ SS-(α-MeF)$^{11}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 8 | H-(Aib)$^2$-EG-(S)$^5$-(α-MeF)-(S)$^5$-SDV$^{10}$ SS-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 9 | H-(Aib)$^2$-EG-(S)$^5$-(α-MeF)-(S)$^5$-5-(E)$^9$-V$^{10}$ SS-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 10 | H-(Aib)$^2$-EG-(S)$^5$-(α-MeF)-TSDV$^{10}$ SS-(α-MeF)$^{13}$-(V)$^{14}$-E$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 11 | H-(Aib)$^2$-EG-(S)$^5$-(α-MeF)-TSDV$^{10}$ SS-(α-MeF)$^{13}$-LE$^{15}$ G-(E)$^{17}$-AA-(α-MeK)$^{20}$ E-(α-MeF)$^{22}$-(V)$^{23}$-A-(α-MeF)$^{25}$-(V)$^{26}$-V-(α-MeK)$^{28}$-G-(G)$^{30}$ |
| | 12 | H-(Aib)$^2$-EG-(S)$^5$-(α-MeF)-(S)$^5$-S-(E)$^9$-V$^{10}$ SS-(α-MeF)$^{13}$-(V)$^{14}$-E$^{15}$ G-(E)$^{17}$-AA-(α-MeK)$^{20}$ E-(α-MeF)$^{22}$-(V)$^{23}$-A-(α-MeF)$^{25}$-(V)$^{26}$-V-(α-MeK)$^{29}$-G-(G)$^{30}$ |
| | 13 | H-(Aib)$^2$-QG-(S)$^5$-(α-MePhe)-TSD-K$^{10}$(γE-Palmitoyl)-SE-(α-MePhe)$^{13}$-LD$^{15}$ SERAR$^{20}$ D-(α-MePhe)$^{22}$-VA-(α-MePhe)$^{25}$-LEAGG$^{30}$ |
| | 14 | H-(Aib)$^2$-QG-(S)$^5$-(α-MePhe)-TSD-(α-MePhe)$^{10}$-SK-(α-MePhe)$^{13}$-LD$^{15}$ SRRAQ$^{20}$ D-(α-MePhe)$^{22}$-VQ-(α-MePhe)$^{25}$-LMNT$^{29}$ |
| | 15 | Y-(Aib)$^2$-EG-(S)$^5$-(α-MePhe)-ISD-(α-MePhe)$^{10}$-SIAMD$^{15}$ KIHQQ$^{20}$ D-(α-MePhe)$^{22}$-VN-(α-MePhe)$^{25}$-LLAQK$^{30}$ |
| | 16 | H-(Aib)$^2$-EG-(S)$^5$-(α-MeF)-T-(α-MeS)-DV$^{10}$-SS-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |

TABLE 1-continued

Substituted and Mono-lipidated Peptide Sequences

| SEQ ID NO | Peptide |
|---|---|
| 17 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 18 | H-(Aib)$^2$-EG-(S)$^5$-(α-MeF)-T-(α-MeS)-DV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 19 | H-(Aib)$^2$-EGT$^5$ FT-(α-MeSer)-DV$^{10}$ SSYLE$^{15}$ GQAAK$^{20}$ EFIAW$^{25}$ LVKGR$^{30}$ |
| 20 | H-(Aib)$^2$-EGT$^5$ FT-(Aib)$^8$-DV$^{10}$ SSYLE$^{15}$ GQAAK$^{20}$ EFIAW$^{25}$ LVKGR$^{30}$ |
| 21 | H-(Aib)$^2$-EGT$^5$ FTSDV$^{10}$ (α-MeSer)$^{11}$-SYLE$^{15}$ GQAAK$^{20}$ EFIAW$^{25}$ LVKGR$^{30}$ |
| 22 | H-(Aib)$^2$-EGT$^5$ FTSDV$^{10}$ (Aib)$^{11}$-SYLE$^{15}$ GQAAK$^{20}$ EFIAW$^{25}$ LVKGR$^{30}$ |
| 23 | H-(Aib)$^2$-EGT$^5$ FT-(α-MeSer)-DV$^{10}$-(α-MeSer)$^{11}$-SYLE$^{15}$ GQAAK$^{20}$ EFIAW$^{25}$ LVKGR$^{30}$ |
| 24 | H-(Aib)$^2$-EGT$^5$ FT-(Aib)$^8$-DV$^{10}$-(Aib)$^{11}$-SYLE$^{15}$ GQAAK$^{20}$ EFIAW$^{25}$ LVKGR$^{30}$ |
| 25 | H-(Aib)$^2$-EG-(S)$^5$-(α-MeF)-T-(G)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{25}$-V-(α-MeK)$^{28}$-G-(G)$^{30}$ |
| 26 | H-(Aib)$^2$-EG-(S)$^5$-(α-MeF)-T-(A)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 27 | H-(Aib)$^2$-EG-(S)$^5$-(α-MeF)-T-(D)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 28 | H-(Aib)$^2$-EG-(S)$^5$-(α-MeF)-T-(E)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 29 | H-(Aib)$^2$-EG-(S)$^5$-(α-MeF)-T-(T)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 30 | H-(Aib)$^2$-EG-(S)$^5$-(α-MeF)-T-(V)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| 31 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-PEG)$_2$-(PEG)$_2$-ε-γE-Stearate) |
| 32 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-Palmitoyl) |
| 33 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-ε-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| 34 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-Palmitoyl)$^{20}$ E-(α-MeF)$^{22}$-IA-(α-MeF)$^{25}$-(V)$^{26}$-V-(α-MeK)$^{28}$-G-(G)$^{30}$ |
| 35 | H-(Aib)$^2$-EG-(S)$^5$-(α-MeF)-T-(D)-DV$^{10}$-(α-MeSer)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-Palmitoyl) |
| 36 | H-(Aib)$^2$-EG-(S)$^5$-(α-MeF)-T-(D)-DV$^{10}$-(α-MeSer)$^{11}$-S-(α-MeF)$^{13}$-LE$^{15}$ G-(E)$^{17}$-AAK(ε-PEG)$_2$-(PEG)$_2$-ε-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| 37 | H-(Aib)$^2$-EG-(S)$^5$-(α-MeF)-T-(D)-DV$^{10}$-(α-MeSer)$^{11}$-S-(α-MeF)$^{13}$-LE$^{15}$ G-(E)$^{17}$-AAK(ε-γE-Palmitoyl)$^{20}$ E-(α-MeF)$^{22}$-IA-(α-MeF)$^{25}$-(V)$^{26}$-V-(α-MeK)$^{28}$-G-(G)$^{30}$ |
| 38 | H-(Aib)$^2$-EG-(S)$^5$-(α-MeF)-TSDV$^{10}$ SS-(α-MeF)$^{13}$-LE$^{15}$ G-(E)$^{17}$-AAK$^{20}$ E-(α-MeF)$^{22}$-IA-(α-MeF)$^{25}$ (V)$^{26}$-VKG-(G)$^{30}$-K(ε-PEG)$_2$-(PEG)$_2$-ε-γE-Stearate) |
| 39 | H-(Aib)$^2$-EG-(S)$^5$-(α-MeF)-TSDV$^{10}$ SS-(α-MeF)$^{13}$-LE$^{15}$ G-(E)$^{17}$-AAK$^{20}$ E-(α-MeF)$^{22}$-IA-(α-MeF)$^{25}$ (V)$^{26}$-VKG-(G)$^{30}$-K(ε-γE-Palmitoyl) |
| 40 | H-(Aib)$^2$-EG-(S)$^5$-(α-MeF)-TSDV$^{10}$ SS-(α-MeF)$^{13}$-LE$^{15}$ G-(E)$^{17}$-AAK(ε-PEG)$_2$-(PEG)$_2$-ε-γE-Stearate)$^{20}$ E-(α-MeF)$^{22}$-IA-(α-MeF)$^{25}$ (V)$^{26}$-VKG-(G)$^{30}$ |
| 41 | H-(Aib)$^2$-EG-(S)$^5$-(α-MeF)-TSDV$^{10}$ SS-(α-MeF)$^{13}$-LE$^{15}$ G-(E)$^{17}$-AAK(ε-γE-Palmitoyl)$^{20}$ E-(α-MeF)$^{22}$-IA-(α-MeF)$^{25}$ (V)$^{26}$-VKG-(G)$^{30}$ |
| 42 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(E)$^{20}$ E-(α-MeF)$^{22}$-IA-(α-MeF)$^{25}$-(V)$^{26}$-V-(α-MeK)$^{28}$-G-(G)$^{30}$ |

TABLE 1-continued

Substituted and Mono-lipidated Peptide Sequences

| SEQ ID NO | Peptide |
|---|---|
| 43 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(E)$^{28}$-G-(G)$^{30}$ |
| 44 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(E)$^{20}$ E-(α-MeF)$^{22}$-IA-(α-MeF)$^{25}$-(V)$^{26}$-V-(E)$^{28}$-G-(G)$^{30}$ |
| 45 | H-(Aib)$^2$-EG-(S)$^5$-FTSDV$^{10}$-(α-MeS)$^{11}$-S-(α-MeF)$^{13}$-LE$^{15}$ G-(E)$^{17}$-AAK(ε-PEG)$_2$-(PEG)$_2$-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| 46 | H-(Aib)$^2$-EG-(S)$^5$-(α-MeF)-TSDV$^{10}$-SS-(α-MeF)$^{13}$-LE$^{15}$ G-(E)$^{17}$-AAK(ε-PEG)$_2$-(PEG)$_2$-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| 47 | H-(Aib)$^2$-EG-(S)$^5$-(α-MeF)-TSDV$^{10}$-(α-MeS)$^{11}$-SYLE$^{15}$ G-(E)$^{17}$-AAK(ε-PEG)$_2$-(PEG)$_2$-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| 48 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-γE-Stearate)$^{20}$ EFIA-(α-MeF)$^{25}$-(V)$^{26}$-V-(α-MeK)$^{28}$-G-(G)$^{30}$ |
| 49 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-γE-Stearate)$^{20}$ E-(α-MeF)$^{22}$-IAW-(V)$^{26}$-V-(α-MeK)$^{28}$-G-(G)$^{30}$ |
| 50 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-γE-Stearate)$^{20}$ E-(α-MeF)$^{22}$-IA-(α-MeF)$^{25}$-(V)$^{26}$-VKG-(G)$^{30}$ |
| 51 | H-(Aib)$^2$-EG-(S)$^5$-FTSDV$^{10}$-(α-MeS)$^{11}$-S-(α-MeF)$^{13}$-LE$^{15}$ G-(E)$^{17}$-AAK(ε-PEG)$_2$-(PEG)$_2$-(PEG)$_2$-Stearoyl)$^{20}$ E-(α-MeF)$^{22}$-IA-(α-MeF)$^{25}$-(V)$^{26}$-V-(α-MeK)$^{28}$-G-(G)$^{30}$ |
| 52 | H-(Aib)$^2$-EG-(S)$^5$-(α-MeF)-TSDV$^{10}$-SS-(α-MeF)$^{13}$-LE$^{15}$ G-(E)$^{17}$-AAK(ε-PEG)$_2$-(PEG)$_2$-(PEG)$_2$-Stearoyl)$^{20}$ E-(α-MeF)$^{22}$-IA-(α-MeF)$^{25}$-(V)$^{26}$-V-(α-MeK)$^{28}$-G-(G)$^{30}$ |
| 53 | H-(Aib)$^2$-EG-(S)$^5$-(α-MeF)-TSDV$^{10}$-(α-MeS)$^{11}$-SYLE$^{15}$ G-(E)$^{17}$-AAK(ε-PEG)$_2$-(PEG)$_2$-(PEG)$_2$-Stearoyl)$^{20}$ E-(α-MeF)$^{22}$-IA-(α-MeF)$^{25}$-(V)$^{26}$-V-(α-MeK)$^{28}$-G-(G)$^{30}$ |
| 54 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-(PEG)$_2$-Stearoyl)$^{20}$ EFIA-(α-MeF)$^{25}$-(V)$^{26}$-V-(α-MeK)$^{28}$-G-(G)$^{30}$ |
| 55 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-(PEG)$_2$-Stearoyl)$^{20}$ E-(α-MeF)$^{22}$-IAW-(V)$^{26}$-V-(α-MeK)$^{28}$-G-(G)$^{30}$ |
| 56 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-PEG)$_2$-(PEG)$_2$-(PEG)$_2$-Stearoyl)$^{20}$ E-(α-MeF)$^{22}$-IA-(α-MeF)$^{25}$-(V)$^{26}$-VKG-(G)$^{30}$ |
| 57 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-K$^{20}$-E-(α-MeF)$^{22}$-IA-(α-MeF)$^{25}$-(V)$^{26}$-V-(E)$^{28}$-G-(G)$^{30}$ |
| 58 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(E)$^{20}$-E-(α-MeF)$^{22}$-IA-(α-MeF)$^{25}$-(V)$^{26}$-V-(E)$^{28}$-G-(G)$^{30}$ |
| 59 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(Aib)$^{20}$ E-(α-MeF)$^{22}$-IA-(α-MeF)$^{25}$-(V)$^{26}$-V-(E)$^{22}$-G-(G)$^{30}$ |
| 60 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(α-MeK)$^{20}$ E-(α-MeF)$^{22}$-IA-(α-MeF)$^{25}$-(V)$^{26}$-V-(E)$^{28}$-G-(G)$^{30}$ |
| 61 | H-(Aib)$^2$-EG-(S)$^5$-(α-MeF)-TSDV$^{10}$-S-K(ε-(PEG)$_2$-(PEG)$_2$-(PEG)$_2$-Stearoyl)$^{12}$-YLE$^{15}$ G-(E)$^{17}$-AA-K$^{20}$-E-(α-MeF)$^{22}$-IA-(α-MeF)$^{25}$-(V)$^{26}$-V-(E)$^{28}$-G-(G)$^{30}$ |
| 62 | H-(Aib)$^2$-EG-(S)$^5$-(α-MeF)-TSDV$^{10}$-S-K(ε-(PEG)$_2$-(PEG)$_2$-(PEG)$_2$-Stearoyl)$^{12}$-YLE$^{15}$ G-(E)$^{17}$-AA-(E)$^{20}$-E-(α-MeF)$^{22}$-IA-(α-MeF)$^{25}$-(V)$^{26}$-V-(E)$^{28}$-G-(G)$^{30}$ |
| 63 | H-(Aib)$^2$-EG-(S)$^5$-(α-MeF)-TSDV$^{10}$-S-K(ε-(PEG)$_2$-(PEG)$_2$-(PEG)$_2$-Stearoyl)$^{12}$-YLE$^{15}$ G-(E)$^{17}$-AA-(Aib)$^{20}$ E-(α-MeF)$^{22}$-IA-(α-MeF)$^{25}$-(V)$^{26}$-V-(E)$^{28}$-G-(G)$^{30}$ |
| 64 | H-(Aib)$^2$-EG-(S)$^5$-(α-MeF)-TSDV$^{10}$-S-K(ε-(PEG)$_2$-(PEG)$_2$-(PEG)$_2$-Stearoyl)$^{12}$-YLE$^{15}$ G-(E)$^{17}$-AA-(α-MeK)$^{20}$ E-(α-MeF)$^{22}$-IA-(α-MeF)$^{25}$-(V)$^{26}$-V-(E)$^{28}$-G-(G)$^{30}$ |
| 65 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-K$^{20}$-EFI-K(-ε-(PEG)$_2$-(PEG)$_2$-γE-Stearate)$^{24}$-W$^{25}$-(V)$^{26}$-V-(E)$^{28}$-G-(G)$^{30}$ |
| 66 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(E)$^{20}$ EFI-K(-ε-(PEG)$_2$-(PEG)$_2$-γE-Stearate)$^{24}$-W$^{25}$-(V)$^{26}$-V-(E)$^{28}$-G-(G)$^{30}$ |

TABLE 1-continued

Substituted and Mono-lipidated Peptide Sequences

| ID | SEQ ID NO | Peptide |
|---|---|---|
| | 67 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(Aib)$^{20}$ EFI-K(-ε-(PEG)$_2$-(PEG)$_2$-γE-Stearate)$^{24}$-W$^{25}$-(V)$^{26}$-V-(E)$^{28}$-G-(G)$^{30}$ |
| | 68 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ EFI-K(-ε-(PEG)$_2$-(PEG)$_2$-γE-Stearate)$^{24}$-W$^{25}$-(V)$^{26}$-V-(E)$^{28}$-G-(G)$^{30}$ |
| | 69 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(A)$^{20}$ EFI-K(-ε-(PEG)$_2$-(PEG)$_2$-γE-Stearate)$^{24}$-W$^{25}$-(V)$^{26}$-V-(E)$^{28}$-G-(G)$^{30}$ |
| | 70 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-K(ε-γE-Palmitoyl)$^{30}$ |
| | 71 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-K(ε-γE-Palmitoyl)$^{28}$-(G)$^{30}$ |
| | 72 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-K(ε-γE-Palmitoyl)$^{28}$-G-(G)$^{30}$ |
| | 73 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-K(ε-γE-Palmitoyl)$^{27}$-(α-MeK)$^{28}$-G-(G)$^{30}$ |
| | 74 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-K(ε-γE-Palmitoyl)$^{26}$-V-(α-MeK)$^{28}$-G-(G)$^{30}$ |
| | 75 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-K(ε-γE-Palmitoyl)$^{25}$-(V)$^{26}$-V-(α-MeK)$^{28}$-G-(G)$^{30}$ |
| | 76 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IK(ε-γE-Palmitoyl)$^{24}$-(α-MeF)$^{25}$-(V)$^{26}$-V-(α-MeK)$^{28}$-G-(G)$^{30}$ |
| | 77 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-K(ε-γE-Palmitoyl)$^{23}$-A-(α-MeF)$^{25}$-(V)$^{26}$-V-(α-MeK)$^{28}$ G-(G)$^{30}$ |
| | 78 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-K(ε-γE-Palmitoyl)$^{22}$-IA-(α-MeF)$^{25}$-(V)$^{26}$-V-(α-MeK)$^{28}$ G-(G)$^{30}$ |
| | 79 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ K(ε-γE-Palmitoyl)$^{21}$-(α-MeF)$^{22}$-IA-(α-MeF)$^{25}$-(V)$^{26}$-V-(α-MeK)$^{28}$ G-(G)$^{30}$ |
| | 80 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-K(ε-γE-Palmitoyl)$^{20}$-E-(α-MeF)$^{22}$-IA-(α-MeF)$^{25}$-(V)$^{26}$-V-(α-MeK)$^{28}$ G-(G)$^{30}$ |
| | 81 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AK(ε-γE-Palmitoyl)$^{19}$-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 82 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-K(ε-γE-Palmitoyl)$^{18}$-A-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 83 | H-(Aib)$^2$-EG-(S)$^5$-(α-MeF)-TSDV$^{10}$-(α-MeS)$^{11}$-S-(α-MeF)$^{13}$-LE$^{15}$ G-K(ε-γE-Palmitoyl)$^{17}$-AA-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 84 | H-(Aib)$^2$-EG-(S)$^5$-(α-MeF)-TSDV$^{10}$-(α-MeS)$^{11}$-S-(α-MeF)$^{13}$-LE$^{15}$ K(ε-γE-Palmitoyl)$^{16}$-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 85 | H-(Aib)$^2$-EG-(S)$^5$-(α-MeF)-TSDV$^{10}$-(α-MeS)$^{11}$-S-(α-MeF)$^{13}$-L-K(ε-γE-Palmitoyl)$^{15}$-G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 86 | H-(Aib)$^2$-EG-(S)$^5$-(α-MeF)-TSDV$^{10}$-(α-MeS)$^{11}$-S-(α-MeF)$^{13}$-K(ε-γE-Palmitoyl)$^{14}$-EG-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 87 | H-(Aib)$^2$-EG-(S)$^5$-(α-MeF)-TSDV$^{10}$-(α-MeS)$^{11}$-S-K(ε-γE-Palmitoyl)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 88 | H-(Aib)$^2$-EG-(S)$^5$-(α-MeF)-TSDV$^{10}$-(α-MeS)$^{11}$-K(ε-γE-Palmitoyl)$^{12}$-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 89 | H-(Aib)$^2$-EG-(S)$^5$-(α-MeF)-TSDV$^{10}$-K(ε-γE-Palmitoyl)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 90 | H-(Aib)$^2$-EG-(S)$^5$-(α-MeF)-TSD-K(ε-γE-Palmitoyl)$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |

TABLE 1-continued

Substituted and Mono-lipidated Peptide Sequences

| ID | SEQ ID NO | Peptide |
|---|---|---|
| | 91 | H-(Aib)$^2$-EG-(S)$^5$-(α-MeF)-TS-K(ε-γE-Palmitoyl)$^9$-V-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 92 | H-(Aib)$^2$-EG-(S)$^5$-(α-MeF)-T-K(ε-γE-Palmitoyl)-DV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 93 | H-(Aib)$^2$-EG-(S)$^5$-(α-MeF)-K(ε-γE-Palmitoyl)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 94 | H-(Aib)$^2$-EG-(S)$^5$-K(ε-γE-Palmitoyl)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 95 | H-(Aib)$^2$-EG-K(ε-γE-Palmitoyl)-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 96 | H-(Aib)$^2$-E-K(ε-γE-Palmitoyl)-(S)$^5$-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 97 | H-(Aib)$^2$-K(ε-γE-Palmitoyl)-G-(S)$^5$-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 98 | H-K(ε-γE-Palmitoyl)-EG-(S)$^5$-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 99 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-K(ε-(PEG)$_2$-(PEG)$_2$-γE-Stearate)$^{30}$ |
| | 100 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-K(ε-(PEG)$_2$-(PEG)$_2$-γE-Stearate)$^{29}$-(G)$^{30}$ |
| | 101 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-K(ε-(PEG)$_2$-(PEG)$_2$-γE-Stearate)$^{28}$-G-(G)$^{30}$ |
| | 102 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-K(ε-(PEG)$_2$-(PEG)$_2$-γE-Stearate)$^{25}$-(α-MeK)$^{28}$-G-(G)$^{30}$ |
| | 103 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-K(ε-(PEG)$_2$-(PEG)$_2$-γE-Stearate)$^{26}$-V-(α-MeK)$^{28}$-G-(G)$^{30}$ |
| | 104 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-K(ε-(PEG)$_2$-(PEG)$_2$-γE-Stearate)$^{25}$-(V)$^{26}$-V-(α-MeK)$^{28}$ G-(G)$^{30}$ |
| | 105 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IK(ε-(PEG)$_2$-(PEG)$_2$-γE-Stearate)$^{24}$-(α-MeF)$^{25}$-(V)$^{26}$-V-(α-MeK)$^{28}$ G-(G)$^{30}$ |
| | 106 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-K(ε-(PEG)$_2$-(PEG)$_2$-γE-Stearate)$^{23}$-A-(α-MeF)$^{25}$-(V)$^{26}$-V-(α-MeK)$^{28}$ G-(G)$^{30}$ |
| | 107 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-K(ε-(PEG)$_2$-(PEG)$_2$-γE-Stearate)$^{22}$-IA-(α-MeF)$^{25}$-(V)$^{26}$-V-(α-MeK)$^{28}$ G-(G)$^{30}$ |
| | 108 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ K(ε-(PEG)$_2$-(PEG)$_2$-γE-Stearate)$^{21}$-(α-MeF)$^{22}$-IA-(α-MeF)$^{25}$-(V)$^{26}$-V-(α-MeK)$^{28}$ G-(G)$^{30}$ |
| | 109 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-K(ε-(PEG)$_2$-(PEG)$_2$-γE-Palmitate)$^{20}$-E-(α-MeF)$^{22}$-IA-(α-MeF)$^{25}$-(V)$^{26}$-V-(α-MeK)$^{28}$ G-(G)$^{30}$ |
| | 110 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AK(ε-(PEG)$_2$-(PEG)$_2$-γE-Stearate)$^{19}$-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 111 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-K(ε-(PEG)$_2$-(PEG)$_2$-γE-Stearate)$^{18}$-A-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 112 | H-(Aib)$^2$-EG-(S)$^5$-(α-MeF)-TSDV$^{10}$-(α-MeS)$^{11}$-S-(α-MeF)$^{13}$-LE$^{15}$ G-K(ε-(PEG)$_2$-(PEG)$_2$-γE-Stearate)$^{17}$-AA-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 113 | H-(Aib)$^2$-EG-(S)$^5$-(α-MeF)-TSDV$^{10}$-(α-MeS)$^{11}$-S-(α-MeF)$^{13}$-LE$^{15}$ K(ε-(PEG)$_2$-(PEG)$_2$-γE-Stearate)$^{16}$-(E)$^{17}$-AA-(α-MeK)$^{20}$ E-(α-MeF)$^{22}$-IA-(α-MeF)$^{25}$-(V)$^{26}$-V-(α-MeK)$^{28}$ G-(G)$^{30}$ |
| | 114 | H-(Aib)$^2$-EG-(S)$^5$-(α-MeF)-TSDV$^{10}$-(α-MeS)$^{11}$-S-(α-MeF)-L-K(ε-(PEG)$_2$-(PEG)$_2$-γE-Stearate)$^{15}$-G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |

TABLE 1-continued

Substituted and Mono-lipidated Peptide Sequences

| ID | SEQ ID NO | Peptide |
|---|---|---|
| | 115 | H-(Aib)$^2$-EG-(S)$^5$-(α-MeF)-TSDV$^{10}$-(α-MeS)$^{11}$-S-(α-MeF)$^{13}$-K(ε-(PEG)$_2$-(PEG)$_2$-γE-Stearate)$^{14}$-EG-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 116 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearate)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 117 | H-(Aib)$^2$-EG-(S)$^5$-(α-MeF)-TSDV$^{10}$-(α-MeS)$^{11}$-K(ε-(PEG)$_2$-(PEG)$_2$-γE-Stearate)$^{12}$-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 118 | H-(Aib)$^2$-EG-(S)$^5$-(α-MeF)-TSDV$^{10}$-K(ε-(PEG)$_2$-(PEG)$_2$-γE-Stearate)$^{11}$-5-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 119 | H-(Aib)$^2$-EG-(S)$^5$-(α-MeF)-TSD-K(ε-(PEG)$_2$-(PEG)$_2$-γE-Stearate)$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 120 | H-(Aib)$^2$-EG-(S)$^5$-(α-MeF)-TS-K(ε-(PEG)$_2$-(PEG)$_2$-γE-Stearate)$^9$-V-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$ |
| | 121 | H-(Aib)$^2$-EG-(S)$^5$-(α-MeF)-T-K(ε-(PEG)$_2$-(PEG)$_2$-γE-Stearate)-DV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)-G-(G)$^{28}$ 30 |
| | 122 | H-(Aib)$^2$-EG-(S)$^5$-(α-MeF)-K(ε-(PEG)$_2$-(PEG)$_2$-γE-Stearate)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{25}$-G-(G)$^{30}$ |
| | 123 | H-(Aib)$^2$-EG-(S)$^5$-K(ε-(PEG)$_2$-(PEG)$_2$-γE-Stearate)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{25}$-G-(G)$^{30}$ |
| | 124 | H-(Aib)$^2$-EG-K(ε-(PEG)$_2$-(PEG)$_2$-γE-Stearate)-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{25}$-G-(G)$^{30}$ |
| | 125 | H-(Aib)$^2$-E-K(ε-(PEG)$_2$-(PEG)$_2$-γE-Stearate) 4-(S)$^5$-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{25}$-G-(G)$^{30}$ |
| | 126 | H-(Aib)$^2$-K(ε-(PEG)$_2$-(PEG)$_2$-γE-Stearate)-G-(S)$^5$-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{25}$-G-(G)$^{30}$ |
| | 127 | H-K(ε-(PEG)$_2$-(PEG)$_2$-γE-Stearate)-EG-(S)$^5$-(α-MeF)-TSDV-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{25}$-G-(G)$^{30}$ |
| | 128 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 129 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 130 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-γE-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 131 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-Ahx-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 132 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-Ahx-Ahx-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 133 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-Ahx-Ahx-Ahx-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 134 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-Lauroyl)$^{20}$ E-(α-MeF)$^{22}$-IA-(α-MeF)$^{25}$-(V)$^{26}$-V-(α-MeK)$^{25}$-G-(G)$^{30}$ |
| | 135 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-Lauroyl)$^{20}$ E-(α-MeF)$^{22}$-IA-(α-MeF)$^{25}$-(V)$^{26}$-V-(α-MeK)$^{28}$-G-(G)$^{30}$ |
| | 136 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-(PEG)$_2$-Lauroyl)$^{20}$ E-(α-MeF)$^{22}$-IA-(α-MeF)$^{25}$-(V)$^{26}$-V-(α-MeK)$^{28}$-G-(G)$^{30}$ |
| | 137 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 138 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |

TABLE 1-continued

Substituted and Mono-lipidated Peptide Sequences

| ID | SEQ ID NO | Peptide |
|---|---|---|
| | 139 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-γE-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 140 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 141 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Ahx-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 142 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Ahx-Ahx-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 143 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 144 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 145 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-(PEG)$_2$-12-(4-carboxyphenoxy)dodecanoyl)$^{20}$ E-(α-MeF)$^{22}$-IA-(α-MeF)$^{25}$-(V)$^{26}$-V-(α-MeK)$^{28}$-G-(G)$^{30}$ |
| | 146 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 147 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 148 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-γE-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 149 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 150 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Ahx-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 151 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Ahx-Ahx-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 152 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 153 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 154 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-(PEG)$_2$-Stearoyl)$^{20}$ E-(α-MeF)$^{22}$-IA-(α-MeF)$^{25}$-(V)$^{26}$-V-(α-MeK)$^{28}$-G-(G)$^{30}$ |
| | 155 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| | 156 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| | 157 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-γE-γE-γE-Stearate)$^{20}$ E-(α-MeF)$^{22}$-IA-(α-MeF)$^{25}$-(V)$^{26}$-V-(α-MeK)$^{28}$-G-(G)$^{30}$ |
| | 158 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Stearate)$^{20}$ E-(α-MeF)$^{22}$-IA-(α-MeF)$^{25}$-(V)$^{26}$-V-(α-MeK)$^{28}$-G-(G)$^{30}$ |
| | 159 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Ahx-Stearate)$^{20}$ E-(α-MeF)$^{22}$-IA-(α-MeF)$^{25}$-(V)$^{26}$-V-(α-MeK)$^{28}$-G-(G)$^{30}$ |
| | 160 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(S-Ahx-Ahx-Ahx-Stearate)$^{20}$ E-(α-MeF)$^{22}$-IA-(α-MeF)$^{25}$-(V)$^{26}$-V-(α-MeK)$^{28}$-G-(G)$^{30}$ |
| | 161 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-Stearate)$^{20}$ E-(α-MeF)$^{22}$-IA-(α-MeF)$^{25}$-(V)$^{26}$-V-(α-MeK)$^{28}$-G-(G)$^{30}$ |
| | 162 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-Stearate)$^{20}$ E-(α-MeF)$^{22}$-IA-(α-MeF)$^{25}$-(V)$^{26}$-V-(α-MeK)$^{28}$-G-(G)$^{30}$ |

TABLE 1-continued

Substituted and Mono-lipidated Peptide Sequences

| SEQ ID NO | Peptide |
|---|---|
| 163 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AAK(ε-(PEG)$_2$-(PEG)$_2$-(PEG)$_2$-Stearate)$^{20}$ E-(α-MeF)$^{22}$-IA-(α-MeF)$^{25}$-(V)$^{26}$-V-(α-MeK)$^{28}$-G-(G)$^{30}$ |
| 164 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-Lauroyl)$^{28}$-G-(G)$^{30}$ |
| 165 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-Lauroyl)$^{28}$-G-(G)$^{30}$ |
| 166 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-γE-Lauroyl)$^{28}$-G-(G)$^{30}$ |
| 167 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Lauroyl)$^{28}$-G-(G)$^{30}$ |
| 168 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Lauroyl)$^{28}$-G-(G)$^{30}$ |
| 169 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Ahx-Lauroyl)$^{28}$-G-(G)$^{30}$ |
| 170 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-Lauroyl)$^{28}$-G-(G)$^{30}$ |
| 171 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-Lauroyl)$^{28}$-G-(G)$^{30}$ |
| 172 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-(PEG)$_2$-Lauroyl)$^{28}$-G-(G)$^{30}$ |
| 173 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-Dodecylbenzoate)$^{28}$-G-(G)$^{30}$ |
| 174 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-Dodecylbenzoate)$^{28}$-G-(G)$^{30}$ |
| 175 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-γE-Dodecylbenzoate)$^{28}$-G-(G)$^{30}$ |
| 176 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Dodecylbenzoate)$^{28}$-G-(G)$^{30}$ |
| 177 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Dodecylbenzoate)$^{28}$-G-(G)$^{30}$ |
| 178 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Ahx-Dodecylbenzoate)$^{28}$-G-(G)$^{30}$ |
| 179 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-Dodecylbenzoate)$^{28}$-G-(G)$^{30}$ |
| 180 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-Dodecylbenzoate)$^{28}$-G-(G)$^{30}$ |
| 181 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-(PEG)$_2$-Dodecylbenzoate)$^{28}$-G-(G)$^{30}$ |
| 182 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-Stearoyl)$^{28}$-G-(G)$^{30}$ |
| 183 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-Stearoyl)$^{28}$-G-(G)$^{30}$ |
| 184 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-γE-Stearoyl)$^{28}$-G-(G)$^{30}$ |
| 185 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Stearoyl)$^{28}$-G-(G)$^{30}$ |
| 186 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Stearoyl)$^{28}$-G-(G)$^{30}$ |

TABLE 1-continued

Substituted and Mono-lipidated Peptide Sequences

| SEQ ID NO | Peptide |
|---|---|
| 187 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Ahx-Stearoyl)$^{28}$-G-(G)$^{30}$ |
| 188 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-Stearoyl)$^{28}$-G-(G)$^{30}$ |
| 189 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-Stearoyl)$^{28}$-G-(G)$^{30}$ |
| 190 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-(PEG)$_2$-Stearoyl)$^{28}$-G-(G)$^{30}$ |
| 191 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-Stearate)$^{28}$-G-(G)$^{30}$ |
| 192 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-Stearate)$^{28}$-G-(G)$^{30}$ |
| 193 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-γE-γE-γE-Stearate)$^{28}$-G-(G)$^{30}$ |
| 194 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Stearate)$^{28}$-G-(G)$^{30}$ |
| 195 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Stearate)$^{28}$-G-(G)$^{30}$ |
| 196 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-Ahx-Ahx-Ahx-Stearate)$^{28}$-G-(G)$^{30}$ |
| 197 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-Stearate)$^{28}$-G-(G)$^{30}$ |
| 198 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-Stearate)$^{28}$-G-(G)$^{30}$ |
| 199 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-VK(ε-(PEG)$_2$-(PEG)$_2$-(PEG)$_2$-Stearate)$^{28}$-G-(G)$^{30}$ |
| 200 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-Lauroyl)$^{31}$ |
| 201 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-Lauroyl)$^{31}$ |
| 202 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE--E-Lauroyl)$^{31}$ |
| 203 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Lauroyl)$^{31}$ |
| 204 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-Lauroyl)$^{31}$ |
| 205 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-Ahx-Lauroyl)$^{31}$ |
| 206 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-Lauroyl)$^{31}$ |
| 207 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-(PEG)$_2$-Lauroyl)$^{31}$ |
| 208 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-(PEG)$_2$-(PEG)$_2$-Lauroyl)$^{31}$ |
| 209 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-12-(4-carboxyphenoxy)dodecanoyl)$^{31}$ |
| 210 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-12-(4-carboxyphenoxy)dodecanoyl)$^{31}$ |

TABLE 1-continued

Substituted and Mono-lipidated Peptide Sequences

| ID | SEQ ID NO | Peptide |
|---|---|---|
| | 211 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-γE-12-(4-carboxyphenoxy)dodecanoyl)$^{31}$ |
| | 212 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-12-(4-carboxyphenoxy)dodecanoyl)$^{31}$ |
| | 213 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-12-(4-carboxyphenoxy)dodecanoyl)$^{31}$ |
| | 214 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-Ahx-12-(4-carboxyphenoxy)dodecanoyl)$^{31}$ |
| | 215 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-12-(4-carboxyphenoxy)dodecanoyl)$^{31}$ |
| | 216 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-(PEG)$_2$-12-(4-carboxyphenoxy)dodecanoyl)$^{31}$ |
| | 217 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-((x-MeK)$^{28}$-G-(G)$^{30}$-K(ε-(PEG)$_2$-(PEG)$_2$-(PEG)$_2$-12-(4-carboxyphenoxy)dodecanoyl)$^{31}$ |
| | 218 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-Stearoyl)$^{31}$ |
| | 219 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-Stearoyl)$^{31}$ |
| | 220 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-γE-Stearoyl)$^{31}$ |
| | 221 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Stearoyl)$^{31}$ |
| | 222 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-Stearoyl)$^{31}$ |
| | 223 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)-K(ε-Ahx-Ahx-Ahx-Stearoyl)$^{31}$ |
| | 224 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-Stearoyl)$^{31}$ |
| | 225 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-(PEG)$_2$-Stearoyl)$^{31}$ |
| | 226 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)6-K(ε-(PEG)$_2$-(PEG)$_2$-(PEG)$_2$-Stearoyl)$^{31}$ |
| | 227 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-Stearate)$^{31}$ |
| | 228 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-Stearate)$^{31}$ |
| | 229 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-γE-γE-γE-Stearate)$^{31}$ |
| | 230 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Stearate)$^{31}$ |
| | 231 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-Stearate)$^{31}$ |
| | 232 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Ahx-Ahx-Ahx-Stearate)$^{31}$ |
| | 233 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)6-K(ε-(PEG)$_2$-Stearate)$^{31}$ |
| | 234 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-(PEG)$_2$-(PEG)$_2$-Stearate)$^{31}$ |

TABLE 1-continued

Substituted and Mono-lipidated Peptide Sequences

| ID | SEQ ID NO | Peptide |
|---|---|---|
| | 235 | H-(Aib)$^2$-EG-(S)$^5$-(α-MeF)-TSDV$^{10}$-(α-MeS)$^{11}$-S-(α-MeF)$^{13}$-LE$^{15}$ G-(E)$^{17}$-AA-(α-MeK)$^{20}$ E-(α-MeF)$^{22}$-IA-(α-MeF)$^{25}$-(V)$^{26}$-V-(α-MeK)$^{28}$-G-(G)6-K(ε-(PEG)$_2$-(PEG)$_2$-(PEG)$_2$-Stearate)$^{31}$ |

In certain embodiments, lipidated GLP-1 peptide analogs are provided comprising at least two lipid modified amino acid residues, such as those shown in Table 2. In certain embodiments, lipidated GLP-1 peptide analogs contain two lipidated amino acid residues. Bis-lipidated GLP-1 peptide analogs disclosed herein can be substantially resistant to proteolytic degradation. For example, in certain embodiments the bis-lipidated peptide is substantially resistant to DPP-IV, neprilysin, α-chymotrypsin, plasmin, thrombin, kallikrein, trypsin, elastase, and/or pepsin degradation. Bis-lipidated GLP-1 peptide analogs disclosed herein can maintain substantially the same or exhibit increased receptor potency and selectivity as a corresponding non-lipidated GLP-1 peptide or GLP-1 peptide analog.

A bis-lipidated peptide is lipid modified at two amino acid residues. In certain embodiments, this can be at two K (lysine) residues, at two C (cysteine) residues, or at one K and one C residue in the same peptide. In certain embodiments, two K residues are lipid modified. Thus, certain embodiments provide for an isolated polypeptide comprising the amino acid sequence:

(SEQ ID NO: 4)
H X2 E G X5 X6 T S D X10 X11 X12 X13 X14 E G X17 A

A X20 E X22 I X24 X25 X26 V X28 G X30;

wherein X2 is A or Aib;
X5 is T or S;
X6 is F or an alpha-methyl functionalized amino acid;
X10 is V or a lipid modified K;
X11 is S or an alpha-methyl functionalized amino acid;
X12 is S or a lipid modified K;
X13 is Y, F, or a lipid modified K;
X14 is L or a lipid modified K;
X17 is Q or E;
X20 is K, E, or an alpha-methyl functionalized amino acid;
X22 is F, norleucine, tyrosine methyl ester, or an alpha-methyl functionalized amino acid;
X24 is A or a lipid modified K;
X25 is W, F, or a lipid modified K;
X26 is L, V, or a lipid modified K;
X28 is K or E; and
X30 is R or G, wherein the polypeptide comprises two lipid modified K residues, and wherein one of X10, X12, X13, or X14 is a lipid modified K residue and one of X24, X25, or X26 is a lipid modified K residue.

In certain embodiments, a bis-lipidated peptide comprises one or more aminoisobutyric acid (Aib) substitutions. In certain embodiments of a peptide comprising the amino acid sequence of SEQ ID NO: 4: X2 is Aib. In certain embodiments, an alpha-methyl functionalized amino acid is one of α-MeF, α-MeS, or α-MeK.

The lipid modified K residues can be attached to a variety of lipids or lipid moieties such as any of those described herein. Example include those selected from the group consisting of: K(ε-(PEG)$_2$-(PEG)$_2$-γE-Lauroyl); K(ε-(PEG)$_2$-(PEG)$_2$-γE-Palmitate); K(ε-(PEG)$_2$-(PEG)$_2$-γE-Myristoyl); K(ε-(PEG)$_2$-(PEG)$_2$-γE-Palmitoyl); K(ε-(PEG)$_2$-(PEG)$_2$-γE-Stearoyl); K(ε-(PEG)$_2$-(PEG)$_2$-γE-Stearate); and any combination thereof. The lipid modification of the K residues can be the same or different. In certain embodiments, they are the same. Thus, in certain embodiments, at least two lipid modified K residues can both be K(ε-(PEG)$_2$-(PEG)$_2$-γE-Lauroyl); both be K(ε-(PEG)$_2$-(PEG)$_2$-γE-Palmitate); both be K(ε-(PEG)$_2$-(PEG)$_2$-γE-Myristoyl); both be K(ε-(PEG)$_2$-(PEG)$_2$-γE-Palmitoyl); both be K(ε-(PEG)$_2$-(PEG)$_2$-γE-Stearoyl); or both be K(ε-(PEG)$_2$-(PEG)$_2$-γE-Stearate). In certain embodiments of a peptide comprising the amino acid sequence of SEQ ID NO: 4: both modified residues can be K(ε-(PEG)$_2$-(PEG)$_2$-γE-Lauroyl); both can be K(ε-(PEG)$_2$-(PEG)$_2$-γE-Palmitate); both can be K(ε-(PEG)$_2$-(PEG)$_2$-γE-Myristoyl); both can be K(ε-(PEG)$_2$-(PEG)$_2$-γE-Palmitoyl); both can be K(ε-(PEG)$_2$-(PEG)$_2$-γE-Stearoyl); or both can be K(ε-(PEG)$_2$-(PEG)$_2$-γE-Stearate).

In certain embodiments, amino acid lipid modification of a peptide comprising the amino acid sequence of SEQ ID NO: 4 occurs in two distinct regions: one amino acid at position X10, X12, X13, or X14 is a lipid modified K residue and another amino acid at position X24, X25, or X26 is a lipid modified K residue. Thus, in certain embodiments:
X10 is a lipid modified K and one of X24, X25, or X26 is a lipid modified K;
X12 is a lipid modified K and one of X24, X25, or X26 is a lipid modified K;
X13 is a lipid modified K and one of X24, X25, or X26 is a lipid modified K;
X14 is a lipid modified K and one of X24, X25, or X26 is a lipid modified K;
X24 is a lipid modified K and one of X10, X12, X13, or X14 is a lipid modified K;
X25 is a lipid modified K and one of X10, X12, X13, or X14 is a lipid modified K; or
X26 is a lipid modified K and one of X10, X12, X13, or X14 is a lipid modified K.

The number, position, and identity of an alpha-methyl functionalized amino acid in a bis-lipidated polypeptide comprising the amino acid sequence of SEQ ID NO: 4 can vary. In certain embodiments, position X6 is α-MeF; X11 is α-MeS; X20 is α-MeK; and/or X22 is α-MeF. In certain embodiments, X6 is α-MeF. In certain embodiments, X6 is α-MeF and X11 is α-MeS. In certain embodiments, X6 is α-MeF and X20 is α-MeK. In certain embodiments, X6 is α-MeF, X11 is α-MeS, X20 is α-MeK, and X22 is α-MeF.

In certain embodiments, the number, position, and identity of an alpha-methyl functionalized amino acid in a bis-lipidated polypeptide comprising the amino acid sequence of SEQ ID NO: 4 can vary along with the position of the lipid modified amino acid residues. In certain embodiments where X13 is a lipid modified K and one of X24, X25, or X26 is a lipid modified K, X6 is α-MeF and X11 is α-MeS. In certain embodiments where X14 is a lipid modified K and one of X24, X25, or X26 is a lipid modified K, X6 is α-MeF and X11 is α-MeS.

In certain embodiments of a peptide comprising the GLP-1-derived amino acid sequence of SEQ ID NO: 4, one or more wild-type GLP-1 sequence amino acids can be substituted with another naturally occurring amino acid. For example, in certain embodiments, the wild-type T residue at position X5 is substituted with S. In certain embodiments, the wild-type Q, K, and R residues at positions X17, X28, and X30, respectively, can be substituted with E, E, and G, respectively.

In certain embodiments of a peptide comprising the amino acid sequence of SEQ ID NO: 4; the peptide comprises the amino acid sequence of SEQ ID NO: 252 (Table 2); SEQ ID NO: 263 (Table 2); SEQ ID NO: 269 (Table 2); SEQ ID NO: 405 (Table 2); SEQ ID NO: 408 (Table 2); SEQ ID NO: 409 (Table 2); or SEQ ID NO: 410 (Table 2).

In certain embodiments, a peptide comprising the amino acid sequence of SEQ ID NO: 4, 252, 263, 269, 405, 408, 409, or 410 is substantially resistant to proteolytic degradation. For example, in certain embodiments the peptide is substantially resistant to DPP-IV, neprilysin, α-chymotrypsin, plasmin, thrombin, kallikrein, trypsin, elastase, and/or pepsin degradation. In certain embodiments, a peptide comprising the amino acid sequence of SEQ ID NO: 4, 252, 263, 269, 405, 408, 409, or 410 at least maintains substantially the same receptor potency as compared to a corresponding non-lipidated peptide. In certain embodiments, a peptide comprising the amino acid sequence of SEQ ID NO: 4, 252, 263, 269, 405, 408, 409, or 410 at least maintains substantially the same receptor potency and selectivity as a compared to corresponding non-lipidated peptide.

TABLE 2

Bis-lipidated Peptide Sequences

| ID | SEQ ID NO | |
|---|---|---|
| GLP-1 (7-36) | 1 | HAEGT$^5$ FTSDV$^{10}$ SSYLE$^{15}$ GQAAK$^{20}$ EFIAW$^{25}$ LVKGR$^{30}$-amide |
| bis- | 4 | H X2 E G X5 X6 T S D X10 X11 X12 X13 X14 E G X17 A A X20 E F I X24 X25 X26 V X28 G X30 |
| | 236 | H-(Aib)$^2$-EGT$^5$ FTSDV$^{10}$ S-K(ε-(PEG)$_2$-(PEG)$_2$-γE-Lauroyl)$^{22}$-YLE$^{15}$ G-(E)$^{17}$-AA-(E)$^{20}$-EFI-K(ε-(PEG)$_2$-(PEG)$_2$-γE-Lauroyl)$^{24}$-W$^{25}$ (V)$^{26}$-V-(E)$^{28}$-G-(G)$^{30}$ |
| | 237 | H-(Aib)$^2$-EGT$^5$ FTSDV$^{10}$ S-K(ε-(PEG)$_2$-(PEG)$_2$-γE-Lauroyl)$^{12}$-(F)$^{13}$-LE$^{15}$ G-(E)$^{17}$-AA-(E)$^{20}$ EFI-K(ε-(PEG)$_2$-(PEG)$_2$-γE-Lauroyl)$^{24}$-W$^{25}$ (V)$^{26}$-V-(E)$^{28}$-G-(G)$^{30}$ |
| | 238 | H-(Aib)$^2$-EGT$^5$ FTSDV$^{10}$ S-K(ε-(PEG)$_2$-(PEG)$_2$-γE-Lauroyl)$^{12}$-YLE$^{15}$ G-(E)$^{17}$-AA-(E)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 239 | H-(Aib)$^2$-EGT$^5$ FTSDV$^{10}$ S-K(ε-(PEG)$_2$-(PEG)$_2$-γE-Lauroyl)$^{12}$-(F)$^{13}$-LE$^{15}$ G-(E)$^{17}$-AA-(E)$^{20}$-EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 240 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(E)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 241 | H-(Aib)$^2$-EG-(S)$^5$-(α-MeF)-TSDV$^{10}$-S-K(ε-(PEG)$_2$-(PEG)$_2$-γE-Lauroyl)$^{12}$-(F)$^{13}$-LE$^{15}$ G-(E)$^{17}$-AA-(E)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 242 | H-(Aib)$^2$-EGT$^5$ FTSDV$^{10}$ S-K(ε-(PEG)$_2$-(PEG)$_2$-γE-Palmitate)$^{12}$-YLE$^{15}$ G-(E)$^{17}$-AA-(E)$^{20}$-EFI-K(ε-(PEG)$_2$-(PEG)$_2$-γE-Palmitate)$^{24}$-W25 (V)$^{26}$-V-(E)$^{28}$-G-(G)$^{30}$ |
| | 243 | H-(Aib)$^2$-EGT$^5$ FTSDV$^{10}$ S-K(ε-(PEG)$_2$-(PEG)$_2$-γE-Palmitate)$^{12}$-(F)$^{13}$-LE$^{15}$ G-(E)$^{17}$-AA-(E)$^{20}$ EFI-K(ε-(PEG)$_2$-(PEG)$_2$-γE-Palmitate)$^{24}$-W$^{25}$ (V)$^{26}$-V-(E)$^{28}$-G-(G)$^{30}$ |
| | 244 | H-(Aib)$^2$-EGT$^5$ FTSDV$^{10}$ S-K(ε-(PEG)$_2$-(PEG)$_2$-γE-Palmitate)$^{12}$-YLE$^{15}$ G-(E)$^{17}$-AA-(E)$^{20}$ EFI-K(S-(PEG)$_2$-(PEG)$_2$-γE-Palmitate)$^{24}$-(F)$^{25}$-(V)$^{26}$-V-(E)$^{28}$-G-(G)$^{30}$ |
| | 245 | H-(Aib)$^2$-EGT$^5$ FTSDV$^{10}$ S-K(ε-(PEG)$_2$-(PEG)$_2$-γE-Palmitate)$^{12}$-(F)$^{13}$-LE$^{15}$ G-(E)$^{17}$-AA-(E)$^{20}$-EFI-K(ε-(PEG)$_2$-(PEG)$_2$-γE-Palmitate)$^{24}$-(F)$^{25}$-(V)$^{26}$-V-(E)$^{28}$-G-(G)$^{30}$ |
| | 246 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(E)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 247 | H-(Aib)$^2$-EG-(S)$^5$-(α-MeF)-TSDV$^{10}$-S-K(ε-(PEG)$_2$-(PEG)$_2$-γE-Palmitate)$^{12}$-(F)$^{13}$-LE$^{15}$ G-(E)$^{17}$-AA-(E)$^{20}$ EFI-K(ε-(PEG)$_2$-(PEG)$_2$-γE-Palmitate)$^{24}$-(E)$^{25}$-(V)$^{26}$-V-(E)$^{28}$-G-(G)$^{30}$ |
| | 248 | H-(Aib)$^2$-EG-(S)$^5$-(α-MeF)-TSDV$^{10}$-S-K(ε-(PEG)$_2$-(PEG)$_2$-γE-Lauroyl)$^{12}$-(F)$^{13}$-LE$^{15}$ G-(E)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 249 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(α-MeK)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 250 | H-(Aib)$^2$-EG-(S)$^5$-(α-MeF)-TSDV$^{10}$-S-K(ε-(PEG)$_2$-(PEG)$_2$-γE-Palmitate)$^{12}$-(F)$^{13}$-LE$^{15}$ G-(E)$^{17}$-AA-(α-MeK)$^{20}$ EFI-K(ε-(PEG)$_2$-(PEG)$_2$-γE-Palmitate)$^{24}$-(E)$^{25}$-(V)$^{26}$-V-(E)$^{28}$-G-(G)$^{30}$ |

TABLE 2-continued

Bis-lipidated Peptide Sequences

| ID | SEQ ID NO | |
|---|---|---|
| | 251 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(α-MeK)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 252 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 253 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(α-MeK)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 254 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(α-MeK)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 255 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(α-MeK)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 256 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(α-MeK)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 257 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 258 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(α-MeK)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 259 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(α-MeK)$^{20}$ EFT-K(ε-(PEG)$_2$-(PEG)$_2$-γE-Palmitate)$^{24}$-W$^{25}$-(V)$^{26}$-V-(E)$^{28}$-G-(G)$^{30}$ |
| | 260 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(α-MeK)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 261 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(α-MeK)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 262 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(α-MeK)$^{20}$ EFT-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 263 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 264 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(α-MeK)$^{20}$ EFIAW$^{25}$-K(-ε-(PEG)$_2$-(PEG)$_2$-γE-Lauroyl)$^{26}$-V-(E)$^{28}$-G-(G)$^{30}$ |
| | 265 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(α-MeK)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 266 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(α-MeK)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 267 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(α-MeK)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 268 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(α-MeK)$^{20}$ EFT-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 269 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 270 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(α-MeK)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 271 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(α-MeK)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 272 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(α-MeK)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 273 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(α-MeK)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 274 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(E)$^{20}$ EFIA-K(ε-(PEG)$_2$-(PEG)$_2$-γE-Lauroyl)$^{25}$-(V)$^{26}$-V-(E)$^{25}$-G-(G)$^{30}$ |
| | 275 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(E)$^{20}$ EFIAW$^{25}$-K(ε-(PEG)$_2$-(PEG)$_2$-γE-Lauroyl)$^{26}$-V-(E)$^{28}$-G-(G)$^{30}$ |

TABLE 2-continued

Bis-lipidated Peptide Sequences

| ID | SEQ ID NO | |
|---|---|---|
| | 276 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(E)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 277 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(E)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 278 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(E)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 279 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(E)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 280 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(E)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 281 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(E)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 282 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(E)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 283 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(E)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 284 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(E)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 285 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(E)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 286 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)'-AA-(E)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 287 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(E)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 288 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(E)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 289 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(E)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 290 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(E)$^{20}$ EFI-K(-ε-(PEG)$_2$-(PEG)$_2$-γE-Lauroyl)$^{24}$-W$^{25}$-(V)$^{26}$-V-(E)$^{28}$-G-(G)$^{30}$ |
| | 291 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(E)$^{20}$ EFIA-K(-ε-(PEG)$_2$-(PEG)$_2$-γE-Lauroyl)$^{25}$-(V)$^{26}$-V-(E)$^{28}$-G-(G)$^{30}$ |
| | 292 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(E)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 293 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(E)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 294 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(E)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 295 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{14}$-AA-(E)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 296 | H-(Aib)$^2$-EG-(S)$^5$-(α-MeF)-TSDV$^{10}$-S-K(ε-(PEG)$_2$-(PEG)$_2$-γE-Myristoyl)$^{12}$-YLE$^{15}$ G-(E)$^{17}$-AA-(E)$^{20}$ EFI-K(ε-(PEG)$_2$-(PEG)$_2$-γE-Myristoyl)$^{24}$-W$^{25}$-(V)$^{26}$-V-(E)$^{28}$-G-(G)$^{30}$ |
| | 297 | H-(Aib)$^2$-EG-(S)$^5$-(α-MeF)-TSDV$^{10}$-S-K(ε-(PEG)$_2$-(PEG)$_2$-γE-Palmitoyl)$^{12}$-YLE$^{15}$ G-(E)$^{14}$-AA-(E)$^{20}$ EFI-K(ε-(PEG)$_2$-(PEG)$_2$-γE-Palmitoyl)$^{24}$-W$^{25}$-(V)$^{26}$-V-(E)$^{28}$-G-(G)$^{30}$ |
| | 298 | H-(Aib)$^2$-EG-(S)$^5$-(α-MeF)-TSDV$^{10}$-S-K(ε-(PEG)$_2$-(PEG)$_2$-γE-Stearoyl)$^{12}$-YLE$^{15}$ G-(E)$^{17}$-AA-(E)$^{20}$ EFI-K(ε-(PEG)$_2$-(PEG)$_2$-γE-Stearoyl)$^{24}$-W$^{25}$-(V)$^{26}$-V-(E)$^{28}$-G-(G)$^{30}$ |
| | 299 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(E)$^{20}$ EFI-K(ε-(PEG)$_2$-(PEG)$_2$-γE-Stearate)$^{24}$-W$^{25}$-(V)$^{26}$-V-(E)$^{28}$-G-(G)$^{30}$ |
| | 300 | H-(Aib)$^2$-EG-(S)$^5$-(α-MeF)-TSDV$^{10}$-S-K(ε-(PEG)$_2$-(PEG)$_2$-γE-Myristoyl)$^{12}$-(F)$^{13}$-LE$^{15}$ G-(E)$^{17}$-AA-(E)$^{20}$ EFI-K(ε-(PEG)$_2$-(PEG)$_2$-γE-Myristoyl)$^{24}$-(F)$^{25}$-(V)$^{26}$-V-(E)$^{28}$-G-(G)$^{30}$ |

TABLE 2-continued

Bis-lipidated Peptide Sequences

| ID | SEQ ID NO | |
|---|---|---|
| | 301 | H-(Aib)$^2$-EG-(S)$^5$-(α-MeF)-TSDV$^{10}$-S-K(ε-(PEG)$_2$-(PEG)$_2$-γE-Palmitoyl)$^{12}$-(F)$^{13}$-LE$^{15}$ G-(E)$^{17}$-AA-(E)$^{20}$ EFI-K(ε-(PEG)$_2$-(PEG)$_2$-γE-Palmitoyl)$^{24}$-(F)$^{25}$-(V)$^{26}$-V-(E)$^{28}$-G-(G)$^{30}$ |
| | 302 | H-(Aib)$^2$-EG-(S)$^5$-(α-MeF)-TSDV$^{10}$-S-K(ε-(PEG)$_2$-(PEG)$_2$-γE-Stearoyl)$^{12}$-(F)$^{13}$-LE$^{15}$ G-(E)$^{17}$-AA-(E)$^{20}$ EFI-K(ε-(PEG)$_2$-(PEG)$_2$-γE-Stearoyl)$^{24}$-(F)$^{25}$-(V)$^{26}$-V-(E)$^{28}$-G-(G)$^{30}$ |
| | 303 | H-(Aib)$^2$-EG-(S)$^5$-(α-MeF)-TSDV$^{10}$-S-K(ε-(PEG)$_2$-(PEG)$_2$-γE-Stearate)$^{12}$-(F)$^{13}$-LE$^{15}$ G-(E)$^{17}$-AA-(E)$^{20}$ EFI-K(ε-(PEG)$_2$-(PEG)$_2$-γE-Stearate)$^{24}$-(F)$^{25}$-(V)$^{26}$-V-(E)$^{28}$-G-(G)$^{30}$ |
| | 304 | H-(Aib)$^2$-EG-(S)$^5$-(α-MeF)-TSDV$^{10}$-S-K(ε-(PEG)$_2$-(PEG)$_2$-γE-Myristoyl)$^{12}$-YLE$^{15}$ G-(E)$^{17}$-AA-(α-MeK)$^{20}$ EFI-K(ε-(PEG)$_2$-(PEG)$_2$-γE-Myristoyl)$^{24}$-W$^{25}$-(V)$^{26}$-V-(E)$^{28}$-G-(G)$^{30}$ |
| | 305 | H-(Aib)$^2$-EG-(S)$^5$-(α-MeF)-TSDV$^{10}$-S-K(ε-(PEG)$_2$-(PEG)$_2$-γE-Palmitoyl)$^{12}$-YLE$^{15}$ G-(E)$^{17}$-AA-(α-MeK)$^{20}$ EFI-K(ε-(PEG)$_2$-(PEG)$_2$-γE-Palmitoyl)$^{24}$-W$^{25}$-(V)$^{26}$-V-(E)$^{28}$-G-(G)$^{30}$ |
| | 306 | H-(Aib)$^2$-EG-(S)$^5$-(α-MeF)-TSDV$^{10}$-S-K(ε-(PEG)$_2$-(PEG)$_2$-γE-Stearoyl)$^{12}$-YLE$^{15}$ G-(E)$^{17}$-AA-(-MeK)$^{20}$ EFI-K(ε-(PEG)$_2$-(PEG)$_2$-γE-Stearoyl)$^{24}$-W$^{25}$-(V)$^{26}$-V-(E)$^{28}$-G-(G)$^{30}$ |
| | 307 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(α-MeK)$^{20}$ EFI-K(ε-(PEG)$_2$-(PEG)$_2$-γE-Stearate)$^{24}$-W$^{25}$-(V)$^{26}$-V-(E)$^{28}$-G-(G)$^{30}$ |
| | 308 | H-(Aib)$^2$-EG-(S)$^5$-(α-MeF)-TSDV$^{10}$-S-K(ε-(PEG)$_2$-(PEG)$_2$-γE-Myristoyl)$^{12}$-(F)$^{13}$-LE$^{15}$ G-(E)$^{17}$-AA-(α-MeK)$^{20}$ EFI-K(ε-(PEG)$_2$-(PEG)$_2$-γE-Myristoyl)$^{24}$-(F)$^{25}$-(v)$^{26}$-V-(E)$^{28}$-G-(G)$^{30}$ |
| | 309 | H-(Aib)$^2$-EG-(S)$^5$-(α-MeF)-TSDV$^{10}$-S-K(ε-(PEG)$_2$-(PEG)$_2$-γE-Palmitoyl)$^{12}$-(F)$^{13}$-LE$^{15}$ G-(E)$^{17}$-AA-(α-MeK)$^{20}$ EFI-K(ε-(PEG)$_2$-(PEG)$_2$-γE-Palmitoyl)$^{24}$-(F)$^{25}$-(V)$^{26}$-V-(E)$^{28}$-G-(G)$^{30}$ |
| | 310 | H-(Aib)$^2$-EG-(S)$^5$-(α-MeF)-TSDV$^{10}$-S-K(ε-(PEG)$_2$-(PEG)$_2$-γE-Stearoyl)$^{12}$-(F)$^{13}$-LE$^{15}$ G-(E)$^{17}$-AA-(α-MeK)$^{20}$ EFI-K(ε-(PEG)$_2$-(PEG)$_2$-γE-Stearoyl)$^{24}$-(F)$^{25}$-(V)$^{26}$-V-(E)$^{28}$-G-(G)$^{30}$ |
| | 311 | H-(Aib)$^2$-EG-(S)$^5$-(α-MeF)-TSDV$^{10}$-S-K(ε-(PEG)$_2$-(PEG)$_2$-γE-Stearate)$^{12}$-(F)$^{13}$-LE$^{15}$ G-(E)$^{17}$-AA-(α-MeK)$^{20}$ EFI-K(ε-(PEG)$_2$-(PEG)$_2$-γE-Stearate)$^{24}$-(F)$^{25}$-(V)$^{26}$-V-(E)$^{28}$-G-(G)$^{30}$ |
| | 312 | H-(Aib)$^2$-EG-(S)$^5$-(α-MeF)-TSDV$^{10}$-S-K(ε-(PEG)$_2$-(PEG)$_2$-γE-Lauroyl)$^{12}$-(F)$^{13}$-LE$^{15}$ G-(E)$^{17}$-AA-(Aib)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 313 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(Aib)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 314 | H-(Aib)$^2$-EG-(S)$^5$-(α-MeF)-TSDV$^{10}$-S-K(ε-(PEG)$_2$-(PEG)$_2$-γE-Palmitate)$^{12}$-(F)$^{13}$-LE$^{15}$ G-(E)$^{17}$-AA-(Aib)$^{20}$ EFI-K(ε-(PEG)$_2$-(PEG)$_2$-γE-Palmitate)$^{24}$-(F)$^{25}$-(V)$^{26}$-V-(E)$^{28}$-G-(G)$^{30}$ |
| | 315 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(Aib)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 316 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(Aib)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 317 | H-(Aib)$^2$-EG-(S)$^5$-(α-MeF)-TSDV$^{10}$-S-K(ε-(PEG)$_2$-(PEG)$_2$-γE-Lauroyl)$^{12}$-YLE$^{15}$ G-(E)$^{17}$-AA-(Aib)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 318 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(Aib)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 319 | H-(Aib)$^2$-EG-(S)$^5$-(α-MeF)-TSDV$^{10}$-S-K(ε-(PEG)$_2$-(PEG)$_2$-γE-Palmitate)$^{12}$-YLE$^{15}$ G-(E)$^{17}$-AA-(Aib)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 320 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(Aib)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 321 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(Aib)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 322 | H-(Aib)$^2$-EG-(S)$^5$-(α-MeF)-TSD-K(ε-(PEG)$_2$-(PEG)$_2$-γE-Lauroyl)$^{10}$-SSYLE$^{15}$ G-(E)$^{17}$-AA-(Aib)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 323 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(Aib)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 324 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(Aib)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 325 | H-(Aib)$^2$-EG-(S)$^5$-(α-MeF)-TSD-K(ε-(PEG)$_2$-(PEG)$_2$-γE-Palmitate)$^{10}$-SSYLE$^{15}$ G-(E)$^{17}$-AA-(Aib)$^{20}$ EFIAW$^{25}$-K(ε-(PEG)$_2$-(PEG)$_2$-γE-Palmitate)$^{26}$-V-(E)$^{28}$-G-(G)$^{30}$ |

TABLE 2-continued

Bis-lipidated Peptide Sequences

| ID | SEQ ID NO | |
|---|---|---|
| | 326 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(Aib)$^{20}$ EFI-K(ε-(PEG)$_2$-(PEG)$_2$-γE-Lauroyl)$^{24}$-W$^{25}$-(V)$^{26}$-V-(E)$^{28}$-G-(G)$^{30}$ |
| | 327 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(Aib)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 328 | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{13}$-LE$^{15}$ G-(E)$^{17}$-AA-(Aib)$^{20}$ EFIAW$^{25}$-K(ε-(PEG)$_2$-(PEG)$_2$-γE-Lauroyl)$^{26}$-V-(E)$^{28}$-G-(G)$^{30}$ |
| | 329 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(Alb)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 330 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(Alb)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 331 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitate)$^{13}$-LE$^{15}$ G-(E)$^{17}$-AA-(Aib)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 332 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(Aib)$^{20}$ EFI-K(-E-(PEG)$_2$-(PEG)$_2$-γE-Lauroyl)$^{24}$-W$^{25}$-(V)$^{26}$-V-(E)$^{28}$-G-(G)$^{30}$ |
| | 333 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(Aib)$^{20}$ EFIA-K(-E-(PEG)$_2$-(PEG)$_2$-γE-Lauroyl)$^{25}$-(V)$^{26}$-V-(E)$^{28}$-G-(G)$^{30}$ |
| | 334 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Lauroyl)$^{14}$-E$^{15}$ G-(E)$^{17}$-AA-(Aib)$^{20}$ EFIAW$^{25}$-K(-E-(PEG)$_2$-(PEG)$_2$-γE-Lauroyl)$^{26}$-V-(E)$^{28}$-G-(G)$^{30}$ |
| | 335 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(Alb)$^{20}$ EFI-K(ε-(PEG)$_2$-(PEG)$_2$-γE-Palmitate)$^{24}$-W$^{25}$-(V)$^{26}$-V-(E)$^{28}$-G-(G)$^{30}$ |
| | 336 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(Alb)$^{20}$ EFIA-K(ε-(PEG)$_2$-(PEG)$_2$-γE-Palmitate)$^{25}$-(V)$^{26}$-V-(E)$^{28}$-G-(G)$^{30}$ |
| | 337 | H-(Aib)$^2$-EG-(S)$^5$-(α-MeF)-TSDV$^{10}$-(α-MeS)$^{11}$-SY-K(ε-(PEG)$_2$-(PEG)$_2$-γE-Palmitate)$^{14}$-E$^{15}$ G-(E)$^{17}$-AA-(Aib)$^{20}$ EFIAW$^{25}$-K(ε-(PEG)$_2$-(PEG)$_2$-γE-Palmitate)$^{26}$-V-(E)$^{28}$-G-(G)$^{30}$ |
| | 338 | H-(Aib)$^2$-EG-(S)$^5$-(α-MeF)-TSDV$^{10}$-S-K(ε-(PEG)$_2$-(PEG)$_2$-γE-Myristoyl)$^{12}$-YLE$^{15}$ G-(E)$^{17}$-AA-(Aib)$^{20}$ EFI-K(ε-(PEG)$_2$-(PEG)$_2$-γE-Myristoyl)$^{24}$-W$^{25}$-(V)$^{26}$-V-(E)$^{28}$-G-(G)$^{30}$ |
| | 339 | H-(Aib)$^2$-EG-(S)$^5$-(α-MeF)-TSDV$^{10}$-S-K(ε-(PEG)$_2$-(PEG)$_2$-γE-Palmitoyl)$^{12}$-YLE$^{15}$ G-(E)$^{17}$-AA-(Aib)$^{20}$ EFI-K(ε-(PEG)$_2$-(PEG)$_2$-γE-Palmitoyl)$^{24}$-W$^{25}$-(V)$^{26}$-V-(E)$^{28}$-G-(G)$^{30}$ |
| | 340 | H-(Aib)$^2$-EG-(S)$^5$-(α-MeF)-TSDV$^{10}$-S-K(ε-(PEG)$_2$-(PEG)$_2$-γE-Stearoyl)$^{12}$-YLE$^{15}$ G-(E)$^{17}$-AA-(Aib)$^{20}$ EFI-K(ε-(PEG)$_2$-(PEG)$_2$-γE-Stearoyl)$^{24}$-W$^{25}$-(V)$^{26}$-V-(E)$^{28}$-G-(G)$^{30}$ |
| | 341 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(Aib)$^{20}$ EFI-K(ε-(PEG)$_2$-(PEG)$_2$-γE-Stearate)$^{24}$-W$^{25}$-(V)$^{26}$-V-(E)$^{28}$-G-(G)$^{30}$ |
| | 342 | H-(Aib)$^2$-EG-(S)$^5$-(α-MeF)-TSDV$^{10}$-S-K(ε-(PEG)$_2$-(PEG)$_2$-γE-Myristoyl)-(F)$^{13}$-LE$^{15}$ G-(E)$^{17}$-AA-(Aib)$^{20}$ EFI-K(ε-(PEG)$_2$-(PEG)$_2$-γE-Myristoyl)$^{24}$-(F)$^{25}$-(V)$^{26}$-V-(E)$^{28}$-G-(G)$^{30}$ |
| | 343 | H-(Aib)$^2$-EG-(S)$^5$-(α-MeF)-TSDV$^{10}$-S-K(ε-(PEG)$_2$-(PEG)$_2$-γE-Palmitoyl)$^{12}$-(F)$^{13}$-LE$^{15}$ G-(E)$^{17}$-AA-(Aib)$^{20}$ EFI-K(ε-(PEG)$_2$-(PEG)$_2$-γE-Palmitoyl)$^{24}$-(F)$^{25}$-(V)$^{26}$-V-(E)$^{28}$-G-(G)$^{30}$ |
| | 344 | H-(Aib)$^2$-EG-(S)$^5$-(α-MeF)-TSDV$^{10}$-S-K(ε-(PEG)$_2$-(PEG)$_2$-γE-Stearoyl)$^{12}$-(F)$^{13}$-LE$^{15}$ G-(E)$^{17}$-AA-(Aib)$^{20}$ EFI-K(ε-(PEG)$_2$-(PEG)$_2$-γE-Stearoyl)$^{24}$-(F)$^{25}$-(V)$^{26}$-V-(E)$^{28}$-G-(G)$^{30}$ |
| | 345 | H-(Aib)$^2$-EG-(S)$^5$-(α-MeF)-TSDV$^{10}$-S-K(ε-(PEG)$_2$-(PEG)$_2$-γE-Stearate)$^{12}$-(F)$^{13}$-LE$^{15}$ G-(E)$^{17}$-AA-(Aib)$^{20}$ EFI-K(ε-(PEG)$_2$-(PEG)$_2$-γE-Stearate)$^{24}$-(F)$^{25}$-(V)$^{26}$-V-(E)$^{28}$-G-(G)$^{30}$ |
| | 346 | H-(Aib)$^2$-EG-(S)$^5$-(α-MeF)-TSDV$^{10}$-S-K(ε-(PEG)$_2$-(PEG)$_2$-γE-Myristoyl)$^{12}$-YLE$^{15}$ G-(E)$^{17}$-AA-(E)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 347 | H-(Aib)$^2$-EG-(S)$^5$-(α-MeF)-TSDV$^{10}$-S-K(ε-(PEG)$_2$-(PEG)$_2$-γE-Palmitoyl)$^{12}$-YLE$^{15}$ G-(E)$^{17}$-AA-(E)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 348 | H-(Aib)$^2$-EG-(S)$^5$-(α-MeF)-TSDV$^{10}$-S-K(ε-(PEG)$_2$-(PEG)$_2$-γE-Stearoyl)$^{12}$-YLE$^{15}$ G-(E)$^{17}$-AA-(E)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 349 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(E)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 350 | H-(Aib)$^2$-EG-(S)$^5$-(α-MeF)-TSDV$^{10}$-S-K(ε-(PEG)$_2$-(PEG)$_2$-γE-Myristoyl)$^{12}$-(F)$^{13}$-LE$^{15}$ G-(E)$^{17}$-AA-(E)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |

TABLE 2-continued

Bis-lipidated Peptide Sequences

| ID | SEQ ID NO | |
|---|---|---|
| | 351 | H-(Aib)$^2$-EG-(S)$^5$-(α-MeF)-TSDV$^{10}$-S-K(ε-(PEG)$_2$-(PEG)$_2$-γE-Palmitoyl)$^{12}$-(F)$^{13}$-LE$^{15}$ G-(E)$^{17}$-AA-(E)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 352 | H-(Aib)$^2$-EG-(S)$^5$-(α-MeF)-TSDV$^{10}$-S-K(ε-(PEG)$_2$-(PEG)$_2$-γE-Stearoyl)$^{12}$-(F)$^{13}$-LE$^{15}$ G-(E)$^{17}$-AA-(E)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 353 | H-(Aib)$^2$-EG-(S)$^5$-(α-MeF)-TSDV$^{10}$-S-K(ε-(PEG)$_2$-(PEG)$_2$-γE-Stearate)$^{12}$-(F)$^{13}$-LE$^{15}$ G-(E)$^{18}$-AA-(E)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 354 | H-(Aib)$^2$-EG-(S)$^5$-(α-MeF)-TSDV$^{10}$-S-K(ε-(PEG)$_2$-(PEG)$_2$-γE-Myristoyl)$^{12}$-YLE$^{15}$ G-(E)$^{18}$-AA-(α-MeK)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 355 | H-(Aib)$^2$-EG-(S)$^5$-(α-MeF)-TSDV$^{10}$-S-K(ε-(PEG)$_2$-(PEG)$_2$-γE-Palmitoyl)$^{12}$-YLE$^{15}$ G-(E)$^{18}$-AA-(α-MeK)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 356 | H-(Aib)$^2$-EG-(S)$^5$-(α-MeF)-TSDV$^{10}$-S-K(ε-(PEG)$_2$-(PEG)$_2$-γE-Stearoyl)$^{12}$-YLE$^{15}$ G-(E)$^{17}$-AA-(α-MeK)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 357 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(α-MeK)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 358 | H-(Aib)$^2$-EG-(S)$^5$-(α-MeF)-TSDV$^{10}$-S-K(ε-(PEG)$_2$-(PEG)$_2$-γE-Myristoyl)$^{12}$-(F)$^{13}$-LE$^{15}$ G-(E)$^{17}$-AA-(α-MeK)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 359 | H-(Aib)$^2$-EG-(S)$^5$-(α-MeF)-TSDV$^{10}$-S-K(ε-(PEG)$_2$-(PEG)$_2$-γE-Palmitoyl)$^{12}$-(F)$^{13}$-LE$^{15}$ G-(E)$^{17}$-AA-(α-MeK)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 360 | H-(Aib)$^2$-EG-(S)$^5$-(α-MeF)-TSDV$^{10}$-S-K(ε-(PEG)$_2$-(PEG)$_2$-γE-Stearoyl)$^{12}$-(F)$^{13}$-LE$^{15}$ G-(E)$^{17}$-AA-(α-MeK)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 361 | H-(Aib)$^2$-EG-(S)$^5$-(α-MeF)-TSDV$^{10}$-S-K(ε-(PEG)$_2$-(PEG)$_2$-γE-Stearate)$^{12}$-(F)$^{13}$-LE$^{15}$ G-(E)$^{17}$-AA-(α-MeK)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 362 | H-(Aib)$^2$-EG-(S)$^5$-(α-MeF)-TSDV$^{10}$-S-K(ε-(PEG)$_2$-(PEG)$_2$-γE-Myristoyl)$^{12}$-YLE$^{15}$ G-(E)$^{17}$-AA-(Aib)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 363 | H-(Aib)$^2$-EG-(S)$^5$-(α-MeF)-TSDV$^{10}$-S-K(ε-(PEG)$_2$-(PEG)$_2$-γE-Palmitoyl)$^{12}$-YLE$^{15}$ G-(E)$^{17}$-AA-(Aib)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 364 | H-(Aib)$^2$-EG-(S)$^5$-(α-MeF)-TSDV$^{10}$-S-K(ε-(PEG)$_2$-(PEG)$_2$-γE-Stearoyl)$^{12}$-YLE$^{15}$ G-(E)$^{17}$-AA-(Aib)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 365 | H-(Aib)$^2$-EG-(S)$^5$-(α-MeF)-TSDV$^{10}$-S-K(ε-(PEG)$_2$-(PEG)$_2$-γE-Stearate)$^{12}$-YLE$^{15}$ G-(E)$^{17}$-AA-(Aib)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 366 | H-(Aib)$^2$-EG-(S)$^5$-(α-MeF)-TSDV$^{10}$-S-K(ε-(PEG)$_2$-(PEG)$_2$-γE-Myristoyl)$^{12}$-(F)$^{13}$-LE$^{15}$ G-(E)$^{17}$-AA-(Aib)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 367 | H-(Aib)$^2$-EG-(S)$^5$-(α-MeF)-TSDV$^{10}$-S-K(ε-(PEG)$_2$-(PEG)$_2$-γE-Palmitoyl)$^{12}$-(F)$^{13}$-LE$^{15}$ G-(E)$^{17}$-AA-(Aib)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 368 | H-(Aib)$^2$-EG-(S)$^5$-(α-MeF)-TSDV$^{10}$-S-K(ε-(PEG)$_2$-(PEG)$_2$-γE-Stearoyl)$^{12}$-(F)$^{13}$-LE$^{15}$ G-(E)$^{17}$-AA-(Aib)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 369 | H-(Aib)$^2$-EG-(S)$^5$-(α-MeF)-TSDV$^{10}$-S-K(ε-(PEG)$_2$-(PEG)$_2$-γE-Stearate)$^{12}$-(F)$^{13}$-LE$^{15}$ G-(E)$^{17}$-AA-(Aib)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 370 | H-(Aib)$^2$-EG-(S)$^5$-(α-MeF)-TSDV$^{10}$-(α-MeS)$^{11}$-S-K(ε-(PEG)$_2$-(PEG)$_2$-γE-Myristoyl)$^{13}$-LE$^{15}$ G-(E)$^{17}$-AA-(α-MeK)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 371 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitoyl)$^{13}$-LE$^{15}$ G-(E)$^{17}$-AA-(α-MeK)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 372 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearoyl)$^{13}$-LE$^{15}$ G-(E)$^{17}$-AA-(α-MeK)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 373 | H-(Aib)$^2$-EG-(S)$^5$-(α-MeF)-TSDV$^{10}$-(α-MeS)$^{11}$-S-K(ε-(PEG)$_2$-(PEG)$_2$-γE-Laurate)$^{13}$-LE$^{15}$ G-(E)$^{17}$-AA-(α-MeK)$^{20}$ EFIA-K(ε-(PEG)$_2$-(PEG)$_2$-γE-Laurate)$^{25}$-(V)$^{26}$-V-(E)$^{28}$-G-(G)$^{30}$ |
| | 374 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearate)$^{13}$-LE$^{15}$ G-(E)$^{17}$-AA-(α-MeK)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 375 | H-(Aib)$^2$-EG-(S)$^5$-(α-MeF)-TSDV$^{10}$-(α-MeS)$^{11}$-S-K(ε-(PEG)$_2$-(PEG)$_2$-γE-Myristoyl)$^{13}$-LE$^{15}$ G-(E)$^{17}$-AA-(E)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |

TABLE 2-continued

Bis-lipidated Peptide Sequences

| ID | SEQ ID NO | |
|---|---|---|
| | 376 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitoyl)$^{13}$-LE$^{15}$ G-(E)$^{17}$-AA-(E)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 377 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearoyl)$^{13}$-LE$^{15}$ G-(E)$^{17}$-AA-(E)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 378 | H-(Aib)$^2$-EG-(S)$^5$-(α-MeF)-TSDV$^{10}$-(α-MeS)$^{11}$-S-K(ε-(PEG)$_2$-(PEG)$_2$-γE-Laurate)$^{13}$-LE$^{15}$ G-(E)$^{17}$-AA-(E)$^{20}$ EFIA-K(ε-(PEG)$_2$-(PEG)$_2$-γE-Laurate)$^{25}$-(V)$^{26}$-V-(E)$^{28}$-G-(G)$^{30}$ |
| | 379 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearate)$^{13}$-LE$^{15}$ G-(E)$^{17}$-AA-(E)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 380 | H-(Aib)$^2$-EG-(S)$^5$-(α-MeF)-TSDV$^{10}$-(α-MeS)$^{11}$-S-K(ε-(PEG)$_2$-(PEG)$_2$-γE-Myristoyl)$^{13}$-LE$^{15}$ G-(E)$^{17}$-AA-(Aib)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| | 381 | H-(Aib)$^2$-EG-(S)$^5$-(α-MeF)-TSDV$^{10}$-(α-MeS)$^{11}$-S-K(ε-(PEG)$_2$-(PEG)$_2$-γE-Palmitoyl)$^{13}$-LE$^{15}$ G-(E)$^{17}$-AA-(Aib)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| | 382 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearoyl)$^{13}$-LE$^{15}$ G-(E)$^{17}$-AA-(Aib)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| | 383 | H-(Aib)$^2$-EG-(S)$^5$-(α-MeF)-TSDV$^{10}$-(α-MeS)$^{11}$-S-K(ε-(PEG)$_2$-(PEG)$_2$-γE-Laurate)$^{13}$-LE$^{15}$ G-(E)$^{17}$-AA-(Aib)$^{20}$ EFIA-K(ε-(PEG)$_2$-(PEG)$_2$-γE-Laurate)$^{25}$-(V)$^{26}$-V-(E)$^{28}$-G-(G)$^{30}$ |
| | 384 | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearate)$^{13}$-LE$^{15}$ G-(E)$^{17}$-AA-(Aib)$^{20}$ EFIA-K(ε-(PEG)$_2$-(PEG)$_2$-γE-Stearate)$^{25}$-(V)$^{26}$-V-(E)$^{28}$-G-(G)$^{30}$ |
| | 385 | H-(Aib)$^2$-EG-(S)$^5$-(α-MeF)-TSDV$^{10}$-(α-MeS)$^{11}$-S-K(ε-γE-Lauroyl)$^{13}$-LE$^{15}$ G-(E)$^{17}$-AA-(α-MeK)$^{20}$ EFIA-K(ε-γE-Lauroyl)$^{25}$-(V)$^{26}$-V-(E)$^{28}$-G-(G)$^{30}$ |
| | 386 | H-(Aib)$^2$-EG-(S)$^5$-(α-MeF)-TSDV$^{10}$-(α-MeS)$^{11}$-S-K(ε-γE-Myristoyl)$^{13}$-LE$^{15}$ G-(E)$^{17}$-AA-(α-MeK)$^{20}$ EFIA-K(ε-γE-Myristoyl)$^{25}$-(V)$^{26}$-V-(E)$^{28}$-G-(G)$^{30}$ |
| | 387 | H-(Aib)$^2$-EG-(S)$^5$-(α-MeF)-TSDV$^{10}$-(α-MeS)$^{11}$-S-K(ε-γE-Palmitoyl)$^{13}$-LE$^{15}$ G-(E)$^{17}$-AA-(α-MeK)$^{20}$ EFIA-K(ε-γE-Palmitoyl)$^{25}$-(V)$^{26}$-V-(E)$^{28}$-G-(G)$^{30}$ |
| | 388 | H-(Aib)$^2$-EG-(S)$^5$-(α-MeF)-TSDV$^{10}$-(α-MeS)$^{11}$-S-K(ε-γE-Stearoyl)$^{13}$-LE$^{15}$ G-(E)$^{17}$-AA-(α-MeK)$^{20}$ EFIA-K(ε-γE-Stearoyl)$^{25}$-(V)$^{26}$-V-(E)$^{28}$-G-(G)$^{30}$ |
| | 389 | H-(Aib)$^2$-EG-(S)$^5$-(α-MeF)-TSDV$^{10}$-(α-MeS)$^{11}$-S-K(ε-(PEG)$_2$-γE-Lauroyl)$^{13}$-LE$^{15}$ G-(E)$^{17}$-AA-(α-MeK)$^{20}$ EFIA-K(ε-(PEG)$_2$-γE-Lauroyl)$^{25}$-(V)$^{26}$-V-(E)$^{28}$-G-(G)$^{30}$ |
| | 390 | H-(Aib)$^2$-EG-(S)$^5$-(α-MeF)-TSDV$^{10}$-(α-MeS)$^{11}$-S-K(ε-(PEG)$_2$-γE-Myristoyl)$^{13}$-LE$^{15}$ G-(E)$^{17}$-AA-(α-MeK)$^{20}$ EFIA-K(ε-(PEG)$_2$-γE-Myristoyl)$^{25}$-(V)$^{26}$-V-(E)$^{28}$-G-(G)$^{30}$ |
| | 391 | H-(Aib)$^2$-EG-(S)$^5$-(α-MeF)-TSDV$^{10}$-(α-MeS)$^{11}$-S-K(ε-(PEG)$_2$-γE-Palmitoyl)$^{13}$-LE$^{15}$ G-(E)$^{17}$-AA-(α-MeK)$^{20}$ EFIA-K(ε-(PEG)$_2$-γE-Palmitoyl)$^{25}$-(V)$^{26}$-V-(E)$^{28}$-G-(G)$^{30}$ |
| | 392 | H-(Aib)$^2$-EG-(S)$^5$-(α-MeF)-TSDV$^{10}$-(α-MeS)$^{11}$-S-K(ε-(PEG)$_2$-γE-Stearoyl)$^{13}$-LE$^{15}$ G-(E)$^{17}$-AA-(α-MeK)$^{20}$ EFIA-K(ε-(PEG)$_2$-γE-Stearoyl)$^{26}$-(V)$^{26}$-V-(E)$^{28}$-G-(G)$^{30}$ |
| | 393 | H-(Aib)$^2$-EG-(S)$^5$-(α-MeF)-TSDV$^{10}$-SS-K(ε-γE-Lauroyl)$^{13}$-LE$^{15}$ G-(E)$^{17}$-AA-(α-MeK)$^{20}$ EFIA-K(ε-γE-Lauroyl)$^{26}$-(V)$^{26}$-V-(E)$^{28}$-G-(G)$^{30}$ |
| | 394 | H-(Aib)$^2$-EG-(S)$^5$-(α-MeF)-TSDV$^{10}$-SS-K(ε-γE-Myristoyl)$^{13}$-LE$^{15}$ G-(E)$^{17}$-AA-(α-MeK)$^{20}$ EFIA-K(ε-γE-Myristoyl)$^{25}$-(V)$^{26}$-V-(E)$^{28}$-G-(G)$^{30}$ |
| | 395 | H-(Aib)$^2$-EG-(S)$^5$-(α-MeF)-TSDV$^{10}$-SS-K(ε-γE-Palmitoyl)$^{13}$-LE$^{15}$ G-(E)$^{17}$-AA-(α-MeK)$^{20}$ EFIA-K(ε-γE-Palmitoyl)$^{25}$-(V)$^{26}$-V-(E)$^{28}$-G-(G)$^{30}$ |
| | 396 | H-(Aib)$^2$-EG-(S)$^5$-(α-MeF)-TSDV$^{10}$-SS-K(ε-γE-Stearoyl)$^{13}$-LE$^{15}$ G-(E)$^{17}$-AA-(α-MeK)$^{20}$ EFIA-K(ε-γE-Stearoyl)$^{25}$-(V)$^{26}$-V-(E)$^{28}$-G-(G)$^{30}$ |
| | 397 | H-(Aib)$^2$-EG-(S)$^5$-(α-MeF)-TSDV$^{10}$-SS-K(ε-(PEG)$_2$-γE-Lauroyl)$^{13}$-LE$^{15}$ G-(E)$^{17}$-AA-(α-MeK)$^{20}$ EFIA-K(ε-(PEG)$_2$-γE-Lauroyl)$^{26}$-(V)$^{26}$-V-(E)$^{28}$-G-(G)$^{30}$ |
| | 398 | H-(Aib)$^2$-EG-(S)$^5$-(α-MeF)-TSDV$^{10}$-SS-K(ε-(PEG)$_2$-γE-Myristoyl)$^{13}$-LE$^{15}$ G-(E)$^{17}$-AA-(α-MeK)$^{20}$ EFIA-K(ε-(PEG)$_2$-γE-Myristoyl)$^{26}$-(V)$^{26}$-V-(E)$^{28}$-G-(G)$^{30}$ |
| | 399 | H-(Aib)$^2$-EG-(S)$^5$-(α-MeF)-TSDV$^{10}$-SS-K(ε-(PEG)$_2$-γE-Palmitoyl)$^{13}$-LE$^{15}$ G-(E)$^{17}$-AA-(α-MeK)$^{20}$ EFIA-K(ε-(PEG)$_2$-γE-Palmitoyl)$^{25}$-(V)$^{26}$-V-(E)$^{28}$-G-(G)$^{30}$ |
| | 400 | H-(Aib)$^2$-EG-(S)$^5$-(α-MeF)-TSDV$^{10}$-SS-K(ε-(PEG)$_2$-γE-Stearoyl)$^{13}$-LE$^{15}$ G-(E)$^{17}$-AA-(α-MeK)$^{20}$ EFIA-K(ε-(PEG)$_2$-γE-Stearoyl)$^{26}$-(V)$^{26}$-V-(E)$^{28}$-G-(G)$^{30}$ |

TABLE 2-continued

Bis-lipidated Peptide Sequences

| ID | SEQ ID NO | |
|---|---|---|
| 401 | | H-(Aib)$^2$-EG-(S)$^5$-(α-MeF)-TSDV$^{10}$-SS-K(ε-(PEG)$_2$-(PEG)$_2$-γE-Lauroyl)$^{23}$-LE$^{15}$ G-(E)$^{27}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| 402 | | H-(Aib)$^2$-EG-(S)$^5$-(α-MeF)-TSDV$^{10}$-SS-K(ε-(PEG)$_2$-(PEG)$_2$-γE-Myristoyl)$^{23}$-LE$^{15}$ G-(E)$^{27}$-AA-(α-MeK)$^{20}$ EFIA-K(ε-(PEG)$_2$-(PEG)$_2$-γE-Myristoyl)$^{25}$-(V)$^{26}$-V-(E)$^{28}$-G-(G)$^{30}$ |
| 403 | | H-(Aib)$^2$-EG-(S)$^5$-(α-MeF)-TSDV$^{10}$-SS-K(ε-(PEG)$_2$-(PEG)$_2$-γE-Palmitoyl)$^{23}$-LE$^{15}$ G-(E)$^{27}$-AA-(α-MeK)$^{20}$ EFIA-K(ε-(PEG)$_2$-(PEG)$_2$-γE-Palmitoyl)$^{25}$-(V)$^{26}$-V-(E)$^{28}$-G-(G)$^{30}$ |
| 404 | | H-(Aib)$^2$-EG-(S)$^5$-(α-MeF)-TSDV$^{10}$-SS-K(ε-(PEG)$_2$-(PEG)$_2$-γE-Stearoyl)$^{23}$-LE$^{15}$ G-(E)$^{27}$-AA-(α-MeK)$^{20}$ EFIA-K(ε-(PEG)$_2$-(PEG)$_2$-γE-Stearoyl)$^{25}$-(V)$^{26}$-V-(E)$^{28}$-G-(G)$^{30}$ |
| 405 | | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{23}$-LE$^{15}$ G-(E)$^{17}$-AA-(α-MeK)$^{20}$ E-(α-MeF)$^{22}$IA-K(ε-(PEG)$_2$-(PEG)$_2$-γE-Lauroyl)$^{25}$-(V)$^{26}$-V-(E)$^{28}$-G-(G)$^{30}$ |
| 406 | | H-(Aib)$^2$-EG-(S)$^5$-(α-MeF)-TSDV$^{10}$-(α-MeS)$^{22}$-S-K(ε-(PEG)$_2$-(PEG)$_2$-γE-Lauroyl)$^{23}$-LE$^{15}$ G-(E)$^{17}$-AA-(α-MeK)$^{20}$ E-(Tyr (OMe)$^{22}$K(ε-(PEG)$_2$-(PEG)$_2$-γE-Lauroyl)$^{25}$-(V)$^{26}$-V-(E)$^{28}$-G-(G)$^{30}$ |
| 407 | | H-(Aib)$^2$-EG-(S)$^5$-(α-MeF)-TSDV$^{10}$-(α-MeS)$^{11}$-S-K(ε-(PEG)$_2$-(PEG)$_2$-γE-Lauroyl)$^{23}$-LE$^{15}$ G-(E)$^{17}$-AA-(α-MeK)$^{20}$ E-(Nle)$^{22}$IA-K(ε-(PEG)$_2$-(PEG)$_2$-γE-Lauroyl)$^{25}$-(V)$^{26}$-V-(E)$^{28}$-G-(G)$^{30}$ |
| 408 | | H-(Aib)$^2$-EG-(S)$^5$-(α-MeF)-TSDV$^{10}$-(α-MeS)$^{11}$-S-K(ε-(PEG)$_2$-(PEG)$_2$-γE-Myristoyl)$^{23}$-LE$^{15}$ G-(E)$^{27}$-AA-(α-MeK)$^{20}$ E-(α-MeF)$^{22}$IA-K(ε-(PEG)$_2$-(PEG)$_2$-γE-Myristoy l)$^{25}$-(V)$^{26}$-V-(E)$^{28}$-G-(G)$^{30}$ |
| 409 | | H-(Aib)$^2$-EG-(S)$^5$-(α-MeF)-TSDV$^{10}$-(α-MeS)$^{22}$-S-K(ε-(PEG)$_2$-(PEG)$_2$-γE-Palmitoyl)$^{23}$-LE$^{15}$ G-(E)$^{27}$-AA-(α-MeK)$^{20}$ E-(α-MeF)$^{22}$IA-K(ε-(PEG)$_2$-(PEG)$_2$-γE-Palmitoyl)$^{25}$-(V)$^{26}$-V-(E)$^{28}$-G-(G)$^{30}$ |
| 410 | | H-(Aib)$^2$-EG-(S)$^5$-(α-MeF)-TSDV$^{10}$-(α-MeS)$^{11}$-S-K(ε-(PEG)$_2$-(PEG)$_2$-γE-Stearoyl)$^{23}$-LE$^{15}$ G-(E)$^{17}$-AA-(α-MeK)$^{20}$ E-(α-MeF)$^{22}$IA-K(ε-(PEG)$_2$-(PEG)$_2$-γE-Stearoyl)$^{25}$-(V)$^{26}$-V-(E)$^{28}$-G-(G)$^{30}$ |
| 411 | | H-(Aib)$^2$-EG-(S)$^5$-(α-MeF)-TSDV$^{10}$-(α-MeS)$^{22}$-S-K(ε-(PEG)$_2$-(PEG)$_2$-γE-Laurate)$^{23}$-LE$^{15}$ G-(E)$^{17}$-AA-(α-MeK)$^{20}$ E-(α-MeF)$^{22}$IA-K(ε-(PEG)$_2$-(PEG)$_2$-γE-Laurate)$^{25}$-(V)$^{26}$-V-(E)$^{28}$-G-(G)$^{30}$ |
| 412 | | H-(Aib)$^2$-EG-(S)$^5$-(α-MeF)-TSDV$^{10}$-(α-MeS)$^{11}$-S-K(ε-(PEG)$_2$-(PEG)$_2$-γE-Myristate)$^{23}$-LE$^{15}$ G-(E)$^{27}$-AA-(α-MeK)$^{20}$ E-(α-MeF)$^{22}$IA-K(ε-(PEG)$_2$-(PEG)$_2$-γE-Myristate)$^{25}$-(V)$^{26}$-V-(E)$^{28}$-G-(G)$^{30}$ |
| 413 | | H-(Aib)$^2$-EG-(S)$^5$-(α-MeF)-TSDV$^{10}$-(α-MeS)-S-K(ε-(PEG)$_2$-(PEG)$_2$-γE-Palmitate)$^{13}$-LE$^{15}$ G-(E)$^{17}$-AA-(α-MeK)$^{20}$ E-(α-MeF)$^{22}$IA-K(ε-(PEG)$_2$-(PEG)$_2$-γE-Palmitate)$^{25}$-(V)$^{26}$-V-(E)$^{28}$-G-(G)$^{30}$ |
| 414 | | H-(Aib)$^2$-EG-(S)$^5$-(α-MeF)-TSDV$^{10}$-(α-MeS)-S-K(ε-(PEG)$_2$-(PEG)$_2$-γE-Stearate)$^{13}$-LE$^{15}$ G-(E)$^{17}$-AA-(α-MeK)$^{20}$ E-(α-MeF)$^{22}$IA-K(ε-(PEG)$_2$-(PEG)$_2$-γE-Stearate)$^{25}$-(V)$^{26}$-V-(E)$^{28}$-G-(G)$^{30}$ |
| 415 | | H-(Aib)$^2$-EG-( 5)-(α-MeF)-TSDV$^{10}$-(α-MeS)$^{11}$-S-K(ε-(PEG)$_2$-γE-Lauroyl)$^{13}$-LE$^{15}$ G-(E)$^{17}$-AA-(α-MeK)$^{20}$ E-(α-MeF)$^{22}$IA-K(ε-(PEG)$_2$-γE-Lauroyl)$^{25}$-(V)$^{26}$-V-(E)$^{28}$-G-(G)$^{30}$ |
| 416 | | H-(Aib)$^2$-EG-(S)$^5$-(α-MeF)-TSDV$^{10}$-(α-MeS)$^{11}$-S-K(ε-(PEG)$_2$-γE-Myristoyl)$^{13}$-LE$^{15}$ G-(E)$^{17}$-AA-(α-MeK)$^{20}$ E-(α-MeF)$^{22}$ IA-K(ε-(PEG)$_2$-γE-Myristoyl)$^{25}$-(V)$^{26}$-V-(E)$^{28}$-G-(G)$^{30}$ |
| 417 | | H-(Aib)$^2$-EG-(S)$^5$-(α-MeF)-TSDV$^{10}$-(α-MeS)$^{11}$-S-K(ε-(PEG)$_2$-γE-Palmitoyl)$^{13}$-LE$^{15}$ G-(E)$^{17}$-AA-(α-MeK)$^{20}$ E-(α-MeF)$^{22}$ IA-K(ε-(PEG)$_2$-γE-Palmitoyl)$^{25}$-(V)$^{26}$-V-(E)$^{28}$-G-(G)$^{30}$ |
| 418 | | H-(Aib)$^2$-EG-(S)$^5$-(α-MeF)-TSDV$^{10}$-(α-MeS)$^{11}$-S-K(ε-(PEG)$_2$-γE-Stearoyl)$^{13}$-LE$^{15}$ G-(E)$^{17}$-AA-(α-MeK)$^{20}$ E-(α-MeF)$^{22}$IA-K(ε-(PEG)$_2$-γE-Stearoyl)$^{25}$-(V)$^{26}$-V-(E)$^{28}$-G-(G)$^{30}$ |
| 419 | | H-(Aib)$^2$-EG-(S)$^5$-(α-MeF)-TSDV$^{10}$-(α-MeS)$^{11}$-S-K(ε-(PEG)$_2$-γE-Laurate)$^{13}$-LE$^{15}$ G-(E)$^{17}$-AA-(α-MeK)$^{20}$ E-(α-MeF)$^{22}$IA-K(ε-(PEG)$_2$-γE-Laurate)$^{25}$-(V)$^{26}$-V-(E)$^{28}$-G-(G)$^{30}$ |
| 420 | | H-(Aib)$^2$-EG-(S)$^5$-(α-MeF)-TSDV$^{10}$-(α-MeS)$^{11}$-S-K(ε-(PEG)$_2$-γE-Myristate)$^{13}$-LE$^{15}$ G-(E)$^{17}$-AA-(α-MeK)$^{20}$ E-(α-MeF)$^{22}$ IA-K(ε-(PEG)$_2$-γE-Myristate)$^{25}$-(V)$^{26}$-V-(E)$^{28}$-G-(G)$^{30}$ |
| 421 | | H-(Aib)$^2$-EG-(S)$^5$-(α-MeF)-TSDV$^{10}$-(α-MeS)$^{11}$-S-K(ε-(PEG)$_2$-γE-Palmitate)$^{13}$-LE$^{15}$ G-(E)$^{17}$-AA-(α-MeK)$^{20}$ E-(α-MeF)$^{22}$ IA-K(ε-(PEG)$_2$-γE-Palmitate)$^{25}$-(V)$^{26}$-V-(E)$^{28}$-G-(G)$^{30}$ |
| 422 | | H-(Aib)$^2$-EG-(S)$^5$-(α-MeF)-TSDV$^{10}$-(α-MeS)-S-K(ε-(PEG)$_2$-γE-Stearate)$^{13}$-LE$^{15}$ G-(E)$^{17}$-AA-(α-MeK)$^{20}$ E-(α-MeF)$^{22}$IA-K(ε-(PEG)$_2$-γE-Stearate)$^{25}$-(V)$^{26}$-V-(E)$^{28}$-G-(G)$^{30}$ |
| 423 | | H-(Aib)$^2$-EG-(S)$^5$-(α-MeF)-TSDV$^{10}$-(α-MeS)$^{11}$-S-K(ε-γE-Lauroyl)$^{13}$-LE$^{15}$ G-(E)$^{17}$-AA-(α-MeK)$^{20}$ E-(α-MeF)$^{22}$IA-K(ε-γE-Lauroyl)$^{25}$-(V)$^{26}$-V-(E)$^{28}$-G-(G)$^{30}$ |
| 424 | | H-(Aib)$^2$-EG-(S)$^5$-(α-MeF)-TSDV$^{10}$-(α-MeS)$^{11}$-S-K(ε-γE-Myristoyl)$^{13}$-LE$^{15}$ G-(E)$^{17}$-AA-(α-MeK)$^{20}$ E-(α-MeF)$^{22}$IA-K(ε-γE-Myristoyl)$^{25}$-(V)$^{26}$-V-(E)$^{28}$-G-(G)$^{30}$ |
| 425 | | H-(Aib)$^2$-EG-(S)$^5$-(α-MeF)-TSDV$^{10}$-(α-MeS)$^{11}$-S-K(ε-γE-Palmitoyl)$^{13}$-LE$^{15}$ G-(E)$^{17}$-AA-(α-MeK)$^{20}$ E-(α-MeF)$^{22}$IA-K(ε-γE-Palmitoyl)$^{25}$-(V)$^{26}$-V-(E)$^{28}$-G-(G)$^{30}$ |

TABLE 2-continued

Bis-lipidated Peptide Sequences

| ID | SEQ ID NO | |
|---|---|---|
| | 426 | H-(Aib)$^2$-EG-(S)$^5$-(α-MeF)-TSDV$^{10}$-(α-MeS)$^{11}$-S-K(ε-γE-Stearoyl)$^{13}$-LE$^{15}$ G-(E)$^{17}$-AA-(α-MeK)$^{20}$ E-(α-MeF)$^{22}$IA-K(ε-γE-Stearoyl)$^{25}$-(V)$^{26}$-V-(E)$^{28}$-G-(G)$^{30}$ |
| | 427 | H-(Aib)$^2$-EG-(S)$^5$-(α-MeF)-TSDV$^{10}$-(α-MeS)$^{11}$-S-K(ε-γE-Laurate)$^{13}$-LE$^{15}$ G-(E)$^{17}$-AA-(α-MeK)$^{20}$ E-(α-MeF)$^{22}$IA-K(ε-γE-Laurate)$^{25}$-(V)$^{26}$-V-(E)$^{28}$-G-(G)$^{30}$ |
| | 428 | H-(Aib)$^2$-EG-(S)$^5$-(α-MeF)-TSDV$^{10}$-(α-MeS)$^{11}$-S-K(ε-γE-Myristate)$^{13}$-LE$^{15}$ G-(E)$^{17}$-AA-(α-MeK)$^{20}$ E-(α-MeF)$^{22}$IA-K(ε-γE-Myristate)$^{25}$-(V)$^{26}$-V-(E)$^{28}$-G-(G)$^{30}$ |
| | 429 | H-(Aib)$^2$-EG-(S)$^5$-(α-MeF)-TSDV$^{10}$-(α-MeS)$^{11}$-S-K(ε-γE-Palmitate)$^{13}$-LE$^{15}$ G-(E)$^{17}$-AA-(α-MeK)$^{20}$ E-(α-MeF)$^{22}$IA-K(ε-γE-Palmitate)$^{25}$-(V)$^{26}$-V-(E)$^{28}$-G-(G)$^{30}$ |
| | 430 | H-(Aib)$^2$-EG-(S)$^5$-(α-MeF)-TSDV$^{10}$-(α-MeS)$^{11}$-S-K(ε-γE-Stearate)$^{13}$-LE$^{15}$ G-(E)$^{17}$-AA-(α-MeK)$^{20}$ E-(α-MeF)$^{22}$IA-K(ε-γE-Stearate)$^{25}$-(V)$^{26}$-V-(E)$^{28}$-G-(G)$^{30}$ |
| | 431 | H-(Aib)$^2$-EG-(S)$^5$-(α-MeF)-TSDV$^{10}$-(α-MeS)$^{11}$-S-K(ε-Lauroyl)$^{13}$-LE$^{15}$ G-(E)$^{17}$-AA-(α-MeK)$^{20}$ E-(α-MeF)$^{22}$ IA-K(ε-Lauroyl)$^{25}$-(V)$^{26}$-V-(E)$^{28}$-G-(G)$^{30}$ |
| | 432 | H-(Aib)$^2$-EG-(S)$^5$-(α-MeF)-TSDV$^{10}$-(α-MeS)$^{11}$-S-K(ε-Myristoyl)$^{13}$-LE$^{15}$ G-(E)$^{17}$-AA-(α-MeK)$^{20}$ E-(α-MeF)$^{22}$IA-K(ε-Myristoyl)$^{25}$-(V)$^{26}$-V-(E)$^{28}$-G-(G)$^{30}$ |
| | 433 | H-(Aib)$^2$-EG-(S)$^5$-(α-MeF)-TSDV$^{10}$-(α-MeS)$^{11}$-S-K(ε-Palmitoyl)$^{13}$-LE$^{15}$ G-(E)$^{17}$-AA-(α-MeK)$^{20}$ E-(α-MeF)$^{22}$IA-K(ε-Palmitoyl)$^{25}$-(V)$^{26}$-V-(E)$^{28}$-G-(G)$^{30}$ |
| | 434 | H-(Aib)$^2$-EG-(S)$^5$-(α-MeF)-TSDV$^{10}$-(α-MeS)$^{11}$-S-K(ε-Stearoyl)$^{13}$-LE$^{15}$ G-(E)$^{17}$-AA-(α-MeK)$^{20}$ E-(α-MeF)$^{22}$IA-K(ε-Stearoyl)$^{25}$-(V)$^{26}$-V-(E)$^{28}$-G-(G)$^{30}$ |
| | 435 | H-(Aib)$^2$-EG-(S)$^5$-(α-MeF)-TSDV$^{10}$-(α-MeS)$^{11}$-S-K(ε-Laurate)$^{13}$-LE$^{15}$ G-(E)$^{17}$-AA-(α-MeK)$^{20}$ E-(α-MeF)$^{22}$ IA-K(ε-Laurate)$^{25}$-(V)$^{26}$-V-(E)$^{28}$-G-(G)$^{30}$ |
| | 436 | H-(Aib)$^2$-EG-(S)$^5$-(α-MeF)-TSDV$^{10}$-(α-MeS)$^{11}$-S-K(ε-Myristate)$^{13}$-LE$^{15}$ G-(E)$^{17}$-AA-(α-MeK)$^{20}$ E-(α-MeF)$^{22}$IA-K(ε-Myristate)$^{25}$-(V)$^{26}$-V-(E)$^{28}$-G-(G)$^{30}$ |
| | 437 | H-(Aib)$^2$-EG-(S)$^5$-(α-MeF)-TSDV$^{10}$-(α-MeS)$^{11}$-S-K(S-Palmitate)$^{13}$-LE$^{15}$ G-(E)$^{15}$-AA-(α-MeK)$^{20}$ E-(α-MeF)$^{22}$IA-K(S-Palmitate)$^{25}$-(V)$^{26}$-V-(E)$^{28}$-G-(G)$^{30}$ |
| | 438 | H-(Aib)$^2$-EG-(S)$^5$-(α-MeF)-TSDV$^{10}$-(α-MeS)$^{11}$-S-K(ε-Stearate)$^{13}$-LE$^{15}$ G-(E)$^{15}$-AA-(α-MeK)$^{20}$ E-(α-MeF)$^{22}$IA-K(ε-Stearate)$^{25}$-(V)$^{26}$-V-(E)$^{25}$-G-(G)$^{30}$ |

In certain embodiments, lipidated GLP-1 peptide analogs are provided comprising at least three lipid modified amino acid residues, such as those shown in Table 3. In certain embodiments, lipidated GLP-1 peptide analogs contain three lipidated amino acid residues. Tris-lipidated GLP-1 peptide analogs disclosed herein can be substantially resistant to proteolytic degradation. For example, in certain embodiments the tris-lipidated peptide is substantially resistant to DPP-IV, neprilysin, α-chymotrypsin, plasmin, thrombin, kallikrein, trypsin, elastase, and/or pepsin degradation. Tris-lipidated GLP-1 peptide analogs disclosed herein can maintain substantially the same or exhibit increased receptor potency and selectivity as a corresponding non-lipidated GLP-1 peptide or GLP-1 peptide analog.

A tris-lipidated peptide is lipid modified at three amino acid residues. In certain embodiments, this can be at three K (lysine) residues, at three C (cysteine) residues, or at one K, one C residue, and a third K or C residue in the same peptide. In certain embodiments, three K residues are lipid modified. Thus, certain embodiments provide for an isolated polypeptide comprising the amino acid sequence:

(SEQ ID NO: 487)
H (Aib)E G S (α-MeF) T S D X10 X11 X12 X13 X14 E
X16 X17 X18 A (α-MeK) X21 F I X24 X25 X26 V E G G;

wherein X10 is V or a lipid modified K;
X11 is S or an alpha-methyl functionalized amino acid;
X12 is S or a lipid modified K;
X13 is Y or a lipid modified K;
X14 is L or a lipid modified K;
X16 is G or a lipid modified K;
X17 is E or a lipid modified K;
X18 is A or a lipid modified K;
X21 is E or a lipid modified K;
X24 is A or a lipid modified K;
X25 is F or a lipid modified K;
X26 is V or a lipid modified K; and
wherein the polypeptide comprises three lipid modified K residues, and wherein one of X10, X12, X13, or X14 is a lipid modified K residue and one of X16, X17, X18, or X21 is a lipid modified K residue and one of X24, X25, or X26 is a lipid modified K residue.

The lipid modified K residues can be attached to a variety of lipids or lipid moieties such as any of those described herein. Example include those selected from the group consisting of: K(ε-(PEG)$_2$-(PEG)$_2$-γE-Lauroyl); K(ε-(PEG)$_2$-(PEG)$_2$-γE-Palmitate); K(ε-(PEG)$_2$-(PEG)$_2$-γE-Myristoyl); K(ε-(PEG)$_2$-(PEG)$_2$-γE-Palmitoyl); K(ε-(PEG)$_2$-(PEG)$_2$-γE-Stearoyl); K(ε-(PEG)$_2$-(PEG)$_2$-γE-Stearate); and any combination thereof. The lipid modification of the K residues can be the same or different.

In certain embodiments, they are the same. Thus, in certain embodiments, at least three lipid modified K residues can all be K(ε-(PEG)$_2$-(PEG)$_2$-γE-Lauroyl); all be K(ε-(PEG)$_2$-(PEG)$_2$-γE-Palmitate); all be K(ε-(PEG)$_2$-(PEG)$_2$-γE-Myristoyl); all be K(ε-(PEG)$_2$-(PEG)$_2$-γE-Palmitoyl); all be K(ε-(PEG)$_2$-(PEG)$_2$-γE-Stearoyl); or all be K(ε-(PEG)$_2$-(PEG)$_2$-γE-Stearate). In certain embodiments of a peptide comprising the amino acid sequence of SEQ ID NO: 487: all modified residues can be K(ε-(PEG)$_2$-(PEG)$_2$-γE-Lauroyl); all can be K(ε-(PEG)$_2$-(PEG)$_2$-γE-Palmitate); all can be K(ε-(PEG)$_2$-(PEG)$_2$-γE-Myristoyl); all can be K(ε-(PEG)$_2$-(PEG)$_2$-γE-Palmitoyl); all can be K(ε-(PEG)$_2$-(PEG)$_2$-γE-Stearoyl); or all can be K(ε-(PEG)$_2$-(PEG)$_2$-γE-Stearate).

TABLE 3

Tris-lipidated Peptide Sequences

| ID | Seq ID No | |
|---|---|---|
| GLP-1 (7-36) | 1 | HAEGT$^5$ FTSDV$^{10}$ SSYLE$^{15}$ GQAAK)$^{28}$EFIAW$^{25}$ LVKGR$^{30}$-amide |
| Tris- | 487 | H (Aib) E G S (α-MeF) T S D X10 X11 X12 X13 X14 E X16 X17 X18 A(α-MeK) X21 F I X24 X25 X26 V E G G |
| | 439 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-K(ε-(PEG)$_2$-(PEG)$_2$-γE-Lauroyl)$^{16}$-(E)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 440 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-K(ε-(PEG)$_2$-(PEG)$_2$-γE-Lauroyl)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 441 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-(E)$^{17}$-K(ε-(PEG)$_2$-(PEG)$_2$-γE-Lauroyl)$^{18}$-A-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 442 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-(E)$^{17}$-AA-(α-MeK)$^{20}$ K(ε-(PEG)$_2$-(PEG)$_2$-γE-Lauroyl)$^{21}$-FI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 443 | H-(Aib)$^2$-EG-(5)$^5$-(α-MeF)$^6$-TSDV$^{10}$-S-K(ε-(PEG)$_2$-(PEG)$_2$-γE-Lauroyl)$^{12}$-YLE$^{15}$-K(ε-(PEG)$_2$-(PEG)$_2$-γE-Lauroyl)$^{16}$-(E)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 444 | H-(Aib)$^2$-EG-(5)$^5$-(α-MeF)$^6$-TSDV$^{10}$-S-K(ε-(PEG)$_2$-(PEG)$_2$-γE-Lauroyl)$^{12}$-YLE$^{15}$-G-K(ε-(PEG)$_2$-(PEG)$_2$-γE-Lauroyl)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 445 | H-(Aib)$^2$-EG-(5)$^5$-(α-MeF)$^6$-TSDV$^{10}$-S-K(ε-(PEG)$_2$-(PEG)$_2$-γE-Lauroyl)$^{12}$-YLE$^{15}$-G-(E)$^{17}$-K(ε-(PEG)$_2$-(PEG)$_2$-γE-Lauroyl)$^{18}$-A-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 446 | H-(Aib)$^2$-EG-(5)$^5$-(α-MeF)$^6$-TSDV$^{10}$-S-K(ε-(PEG)$_2$-(PEG)$_2$-γE-Lauroyl)$^{12}$-YLE$^{15}$-G-(E)$^{17}$-AA-(α-MeK)$^{20}$ K(ε-(PEG)$_2$-(PEG)$_2$-γE-Lauroyl)$^{21}$-FI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 447 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-K(ε-(PEG)$_2$-(PEG)$_2$-γE-Lauroyl)$^{16}$-(E)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 448 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-K(ε-(PEG)$_2$-(PEG)$_2$-γE-Lauroyl)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 449 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-(E)$^{17}$-K(ε-(PEG)$_2$-(PEG)$_2$-γE-Lauroyl)$^{18}$-A-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 450 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-(E)$^{17}$-AA-(α-MeK)$^{20}$ K(ε-(PEG)$_2$-(PEG)$_2$-γE-Lauroyl) 22-FI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 451 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-K(ε-(PEG)$_2$-(PEG)$_2$-γE-Lauroyl)$^{16}$-(E)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 452 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-K(ε-(PEG)$_2$-(PEG)$_2$-γE-Lauroyl)$^{17}$-AA-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 453 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-(E)$^{17}$-K(ε-(PEG)$_2$-(PEG)$_2$-γE-Lauroyl)$^{18}$-A-(α-MeK)$^{20}$ EFI-K(ε-(PEG)$_2$-(PEG)$_2$-γE-Lauroyl)$^{24}$-(F)$^{25}$-(V)$^{26}$-V-(E)$^{28}$-G-(G)$^{30}$ |

TABLE 3-continued

Tris-lipidated Peptide Sequences

| ID | Seq ID No | |
|---|---|---|
| | 454 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-(E)$^{17}$-AA-(α-MeK)$^{20}$ K(ε-(PEG)$_2$-(PEG)$_2$-γE-Lauroyl)22-FI-K(ε-(PEG)$_2$-(PEG)$_2$-γE-Lauroyl)$^{24}$-(F)$^{25}$-(V)$^{26}$-V-(E)$^{28}$-G-(G)$^{30}$ |
| | 455 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-K(ε-(PEG)$_2$-(PEG)$_2$-γE-Lauroyl)$^{16}$-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 456 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-K(ε-(PEG)$_2$-(PEG)$_2$-γE-Lauroyl)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 457 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-(E)$^{17}$-K(ε-(PEG)$_2$-(PEG)$_2$-γE-Lauroyl)$^{18}$-A-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 458 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-(E)$^{17}$-AA-(α-MeK)$^{20}$ K(ε-(PEG)$_2$-(PEG)$_2$-γE-Lauroyl)$^{21}$-FIA-K(ε-(PEG)$_2$-(PEG)$_2$-γE-Lauroyl)$^{25}$-(V)$^{26}$-V-(E)$^{28}$-G-(G)$^{30}$ |
| | 459 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-K(ε-(PEG)$_2$-(PEG)$_2$-γE-Lauroyl)$^{16}$-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 460 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-G-K(ε-(PEG)$_2$-(PEG)$_2$-γE-Lauroyl)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 461 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-G-(E)$^{17}$-K(ε-(PEG)$_2$-(PEG)$_2$-γE-Lauroyl)$^{18}$-A-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 462 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-G-(E)$^{17}$-AA-(α-MeK)$^{20}$ K(ε-(PEG)$_2$-(PEG)$_2$-γE-Lauroyl)$^{21}$-FIA-K(ε-(PEG)$_2$-(PEG)$_2$-γE-Lauroyl)$^{25}$-(V)$^{26}$-V-(E)$^{28}$-G-(G)$^{30}$ |
| | 463 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-K(ε-(PEG)$_2$-(PEG)$_2$-γE-Lauroyl)$^{16}$-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 464 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-K(ε-(PEG)$_2$-(PEG)$_2$-γE-Lauroyl)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 465 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-(E)$^{17}$-K(ε-(PEG)$_2$-(PEG)$_2$-γE-Lauroyl)$^{18}$-A-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 466 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-(E)$^{17}$-AA-(α-MeK)$^{20}$ K(ε-(PEG)$_2$-(PEG)$_2$-γE-Lauroyl)$^{21}$-FIA-K(ε-(PEG)$_2$-(PEG)$_2$-γE-Lauroyl)$^{25}$-(V)$^{26}$-V-(E)$^{28}$-G-(G)$^{30}$ |
| | 467 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-K(ε-(PEG)$_2$-(PEG)$_2$-γE-Lauroyl)$^{16}$-(E)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 468 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-K(ε-(PEG)$_2$-(PEG)$_2$-γE-Lauroyl)$^{17}$-AA-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 469 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-(E)$^{17}$-K(ε-(PEG)$_2$-(PEG)$_2$-γE-Lauroyl)$^{18}$-A-(α-MeK)$^{20}$ EFIA-K(ε-(PEG)$_2$-(PEG)$_2$-γE-Lauroyl)$^{25}$-(V)$^{26}$-V-(E)$^{28}$-G-(G)$^{30}$ |
| | 470 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-(E)$^{17}$-AA-(α-MeK)$^{20}$ K(ε-(PEG)$_2$-(PEG)$_2$-γE-Lauroyl)$^{21}$-FIA-K(ε-(PEG)$_2$-(PEG)$_2$-γE-Lauroyl)$^{25}$-(V)$^{26}$-V-(E)$^{28}$-G-(G)$^{30}$ |
| | 471 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-K(ε-(PEG)$_2$-(PEG)$_2$-γE-Lauroyl)$^{16}$-(E)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 472 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-K(ε-(PEG)$_2$-(PEG)$_2$-γE-Lauroyl)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 473 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-(E)$^{17}$-K(ε-(PEG)$_2$-(PEG)$_2$-γE-Lauroyl)$^{18}$-A-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |

TABLE 3-continued

Tris-lipidated Peptide Sequences

| ID | Seq ID No | |
|---|---|---|
| | 474 | H-(Aib)$^2$-EG-(S)$^5$-(α-MeF)$^6$-TSD-K(ε-(PEG)$_2$-(PEG)$_2$-γE-Lauroyl)$^{10}$-SSYLE$^{15}$-G-(E)$^{17}$-AA-(α-MeK)$^{20}$ K(ε-(PEG)$_2$-(PEG)$_2$-γE-Lauroyl)$^{21}$-FIA-(F)$^{25}$-K(ε-(PEG)$_2$-(PEG)$_2$-γE-Lauroyl)$^{26}$-V-(E)$^{28}$-G-(G)$^{30}$ |
| | 475 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-K(ε-(PEG)$_2$-(PEG)$_2$-γE-Lauroyl)$^{16}$-(E)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 476 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-G-K(ε-(PEG)$_2$-(PEG)$_2$-γE-Lauroyl)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 477 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-G-(E)$^{17}$-K(ε-(PEG)$_2$-(PEG)$_2$-γE-Lauroyl)$^{18}$-A-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 478 | H-(Aib)$^2$-EG-(S)$^5$-(α-MeF)$^6$-TSDV$^{10}$-S-K(ε-(PEG)$_2$-(PEG)$_2$-γE-Lauroyl)$^{12}$-YLE$^{15}$-G-(E)$^{17}$-AA-(α-MeK)$^{20}$ K(ε-(PEG)$_2$-(PEG)$_2$-γE-Lauroyl)$^{21}$-FIA-(F)$^{25}$-K(ε-(PEG)$_2$-(PEG)$_2$-γE-Lauroyl)$^{26}$-V-(E)$^{28}$-G-(G)$^{30}$ |
| | 479 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-K(ε-(PEG)$_2$-(PEG)$_2$-γE-Lauroyl)$^{16}$-(E)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 480 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-K(ε-(PEG)$_2$-(PEG)$_2$-γE-Lauroyl)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 481 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-(E)$^{17}$-K(ε-(PEG)$_2$-(PEG)$_2$-γE-Lauroyl)$^{18}$-A-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 482 | H-(Aib)$^2$-EG-(S)$^5$-(α-MeF)$^6$-TSDV$^{10}$-(α-MeS)$^{11}$-S-K(ε-(PEG)$_2$-(PEG)$_2$-γE-Lauroyl)$^{13}$-LE$^{15}$-G-(E)$^{17}$-AA-(α-MeK)$^{20}$ K(ε-(PEG)$_2$-(PEG)$_2$-γE-Lauroyl)$^{21}$-FIA-(F)$^{25}$-K(ε-(PEG)$_2$-(PEG)$_2$-γE-Lauroyl)$^{26}$-V-(E)$^{28}$-G-(G)$^{30}$ |
| | 483 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-K(ε-(PEG)$_2$-(PEG)$_2$-γE-Lauroyl)$^{16}$-(E)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 484 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-K(ε-(PEG)$_2$-(PEG)$_2$-γE-Lauroyl)$^{17}$-AA-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 485 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-(E)$^{17}$-K(ε-(PEG)$_2$-(PEG)$_2$-γE-Lauroyl)$^{18}$-A-(α-MeK)$^{20}$ EFIA-(F)$^{25}$-K(ε-(PEG)$_2$-(PEG)$_2$-γE-Lauroyl)$^{26}$-V-(E)$^{28}$-G-(G)$^{30}$ |
| | 486 | H-(Aib)$^2$-EG-(S)$^5$-(α-MeF)$^6$-TSDV$^{10}$-(α-MeS)$^{11}$-SY-K(ε-(PEG)$_2$-(PEG)$_2$-γE-Lauroyl)$^{14}$-E$^{15}$-G-(E)$^{17}$-AA-(α-MeK)$^{20}$ K(ε-(PEG)$_2$-(PEG)$_2$-γE-Lauroyl)$^{21}$-FIA-(F)$^{25}$-K(ε-(PEG)$_2$-(PEG)$_2$-γE-Lauroyl)$^{26}$-V-(E)$^{28}$-G-(G)$^{30}$ |
| | 487 | H-(Aib)-EGS-(α-MeF)-TSD-X10-X11-X12-X13-X14-E-X16-X17-X18-A-(α-MeK)-X21-FI-X24-X25-X26-VEGG |

The C-terminus of a peptide is generally either a free carboxylic acid or an amide. Thus, in certain aspects, any one of the peptides in Tables 1, 2, and 3 can either have a C-terminal acid or a C-terminal amide. In certain aspects, any one of the peptides in Tables 1, 2, and 3 comprises a C-terminal acid. In certain aspects, any one of the peptides in Tables 1, 2, and 3 comprises a C-terminal amide.

Linkers used in various polypeptides provided herein can facilitate formation of a structure. In some aspects, a polypeptide linker can comprise 1-50 amino acids, 1-25 amino acids, 25-50 amino acids, or 30-50 amino acids. Generally longer linkers correlate with higher activity (more flexible), but also decreased stability as the peptide becomes more exposed. Linkers can comprise, e.g., (Gly-Ser)n, residues, where n is an integer of at least one, and up to, e.g., 4, 5, 6, 10, 20, 50, 100, or more, optionally with some Glu or Lys residues dispersed throughout to increase solubility. Alternatively, certain linkers do not comprise any Serine residues, e.g., where the linker is subject to O-linked glycosylation. In some aspects, linkers can contain cysteine residues, for example, if dimerization of linkers is used to bring two or more agonist polypeptides into a dimeric configuration. In some aspects, an agonist polypeptide can comprise at least one, two, three, four, or more linkers. The length and amino acid sequence of a linker can be readily selected and optimized.

Methods of Preparing Lipidated Peptides

While various methods of attaching lipids and lipid moieties to peptides are known, provided herein is at least one representative method of preparing lipidated peptides.

In certain embodiments, lipidated peptides can be prepared as C-terminal carboxamides, such as on NovaSyn®

TGR resin. In certain embodiments, amino acids (both natural and unnatural) can be coupled at ambient temperature, such as by using HCTU/DIPEA in NMP, capping residual functionality with a solution of acetic anhydride and pyridine. In such methods, the N-Fmoc group can be deblocked using piperidine in DMF (20% v/v) at ambient temperature and the C-terminal residue incorporated as the N-Boc-protected form, e.g. Boc-His(Trt)-OH or Boc-Tyr(tBu)-OH or equivalent. At the position(s) of lipidation Fmoc-Lys(Mmt)-OH can be incorporated into the peptide backbone during automated assembly and upon completion the Mmt protecting group(s) can be removed manually and selectively by treatment of the synthesis resin with 1% TFA, 2% TIPS, DCM (10×1 minute, 20.0 mL/g). The acidified resin can be quenched, such as with 5% DIPEA/NMP, and the exposed lysine amino-function(s) acylated, PEGylated or lipidated as required prior to peptide cleavage.

Crude peptides can be cleaved from the resin support by treatment with a suitable cleavage cocktail. In certain embodiments the cocktail consists of TFA (95% v/v), TIPS (2.5% v/v), and water (2.5% v/v) with agitation (3×1 hour at ambient temperature). Cleavage aliquots can be combined, concentrated by rotary evaporation and precipitated by addition of cold diethyl ether, isolating the solids by centrifugation. The crude peptides can be dried under a flow of dry nitrogen, reconstituted in a suitable aqueous buffer and filtered prior to chromatographic purification.

Crude mono-lipidated peptides can be dissolved in a solution of acetic acid/acetonitrile/water (1:5:50 v/v) and filtered. The crude filtrates can be chromatographed, such as over an Agilent Polaris C8-A stationary phase (21.2×250 mm, 5 micron) eluting with a linear solvent gradient of 10-70%, 15-80% or 20-90% MeCN (0.1% TFA v/v) in water (0.1% TFA v/v) over 30 minutes using a Varian SD-1 PrepStar binary pump system, monitoring by UV absorption at 210 nm. The peptide-containing fractions can then be pooled, frozen (dry-ice/acetone) and lyophilized.

Crude bis-lipidated peptides can be dissolved, such as in 0.1M ammonium bicarbonate solution (1:5 acetonitrile/water v/v, pH 8.0) and filtered. The crude filtrates can be chromatographed, such as over a Waters X-Bridge C18 stationary phase (19.0×250 mm, 5 micron) eluting with a linear solvent gradient of 20-90% B against A over 30 minutes using a Varian SD-1 PrepStar binary pump system, monitoring by UV absorption at 210 nm. (A=0.1M ammonium bicarbonate in water, B=0.1M ammonium bicarbonate in 1:2 water/acetonitrile). The peptide-containing fractions can then pooled, frozen (dry-ice/acetone) and lyophilized.

The peptide sequence can be a GLP-1 analog sequence such as those disclosed in Tables 1 and 2. The lipid or lipid moiety can be any such as disclosed herein, including but not limited to: K(ε-(PEG)$_2$-(PEG)$_2$-γE-Stearate); K(ε-γE-Palmitoyl); K(ε-(PEG)$_2$-(PEG)$_2$-γE-Stearate); K(γE-Palmitoyl); K(ε-(PEG)$_2$-(PEG)$_2$-(PEG)$_2$-Stearoyl); K(ε-γE-Lauroyl); K(ε-γE-γE-Lauroyl); K(ε-γE-γE-γE-Lauroyl); K(ε-Ahx-Lauroyl); K(ε-Ahx-Ahx-Lauroyl); K(ε-Ahx-Ahx-Ahx-Lauroyl); K(ε-(PEG)$_2$-Lauroyl); K(ε-(PEG)$_2$-(PEG)$_2$-Lauroyl); K(ε-(PEG)$_2$-(PEG)$_2$-(PEG)$_2$-Lauroyl); K(ε-γE-12-(4-carboxyphenoxy)dodecanoyl); K(ε-γE-γE-12-(4-carboxyphenoxy)dodecanoyl); K(ε-γE-γE-γE-12-(4-carboxyphenoxy)dodecanoyl); K(ε-Ahx-12-(4-carboxyphenoxy)dodecanoyl); K(ε-Ahx-Ahx-12-(4-carboxyphenoxy)dodecanoyl); K(ε-Ahx-Ahx-Ahx-12-(4-carboxyphenoxy)dodecanoyl); K(ε-(PEG)$_2$-12-(4-carboxyphenoxy)dodecanoyl); K(ε-(PEG)$_2$-(PEG)$_2$-12-(4-carboxyphenoxy)dodecanoyl); K(ε-(PEG)$_2$-(PEG)$_2$-PEG)$_2$-12-(4-carboxyphenoxy)dodecanoyl); K(ε-γE-Stearoyl); K(ε-γE-γE-Stearoyl); K(ε-γE-γE-γE-Stearoyl); K(ε-Ahx-Stearoyl); K(ε-Ahx-Ahx-Stearoyl); K(ε-Ahx-Ahx-Ahx-Stearoyl); K(ε-(PEG)$_2$-Stearoyl); K(ε-(PEG)$_2$-(PEG)$_2$-Stearoyl); K(ε-(PEG)$_2$-(PEG)$_2$-(PEG)$_2$-Stearoyl); K(ε-γE-Stearate); K(ε-γE-γE-Stearate); K(ε-γE-γE-γE-Stearate); K(ε-Ahx-Stearate); K(ε-Ahx-Ahx-Stearate); K(ε-Ahx-Ahx-Ahx-Stearate); K(ε-(PEG)$_2$-Stearate); K(ε-(PEG)$_2$-(PEG)$_2$-Stearate); K(ε-(PEG)$_2$-(PEG)$_2$-(PEG)$_2$-Stearate), and any combination thereof.

Methods of Preparing Synthetic Peptides

Also provided are methods of preparing synthetic peptides.

In some embodiments, the methods suitably comprise identifying at least one native amino acid residue in the peptide for substitution. In other embodiments, the methods suitably comprise identifying at least two native amino acid residues in the peptide for substitution. Alpha-methyl functionalized amino acids can then substituted for the identified native amino acid residues.

As described throughout, the synthetic peptides prepared by the methods provided herein suitably maintain substantially the same or exhibit increased receptor potency and in some cases selectivity as a corresponding synthetic peptide that does not comprise the substitutions. In addition, the synthetic peptides prepared according to the methods described herein can also be substantially resistant to proteolytic degradation.

Suitably in the methods provided herein the substituted alpha-methyl functionalized amino acids correspond to the substituted native amino acid residues, and in additional embodiments, the substituted alpha-methyl functionalized amino acids correspond to the same class as the substituted native amino acid residues.

In further embodiments, the substituted alpha-methyl functionalized amino acids can be alpha-methyl phenylalanine. In exemplary embodiments, alpha-methyl phenylalanine is substituted for corresponding native amino acids, though in further embodiments of the methods, the alpha-methyl phenylalanine do not have to correspond to the same native amino acids for which the substitution is occurring.

In certain embodiments, the synthetic peptides prepared according to the methods described herein can be substantially resistant to one or more of DPP-IV, neprilysin, α-chymotrypsin, plasmin, thrombin, kallikrein, trypsin, elastase and pepsin degradation.

In embodiments, synthetic peptides can be prepared as C-terminal carboxamides on NOVASYN® TGR resin. Amino acids (both natural and unnatural) can be coupled at ambient temperature using HCTU/DIPEA in NMP, capping residual functionality with a solution of acetic anhydride and pyridine. Fmoc is suitably deblocked in using piperidine in DMF at ambient temperature.

As described herein, identifying at least one native amino acid residue in the peptide for substitution suitably comprises identifying amino acids at sites susceptible to enzymatic cleavage. Exemplary methods of identifying amino acids at sites susceptible to enzymatic cleavage are well known in the art. In certain embodiments, methods of identifying amino acids at sites susceptible to enzymatic cleavage suitably comprise exposing a natural peptide (e.g., a wild-type peptide) to a single enzyme under conditions in which the enzyme is active (e.g., suitable pH, buffer conditions, temperature, etc.) for a pre-determined amount of time and measuring the enzymatic degradation products of the peptide. Exemplary methods for measuring the enzymatic degradation products include, for example, reverse-phase liquid chromatography-mass spectrometry.

Peptide solutions can be added to solutions of a protease. The peptide and enzyme can be co-incubated, suitably at about 37° C. Aliquots of the incubated peptide-enzyme mixture can be withdrawn periodically, quenched to arrest proteolytic activity, and analyzed by liquid chromatography-mass spectrometry (LC/MS). Analytes can be detected by both UV absorption (e.g., at 210 nm) and by ionization using a mass detector (ESI+ mode). Peptidic species (fragments) deriving from enzymatic cleavage of peptides can be analyzed post-process, and their molecular masses can be used to identify the precise cleavage position (highlighting the scissile bond in each case).

In certain embodiments, the methods described herein can be used to prepare any class of peptide having the recited characteristics.

In certain embodiments, the methods can be used to prepare incretin class peptides.

Synthetic incretin class peptides that can be prepared as described herein include, but are not limited to, glucagon-like peptide 1 (GLP-1), a glucose-dependent insulinotropic peptide (GIP), an exenatide peptide, plus glucagon, secretins, tenomodulin and oxyntomodulin.

Additional classes of peptides can be prepared as described herein.

In embodiments, the methods can be used to prepare synthetic GLP-1 peptides. In further embodiments, the methods can be used to prepare synthetic insulin.

In further embodiments, methods of preparing a proteolytically stable peptide are provided. Suitably, such methods comprise exposing a peptide to one or more proteases, identifying at least two native amino acid residues which are sites susceptible to proteolytic cleavage, and substituting alpha-methyl functionalized amino acids for the identified amino acid residues.

As described throughout, suitably such methods provide a synthetic peptide that maintains substantially the same or exhibits increased receptor potency and in some cases selectivity as a corresponding synthetic peptide that does not comprise the substitution(s). In further embodiments, the methods also provide a synthetic peptide that is substantially resistant to proteolytic degradation.

Suitably in the methods provided herein, the substituted alpha-methyl functionalized amino acids correspond to the substituted native amino acid residues, and in additional embodiments, the substituted alpha-methyl functionalized amino acids correspond to the same class as the substituted native amino acid residues.

In still further embodiments, the substituted alpha-methyl functionalized amino acids can be selected from alpha-methyl functionalized Histidine, alpha-methyl functionalized Alanine, alpha-methyl functionalized Isoleucine, alpha-methyl functionalized Arginine, alpha-methyl functionalized Leucine, alpha-methyl functionalized Asparagine, alpha-methyl functionalized Lysine, alpha-methyl functionalized Aspartic acid, alpha-methyl functionalized Methionine, alpha-methyl functionalized Cysteine, alpha-methyl functionalized Phenylalanine, alpha-methyl functionalized Glutamic acid, alpha-methyl functionalized Threonine, alpha-methyl functionalized Glutamine, alpha-methyl functionalized Tryptophan, alpha-methyl functionalized Glycine, alpha-methyl functionalized Valine, alpha-methyl functionalized Ornithine, alpha-methyl functionalized Proline, alpha-methyl functionalized Selenocysteine, alpha-methyl functionalized Serine and alpha-methyl functionalized Tyrosine.

In further embodiments, the substituted alpha-methyl functionalized amino acids can be alpha-methyl phenylalanine and/or alpha-methyl lysine. In exemplary embodiments, alpha-methyl phenylalanine and/or alpha-methyl lysine can be substituted for corresponding native amino acids, though in further embodiments of the methods, the alpha-methyl phenylalanine and/or alpha-methyl lysine do not have to correspond to the same native amino acids for which the substitution is occurring.

In certain embodiments, the synthetic peptides prepared according to the methods described herein can be substantially resistant to one or more of DPP-IV, neprilysin, α-chymotrypsin, plasmin, thrombin, kallikrein, trypsin, elastase and pepsin degradation.

Formulations Comprising Lipidated Peptides

Also provided are formulations (or pharmaceutical compositions) comprising a lipidated peptide described herein. Suitably such formulations comprise a lipidated peptide as described herein and a carrier. Such formulations can be readily administered in the various methods described throughout. In some embodiments, the formulation comprises a pharmaceutically acceptable carrier.

The term "pharmaceutically acceptable carrier" means one or more non-toxic materials that do not interfere with the effectiveness of the biological activity of the lipidated peptides. The term "carrier" denotes an organic or inorganic ingredient, natural or synthetic, with which the lipidated peptide is combined to facilitate the application.

Formulations as described herein can be formulated for a particular dosage. Dosage regimens can be adjusted to provide the optimum response. It can be useful to formulate parenteral compositions in dosage unit forms for ease of administration and uniformity of dosage. Dosage unit forms as used herein refers to physically discrete units suited as unitary dosages for the subjects to be treated; each unit contains a predetermined quantity of a lipidated peptide calculated to produce a therapeutic effect in association with the required pharmaceutical carrier. The specification for the dosage unit forms are dictated by, and directly dependent on, (a) the unique characteristics of the lipidated peptide and the particular therapeutic effect to be achieved, and (b) the limitations inherent in the art of compounding such a lipidated peptide.

Formulations described herein can be formulated for particular routes of administration, such as oral, nasal, pulmonary, topical (including buccal and sublingual), rectal, vaginal and/or parenteral administration. The formulations can conveniently be presented in unit dosage form and can be prepared by any methods known in the art of pharmacy. The amount of lipidated peptide that can be combined with a carrier material to produce a single dosage form will vary depending upon the subject being treated, and the particular mode of administration. The amount of lipidated peptide that can be combined with a carrier material to produce a single dosage form will generally be that amount of the composition which produces a therapeutic effect.

Methods of Treatment Utilizing Lipidated Peptides

Also provided herein are methods of treating a patient comprising administering a lipidated peptide, e.g., the formulations, described herein to a subject in need thereof.

Suitably subjects that can be administered the lipidated peptides in the various methods described herein are mammals, such as for example, humans, dogs, cats, primates, cattle, sheep, horses, pigs, etc.

Methods by which the lipidated peptides can be administered to the subject in any of the various methods described herein include, but are not limited to, intravenous (IV), intratumoral (IT), intralesional (IL), aerosol, percutaneous, oral, endoscopic, topical, intramuscular (IM), intradermal (ID), intraocular (TO), intraperitoneal (IP), transdermal (TD), intranasal (IN), intracerebral (IC), intraorgan (e.g. intrahepatic), slow release implant, or subcutaneous administration, or via administration using an osmotic or mechanical pump.

Suitably, the lipidated peptides can be administered as soon as possible after a suitable diagnosis, e.g., within hours or days.

As described herein, suitably the various methods can be carried out on mammalian subjects that are humans, including adults of any age and children.

In certain embodiments, the methods of treatment comprise treating a subject (also referred to herein as a patient) diagnosed with diabetes comprising administering a therapeutically effective amount of a suitable lipidated peptide as described herein, suitably a lipidated GLP-1 peptide as described herein.

As used herein, the term "therapeutically effective amount" refers to the amount of a lipidated peptide, or formulation, that is sufficient to reduce the severity of a disease or disorder (or one or more symptoms thereof), ameliorate one or more symptoms of such a disease or disorder, prevent the advancement of such a disease or disorder, cause regression of such a disease or disorder, or enhance or improve the therapeutic effect(s) of another therapy. In some embodiments, the therapeutically effective amount cannot be specified in advance and can be determined by a caregiver, for example, by a physician or other healthcare provider, using various means, for example, dose titration.

In embodiments, methods are provided of treating a patient diagnosed with diabetes comprising administering a therapeutically effective amount of lipidated insulin to a patient.

As described herein, in certain embodiments the methods of administration of the lipidated peptides or formulations described herein can be delivered orally. As described herein, lipidated peptides can be substantially resistant to proteolytic degradation, e.g., degradation by enzymes in the stomach following oral administration.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

EXAMPLES

Example 1: Chemical Synthesis and Testing of Proteolytic-Resistant Lipidated Peptides 1. Introduction The following provides exemplary methods for preparing proteolytic-resistant peptides as described herein.

2. Abbreviations

Boc, tert-butyloxycarbonyl; DCM, dichloromethane; DIPEA, N,N-diisopropylethylamine; DMF, N,N-dimethylformamide; DMSO, dimethylsulfoxide; EK, enterokinase; ESI, electrospray ionisation; Fmoc, 9-fluorenylmethyloxycarbonyl; GIP, gastric inhibitory polypeptide; GLP-1, glucagon-like peptide-1; HCTU, O-(1H-6-chlorobenzotriazole-1-yl)-1,1,3,3-tetramethyluronium hexafluorophosphate; RP-HPLC, reversed-phase high-performance liquid chromatography; $EC_{50}$, half maximal (50%) effective concentration; LC/MS, liquid chromatography-coupled mass spectrometry; MeCN, acetonitrile; Mmt, 4-methoxytrityl; NMP, N-methylpyrrolidinone; Pbf, 2,2,4,6,7-pentamethyldihydrobenzofuran-5-sulfonyl; PBS, phosphate buffered saline; $^t$Bu, tertiary-butyl; TFA, trifluoroacetic acid; TIS, triisopropylsilane; Tris, Tris(hydroxymethyl) aminomethane; Trt, triphenylmethyl; UV, ultraviolet.

3. Experimental 3.1. Peptide Synthesis 3.1.1. Materials

N-α-Fmoc-L-amino acids were obtained from Bachem AG (Switzerland). Unnatural amino acids were obtained from Iris Biotech AG (Germany), prepared by Pharmaron (China), or Peptech corporation (USA). NovaSyn® TGR (TentaGel Rink) and NovaSyn® TGA (TentaGel Wang) synthesis resins were obtained from Novabiochem, Merck Biosciences (Germany). Peptides were prepared by automated synthesis (PTI Prelude) using the Fmoc/$^t$Bu protocol. Asparagine (Asn) and glutamine (Gln) were incorporated as their sidechain trityl (Trt) derivatives. Tryptophan (Trp) and lysine (Lys) were incorporated as their sidechain Boc derivatives. Serine (Ser), threonine (Thr) and tyrosine (Tyr) were incorporated as sidechain $^t$Bu ethers, and aspartate (Asp) and glutamate (Glu) as their sidechain O$^t$Bu esters. Arginine (Arg) was incorporated as the sidechain Pbf derivative. Synthesis reagents were obtained from Sigma-Aldrich, Dorset, United Kingdom. Solvents were obtained from Merck, Darmstadt, Germany at the highest grade available and used without further purification.

3.1.2. Chemical Synthesis of Lipidated Peptides Containing α-Methyl Amino Acids

Unless otherwise stated, peptides were prepared as C-terminal carboxamides on NovaSyn® TGR resin (initial substitution 0.24 mmole/g). Amino acids (both natural and unnatural) were coupled at ambient temperature using HCTU/DIPEA in NMP, capping residual functionality with a solution of acetic anhydride and pyridine. The N-Fmoc group was deblocked using piperidine in DMF (20% v/v) at ambient temperature. The C-terminal residue was incorporated as the N-Boc-protected form, e.g. Boc-His(Trt)-OH or Boc-Tyr(tBu)-OH or equivalent. At the position(s) of lipidation Fmoc-L-Lys(Mmt)-OH was incorporated into the peptide backbone during automated assembly and upon completion the Mmt protecting group(s) were removed manually by treatment of the synthesis resin with 1% TFA, 2% TIPS, DCM (10×1 minute, 20.0 mL/g). The acidified resin was quenched with 5% DIPEA/NMP and the exposed lysine amino-function(s) acylated, PEGylated or lipidated as required prior to peptide cleavage.

3.1.3. Cleavage of Lipidated Peptides

Crude peptides were cleaved from the resin support by treatment with a cocktail consisting of TFA (95% v/v), TIPS (2.5% v/v), water (2.5% v/v) with agitation (3×1 hour at ambient temperature). Cleavage aliquots were combined, concentrated by rotary evaporation and precipitated by addition of cold diethyl ether, isolating the solids by centrifugation. Crude peptides were dried under a flow of dry nitrogen, reconstituted in a suitable buffer and filtered prior to chromatographic purification.

3.1.4. Purification of Crude Mono-Lipidated Peptides

Crude mono-lipidated peptides were dissolved in a solution of acetic acid/acetonitrile/water (1:5:50 v/v) and filtered. The crude filtrates were chromatographed over an Agilent Polaris C8-A stationary phase (21.2×250 mm, 5 micron) eluting with a linear solvent gradient of 10-70%, 15-80% or 20-90% MeCN (0.1% TFA v/v) in water (0.1% TFA v/v) over 30 minutes using a Varian SD-1 PrepStar binary pump system, monitoring by UV absorption at 210 nm. The peptide-containing fractions were pooled, frozen (dry-ice/acetone) and lyophilized.

3.1.5. Purification of Crude Bis-Lipidated Peptides

Crude bis-lipidated peptides were dissolved in 0.1M ammonium bicarbonate solution (1:5 acetonitrile/water v/v, pH 8.0) and filtered. The crude filtrates were chromatographed over a Waters X-Bridge C18 stationary phase (19.0×250 mm, 5 micron) eluting with a linear solvent gradient of 20-90% B against A over 30 minutes using a Varian SD-1 PrepStar binary pump system, monitoring by UV absorption at 210 nm. (A=0.1M ammonium bicarbonate in water, B=0.1M ammonium bicarbonate in 1:2 water/acetonitrile). The peptide-containing fractions were pooled, frozen (dry-ice/acetone) and lyophilized.

3.1.6. Peptide Analysis and Characterization

Purified peptides were characterized by single quadrupole LC/MS using a Waters Mass Lynx 3100 platform. Analytes were chromatographed by elution over a Waters X-Bridge C18 stationary phase (4.6×100 mm, 3 micron) using a generic linear binary gradient of 10-90% MeCN (0.1% TFA v/v) in water (0.1% TFA v/v) over 10 minutes at 1.5 mL min$^{-1}$ at ambient temperature. Analytes were detected by both UV absorption at 210 nm and ionization using a Waters 3100 mass detector (ESP mode), verifying molecular mass against calculated theoretical values. Analytical RP-HPLC spectra were recorded using an Agilent 1260 Infinity binary gradient system. Analytes were chromatographed by elution over an Agilent Polaris C8-A stationary phase (4.6×100 mm, 3 micron) at 1.5 mL min$^{-1}$ using a linear binary gradient of 10-90% MeCN (0.1% TFA v/v) in water (0.1% TFA v/v) over 15 minutes at 40° C.

3.2. Evaluating Proteolytic-Resistance of Peptides Containing α-Methyl Residues Table 3 details several commercially available circulatory and digestive proteases which are likely to contribute to the inactivation of endogenous peptide hormones e.g., GLP-1 through hydrolysis at numerous sites in the unmodified ligands. Several of these proteases were incubated with both native peptides and their modified counterparts containing α-methyl amino acids at known liable sites as described here.

3.3. Preparation of Peptide and Protease Stock Solutions

Neprilysin: 10.0 μg (~10 units) recombinant Neprilysin (R&D Systems: 1182-ZNC-010) was reconstituted to 100 μL (100 μg/mL, ~100 units/mL) in assay buffer (50 mM Tris, 50 mM NaCl, 50 mM NaHCO$_3$, adjusted to pH 8.3) to give the enzyme stock solution. For evaluation of non-lipidated peptides, 10 μL (1 μg, ~1 unit) of neprilysin stock solution was incubated with 100 μL of peptide solution (1.0 mg/mL, ~100 μg of peptide, ~33 μmoles). Ratio enzyme (units):peptide (μmoles)~1:33. For evaluation of lipidated peptides, 100 μL (10 μg, ~10 units) of neprilysin stock solution was incubated with 100 μL of peptide solution (1.0 mg/mL, ~100 μg of peptide, ~25 μmoles). Ratio enzyme (units):peptide (μmoles)~1:2.5.

Pepsin:
Lyophilized porcine pancreatic pepsin (Sigma: P7012) was reconstituted to afford a solution of 200 μg/mL (~500 units/mL) in assay buffer (0.1 M HCl, pH 2.0) to give the enzyme stock solution. For evaluation of non-lipidated peptides, 10 μL (2 μg, ~5 units) of enzyme solution was incubated with 100 μL of peptide solution (1.0 mg/mL, ~100 μg of peptide, ~33 μmoles). Ratio enzyme (units):peptide (μmoles)~1:6. For evaluation of lipidated peptides, 100 μL (20 μg, ~50 units) of enzyme solution was incubated with 100 μL of peptide solution (1.0 mg/mL, ~100 μg of peptide, ~25 μmoles). Ratio enzyme (units):peptide (μmoles)~2:1.

Trypsin:
Lyophilized porcine pancreatic trypsin (Sigma: T1426) was reconstituted to afford a solution of 100 μg/mL (~300 units/mL) in assay buffer (50 mM Tris, 10 mM CaCl$_2$, 150 mM NaCl, 1 mM HCl, adjusted to pH 7.8) to give the enzyme stock solution. For evaluation of non-lipidated peptides, 10 μL (1 μg, ~3 units) of enzyme solution was incubated with 100 μL of peptide solution (1.0 mg/mL, ~100 μg of peptide, ~33 μmoles). Ratio enzyme (units):peptide (μmoles)~1:11. For evaluation of lipidated peptides, 100 μL (10 μg, ~30 units) of enzyme solution was incubated with 100 μL of peptide solution (1.0 mg/mL, ~100 μg of peptide, ~25 μmoles). Ratio enzyme (units):peptide (μmoles)~1.2:1.

α-Chymotrypsin:
10.0 μg (~10 units) recombinant α-chymotrypsin (R&D Systems: 6907-SE-010) was reconstituted to 100 μL (100 μg/mL, ~100 units/mL) in assay buffer (50 mM Tris, 10 mM CaCl$_2$, 150 mM NaCl, 1 mM HCl, adjusted to pH 7.8) to give the enzyme stock solution. For evaluation of non-lipidated peptides, 10 μL (1 μg, ~1 unit) of α-chymotrypsin stock solution was incubated with 100 μL of peptide solution (1.0 mg/mL, ~100 μg of peptide, ~33 μmoles). Ratio enzyme (units):peptide (μmoles)~1:33. For evaluation of lipidated peptides, 100 μL (10 μg, ~10 units) of α-chymotrypsin stock solution was incubated with 100 μL of peptide solution (1.0

TABLE 3

Commercially available purified proteases

| Protease | Distribution | Family | Cleavage Specificity | Notes |
|---|---|---|---|---|
| Neprilysin | Brush border | Zinc metalloprotease | Amino side: Y, F, W | R&D Systems: 1182-ZNC-010 |
| DPP-IV | Brush border | Serine Protease | N-terminal dipeptides | Sigma: D3446 |
| Pepsin | Stomach | Aspartate protease | Amino side: Y, F, W, L | Sigma: P7012 |
| Trypsin | Duodenum | Serine Protease | Carboxyl side: R, K | Sigma: T1426 |
| α-Chymotrypsin | Duodenum | Serine Protease | Carboxyl side: Y, F, W, L, M | R&D Systems: 6907-SE-010 |
| Pancreatic elastase | Duodenum | Serine Protease | Carboxyl side: G, A, S, V, I, L | Sigma: E1250, E7885 | mg/mL, ~100 µg of peptide, ~25 µmoles). Ratio enzyme (units):peptide (µmoles)~1:2.5.

Elastase:

1.0 mg (~5 units) lyophilized porcine pancreatic elastase (Sigma: E7885) was reconstituted to 100 µL (10 mg/mL, ~50 units/mL) in assay buffer (50 mM Tris, 50 mM NaCl, 50 mM NaHCO$_3$) and adjusted to pH 8.1 using NaOH (0.1 M) to give the enzyme stock solution. For evaluation of non-lipidated peptides, 20 µL (200 µg, ~1 unit) of elastase stock solution was incubated with 100 µL of the peptide solution (1.0 mg/mL, ~100 µg of peptide, ~33 µmoles). Ratio enzyme (units):peptide (µmoles)~1:33. For evaluation of lipidated peptides, 100 µL (1000 µg, ~5 units) of elastase stock solution was incubated with 100 µL of the peptide solution (1.0 mg/mL, ~100 µg of peptide, ~25 µmoles). Ratio enzyme (units):peptide (µmoles)~1:5.

3.4 Peptide Proteolysis Procedures 3.4.1 Evaluating Proteolytic-Resistance of Non-Lipidated Peptides to Neprilysin 10.0 µg (~10 units) recombinant Neprilysin (R&D Systems: 1182-ZNC-010) was reconstituted to 100 µL (100 µg/mL, ~100 units/mL) in assay buffer (50 mM Tris, 50 mM NaCl, 50 mM NaHCO$_3$, adjusted to pH 8.3) to give the enzyme stock solution. Peptide stock solutions were prepared to a concentration of 330 µM (~1.0 mg/mL) in assay buffer, pure water or 1×PBS (Dulbecco). 10 µL (1 µg, ~1 unit) of neprilysin stock solution was added to 100 µL of peptide stock solution (1.0 mg/mL, ~100 µg of peptide, ~33 µmoles) and the mixture was co-incubated in a temperature-regulated water bath at 37° C. for the duration of the experiment (ratio enzyme [units]:peptide [µmoles]~1:33). 15 µL aliquots (~15 µg initial peptide) of the peptide-enzyme mixture were periodically withdrawn (t=0, 30 mins, 1 hr, 2 hr, 4 hr, 8 hr, 24 hr) and quenched immediately by addition to an equal volume (15 µL) of 5% TFA (v/v) in 1:1 water/acetonitrile to arrest proteolytic activity. 20 µL aliquots (~10 µg initial peptide) were analyzed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESI+ mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment.

3.4.2 Evaluating Proteolytic-Resistance of Mono- or Bis-Lipidated Peptides to Neprilysin 10.0 µg (~10 units) recombinant Neprilysin (R&D Systems: 1182-ZNC-010) was reconstituted to 100 µL (100 µg/mL, ~100 units/mL) in assay buffer (50 mM Tris, 50 mM NaCl, 50 mM NaHCO$_3$, adjusted to pH 8.3) to give the enzyme stock solution. Peptide stock solutions were prepared to a concentration of 250 µM (~1.0 mg/mL) in assay buffer, pure water or 1×PBS (Dulbecco). 100 µL (10 µg, ~10 units) of neprilysin stock solution was added to 100 µL of peptide stock solution (1.0 mg/mL, ~100 µg of peptide, ~25 µmoles) and the mixture was co-incubated in a temperature regulated bath at 37° C. for the duration of the experiment (ratio enzyme [units]:peptide [µmoles]~1:2.5). 25 µL aliquots (~12.5 µg initial peptide) of the peptide-enzyme mixture were periodically withdrawn (t=0, 30 mins, 1 hr, 2 hr, 4 hr, 8 hr, 24 hr) and quenched immediately by addition to an equal volume (25 µL) of 5% TFA (v/v) in 1:1 water/acetonitrile to arrest proteolytic activity. 25 µL aliquots (~6 µg initial peptide) were analyzed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESP mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment. Table 4 shows the results of this experiment.

TABLE 4

Percentage remaining peptide (AUC at specified time-point by RP-HPLC) upon incubation with neprilysin.

| Peptide | Seq ID | Class | t = 0 | t = 30 min | t = 1 hr | t = 2 hr | t = 4 hr | t = 8 hr | t = 24 hr |
|---|---|---|---|---|---|---|---|---|---|
| | 488 | Un-lipidated | 100% | 63.4% | 38.0% | 13.1% | 2.4% | 1.4% | 0% |
| | 17 | Un-lipidated | 100% | | | | | | |
| | 489 | Mono-lipidated | 100% | | | | | | |
| | 3 | Mono-lipidated | 100% | 100% | 99.8% | 100% | 98.6% | 96.5% | 96.9% |
| | 48 | Mono-lipidated | 100% | 96.8% | 96.5% | 93.0% | 93.9% | 89.5% | 90.0% |
| | 60 | Mono-lipidated | 100% | | | | | | |
| | 68 | Mono-lipidated | 100% | 97.4% | 95.4% | 96.4% | 95.4% | 93.9% | 94.9% |
| | 252 | Bis-lipidated | 100% | 98.1% | 98.2% | 96.0% | 95.2% | 89.4% | 88.1% |
| | 263 | Bis-lipidated | 100% | 98.3% | 99.5% | 97.7% | 92.3% | 91.2% | 91.9% |
| | 269 | Bis-lipidated | 100% | 95.7% | 92.8% | 93.8% | 95.3% | 89.7% | 89.3% |
| Liraglutide | 490 | Mono-lipidated | 100% | 95.6% | 91.7% | 89.6% | 85.5% | 77.9% | 63.7% |
| Semaglutide | 491 | Mono-lipidated | 100% | 93.8% | 92.2% | 84.9% | 78.1% | 61.3% | 29.8% |

3.4.3 Evaluating Proteolytic-Resistance of Non-Lipidated Peptides to Porcine Pancreatic Pepsin Lyophilized porcine pancreatic pepsin (Sigma: P7012) was reconstituted to 200 µg/mL (~500 units/mL) in assay buffer (1.0 M HCl, pH 2.0) to give the enzyme stock solution. Peptides stock solutions were prepared to a concentration of 330 μM (~1.0 mg/mL) in assay buffer, pure water or 1×PBS (Dulbecco). 10 μL (2 μg, ~5 units) of pepsin stock solution was added to 100 μL of peptide solution (1.0 mg/mL, ~100 μg of peptide, ~33 μmoles) and the mixture was co-incubated in a temperature-regulated water bath at 37° C. for the duration of the experiment (ratio enzyme [units]:peptide [μmoles]~1:6). 15 μL aliquots (~15 μg initial peptide) of the peptide-enzyme mixture were periodically withdrawn (t=0, 30 mins, 1 hr, 2 hr, 4 hr, 8 hr, 24 hr) and quenched immediately by addition to an equal volume (15 μL) of 0.1M ammonium bicarbonate solution in water/acetonitrile (1:4, pH 8) to arrest proteolytic activity. 20 μL aliquots (~10 μg initial peptide) were analyzed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESP mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment. Table 5 shows the results of this experiment.

3.4.4 Evaluating Proteolytic-Resistance of Mono- or Bis-Lipidated Peptides to Porcine Pancreatic Pepsin Lyophilized porcine pancreatic pepsin (Sigma: P7012) was reconstituted to 200 μg/mL (~500 units/mL) in assay buffer (1.0 M HCl, pH 2.0) to give the enzyme stock solution. Peptide stock solutions were prepared to a concentration of 250 μM (~1.0 mg/mL) in assay buffer, pure water or 1×PBS (Dulbecco). 50 μL (10 μg, ~25 units) of pepsin stock solution was added to 100 μL of peptide solution (1.0 mg/mL, ~100 μg of peptide, ~25 μmoles) and the mixture was co-incubated in a temperature-regulated water bath at 37° C. for the duration of the experiment (ratio enzyme [units]:peptide [μmoles]~1:1.25 μL aliquots (~17 μg initial peptide) of the peptide-enzyme mixture were periodically withdrawn (t=0, 30 mins, 1 hr, 2 hr, 4 hr, 8 hr, 24 hr) and quenched immediately by addition to an equal volume (25 μL) of 0.1M ammonium bicarbonate solution in water/acetonitrile (1:4, pH 8) to arrest proteolytic activity. 25 μL aliquots (~8 μg initial peptide) were analysed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESP mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment. Table 5 shows the results of this experiment.

TABLE 5

Percentage remaining intact peptide (AUC at specified time-point by RP-HPLC) upon incubation with pepsin.

| Peptide | Seq ID | Class | t = 0 | t = 30 min | t = 1 hr | t = 2 hr | t = 4 hr | t = 8 hr | t = 24 hr |
|---|---|---|---|---|---|---|---|---|---|
|  | 488 | Un-lipidated | 100% | | | | | | |
|  | 17 | Un-lipidated | 100% | | | | | | |
|  | 489 | Mono-lipidated | 100% | | | | | | |
|  | 3 | Mono-lipidated | 100% | 99.4% | 99.3% | 99.1% | 98.9% | 97.4% | 91.3% |
|  | 48 | Mono-lipidated | 100% | 89.1% | 80.8% | 71.4% | 60.6% | 45.9% | 9.4% |
|  | 60 | Mono-lipidated | 100% | 99.9% | 98.5% | 95.5% | 92.1% | 89.8% | 87.0% |
|  | 68 | Mono-lipidated | 100% | 96.5% | 94.7% | 92.2% | 88.2% | 86.0% | 85.3% |
|  | 252 | Bis-lipidated | 100% | 90.6% | 83.2% | 69.7% | 57.7% | 38.8% | 0.7% |
|  | 263 | Bis-lipidated | 100% | 57.7% | 36.0% | 14.3% | 5.1% | 1.1% | 0.0% |
|  | 269 | Bis-lipidated | 100% | 74.9% | 55.8% | 38.6% | 22.4% | 13.4% | 0.0% |
| Liraglutide | 490 | Mono-lipidated | 100% | 12.0% | 0.0% | 0.0% | 0.0% | 0.0% | 0.0% |
| Semaglutide | 491 | Mono-lipidated | 100% | 10.4% | 0.0% | 0.0% | 0.0% | 0.0% | 0.0% |

3.4.5 Evaluating Proteolytic-Resistance of Non-Lipidated Peptides to Porcine Pancreatic Trypsin Lyophilized porcine pancreatic trypsin (Sigma: T7409) was reconstituted to 200 μg/mL (~300 units/mL) in assay buffer (50 mM Tris, 10 mM CaCl$_2$, 150 mM NaCl, 1 mM HCl, adjusted to pH 7.8) to give the enzyme stock solution. Peptide stock solutions were prepared to a concentration of 330 μM (~1.0 mg/mL) in assay buffer, pure water or 1×PBS (Dulbecco). 10 μL (2 μg, ~3 units) of trypsin stock solution was added to 100 μL of peptide stock solution (1.0 mg/mL, ~100 μg of peptide, ~33 μmoles) and the mixture was co-incubated in a temperature-regulated water bath at 37° C. for the duration of the experiment (ratio enzyme [units]: peptide [μmoles]~1:11). 15 μL aliquots (~15 μg initial peptide) of the peptide-enzyme mixture were periodically withdrawn (t=0, 30 mins, 1 hr, 2 hr, 4 hr, 8 hr, 24 hr) and quenched immediately by addition to an equal volume (15 μL) of 5% TFA (v/v) in 1:1 water/acetonitrile to arrest proteolytic activity. 20 μL aliquots (~10 μg initial peptide) were analysed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESP mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment. Table 6 shows the results of this experiment.

3.4.6 Evaluating Proteolytic-Resistance of Mono- or Bis-Lipidated Peptides to Porcine Pancreatic Trypsin Lyophilized porcine pancreatic trypsin (Sigma: T7409) was reconstituted to 200 µg/mL (~300 units/mL) in assay buffer (50 mM Tris, 10 mM CaCl$_2$, 150 mM NaCl, 1 mM HCl, adjusted to pH 7.8) to give the enzyme stock solution. Peptide stock solutions were prepared to a concentration of 250 µM (~1.0 mg/mL) in assay buffer, pure water or 1×PBS (Dulbecco). 50 µL (10 µg, ~15 units) of trypsin stock solution was added to 100 µL of peptide stock solution (1.0 mg/mL, ~100 µg of peptide, ~25 µmoles) and the mixture was co-incubated in a temperature regulated bath at 37° C. for the duration of the experiment (ratio enzyme [units]:peptide [µmoles]~1:1.7). 25 µL aliquots (~17 µg initial peptide) of the peptide-enzyme mixture were periodically withdrawn (t=0, 30 mins, 1 hr, 2 hr, 4 hr, 8 hr, 24 hr) and quenched immediately by addition to an equal volume (25 µL) of 5% TFA (v/v) in 1:1 water/acetonitrile to arrest proteolytic activity. 25 µL aliquots (~8 µg initial peptide) were analysed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESP mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allowed estimation of remaining intact peptide over the time course of the experiment. Table 6 shows the results of this experiment.

3.4.7 Evaluating Proteolytic-Resistance of Non-Lipidated Peptides to α-Chymotrypsin 10.0 µg (~10 units) recombinant α-Chymotrypsin (R&D Systems: 6907-SE-010) is reconstituted to 100 µL (100 µg/mL, ~100 units/mL) in assay buffer (50 mM Tris, 10 mM CaCl$_2$, 150 mM NaCl, 1 mM HCl, adjusted to pH 7.8) to give the enzyme stock solution. Peptide stock solutions are prepared to a concentration of 330 µM (~1.0 mg/mL) in assay buffer, pure water or 1×PBS (Dulbecco). 10 µL (1 µg, ~1 unit) of α-chymotrypsin stock solution is added to 100 µL of peptide stock solution (1.0 mg/mL, ~100 µg of peptide, ~33 µmoles) and the mixture is co-incubated in a temperature-regulated water bath at 37° C. for the duration of the experiment (ratio enzyme [units]:peptide [µmoles]~1:33). 15 µL aliquots (~15 µg initial peptide) of the peptide-enzyme mixture are periodically withdrawn (t=0, 30 mins, 1 hr, 2 hr, 4 hr, 8 hr, 24 hr) and quenched immediately by addition to an equal volume (15 µL) of 5% TFA (v/v) in 1:1 water/acetonitrile to arrest proteolytic activity. 20 µL aliquots (~10 µg initial peptide) are analysed by LC/MS and/or analytical RP-HPLC as follows: LC/MS method: Agilent Polaris C8-A column (4.6×100 mm, 3 micron) elutes with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESP mode). Peptide fragments deriving from enzymatic hydrolysis are identified by molecular weight, allowing location of the site of cleavage. Analytical RP-HPLC method: Agilent Polaris C8-A column (4.6×100 mm, 3 micron) elutes with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allows estimation of remaining intact peptide over the time course of the experiment.

3.4.8 Evaluating Proteolytic-Resistance of Mono- or Bis-Lipidated Peptides to α-Chymotrypsin 10.0 µg (~10 units) recombinant α-chymotrypsin (R&D Systems: 6907-SE-010) is reconstituted to 100 µL (100 µg/mL, ~100 units/mL) in assay buffer (50 mM Tris, 10 mM CaCl$_2$, 150 mM NaCl, 1 mM HCl, adjusted to pH 7.8) to give the enzyme stock solution. Peptide stock solutions are prepared to a concentration of 250 µM (~1.0 mg/mL) in assay buffer, pure water or 1×PBS (Dulbecco). 100 µL (10 µg, ~10 units) of α-chymotrypsin stock solution is added to 100 µL of peptide stock solution (1.0 mg/mL, ~100 µg of peptide, ~25 µmoles) and the mixture is co-incubated in a temperature regulated bath at 37° C. for the duration of the experiment (ratio enzyme [units]:peptide [µmoles]~1:2.5). 25 µL aliquots (~12.5 µg initial peptide) of the peptide-enzyme mixture are periodically withdrawn (t=0, 30 mins, 1

TABLE 6

Percentage remaining intact peptide (AUC at specified time-point by RP-HPLC) upon incubation with trypsin.

| Peptide | Seq ID | Class | t = 0 | t = 30 min | t = 1 hr | t = 2 hr | t = 4 hr | t = 8 hr | t = 24 hr |
|---|---|---|---|---|---|---|---|---|---|
| | 488 | Un-lipidated | 100% | | | | | | |
| | 17 | Un-lipidated | 100% | | | | | | |
| | 489 | Mono-lipidated | 100% | | | | | | |
| | 3 | Mono-lipidated | 100.0% | 90.2% | 86.7% | 82.5% | 79.3% | 76.2% | 74.8% |
| | 48 | Mono-lipidated | 100.0% | 93.0% | 89.2% | 83.5% | 75.6% | 68.9% | 56.5% |
| | 60 | Mono-lipidated | 100.0% | 90.0% | 87.1% | 82.4% | 78.6% | 73.5% | 65.1% |
| | 68 | Mono-lipidated | 100.0% | 92.3% | 86.2% | 76.8% | 48.6% | 39.8% | 27.4% |
| | 252 | Bis-lipidated | 100.0% | 97.2% | 92.5% | 86.0% | 80.1% | 78.1% | 70.2% |
| | 263 | Bis-lipidated | 100.0% | 98.9% | 97.2% | 94.8% | 89.8% | 85.0% | 78.6% |
| | 269 | Bis-lipidated | 100% | 96.8% | 95.2% | 89.9% | 85.2% | 82.9% | 74.7% |
| Liraglutide | 490 | Mono-lipidated | 100.0% | 9.6% | 4.8% | 1.8% | 0.0% | 0.0% | 0.0% |
| Semaglutide | 491 | Mono-lipidated | 100.0% | 0.0% | 0.0% | 0.0% | 0.0% | 0.0% | 0.0% | hr, 2 hr 4 hr, 8 hr, 24 hr) and quenched immediately by addition to an equal volume (25 μL) of 5% TFA (v/v) in 1:1 water/acetonitrile to arrest proteolytic activity. 25 μL aliquots (~6 μg initial peptide) are analysed by LC/MS and/or analytical RP-HPLC as follows: LC/MS method: Agilent Polaris C8-A column (4.6×100 mm, 3 micron) elutes with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESI$^+$ mode). Peptide fragments deriving from enzymatic hydrolysis are identified by molecular weight, allowing location of the site of cleavage. Analytical RP-HPLC method: Agilent Polaris C8-A column (4.6×100 mm, 3 micron) elutes with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allows estimation of remaining intact peptide over the time course of the experiment.

TABLE 7

Percentage remaining intact peptide (AUC at specified time-point by RP-HPLC) upon incubation with α-chymotrypsin.

| Peptide | Seq ID | Class | t = 0 | t = 30 m | t = 1 h | t = 2 h | t = 4 h | t = 8 h | t = 24 h |
|---|---|---|---|---|---|---|---|---|---|
| | 488 | Un-lipidated | 100% | 93.9% | 92.6% | 86.7% | 81.7% | 70.2% | 22.1% |
| | 17 | Un-lipidated | 100% | 91.6% | 87.2% | 86.3% | 86.6% | 87.7% | 82.1% |
| | 3 | Mono-lipidated | 100% | 97.8% | 96.6% | 95.4% | 95.2% | 95.1% | 94.6% |
| | 48 | Mono-lipidated | 100% | 97.8% | 94.6% | 90.9% | 88.8% | 89.4% | 86.4% |
| | 252 | Bis-lipidated | 100% | 96.3% | 96.4% | 94.2% | 91.4% | 86.4% | 77.4% |
| | 263 | Bis-lipidated | 100% | 88.1% | 93.9% | 92.2% | 93.5% | 95.0% | 92.3% |
| | 269 | Bis-lipidated | 100% | 97.1% | 95.8% | 96.0% | 94.2% | 92.6% | 89.4% |
| Liraglutide | 490 | Mono-lipidated | 100% | 95.7% | 95.6% | 91.5% | 89.4% | 84.4% | 73.8% |
| Semaglutide | 491 | Mono-lipidated | 100% | 93.6% | 90.8% | 87.8% | 84.3% | 78.6% | 63.6% |

3.4.9 Evaluating Proteolytic-Resistance of Non-Lipidated Peptides to Porcine Pancreatic Elastase 1.0 mg (~5 units) lyophilized porcine pancreatic elastase (Sigma: E7885) is reconstituted to 100 μL (10 mg/mL, ~50 units/mL) in assay buffer (50 mM Tris, 50 mM NaCl, 50 mM NaHCO$_3$) and adjusted to pH 8.1 using NaOH (1.0 M) to give the enzyme stock solution. Peptide stock solutions are prepared to a concentration of 330 μM (~1.0 mg/mL) in assay buffer, pure water or 1×PBS (Dulbecco). 20 μL (200 μg, ~1 unit) of elastase stock solution is added to 100 μL of peptide stock solution (1.0 mg/mL, ~100 μg of peptide, ~33 μmoles) and the mixture is co-incubated in a temperature-regulated water bath at 37° C. for the duration of the experiment (ratio enzyme [units]:peptide [μmoles] ~1:33). 15 μL aliquots (~15 μg initial peptide) of the peptide-enzyme mixture are periodically withdrawn (t=0, 30 mins, 1 hr, 2 hr, 4 hr, 8 hr, 24 hr) and quenched immediately by addition to an equal volume (15 μL) of 5% TFA (v/v) in 1:1 water/acetonitrile to arrest proteolytic activity. 20 μL aliquots (~10 μg initial peptide) are analysed by LC/MS and/or analytical RP-HPLC as follows: LC/MS method: Agilent Polaris C8-A column (4.6×100 mm, 3 micron) elutes with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESI$^+$ mode). Peptide fragments deriving from enzymatic hydrolysis are identified by molecular weight, allowing location of the site of cleavage. Analytical RP-HPLC method: Agilent Polaris C8-A column (4.6×100 mm, 3 micron) elutes with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allows estimation of remaining intact peptide over the time course of the experiment.

3.4.10 Evaluating Proteolytic-Resistance of Mono- or Bis-Lipidated Peptides to Porcine Pancreatic Elastase 1.0 mg (~5 units) lyophilized porcine pancreatic elastase (Sigma: E7885) are reconstituted to 100 μL (10 mg/mL, ~50 units/mL) in assay buffer (50 mM Tris, 50 mM NaCl, 50 mM NaHCO$_3$) and adjusted to pH 8.1 using NaOH (1.0 M) to give the enzyme stock solution. Peptide stock solutions are prepared to a concentration of 250 μM (~1.0 mg/mL) in assay buffer, pure water or 1×PBS (Dulbecco). 100 μL (1000 μg, ~5 units) of elastase stock solution are added to 100 μL of peptide stock solution (1.0 mg/mL, ~100 μg of peptide, ~25 μmoles) and the mixture is co-incubated in a temperature regulated bath at 37° C. for the duration of the experiment (ratio enzyme [units]:peptide [μmoles]~1:5). 25 μL aliquots (~17 μg initial peptide) of the peptide-enzyme mixture are periodically withdrawn (t=0, 30 mins, 1 hr, 2 hr, 4 hr, 8 hr, 24 hr) and is quenched immediately by addition to an equal volume (25 μL) of 5% TFA (v/v) in 1:1 water/acetonitrile to arrest proteolytic activity. 25 μL aliquots (~8 μg initial peptide) are analysed by LC/MS and/or analytical RP-HPLC as follows: LC/MS method: Agilent Polaris C8-A column (4.6×100 mm, 3 micron) elutes with a linear binary gradient of 10-90% MeCN (0.1% TFA v/v) in water (0.1% TFA v/v) over 30 mins at 1.5 mL min$^{-1}$ at ambient temperature with detection by both UV absorption at 210 nm and ionization using a Waters 3100 mass detector (ESI$^+$ mode). Peptide fragments deriving from enzymatic hydrolysis are identified by molecular weight, allowing location of the site of cleavage. Analytical RP-HPLC method: Agilent Polaris C8-A column (4.6×100 mm, 3 micron) elutes with a linear binary gradient of 10-90% MeCN (0.1% TFA v/v) in water (0.1% TFA v/v) over either 10 or 15 mins at 1.5 mL min$^{-1}$ at 40° C. with detection by UV absorption at 210 nm. Manual integration (AUC) allows estimation of remaining intact peptide over the time course of the experiment.

3.4.11 Evaluating Proteolytic-Resistance of Mono- or Bis-Lipidated Peptides to Fasted-State Simulated Intestinal Fluid (FASSIF/Pancreatin®)

A fresh suspension of FASSIF/P (Fasted-State Simulated Intestinal Fluid+USP Pancreatin®) was prepared according to that described by Galia, Nicolaides, Hörter, Löbenberg, Reppas and Dressman: Pharm. Res. 15 (1998) 698-705. The resulting preparation is proteolytically equivalent to ~375 units/mL (375 kU/L) and was used immediately without storage. Peptides for evaluation (1.0 mg, ~250 nmoles) were initially dissolved in pre-warmed FASSIF without Pancreatin® (200 μL) to which was added pre-warmed fresh FASSIF/Pancreatin® (100 μL) to initiate potential digestion. Following momentary vortexing of the Eppendorf reaction tube the mixture was incubated at 37° C. in a thermostatic waterbath for the duration of the experiment. 25 μL aliquots of the co-incubated peptide-enzyme mixture were periodically withdrawn (t=0, 5 m, 10 m, 15 m, 30 m, 1 h, 2 h) and quenched immediately by addition to a solution of 10% TFA in 1:1 water/acetonitrile (75 μL) to arrest proteolytic activity. Quenched samples were centrifuged (7800 RPM, 3 mins) to pellet solids and 30 μL aliquots of the supernatant solution were analysed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min-1 at ambient temperature with detection by both UV absorption at 210 nm and ionization using a Waters 3100 mass detector (ESI+ mode). Peptide fragments deriving from enzymatic hydrolysis were identified by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min-1 at 40° C. with detection by UV absorption at 210 nm. Manual integration (AUC) allowed estimation of remaining intact peptide over the time course of the experiment.

Reppas and Dressman: Pharm. Res. 15 (1998) 698-705. To the resulting preparation was added human enterokinase (100 μg/mL) to ensure the potential for full zymogen activity of the mixture which was used immediately without storage. Peptides for evaluation (1.0 mg, ~250 nmoles) were initially dissolved in pre-warmed FASSIF without Pancreatin® (200 μL) to which was added pre-warmed fresh FASSIF/Pancreatin® (100 μL) to initiate potential digestion. Following momentary vortexing of the Eppendorf reaction tube the mixture was incubated at 37° C. in a thermostatic waterbath for the duration of the experiment. 25 μL aliquots of the co-incubated peptide-enzyme mixture were periodically withdrawn (t=0, 5 m, 10 m, 15 m, 30 m, 1 h, 2 h) and quenched immediately by addition to a solution of 10% TFA in 1:1 water/acetonitrile (75 μL) to arrest proteolytic activity. Quenched samples were centrifuged (7800 RPM, 3 mins) to pellet solids and 30 μL aliquots of the supernatant solution were analysed by LC/MS and/or analytical RP-HPLC as follows: LC/MS method: Agilent Polaris C8-A column (4.6×100 mm, 3 micron) eluted with a linear binary gradient of 10-90% MeCN (0.1% TFA v/v) in water (0.1% TFA v/v) over 30 mins at 1.5 mL min-1 at ambient temperature with detection by both UV absorption at 210 nm and ionization using a Waters 3100 mass detector (ESI+ mode). Peptide fragments deriving from enzymatic hydrolysis were identi-

TABLE 8

Percentage remaining intact peptide (AUC at specified time-point by RP-HPLC) upon incubation with fasted-state simulated intestinal fluid (FASSIF/P).

| Peptide | Seq ID | Class | t = 0 | t = 5 m | t = 10 m | t = 15 m | t = 30 m | t = 1 h | t = 2 h |
|---|---|---|---|---|---|---|---|---|---|
| | 3 | Mono-lipidated | 100% | 99.6 | 98.3 | 97.6 | 95.7 | 92.1 | 82.3 |
| | 252 | Bis-lipidated | 100% | 66.3 | 39.4 | 19.9 | 3.1 | 0.0 | 0.0 |
| | 263 | Bis-lipidated | 100% | 93.1 | 85.6 | 76.8 | 57.6 | 35.1 | 7.8 |
| | 405 | Bis-lipidated | 100% | 99.5 | 99.0 | 99.4 | 95.7 | 88.7 | 60.4 |
| | 406 | Bis-lipidated | 100% | 93.9 | 85.7 | 75.9 | 56.1 | 33.2 | 7.7 |
| | 407 | Bis-lipidated | 100% | 86.2 | 72.9 | 60.3 | 36.3 | 16.2 | 2.1 |
| Semaglutide | 491 | Mono-lipidated | 100% | 14.8 | 4.0 | 0.0 | 0.0 | 0.0 | 0.0 |

3.4.12 Evaluating Proteolytic-Resistance of Mono- or Bis-Lipidated Peptides to Fasted-State Simulated Intestinal Fluid (FASSIF/Pancreatin®) Following Full Zymogen Activation with Enterokinase A fresh suspension of FASSIF/P (Fasted-State Simulated Intestinal Fluid+USP Pancreatin®) was prepared according to that described by Galia, Nicolaides, Hörter, Löbenberg, fied by molecular weight, allowing location of the site of cleavage. Analytical RP-HPLC method: Agilent Polaris C8-A column (4.6×100 mm, 3 micron) eluted with a linear binary gradient of 10-90% MeCN (0.1% TFA v/v) in water (0.1% TFA v/v) over either 10 or 15 mins at 1.5 mL min-1 at 40° C. with detection by UV absorption at 210 nm. Manual integration (AUC) allowed estimation of remaining intact peptide over the time course of the experiment.

TABLE 9

Percentage remaining intact peptide (AUC at specified time-point by RP-HPLC) upon incubation with fasted-state simulated intestinal fluid (FASSIF) activated with 100 μg/mL enterokinase to ensure full zymogen conversion.

| Peptide | Seq ID | Class | t = 0 | t = 5 m | t = 10 m | t = 15 m | t = 30 m | t = 1 h | t = 2 h | t = 4 h |
|---|---|---|---|---|---|---|---|---|---|---|
| | 3 | Mono-lipidated | 100% | 96.3% | 96.0% | 95.5% | 94.1% | 93.6% | 94.1% | 94.6% |
| | 252 | Bis-lipidated | 100% | 42.5% | 26.8% | 14.6% | 2.4% | 0.0% | 0.0% | 0.0% |
| | 263 | Bis-lipidated | 100% | 94.3% | 86.3% | 74.4% | 56.2% | 29.6% | 8.2% | 1.4% |
| | 269 | Bis-lipidated | 100% | 78.4% | 57.9% | 46.2% | 21.1% | 3.7% | 0.0% | 0.0% |
| | 405 | Bis-lipidated | 100% | 99.5% | 98.9% | 96.8% | 93.2% | 86.7% | 75.7% | 59.4% |
| Semaglutide | 491 | Mono-lipidated | 100% | 10.7% | 3.0% | 0.0% | 0.0% | 0.0% | 0.0% | 0.0% |

4.1 cAMP Assays

The biological activities/receptor potencies of the lipidated GLP-1 analog peptides described herein are suitably tested for biological activity, e.g., stimulation of one or more cellular receptor responses. Stable cell lines expressing human, mouse, rat, or dog GLP-1 receptor (GLP-1R), glucagon receptor (GCGR) or glucose-dependent insulinotropic peptide (gastric inhibitory polypeptide) receptor (GIPR) are generated in HEK293 cells or CHO cells by standard methods. Peptide activation of these various receptors results in downstream accumulation of cAMP second messenger which can be measured in a functional activity assay.

cAMP assays were performed using "assay buffer": Assay Buffer: 0.1% BSA (Sigma # A3059) in HBSS (Sigma # H8264) with 25 mM HEPES, pH 7.4 and containing 0.5 mM IBMX (Sigma #17018).

Low protein binding 384-well plates (Greiner #781280) are used to perform eleven 1 in 5 serial dilutions of test samples which are made in assay buffer. Sample dilutions are made in duplicate.

A frozen cryo-vial of cells expressing the receptor of interest is thawed rapidly in a water-bath, transferred to pre-warmed assay buffer and spun at 240×g for 5 minutes. Cells are re-suspended in assay buffer at a batch-dependent optimized concentration (e.g. hGCGR cells at $2 \times 10^5$ cells/ml, hGLP-1R and hGIPR cells at $1 \times 10^5$ cells/ml).

From the dilution plate, a 5 µL replica is stamped onto a black shallow-well u-bottom 384-well plate (Corning #3676). To this, 5 µL cell suspension is added and the plates incubated at room temperature for 30 minutes.

cAMP levels are measured using a commercially available cAMP dynamic 2 HTRF kit (Cisbio, Cat #62AM4PEJ), following the two step protocol as per manufacturer's recommendations. In brief; anti-cAMP cryptate (donor fluorophore) and cAMP-d2 (acceptor fluorophore) are made up separately by diluting each 1/20 in conjugate & lysis buffer provided in the kit. 5 µL anti-cAMP cryptate is added to wells of the assay plate, and 5 µL cAMP-d2 is added to wells except non-specific binding (NSB) wells, to which conjugate and lysis buffer are added. Plates are incubated at room temperature for one hour and then read on an Envision (Perkin Elmer) using excitation wavelength of 320 nm and emission wavelengths of 620 nm & 665 nm. $EC_{50}$ values of the synthetic peptides determined in cAMP assays are then determined.

In additional experiments for determining biological activity/receptor potency, CHO cells with stable recombinant expression of the human, mouse or rat GCGR or GLP-1 receptor are cultured in assay buffer as above). Cryopreserved cell stocks are prepared in 1× cell freezing medium-DMSO serum free (Sigma Aldrich) at either $1 \times 10^7$ or $2 \times 10^7$/vial and stored at −80° C. Cells are rapidly thawed at 37° C. and then diluted into assay buffer (buffer as above) containing serum albumin at 4.4, 3.2 and 3.2% for human, rat, and mouse serum albumin respectively. Peptides are serially diluted in 100% DMSO and then diluted 100 fold into assay buffer as above containing serum albumin at stated final concentration. Diluted peptides are then transferred into 384 black shallow well microtitre assay plates. Cells are added to the assay plates and incubated for 30 min at room temperature. Following incubation the assay is stopped and cAMP levels measured using the HTRF® dynamic d2 cAMP assay kit available from CisBio Bioassays, as per the manufacturer's guidelines. Plates are read on Perkin Elmer ENVISION® fluorescence plate readers. Human and rat serum albumin are purchased from Sigma Aldrich and mouse serum albumin from Equitech Bio Ltd.

Data is transformed to % Delta F as described in the manufacturer's guidelines and analyzed by 4-parameter logistic fit to determine $EC_{50}$ values. $EC_{50}$ values determined are dependent on both the potency of the peptides tested at the GLP-1 and glucagon receptors in the recombinant cell lines and on the affinity of the peptide for serum albumin, which determines the amount of free peptide. Association with serum albumin increases the $EC_{50}$ value obtained. The fraction of free peptide at plasma concentrations of albumin and the $EC_{50}$ at 0% serum albumin (SA) can be calculated based on the variation in cAMP generation with the SA concentration. To compare the balance of activities at the GLP-1R and GCGR between different peptides and across different conditions, these can be correlated, where the $EC_{50}$'s are related to those of comparator peptides. Tables 7-10 show the results of these experiments.

TABLE 7 cAMP activity of substituted and mono-lipidated peptides

| ID | SEQ ID NO | Primary assay $EC_{50}$ | | | Primary assay $EC_{50}$ | | | Mean pM GLP-1R |
|---|---|---|---|---|---|---|---|---|
| | | Gluc-R | GLP-1R n1 | GIP-R | Gluc-R | GLP-1R n2 | GIP-R | |
| GLP-1 (7-36) | 1 | 2.3E−08 | 2.2E−12 | 2.3E−08 | 2.3E−08 | 3.4E−12 | 2.3E−08 | 2.8 |
| mono- | 2 | | | | | | | |
| | 3 | 2.5E−08 | 6.4E−11 | 2.5E−08 | 2.5E−08 | 1.4E−10 | 2.5E−08 | 100 |
| | 5 | 8.1E−08 | 7.5E−12 | 8.1E−08 | 8.1E−08 | 5.5E−12 | 8.1E−08 | 6.5 |
| | 6 | 2.2E−08 | 4.8E−12 | 2.2E−08 | 2.2E−08 | 5.3E−12 | 2.2E−08 | 5.1 |
| | 7 | 1.0E−07 | 3.5E−10 | 1.0E−07 | 1.0E−07 | 4.3E−10 | 1.0E−07 | 389 |
| | 8 | 7.8E−09 | 7.1E−11 | 2.3E−08 | 1.2E−08 | 1.1E−10 | 2.3E−08 | 88 |
| | 9 | 2.9E−08 | 1.2E−09 | 2.9E−08 | 2.9E−08 | 1.2E−09 | 2.9E−08 | 1195 |
| | 10 | 1.0E−07 | 8.7E−11 | 1.0E−07 | 1.0E−07 | 9.3E−11 | 1.0E−07 | 90 |
| | 11 | 1.0E−07 | 3.2E−11 | 1.0E−07 | 1.0E−07 | 3.2E−11 | 1.0E−07 | 32 |
| | 12 | 1.0E−08 | 2.1E−09 | 4.5E−08 | 1.3E−08 | 2.1E−09 | 4.5E−08 | 2105 |
| | 13 | 7.6E−09 | 2.2E−11 | 6.9E−10 | 4.1E−09 | 9.6E−12 | 6.3E−10 | 16 |
| | 14 | 3.0E−09 | 3.1E−09 | 1.5E−08 | 1.1E−09 | 1.8E−09 | 1.9E−08 | 2445 |
| | 15 | 1.2E−07 | 1.2E−07 | 1.6E−10 | 1.2E−07 | 1.2E−07 | 7.9E−11 | 119000 |
| | 16 | 1.0E−07 | 1.1E−08 | 1.0E−07 | 1.0E−07 | 9.4E−09 | 1.0E−07 | 10120 |
| | 17 | 3.1E−08 | 2.5E−13 | 3.1E−08 | 3.1E−08 | 2.4E−13 | 3.1E−08 | 0.2 |
| | 18 | 1.0E−07 | 4.1E−09 | 1.0E−07 | 1.0E−07 | 5.8E−09 | 1.0E−07 | 4940 |
| | 19 | 1.3E−07 | 3.5E−09 | 1.3E−07 | 1.3E−07 | 3.3E−09 | 1.3E−07 | 3410 |
| | 20 | 2.9E−07 | 1.5E−08 | 2.9E−07 | 2.9E−07 | 1.2E−08 | 2.9E−07 | 13450 |

TABLE 7-continued cAMP activity of substituted and mono-lipidated peptides

| ID | SEQ ID NO | Primary assay EC$_{50}$ | | | Primary assay EC$_{50}$ | | | Mean pM GLP-1R |
|---|---|---|---|---|---|---|---|---|
| | | Gluc-R | GLP-1R n1 | GIP-R | Gluc-R | GLP-1R n2 | GIP-R | |
| | 21 | 3.4E−07 | 1.0E−10 | 3.4E−07 | 3.4E−07 | 1.1E−10 | 3.4E−07 | 108 |
| | 22 | 3.9E−07 | 1.2E−10 | 4.8E−07 | 2.4E−07 | 1.2E−10 | 4.8E−07 | 118 |
| | 23 | 5.4E−07 | 4.0E−09 | 5.4E−07 | 5.4E−07 | 4.9E−09 | 5.4E−07 | 4460 |
| | 24 | 7.4E−07 | 3.3E−09 | 7.4E−07 | 7.4E−07 | 7.9E−09 | 7.4E−07 | 5595 |
| | 25 | 1.0E−07 | 5.0E−10 | 1.0E−07 | 2.2E−08 | 5.9E−10 | 1.0E−07 | 544 |
| | 26 | 1.0E−07 | 9.9E−11 | 1.0E−07 | 3.0E−08 | 1.5E−10 | 1.0E−07 | 123 |
| | 27 | 1.0E−07 | 4.2E−10 | 1.0E−07 | 4.0E−08 | 4.8E−10 | 1.0E−07 | 446 |
| | 28 | 1.0E−07 | 4.6E−09 | 1.0E−07 | 1.0E−07 | 4.7E−09 | 1.0E−07 | 4620 |
| | 29 | 1.0E−07 | 7.8E−10 | 1.0E−07 | 1.0E−07 | 8.2E−10 | 1.0E−07 | 801 |
| | 30 | 1.0E−07 | 8.0E−08 | 1.0E−07 | 1.0E−07 | 9.7E−08 | 1.0E−07 | 88550 |
| | 32 | 9.0E−08 | 3.6E−11 | 9.0E−08 | 9.0E−08 | 1.8E−11 | 9.0E−08 | 27 |
| | 33 | 2.5E−08 | 6.4E−11 | 2.5E−08 | 2.5E−08 | 1.4E−10 | 2.5E−08 | 100 |
| | 34 | 9.3E−08 | 3.9E−11 | 9.3E−08 | 9.3E−08 | 4.8E−11 | 9.3E−08 | 43 |
| | 35 | 8.9E−08 | 4.9E−09 | 8.9E−08 | 2.7E−08 | 1.7E−09 | 2.7E−08 | 3260 |
| | 36 | 8.4E−08 | 6.3E−08 | 8.4E−08 | 2.5E−08 | 2.5E−08 | 2.5E−08 | 44200 |
| | 37 | 9.2E−08 | 7.3E−09 | 9.2E−08 | 2.8E−08 | 1.7E−09 | 2.8E−08 | 4500 |
| | 38 | 2.5E−08 | 6.2E−11 | 2.5E−08 | 2.5E−08 | 8.2E−11 | 2.5E−08 | 72 |
| | 39 | 2.7E−08 | 3.3E−11 | 2.7E−08 | 2.7E−08 | 2.7E−11 | 2.7E−08 | 33 |
| | 40 | 8.5E−08 | 1.8E−09 | 8.5E−08 | 2.6E−08 | 5.7E−10 | 2.6E−08 | 1173 |
| | 41 | 9.4E−08 | 2.4E−10 | 9.4E−08 | 2.8E−08 | 5.1E−11 | 2.8E−08 | 147 |
| | 42 | 3.1E−08 | 6.9E−12 | 3.1E−08 | 3.1E−08 | 1.1E−11 | 3.1E−08 | 8.7 |
| | 43 | 3.1E−08 | 4.5E−13 | 3.1E−08 | 3.1E−08 | 7.1E−13 | 3.1E−08 | 0.6 |
| | 44 | 3.1E−08 | 6.5E−12 | 3.1E−08 | 3.1E−08 | 6.9E−12 | 3.1E−08 | 6.7 |
| | 45 | 2.6E−08 | 3.8E−09 | 2.6E−08 | 2.6E−08 | 3.3E−09 | 2.6E−08 | 3555.0 |
| | 46 | 2.6E−08 | 9.2E−10 | 2.6E−08 | 2.6E−08 | 2.2E−09 | 2.6E−08 | 1555.0 |
| | 47 | 2.5E−08 | 3.7E−11 | 2.5E−08 | 2.5E−08 | 5.0E−11 | 2.5E−08 | 43.3 |
| | 48 | 2.6E−08 | 3.9E−12 | 2.6E−08 | 2.6E−08 | 8.2E−12 | 2.6E−08 | 6.1 |
| | 49 | 2.5E−08 | 9.6E−11 | 2.5E−08 | 2.5E−08 | 1.5E−10 | 2.5E−08 | 123.9 |
| | 50 | 2.6E−08 | 1.7E−10 | 2.6E−08 | 2.6E−08 | 2.6E−10 | 2.6E−08 | 215.5 |
| | 51 | 2.6E−08 | 1.7E−12 | 2.6E−08 | 2.6E−08 | 2.4E−12 | 2.6E−08 | 2.1 |
| | 52 | 2.6E−08 | 1.5E−12 | 2.6E−08 | 2.6E−08 | 2.5E−12 | 2.6E−08 | 2.0 |
| | 53 | 2.6E−08 | 8.3E−13 | 2.6E−08 | 2.6E−08 | 9.0E−13 | 2.6E−08 | 0.9 |
| | 54 | 2.6E−08 | 7.9E−13 | 2.6E−08 | 2.6E−08 | 9.3E−13 | 2.6E−08 | 0.9 |
| | 55 | 2.5E−08 | 1.4E−12 | 2.5E−08 | 2.5E−08 | 2.3E−12 | 2.5E−08 | 1.8 |
| | 56 | 2.6E−08 | 2.9E−12 | 2.6E−08 | 2.6E−08 | 3.5E−12 | 2.6E−08 | 3.2 |
| | 57 | 2.5E−08 | 1.4E−10 | 2.5E−08 | 2.5E−08 | 1.7E−10 | 2.5E−08 | 153 |
| | 58 | 2.5E−08 | 5.2E−09 | 2.5E−08 | 2.5E−08 | 4.3E−09 | 2.5E−08 | 4725 |
| | 59 | 2.56E−08 | 2.43E−10 | 2.56E−08 | 2.56E−08 | 1.79E−10 | 2.56E−08 | 211 |
| | 60 | 2.5E−08 | 4.9E−11 | 2.5E−08 | 2.5E−08 | 5.0E−11 | 2.5E−08 | 49 |
| | 61 | 2.5E−08 | 8.5E−13 | 2.5E−08 | 2.5E−08 | 9.1E−13 | 2.5E−08 | 0.9 |
| | 62 | 2.5E−08 | 2.0E−12 | 2.5E−08 | 2.5E−08 | 1.8E−12 | 2.5E−08 | 1.9 |
| | 63 | 2.57E−08 | 3.21E−12 | 2.57E−08 | 2.57E−08 | 2.55E−12 | 2.57E−08 | 2.9 |
| | 64 | 2.5E−08 | 1.4E−12 | 2.5E−08 | 2.5E−08 | 1.2E−12 | 2.5E−08 | 1.3 |
| | 65 | 2.51E−08 | 1.97E−11 | 2.51E−08 | 2.51E−08 | 1.40E−11 | 2.51E−08 | 16.9 |
| | 66 | 2.51E−08 | 2.03E−10 | 2.51E−08 | 2.51E−08 | 9.79E−11 | 2.51E−08 | 150.5 |
| | 67 | 2.54E−08 | 7.21E−11 | 2.54E−08 | 2.54E−08 | 4.80E−11 | 2.54E−08 | 60.1 |
| | 68 | 2.50E−08 | 2.21E−11 | 2.50E−08 | 2.50E−08 | 1.55E−11 | 2.50E−08 | 18.8 |
| | 69 | 2.55E−08 | 6.61E−11 | 2.55E−08 | 2.55E−08 | 3.99E−11 | 2.55E−08 | 53.0 |
| | 70 | 2.7E−08 | 7.4E−11 | 2.7E−08 | 2.7E−08 | 9.2E−11 | 2.7E−08 | 83 |
| | 71 | 2.7E−08 | 6.2E−12 | 2.7E−08 | 2.7E−08 | 8.0E−12 | 2.7E−08 | 7.1 |
| | 72 | 2.8E−08 | 4.6E−11 | 2.8E−08 | 2.8E−08 | 5.2E−11 | 2.8E−08 | 49 |
| | 73 | 2.8E−08 | 1.3E−10 | 2.8E−08 | 2.8E−08 | 1.6E−10 | 2.8E−08 | 146 |
| | 74 | 2.8E−08 | 2.3E−12 | 2.8E−08 | 2.8E−08 | 2.0E−12 | 2.8E−08 | 2.1 |
| | 75 | 2.8E−08 | 2.0E−12 | 2.8E−08 | 2.8E−08 | 1.4E−12 | 2.8E−08 | 1.7 |
| | 76 | 2.7E−08 | 8.4E−12 | 2.7E−08 | 2.7E−08 | 6.0E−12 | 2.7E−08 | 7.2 |
| | 77 | 2.8E−08 | 1.9E−09 | 2.8E−08 | 2.8E−08 | 1.8E−09 | 2.8E−08 | 1855 |
| | 78 | 2.8E−08 | 1.8E−11 | 2.8E−08 | 2.8E−08 | 9.3E−12 | 2.8E−08 | 14 |
| | 79 | 2.8E−08 | 3.9E−12 | 2.8E−08 | 2.8E−08 | 2.3E−12 | 2.8E−08 | 3.1 |
| | 80 | 2.8E−08 | 3.1E−11 | 2.8E−08 | 2.8E−08 | 1.7E−11 | 2.8E−08 | 24 |
| | 81 | 2.7E−08 | 3.7E−10 | 2.7E−08 | 2.7E−08 | 2.0E−10 | 2.7E−08 | 283 |
| | 82 | 2.7E−08 | 3.0E−12 | 2.7E−08 | 2.7E−08 | 2.0E−12 | 2.7E−08 | 2.5 |
| | 83 | 2.8E−08 | 3.2E−12 | 2.8E−08 | 2.8E−08 | 4.0E−12 | 2.8E−08 | 3.6 |
| | 84 | 2.7E−08 | 7.8E−12 | 2.7E−08 | 2.7E−08 | 8.1E−12 | 2.7E−08 | 8.0 |
| | 85 | 2.8E−08 | 6.6E−11 | 2.8E−08 | 2.8E−08 | 1.4E−10 | 2.8E−08 | 101 |
| | 86 | 2.8E−08 | 1.3E−12 | 2.8E−08 | 2.8E−08 | 1.7E−12 | 2.8E−08 | 1.5 |
| | 87 | 2.8E−08 | 1.6E−12 | 2.8E−08 | 2.8E−08 | 1.6E−12 | 2.8E−08 | 1.6 |
| | 88 | 2.8E−08 | 4.3E−12 | 2.8E−08 | 2.8E−08 | 5.7E−12 | 2.8E−08 | 5.0 |
| | 89 | 2.8E−08 | 4.5E−10 | 2.8E−08 | 2.8E−08 | 6.5E−10 | 2.8E−08 | 548 |
| | 90 | 2.8E−08 | 6.8E−13 | 2.8E−08 | 2.8E−08 | 7.9E−13 | 2.8E−08 | 0.7 |
| | 91 | 2.8E−08 | 2.1E−11 | 2.8E−08 | 2.8E−08 | 2.7E−11 | 2.8E−08 | 24 |
| | 92 | 2.8E−08 | 4.5E−10 | 2.8E−08 | 2.8E−08 | 3.9E−10 | 2.8E−08 | 423 |
| | 93 | 2.8E−08 | 2.8E−08 | 2.8E−08 | 2.8E−08 | 2.8E−08 | 2.8E−08 | 27600 |
| | 94 | 2.8E−08 | 1.4E−10 | 2.8E−08 | 2.8E−08 | 3.2E−10 | 2.8E−08 | 228 |

TABLE 7-continued cAMP activity of substituted and mono-lipidated peptides

| ID | SEQ ID NO | Primary assay $EC_{50}$ | | | Primary assay $EC_{50}$ | | | Mean pM GLP-1R |
|---|---|---|---|---|---|---|---|---|
| | | Gluc-R | GLP-1R n1 | GIP-R | Gluc-R | GLP-1R n2 | GIP-R | |
| | 95 | 2.8E−08 | 2.6E−10 | 2.8E−08 | 2.8E−08 | 1.9E−10 | 2.8E−08 | 224 |
| | 96 | 2.7E−08 | 9.2E−10 | 2.7E−08 | 2.7E−08 | 5.7E−10 | 2.7E−08 | 746 |
| | 97 | 2.8E−08 | 2.8E−08 | 2.8E−08 | 2.8E−08 | 2.8E−08 | 2.8E−08 | 27800 |
| | 98 | 2.8E−08 | 2.8E−08 | 2.8E−08 | 2.8E−08 | 2.8E−08 | 2.8E−08 | 27500 |
| | 99 | 2.5E−08 | 5.8E−11 | 2.5E−08 | 2.49E−08 | 4.93E−11 | 2.49E−08 | 54 |
| | 100 | 2.5E−08 | 1.6E−11 | 2.5E−08 | 2.49E−08 | 1.46E−11 | 2.49E−08 | 15 |
| | 101 | 2.5E−08 | 5.8E−11 | 2.5E−08 | 2.54E−08 | 5.12E−11 | 2.54E−08 | 55 |
| | 102 | 2.5E−08 | 2.4E−11 | 2.5E−08 | 2.52E−08 | 2.06E−11 | 2.52E−08 | 22 |
| | 103 | 2.5E−08 | 4.7E−12 | 2.5E−08 | 2.52E−08 | 4.56E−12 | 2.52E−08 | 5 |
| | 104 | 2.6E−08 | 5.9E−12 | 2.6E−08 | 2.56E−08 | 5.11E−12 | 2.56E−08 | 5 |
| | 105 | 2.5E−08 | 2.1E−11 | 2.5E−08 | 2.50E−08 | 1.48E−11 | 2.50E−08 | 18 |
| | 106 | 2.5E−08 | 6.5E−09 | 2.5E−08 | 2.53E−08 | 5.79E−09 | 2.53E−08 | 6145 |
| | 107 | 2.6E−08 | 8.3E−11 | 2.6E−08 | 2.56E−08 | 7.05E−11 | 2.56E−08 | 77 |
| | 108 | 2.5E−08 | 3.8E−12 | 2.5E−08 | 2.54E−08 | 3.46E−12 | 2.54E−08 | 4 |
| | 109 | 2.6E−08 | 3.4E−11 | 2.6E−08 | 2.56E−08 | 3.46E−11 | 2.56E−08 | 34 |
| | 110 | 2.5E−08 | 6.0E−11 | 2.5E−08 | 2.50E−08 | 6.39E−11 | 2.50E−08 | 62 |
| | 111 | 2.5E−08 | 1.8E−11 | 2.5E−08 | 2.50E−08 | 1.64E−11 | 2.50E−08 | 17 |
| | 112 | 2.5E−08 | 6.1E−12 | 2.5E−08 | 2.54E−08 | 5.07E−12 | 2.54E−08 | 6 |
| | 113 | 2.5E−08 | 1.8E−11 | 2.5E−08 | 2.49E−08 | 1.74E−11 | 2.49E−08 | 18 |
| | 114 | 2.5E−08 | 5.5E−10 | 2.5E−08 | 2.54E−08 | 4.58E−10 | 2.54E−08 | 503 |
| | 115 | 2.5E−08 | 6.0E−12 | 2.5E−08 | 2.53E−08 | 5.39E−12 | 2.53E−08 | 6 |
| | 116 | 2.6E−08 | 9.3E−12 | 2.6E−08 | 2.56E−08 | 9.12E−12 | 2.56E−08 | 9 |
| | 117 | 2.5E−08 | 2.6E−11 | 2.5E−08 | 2.51E−08 | 2.44E−11 | 2.51E−08 | 25 |
| | 118 | 2.5E−08 | 8.1E−10 | 2.5E−08 | 2.52E−08 | 7.58E−10 | 2.52E−08 | 783 |
| | 119 | 2.5E−08 | 1.8E−11 | 2.5E−08 | 2.52E−08 | 1.57E−11 | 2.52E−08 | 17 |
| | 120 | 2.5E−08 | 4.1E−09 | 2.5E−08 | 2.53E−08 | 3.13E−09 | 2.53E−08 | 3635 |
| | 121 | 2.5E−08 | 2.5E−08 | 2.5E−08 | 2.51E−08 | 2.51E−08 | 2.51E−08 | 25100 |
| | 122 | 2.5E−08 | 2.5E−08 | 2.5E−08 | 2.52E−08 | 2.52E−08 | 2.52E−08 | 25200 |
| | 123 | 2.6E−08 | 4.9E−09 | 2.6E−08 | 2.56E−08 | 4.43E−09 | 2.56E−08 | 4655 |
| | 124 | 2.5E−08 | 2.5E−08 | 2.5E−08 | 2.51E−08 | 2.51E−08 | 2.51E−08 | 25100 |
| | 125 | 2.5E−08 | 2.5E−08 | 2.5E−08 | 2.49E−08 | 2.49E−08 | 2.49E−08 | 24900 |
| | 126 | 2.5E−08 | 2.5E−08 | 2.5E−08 | 2.54E−08 | 2.54E−08 | 2.54E−08 | 25400 |
| | 127 | 2.5E−08 | 2.5E−08 | 2.5E−08 | 2.51E−08 | 2.51E−08 | 2.51E−08 | 25100 |
| | 128 | 2.8E−08 | 1.5E−11 | 2.8E−08 | 2.8E−08 | 2.1E−11 | 2.8E−08 | 18.2 |
| | 129 | 2.7E−08 | 1.2E−11 | 2.7E−08 | 2.7E−08 | 1.1E−11 | 2.7E−08 | 11.5 |
| | 130 | 2.6E−08 | 1.6E−11 | 2.6E−08 | 2.6E−08 | 1.3E−11 | 2.6E−08 | 14.4 |
| | 131 | 2.9E−08 | 1.4E−11 | 2.9E−08 | 2.9E−08 | 9.9E−12 | 2.9E−08 | 11.7 |
| | 132 | 2.8E−08 | 1.1E−11 | 2.8E−08 | 2.8E−08 | 7.1E−12 | 2.8E−08 | 9.0 |
| | 133 | 2.7E−08 | 3.4E−11 | 2.7E−08 | 2.7E−08 | 2.5E−11 | 2.7E−08 | 29.4 |
| | 134 | 2.8E−08 | 7.0E−12 | 2.8E−08 | 2.8E−08 | 4.9E−12 | 2.8E−08 | 6.0 |
| | 135 | 2.7E−08 | 5.4E−12 | 2.7E−08 | 2.7E−08 | 4.5E−12 | 2.7E−08 | 5.0 |
| | 136 | 2.6E−08 | 3.5E−12 | 2.6E−08 | 2.6E−08 | 2.5E−12 | 2.6E−08 | 3.0 |
| | 137 | 2.7E−08 | 6.6E−12 | 2.7E−08 | 2.7E−08 | 3.8E−12 | 2.7E−08 | 5.2 |
| | 138 | 2.6E−08 | 1.9E−11 | 2.6E−08 | 2.6E−08 | 1.5E−11 | 2.6E−08 | 17.2 |
| | 139 | 2.6E−08 | 2.9E−11 | 2.6E−08 | 2.6E−08 | 2.2E−11 | 2.6E−08 | 25.5 |
| | 140 | 2.7E−08 | 5.9E−12 | 2.7E−08 | 2.7E−08 | 3.9E−12 | 2.7E−08 | 4.9 |
| | 141 | 2.7E−08 | 8.7E−12 | 2.7E−08 | 2.7E−08 | 5.0E−12 | 2.7E−08 | 6.9 |
| | 142 | 2.6E−08 | 1.2E−11 | 2.6E−08 | 2.6E−08 | 7.9E−12 | 2.6E−08 | 10.1 |
| | 143 | 2.7E−08 | 1.2E−11 | 2.7E−08 | 2.7E−08 | 5.2E−12 | 2.7E−08 | 8.6 |
| | 144 | 2.6E−08 | 1.6E−11 | 2.6E−08 | 2.6E−08 | 9.6E−12 | 2.6E−08 | 12.6 |
| | 145 | 2.5E−08 | 2.7E−11 | 2.5E−08 | 2.5E−08 | 1.5E−11 | 2.5E−08 | 21.0 |
| | 146 | 2.8E−08 | 9.6E−11 | 2.8E−08 | 2.8E−08 | 4.2E−11 | 2.8E−08 | 69.0 |
| | 147 | 2.7E−08 | 3.2E−11 | 2.7E−08 | 2.7E−08 | 1.4E−11 | 2.7E−08 | 23.2 |
| | 148 | 2.6E−08 | 1.6E−11 | 2.6E−08 | 2.6E−08 | 8.7E−12 | 2.6E−08 | 12.1 |
| | 149 | 2.8E−08 | 8.1E−11 | 2.8E−08 | 2.8E−08 | 5.1E−11 | 2.8E−08 | 66.2 |
| | 150 | 2.7E−08 | 2.8E−11 | 2.7E−08 | 2.7E−08 | 2.2E−11 | 2.7E−08 | 25.4 |
| | 151 | 2.6E−08 | 2.2E−11 | 2.6E−08 | 2.6E−08 | 1.5E−11 | 2.6E−08 | 18.2 |
| | 152 | 2.8E−08 | 3.9E−11 | 2.8E−08 | 2.8E−08 | 3.1E−11 | 2.8E−08 | 34.7 |
| | 153 | 2.7E−08 | 7.9E−12 | 2.7E−08 | 2.7E−08 | 5.0E−12 | 2.7E−08 | 6.4 |
| | 154 | 2.6E−08 | 2.8E−12 | 2.6E−08 | 2.6E−08 | 2.3E−12 | 2.6E−08 | 2.5 |
| | 155 | 2.8E−08 | 2.9E−10 | 2.8E−08 | 2.8E−08 | 1.9E−10 | 2.8E−08 | 238.0 |
| | 156 | 2.7E−08 | 1.1E−10 | 2.7E−08 | 2.7E−08 | 1.0E−10 | 2.7E−08 | 105.0 |
| | 157 | 2.6E−08 | 2.4E−10 | 2.6E−08 | 2.6E−08 | 2.2E−10 | 2.6E−08 | 227.0 |
| | 158 | 2.8E−08 | 1.4E−10 | 2.8E−08 | 2.8E−08 | 1.6E−10 | 2.8E−08 | 148.0 |
| | 159 | 2.7E−08 | 2.8E−10 | 2.7E−08 | 2.7E−08 | 2.3E−10 | 2.7E−08 | 254.5 |
| | 160 | 2.6E−08 | 3.9E−10 | 2.6E−08 | 2.6E−08 | 3.2E−10 | 2.6E−08 | 350.5 |
| | 161 | 2.7E−08 | 1.6E−10 | 2.7E−08 | 2.7E−08 | 6.2E−11 | 2.7E−08 | 111.7 |
| | 162 | 2.6E−08 | 5.3E−11 | 2.6E−08 | 2.6E−08 | 5.5E−11 | 2.6E−08 | 54.0 |
| | 163 | 2.5E−08 | 6.3E−11 | 2.5E−08 | 2.5E−08 | 4.9E−11 | 2.5E−08 | 56.0 |
| | 164 | 2.8E−08 | 2.2E−11 | 2.8E−08 | 2.8E−08 | 7.8E−12 | 2.8E−08 | 14.6 |
| | 165 | 2.7E−08 | 1.4E−11 | 2.7E−08 | 2.7E−08 | 6.0E−12 | 2.7E−08 | 10.2 |
| | 166 | 2.6E−08 | 7.2E−12 | 2.6E−08 | 2.6E−08 | 2.7E−12 | 2.6E−08 | 4.9 |
| | 167 | 2.9E−08 | 1.3E−11 | 2.9E−08 | 2.9E−08 | 6.9E−12 | 2.9E−08 | 10.0 |

TABLE 7-continued cAMP activity of substituted and mono-lipidated peptides

| ID | SEQ ID NO | Primary assay EC$_{50}$ | | | Primary assay EC$_{50}$ | | | Mean pM GLP-1R |
|---|---|---|---|---|---|---|---|---|
| | | Gluc-R | GLP-1R n1 | GIP-R | Gluc-R | GLP-1R n2 | GIP-R | |
| | 168 | 2.8E−08 | 5.1E−12 | 2.8E−08 | 2.8E−08 | 2.6E−12 | 2.8E−08 | 3.8 |
| | 169 | 2.7E−08 | 3.4E−12 | 2.7E−08 | 2.7E−08 | 1.7E−12 | 2.7E−08 | 2.6 |
| | 170 | 2.8E−08 | 8.0E−12 | 2.8E−08 | 2.8E−08 | 4.5E−12 | 2.8E−08 | 6.2 |
| | 171 | 2.7E−08 | 2.5E−12 | 2.7E−08 | 2.7E−08 | 1.2E−12 | 2.7E−08 | 1.9 |
| | 172 | 2.6E−08 | 1.5E−12 | 2.6E−08 | 2.6E−08 | 7.2E−13 | 2.6E−08 | 1.1 |
| | 173 | 2.7E−08 | 2.1E−11 | 2.7E−08 | 2.7E−08 | 9.2E−12 | 2.7E−08 | 15.1 |
| | 174 | 2.6E−08 | 2.2E−11 | 2.6E−08 | 2.6E−08 | 1.1E−11 | 2.6E−08 | 16.3 |
| | 175 | 2.6E−08 | 2.3E−11 | 2.6E−08 | 2.6E−08 | 1.2E−11 | 2.6E−08 | 17.4 |
| | 176 | 2.7E−08 | 2.3E−11 | 2.7E−08 | 2.7E−08 | 9.6E−12 | 2.7E−08 | 16.0 |
| | 177 | 2.7E−08 | 6.4E−12 | 2.7E−08 | 2.7E−08 | 3.0E−12 | 2.7E−08 | 4.7 |
| | 178 | 2.6E−08 | 5.0E−12 | 2.6E−08 | 2.6E−08 | 2.3E−12 | 2.6E−08 | 3.6 |
| | 179 | 2.7E−08 | 1.1E−11 | 2.7E−08 | 2.7E−08 | 4.4E−12 | 2.7E−08 | 7.9 |
| | 180 | 2.6E−08 | 3.2E−12 | 2.6E−08 | 2.6E−08 | 1.1E−12 | 2.6E−08 | 2.2 |
| | 181 | 2.5E−08 | 2.1E−12 | 2.5E−08 | 2.5E−08 | 8.3E−13 | 2.5E−08 | 1.5 |
| | 182 | 2.8E−08 | 1.3E−10 | 2.8E−08 | 2.8E−08 | 5.2E−11 | 2.8E−08 | 89.9 |
| | 183 | 2.7E−08 | 6.4E−11 | 2.7E−08 | 2.7E−08 | 1.8E−11 | 2.7E−08 | 40.9 |
| | 184 | 2.6E−08 | 4.7E−11 | 2.6E−08 | 2.6E−08 | 1.2E−11 | 2.6E−08 | 29.5 |
| | 185 | 2.8E−08 | 3.8E−10 | 2.8E−08 | 2.8E−08 | 1.2E−10 | 2.8E−08 | 251.0 |
| | 186 | 2.7E−08 | 1.3E−10 | 2.7E−08 | 2.7E−08 | 5.0E−11 | 2.7E−08 | 87.5 |
| | 187 | 2.6E−08 | 6.4E−11 | 2.6E−08 | 2.6E−08 | 3.1E−11 | 2.6E−08 | 47.4 |
| | 188 | 2.8E−08 | 1.7E−10 | 2.8E−08 | 2.8E−08 | 7.7E−11 | 2.8E−08 | 125.4 |
| | 189 | 2.7E−08 | 3.0E−11 | 2.7E−08 | 2.7E−08 | 1.2E−11 | 2.7E−08 | 20.8 |
| | 190 | 2.6E−08 | 9.7E−12 | 2.6E−08 | 2.6E−08 | 4.7E−12 | 2.6E−08 | 7.2 |
| | 191 | 2.8E−08 | 2.5E−10 | 2.8E−08 | 2.8E−08 | 1.1E−10 | 2.8E−08 | 182.5 |
| | 192 | 2.7E−08 | 1.7E−10 | 2.7E−08 | 2.7E−08 | 6.0E−11 | 2.7E−08 | 113.5 |
| | 193 | 2.6E−08 | 3.3E−10 | 2.6E−08 | 2.6E−08 | 9.5E−11 | 2.6E−08 | 213.0 |
| | 194 | 2.8E−08 | 2.4E−10 | 2.8E−08 | 2.8E−08 | 6.8E−11 | 2.8E−08 | 154.2 |
| | 195 | 2.7E−08 | 1.7E−10 | 2.7E−08 | 2.7E−08 | 4.6E−11 | 2.7E−08 | 107.4 |
| | 196 | 2.6E−08 | 1.9E−10 | 2.6E−08 | 2.6E−08 | 6.3E−11 | 2.6E−08 | 124.6 |
| | 197 | 2.7E−08 | 1.2E−10 | 2.7E−08 | 2.7E−08 | 3.4E−11 | 2.7E−08 | 79.0 |
| | 198 | 2.6E−08 | 4.1E−11 | 2.6E−08 | 2.6E−08 | 1.5E−11 | 2.6E−08 | 27.9 |
| | 199 | 2.5E−08 | 2.9E−11 | 2.5E−08 | 2.5E−08 | 7.5E−12 | 2.5E−08 | 18.3 |

TABLE 8 cAMP activity of substituted and mono-lipidated peptides, cont.

| ID | SEQ ID NO | INS1e assay EC$_{50}$ GLP-1R | | Mean pM GLP-1R |
|---|---|---|---|---|
| | | n1 | n2 | |
| GLP-1 (7-36) | 1 | 7.00E−12 | 2.70E−11 | 17 |
| mono- | 2 | | | |
| | 3 | 3.59E−09 | 3.78E−09 | 3685 |
| | 6 | 1.04E−10 | 1.39E−10 | 122 |
| | 17 | 5.10E−12 | 7.87E−12 | 6 |
| | 33 | 3.59E−09 | 3.78E−09 | 3685 |
| | 42 | 2.07E−10 | 1.67E−10 | 187 |
| | 43 | 1.60E−11 | 1.05E−11 | 13 |
| | 44 | 4.75E−10 | 4.35E−10 | 455 |
| | 45 | 7.61E−08 | 0.000000113 | 94550 |
| | 46 | 5.26E−08 | 8.34E−08 | 68000 |
| | 47 | 7.13E−09 | 1.22E−08 | 9665 |
| | 48 | 7.29E−10 | 8.71E−10 | 800 |
| | 49 | 9.35E−09 | 1.07E−08 | 10025 |
| | 50 | 2.21E−08 | 4.26E−08 | 32350 |
| | 51 | 2.47E−11 | 2.07E−11 | 23 |
| | 52 | 2.14E−11 | 1.93E−11 | 20 |
| | 53 | 6.25E−12 | 8.15E−12 | 7 |
| | 54 | 2.67E−12 | 8.37E−12 | 6 |
| | 55 | 1.25E−11 | 1.01E−11 | 11 |
| | 56 | 3.52E−11 | 7.70E−11 | 56 |
| | 60 | 1.43E−08 | 1.21E−08 | 13200 |
| | 61 | 5.57E−12 | 1.35E−11 | 10 |
| | 62 | 2.09E−10 | 8.37E−11 | 146 |
| | 63 | 2.31E−11 | 3.92E−11 | 31 |
| | 64 | 6.80E−12 | 1.21E−11 | 9 |
| | 65 | 2.57E−09 | 3.74E−09 | 3155 |
| | 66 | 4.56E−08 | 3.88E−08 | 42200 |
| | 67 | 6.15E−09 | 1.81E−08 | 12125 |
| | 68 | 2.69E−09 | 4.87E−09 | 3780 |
| | 69 | 1.92E−08 | 2.50E−08 | 22100 |
| | 71 | 6.04E−10 | 8.41E−10 | 723 |
| | 72 | 4.26E−09 | 8.07E−09 | 6165 |
| | 74 | 7.74E−11 | 1.27E−10 | 102 |
| | 75 | 4.97E−11 | 6.3E−11 | 56 |
| | 76 | 3.26E−10 | 5.31E−10 | 429 |
| | 78 | 3.45E−10 | 3.46E−10 | 346 |
| | 79 | 2.89E−10 | 5.27E−10 | 408 |
| | 80 | 3.89E−09 | 1.33E−09 | 2610 |
| | 82 | 1.51E−10 | 2.38E−10 | 195 |
| | 83 | 1.37E−10 | 2.50E−10 | 194 |
| | 84 | 4.55E−10 | 6.65E−10 | 560 |
| | 86 | 4.53E−11 | 8.45E−11 | 65 |
| | 87 | 4.36E−11 | 6.22E−11 | 53 |
| | 88 | 2.77E−10 | 4.15E−10 | 346 |
| | 90 | 4.34E−11 | 5.86E−11 | 51 |
| | 91 | 1.93E−09 | 3.50E−09 | 2715 |
| | 99 | 1.10E−08 | 5.88E−09 | 8440 |
| | 100 | 2.33E−10 | 1.41E−09 | 822 |
| | 101 | 1.47E−09 | 6.65E−09 | 4060 |
| | 102 | 4.22E−09 | 2.89E−09 | 3555 |
| | 103 | 4.28E−10 | 5.90E−10 | 509 |
| | 104 | 3.91E−10 | 2.70E−10 | 331 |
| | 105 | 2.20E−10 | 1.72E−09 | 970 |
| | 107 | 5.23E−09 | 1.17E−08 | 8465 |
| | 108 | 3.80E−11 | 4.58E−10 | 248 |

TABLE 8-continued cAMP activity of substituted and mono-lipidated peptides, cont.

| ID | SEQ ID NO | INS1e assay EC$_{50}$ GLP-1R n1 | n2 | Mean pM GLP-1R |
|---|---|---|---|---|
| | 109 | 8.35E−09 | 4.32E−09 | 6335 |
| | 110 | 3.16E−08 | 2.31E−08 | 27350 |
| | 111 | 5.01E−10 | 1.11E−09 | 806 |
| | 112 | 2.94E−10 | 4.76E−10 | 385 |
| | 113 | 8.23E−10 | 1.26E−09 | 1042 |
| | 115 | 5.93E−10 | 4.94E−10 | 544 |
| | 116 | 1.61E−09 | 6.10E−10 | 1110 |
| | 117 | 7.65E−10 | 1.67E−09 | 1218 |
| | 119 | 2.71E−09 | 1.45E−09 | 2080 |
| | 132 | 1.29E−10 | 1.15E−10 | 122 |
| | 134 | 1.68E−10 | 7.76E−11 | 123 |
| | 135 | 9.86E−11 | 5.93E−11 | 79 |
| | 136 | 5.26E−11 | 2.15E−11 | 37 |
| | 137 | 6.37E−11 | 3.62E−11 | 50 |
| | 140 | 4.32E−11 | 1.67E−11 | 30 |
| | 141 | 4.47E−11 | 3.67E−11 | 41 |
| | 143 | 4.51E−11 | 2.27E−11 | 34 |
| | 153 | 5.50E−11 | 6.12E−11 | 58 |
| | 154 | 3.23E−11 | 1.71E−11 | 25 |
| | 166 | 2.33E−10 | 6.87E−10 | 460 |
| | 168 | 1.89E−10 | 4.62E−10 | 325.5 |
| | 169 | 9.31E−11 | 2.69E−10 | 181.05 |
| | 170 | 5.48E−10 | 3.76E−10 | 462 |
| | 171 | 8.17E−11 | 1.75E−10 | 128.35 |
| | 172 | 3.96E−11 | 2.8E−11 | 33.8 |
| | 177 | 2.66E−10 | 7.55E−10 | 510.5 |
| | 178 | 3.1E−10 | 2.58E−10 | 284 |
| | 179 | 3.36E−10 | 3.45E−10 | 340.5 |
| | 180 | 6.78E−11 | 5.06E−11 | 59.2 |
| | 181 | 4.53E−11 | 1.14E−10 | 79.65 |
| | 184 | 3.51E−10 | 5.01E−10 | 426 |
| | 189 | 1.14E−10 | 1.73E−10 | 143.5 |
| | 190 | 3.97E−11 | 4.85E−11 | 44.1 |
| | 198 | 1.38E−09 | 8.9E−10 | 1135 |
| | 199 | 7.87E−10 | 2.13E−09 | 1458.5 |

TABLE 9 cAMP activity of bis-lipidated agonist peptides

| ID | SEQ ID NO | Primary assay EC$_{50}$ Gluc-R | GLP-1R n1 | GIP-R | Primary assay EC$_{50}$ Gluc-R | GLP-1R n2 | GIP-R | Mean pM GLP-1R |
|---|---|---|---|---|---|---|---|---|
| GLP-1 (7-36) | 1 | 2.3E−08 | 2.2E−12 | 2.3E−08 | 2.3E−08 | 3.4E−12 | 2.3E−08 | 2.8 |
| bis- | 4 | | | | | | | |
| | 236 | 2.22E−08 | 1.65E−11 | 2.22E−08 | 2.22E−08 | 2.68E−11 | 2.22E−08 | 21.7 |
| | 237 | 2.23E−08 | 1.95E−11 | 2.23E−08 | 2.23E−08 | 2.23E−11 | 2.23E−08 | 20.9 |
| | 238 | 2.24E−08 | 8.75E−12 | 2.24E−08 | 2.24E−08 | 1.32E−11 | 2.24E−08 | 11.0 |
| | 239 | 2.25E−08 | 6.30E−12 | 2.25E−08 | 2.25E−08 | 8.45E−12 | 2.25E−08 | 7.4 |
| | 240 | 2.22E−08 | 1.09E−11 | 2.22E−08 | 2.22E−08 | 1.71E−11 | 2.22E−08 | 14.0 |
| | 241 | 2.25E−08 | 7.55E−12 | 2.25E−08 | 2.25E−08 | 1.16E−11 | 2.25E−08 | 9.6 |
| | 242 | 2.14E−08 | 3.58E−09 | 2.14E−08 | 2.14E−08 | 4.11E−09 | 2.14E−08 | 3845.0 |
| | 243 | 2.15E−08 | 2.93E−09 | 2.15E−08 | 2.15E−08 | 3.48E−09 | 2.15E−08 | 3205.0 |
| | 244 | 2.16E−08 | 7.77E−09 | 2.16E−08 | 2.16E−08 | 1.69E−08 | 2.16E−08 | 12335.0 |
| | 245 | 2.16E−08 | 1.23E−08 | 2.16E−08 | 2.16E−08 | 1.02E−08 | 2.16E−08 | 11250.0 |
| | 246 | 2.14E−08 | 9.99E−10 | 2.14E−08 | 2.14E−08 | 1.80E−09 | 2.14E−08 | 1399.5 |
| | 247 | 2.16E−08 | 1.31E−09 | 2.16E−08 | 2.16E−08 | 2.02E−09 | 2.16E−08 | 1665.0 |
| | 248 | 2.24E−08 | 3.77E−12 | 2.24E−08 | 2.24E−08 | 6.20E−12 | 2.24E−08 | 5.0 |
| | 249 | 2.21E−08 | 4.47E−12 | 2.21E−08 | 2.21E−08 | 6.49E−12 | 2.21E−08 | 5.5 |
| | 250 | 2.16E−08 | 2.92E−11 | 2.16E−08 | 2.16E−08 | 6.10E−11 | 2.16E−08 | 45.1 |
| | 251 | 2.13E−08 | 1.60E−11 | 2.13E−08 | 2.13E−08 | 4.62E−11 | 2.13E−08 | 31.1 |
| | 252 | 2.27E−08 | 2.88E−12 | 2.27E−08 | 2.27E−08 | 2.17E−12 | 2.27E−08 | 2.5 |
| | 253 | 2.23E−08 | 2.34E−11 | 2.23E−08 | 2.23E−08 | 1.77E−11 | 2.23E−08 | 20.6 |
| | 254 | 2.19E−08 | 2.23E−10 | 2.19E−08 | 2.19E−08 | 1.86E−10 | 2.19E−08 | 204.5 |
| | 255 | 2.15E−08 | 5.32E−10 | 2.15E−08 | 2.15E−08 | 3.93E−10 | 2.15E−08 | 462.5 |
| | 256 | 2.22E−08 | 9.46E−12 | 2.22E−08 | 2.22E−08 | 5.57E−12 | 2.22E−08 | 7.5 |
| | 257 | 2.28E−08 | 4.36E−12 | 2.28E−08 | 2.28E−08 | 1.24E−11 | 2.28E−08 | 8.4 |
| | 258 | 2.23E−08 | 5.96E−11 | 2.23E−08 | 2.23E−08 | 1.25E−10 | 2.23E−08 | 92.3 |
| | 259 | 2.14E−08 | 3.39E−10 | 2.14E−08 | 2.14E−08 | 2.87E−10 | 2.14E−08 | 313.0 |
| | 260 | 2.19E−08 | 3.34E−10 | 2.19E−08 | 2.19E−08 | 4.43E−10 | 2.19E−08 | 388.5 |
| | 261 | 2.30E−08 | 4.14E−10 | 2.30E−08 | 2.30E−08 | 4.22E−10 | 2.30E−08 | 418.0 |
| | 262 | 2.25E−08 | 6.73E−12 | 2.25E−08 | 2.25E−08 | 4.14E−12 | 2.25E−08 | 5.4 |
| | 263 | 2.15E−08 | 9.98E−13 | 2.15E−08 | 2.15E−08 | 1.45E−12 | 2.15E−08 | 1.2 |
| | 264 | 2.26E−08 | 1.82E−11 | 2.26E−08 | 2.26E−08 | 7.37E−12 | 2.26E−08 | 12.8 |
| | 265 | 2.16E−08 | 3.91E−11 | 2.16E−08 | 2.16E−08 | 2.80E−11 | 2.16E−08 | 33.6 |
| | 266 | 2.22E−08 | 4.00E−10 | 2.22E−08 | 2.22E−08 | 5.57E−10 | 2.22E−08 | 478.5 |
| | 267 | 2.17E−08 | 6.28E−10 | 2.17E−08 | 2.17E−08 | 5.10E−10 | 2.17E−08 | 569.0 |
| | 268 | 2.22E−08 | 4.46E−12 | 2.22E−08 | 2.22E−08 | 5.05E−12 | 2.22E−08 | 4.8 |
| | 269 | 2.28E−08 | 4.01E−12 | 2.28E−08 | 2.28E−08 | 5.24E−12 | 2.28E−08 | 4.6 |
| | 270 | 2.23E−08 | 2.93E−11 | 2.23E−08 | 2.23E−08 | 3.65E−11 | 2.23E−08 | 32.9 |
| | 271 | 2.14E−08 | 8.91E−10 | 2.14E−08 | 2.14E−08 | 7.50E−10 | 2.14E−08 | 820.5 |
| | 272 | 2.19E−08 | 3.39E−10 | 2.19E−08 | 2.19E−08 | 3.31E−10 | 2.19E−08 | 335.0 |
| | 273 | 2.15E−08 | 7.41E−10 | 2.15E−08 | 2.15E−08 | 7.83E−10 | 2.15E−08 | 762.0 |
| | 405 | 2.15E−08 | 4.05E−12 | 2.15E−08 | 2.15E−08 | 3.66E−12 | 2.15E−08 | 3.9 |
| | 406 | 2.15E−08 | 2.19E−12 | 2.15E−08 | 2.15E−08 | 2.31E−12 | 2.15E−08 | 2.3 |

TABLE 9-continued cAMP activity of bis-lipidated agonist peptides

| ID | SEQ ID NO | Primary assay EC$_{50}$ | | | Primary assay EC$_{50}$ | | | Mean pM GLP-1R |
|---|---|---|---|---|---|---|---|---|
| | | Gluc-R | GLP-1R n1 | GIP-R | Gluc-R | GLP-1R n2 | GIP-R | |
| | 407 | 2.15E−08 | 1.96E−12 | 2.15E−08 | 2.15E−08 | 2.01E−12 | 2.15E−08 | 2.0 |
| | 408 | 2.15E−08 | 9.96E−12 | 2.15E−08 | 2.15E−08 | 7.89E−12 | 2.15E−08 | 8.9 |
| | 409 | 2.15E−08 | 3.95E−11 | 2.15E−08 | 2.15E−08 | 3.26E−11 | 2.15E−08 | 36.1 |
| | 410 | 2.15E−08 | 2.48E−10 | 2.15E−08 | 2.15E−08 | 1.26E−10 | 2.15E−08 | 187.0 |

TABLE 10 cAMP activity of bis-lipidated agonist peptides, cont.

| ID | SEQ ID NO | INS1e assay EC$_{50}$ GLP-1R | | Mean pM GLP-1R |
|---|---|---|---|---|
| | | n1 | n2 | |
| GLP-1 (7-36) bis- | 1 | 7.00E−12 | 2.70E−11 | 17 |
| | 4 | | | |
| | 236 | 1.20E−08 | 1.27E−08 | 12350 |
| | 237 | 1.43E−08 | 2.43E−08 | 19300 |
| | 238 | 1.50E−08 | 1.24E−08 | 13700 |
| | 239 | 1.47E−08 | 1.12E−08 | 12950 |
| | 240 | 6.86E−09 | 5.17E−09 | 6015 |
| | 241 | 5.84E−09 | 6.71E−09 | 6275 |
| | 246 | 7.13E−08 | 7.13E−08 | 71300 |
| | 247 | 7.21E−08 | 7.21E−08 | 72100 |
| | 248 | 3.37E−10 | 4.68E−10 | 403 |
| | 249 | 7.21E−10 | 4.10E−10 | 566 |
| | 250 | 3.67E−08 | 3.94E−08 | 38050 |
| | 251 | 6.47E−09 | 7.85E−09 | 7160 |
| | 252 | 1.84E−10 | 1.66E−10 | 175 |
| | 253 | 2.08E−09 | 2.14E−09 | 2110 |
| | 256 | 1.25E−09 | 1.34E−09 | 1295 |
| | 257 | 8.12E−10 | 3.42E−10 | 577 |
| | 262 | 7.00E−10 | 4.03E−10 | 552 |
| | 263 | 1.20E−10 | 1.44E−10 | 132 |
| | 264 | 9.63E−10 | 1.1E−09 | 1032 |
| | 265 | 1.22E−08 | 5.34E−09 | 8770 |
| | 268 | 1.09E−09 | 1.23E−09 | 1160 |
| | 269 | 2.43E−10 | 1.81E−10 | 212 |
| | 270 | 1.41E−09 | 2.02E−09 | 1715 |
| | 405 | 1.10E−10 | 1.21E−10 | 116 |
| | 406 | 1.01E−10 | 8.72E−11 | 94 |
| | 407 | 1.13E−10 | 9.52E−11 | 104 |
| | 408 | 3.76E−10 | 4.48E−10 | 412 |
| | 409 | 1.83E−10 | 2.49E−10 | 216 |
| | 410 | 6.98E−10 | 8.62E−10 | 780 |

TABLE 11 cAMP activity of tris-lipidated agonist peptides

| ID | SEQ ID NO | Primary assay EC$_{50}$ | | | Primary assay EC$_{50}$ | | | Mean pM GLP-1R |
|---|---|---|---|---|---|---|---|---|
| | | Gluc-R | GLP-1R n1 | GIP-R | Gluc-R | GLP-1R n2 | GIP-R | |
| GLP-1 (7-36) tris- | 1 | 2.3E−08 | 2.2E−12 | 2.3E−08 | 2.3E−08 | 3.4E−12 | 2.3E−08 | 2.8 |
| | 487 | | | | | | | |
| | 439 | 1.95E−08 | 5.99E−11 | 1.95E−08 | 1.95E−08 | 1.34E−10 | 1.95E−08 | 97.0 |
| | 440 | 1.97E−08 | 9.67E−11 | 1.97E−08 | 1.97E−08 | 1.64E−10 | 1.97E−08 | 130.4 |
| | 441 | 1.95E−08 | 1.10E−10 | 1.95E−08 | 1.95E−08 | 2.41E−10 | 1.95E−08 | 175.5 |
| | 442 | 1.97E−08 | 6.09E−11 | 1.97E−08 | 1.97E−08 | 1.03E−10 | 1.97E−08 | 82.0 |
| | 443 | 1.94E−08 | 1.92E−10 | 1.94E−08 | 1.94E−08 | 2.54E−10 | 1.94E−08 | 223.0 |
| | 444 | 1.97E−08 | 1.25E−10 | 1.97E−08 | 1.97E−08 | 1.62E−10 | 1.97E−08 | 143.5 |
| | 445 | 1.95E−08 | 2.42E−10 | 1.95E−08 | 1.95E−08 | 2.77E−10 | 1.95E−08 | 259.5 |
| | 446 | 1.97E−08 | 8.73E−11 | 1.97E−08 | 1.97E−08 | 1.27E−10 | 1.97E−08 | 107.2 |
| | 447 | 1.97E−08 | 1.23E−10 | 1.97E−08 | 1.97E−08 | 1.76E−10 | 1.97E−08 | 149.5 |
| | 448 | 1.99E−08 | 7.88E−11 | 1.99E−08 | 1.99E−08 | 1.06E−10 | 1.99E−08 | 92.4 |
| | 449 | 1.97E−08 | 2.16E−10 | 1.97E−08 | 1.97E−08 | 2.76E−10 | 1.97E−08 | 246.0 |
| | 450 | 1.99E−08 | 2.80E−11 | 1.99E−08 | 1.99E−08 | 7.00E−11 | 1.99E−08 | 49.0 |
| | 451 | 1.97E−08 | 2.88E−11 | 1.97E−08 | 1.95E−08 | 1.58E−10 | 1.95E−08 | 93.4 |
| | 452 | 1.95E−08 | 8.57E−11 | 1.95E−08 | 1.97E−08 | 7.61E−11 | 1.97E−08 | 80.9 |
| | 453 | 1.95E−08 | 6.29E−11 | 1.95E−08 | 1.95E−08 | 1.65E−10 | 1.95E−08 | 114.0 |
| | 454 | 1.97E−08 | 2.21E−11 | 1.97E−08 | 1.97E−08 | 6.52E−11 | 1.97E−08 | 43.7 |
| | 455 | 1.98E−08 | 5.48E−11 | 1.98E−08 | 1.98E−08 | 1.20E−10 | 1.98E−08 | 87.4 |
| | 456 | 1.00E−08 | 1.16E−10 | 2.00E−08 | 2.00E−08 | 2.24E−10 | 2.00E−08 | 170.0 |
| | 457 | 1.98E−08 | 1.27E−10 | 1.98E−08 | 1.98E−08 | 1.56E−10 | 1.98E−08 | 141.5 |
| | 458 | 2.00E−08 | 3.63E−11 | 2.00E−08 | 2.00E−08 | 4.64E−11 | 2.00E−08 | 41.4 |
| | 459 | 1.97E−08 | 8.95E−11 | 1.97E−08 | 1.97E−08 | 1.11E−10 | 1.97E−08 | 100.3 |
| | 460 | 2.00E−08 | 6.74E−11 | 2.00E−08 | 2.00E−08 | 8.88E−11 | 2.00E−08 | 78.1 |
| | 461 | 1.98E−08 | 7.45E−11 | 1.98E−08 | 1.98E−08 | 1.45E−10 | 1.98E−08 | 109.8 |
| | 462 | 2.00E−08 | 3.76E−11 | 2.00E−08 | 2.00E−08 | 5.64E−11 | 2.00E−08 | 47.0 |
| | 463 | 2.00E−08 | 6.95E−11 | 2.00E−08 | 2.00E−08 | 9.44E−11 | 2.00E−08 | 82.0 |
| | 464 | 2.02E−08 | 2.54E−11 | 2.02E−08 | 2.02E−08 | 3.51E−11 | 2.02E−08 | 30.3 |

TABLE 11-continued cAMP activity of tris-lipidated agonist peptides

| ID | SEQ ID NO | Primary assay EC$_{50}$ Gluc-R | GLP-1R n1 | GIP-R | Primary assay EC$_{50}$ Gluc-R | GLP-1R n2 | GIP-R | Mean pM GLP-1R |
|---|---|---|---|---|---|---|---|---|
|  | 465 | 2.00E-08 | 1.01E-10 | 2.00E-08 | 2.00E-08 | 1.33E-10 | 2.00E-08 | 117.0 |
|  | 466 | 2.02E-08 | 1.72E-11 | 2.02E-08 | 2.02E-08 | 2.75E-11 | 2.02E-08 | 22.4 |
|  | 467 | 1.98E-08 | 4.93E-11 | 1.98E-08 | 1.98E-08 | 6.15E-11 | 1.98E-08 | 55.4 |
|  | 468 | 2.00E-08 | 6.24E-11 | 2.00E-08 | 2.00E-08 | 8.45E-11 | 2.00E-08 | 73.5 |
|  | 469 | 1.98E-08 | 4.18E-11 | 1.98E-08 | 1.98E-08 | 4.90E-11 | 1.98E-08 | 45.4 |
|  | 470 | 2.00E-08 | 2.60E-11 | 2.00E-08 | 2.00E-08 | 3.65E-11 | 2.00E-08 | 31.3 |
|  | 471 | 1.96E-08 | 2.77E-10 | 1.96E-08 | 1.96E-08 | 4.70E-10 | 1.96E-08 | 373.5 |
|  | 472 | 1.99E-08 | 2.97E-10 | 1.99E-08 | 1.99E-08 | 2.77E-10 | 1.99E-08 | 287.0 |
|  | 473 | 1.96E-08 | 3.99E-10 | 1.96E-08 | 1.96E-08 | 4.70E-10 | 1.96E-08 | 434.5 |
|  | 474 | 1.99E-08 | 2.79E-10 | 1.99E-08 | 1.99E-08 | 3.00E-10 | 1.99E-08 | 289.5 |
|  | 475 | 1.95E-08 | 2.28E-10 | 1.95E-08 | 1.95E-08 | 3.47E-10 | 1.95E-08 | 287.5 |
|  | 476 | 1.98E-08 | 1.74E-10 | 1.98E-08 | 1.98E-08 | 2.57E-10 | 1.98E-08 | 215.5 |
|  | 477 | 1.96E-08 | 2.26E-10 | 1.96E-08 | 1.96E-08 | 3.02E-10 | 1.96E-08 | 264.0 |
|  | 478 | 1.98E-08 | 1.03E-10 | 1.98E-08 | 1.98E-08 | 1.34E-10 | 1.98E-08 | 118.5 |
|  | 479 | 1.98E-08 | 1.32E-10 | 1.98E-08 | 1.98E-08 | 2.39E-10 | 1.98E-08 | 185.5 |
|  | 480 | 2.00E-08 | 5.60E-11 | 2.00E-08 | 2.00E-08 | 5.89E-11 | 2.00E-08 | 57.5 |
|  | 481 | 1.98E-08 | 1.37E-10 | 1.98E-08 | 1.98E-08 | 1.49E-10 | 1.98E-08 | 143.0 |
|  | 482 | 2.00E-08 | 2.83E-11 | 2.00E-08 | 2.00E-08 | 4.42E-11 | 2.00E-08 | 36.3 |
|  | 483 | 1.96E-08 | 2.29E-10 | 1.96E-08 | 1.96E-08 | 2.58E-10 | 1.96E-08 | 243.5 |
|  | 484 | 1.99E-08 | 1.63E-10 | 1.99E-08 | 1.99E-08 | 1.68E-10 | 1.99E-08 | 165.5 |
|  | 485 | 1.96E-08 | 1.67E-10 | 1.96E-08 | 1.96E-08 | 2.24E-10 | 1.96E-08 | 195.5 |
|  | 486 | 1.99E-08 | 1.65E-10 | 1.99E-08 | 1.99E-08 | 2.59E-10 | 1.99E-08 | 212.0 |

TABLE 12 cAMP activity of tris-lipidated agonist peptides, cont.

| ID | SEQ ID NO | INS1e assay EC$_{50}$ GLP-1R n1 | n2 | Mean pM GLP-1R |
|---|---|---|---|---|
| GLP-1 (7-36) | 1 | 7.00E-12 | 2.70E-11 | 17 |
| tris- | 487 |  |  |  |
|  | 450 | 6.38E-09 | 7.24E-09 | 6810.00 |
|  | 454 | 4.10E-09 | 6.99E-09 | 5545.00 |
|  | 455 | 6.74E-09 | 3.08E-09 | 4910.00 |
|  | 458 | 3.07E-09 | 3.67E-09 | 3370.00 |
|  | 462 | 5.40E-09 | 3.73E-09 | 4565.00 |
|  | 464 | 4.46E-09 | 3.57E-09 | 4015.00 |
|  | 466 | 3.86E-09 | 2.55E-09 | 3205.00 |
|  | 467 | 9.92E-09 | 7.91E-09 | 8915.00 |
|  | 469 | 6.90E-09 | 2.89E-09 | 4895.00 |
|  | 470 | 3.84E-09 | 3.48E-09 | 3660.00 |
|  | 480 | 9.37E-09 | 3.69E-09 | 6530.00 |
|  | 482 | 8.57E-09 | 3.15E-09 | 5860.00 |

TABLE 13

Additional comparative sequences

| Peptide | Seq ID | |
|---|---|---|
|  | 488 | H-(Aib)$^2$-EGT$^5$ FTSDV$^{10}$ SSYLE$^{15}$ GQAAK$^{20}$ EFIAW$^{25}$ LVKGR$^{30}$ |
|  | 489 | H-(Aib)$^2$-EG-(S)$^5$-(α-MeF)$^6$-TSDV$^{10}$ SS-(α-MeF)$^{13}$-LE$^{15}$ GQAA-(α-MeK)$^{20}$ E-(α-MeF)$^{22}$-IA-(α-MeF)$^{25}$-(V)$^{26}$-V-(α-MeK)$^{28}$-G-(G)$^{30}$-K(ε-Palmitoyl) |
| Liraglutide | 490 | HAEGTFTSDVSSYLEGQAAK(ε-γE-palmitoyl) EFIAWLVRGRG-acid |
| Semaglutide | 491 | H-Aib$^2$-EGTFTSDVSSYLEGQAAK(ε-(PEG)$_2$-(PEG)$_2$-γE-stearate)EFIAWLVRGRG-acid |

Examples of comparative sequences are found in Table 13. Additional comparative sequences can be found in International Patent Application No PCT/EP2014/077240, published as WO2015/086686A2, and such sequences are incorporated by reference herein.

All documents, patents, journal articles and other materials cited in the present application are hereby incorporated by reference.

Although the present disclosure provides numerous embodiments including reference to the accompanying drawings, it is to be understood that various changes and modifications can be apparent to those skilled in the art. Such changes and modifications are to be understood as included within the scope of the present disclosure as defined by the appended claims, unless they depart there from.

What is claimed is:

1. An isolated polypeptide comprising the amino acid sequence:
HAibEGS-(αMeF)TSDV-(αMeS)SX13LE-GEAA(αMeK)-E(αMeF)IAX25-VVEGG
X13 is a lipid modified K, and
X25 is a lipid modified K.

2. The polypeptide of claim 1, wherein the peptide comprises a C-terminal amide.

3. The polypeptide of claim 1, wherein the two lipid modified K residues are the same or are different, and are selected from the group consisting of: K(ε-(PEG)$_2$-(PEG)$_2$-γE-Lauroyl), K(ε-(PEG)$_2$-(PEG)$_2$-γE-Myristoyl), K(ε-(PEG)$_2$-(PEG)$_2$-γE-Palmitoyl), K(ε-(PEG)$_2$-(PEG)$_2$-γE-Stearoyl),
and any combination thereof.

4. The polypeptide of claim 1, wherein the polypeptide comprises the amino acid sequence of SEQ ID NO: 405, SEQ ID NO: 408, SEQ ID NO: 409, or SEQ ID NO: 410.

5. A pharmaceutical composition comprising the polypeptide of claim 1 and a carrier.

6. A method of treating or preventing a disease or condition caused or characterized by hypoglycemia or impaired insulin release, wherein an effective amount of the polypeptide of any one of claims 1, 2, 3, 4 or the composition of claim 5 is administered to a subject in need of treatment.

7. The method of claim 6, wherein the disease or condition is diabetes.

8. The method of claim 7, wherein the disease or condition is type-2 diabetes.

9. The method of claim 6, wherein the administration further improves glycemic control, provides body weight control, improves β-cell function and mass, reduces the rate of gastric acid secretion and gastric emptying, or any combination thereof.

10. The method of claim 6, wherein the polypeptide or the pharmaceutical composition is administered orally or by injection.

11. The method of claim 10, wherein the injection is administered subcutaneously or intravenously.

12. The method of claim 6, wherein the peptide or the pharmaceutical composition is administered once per day.

13. The method of claim 6, further comprising administering one or more additional therapies.

14. The method of claim 13, wherein the additional therapy comprises blood sugar monitoring, diet modifications, exercise, insulin, a thiazolidinedione, a sulfonylurea, an incretin, metformin, a glyburide, a dipeptidyl peptidase 4 inhibitor, a bile acid sequestrant, or any combination thereof.

15. The method of claim 14, wherein the subject is human.

* * * * *

SEQUENCE LISTING

<160> NUMBER OF SEQ ID NOS: 492

<210> SEQ ID NO 1
<211> LENGTH: 30
<212> TYPE: PRT

```
<213> ORGANISM: Unknown
<220> FEATURE:
<223> OTHER INFORMATION: Description of Unknown: native GLP-1 (7-36)
      polypeptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (2)..(2)
<223> OTHER INFORMATION: /replace="Aib"
<220> FEATURE:
<221> NAME/KEY: VARIANT
<222> LOCATION: (6)..(6)
<223> OTHER INFORMATION: /replace="any alpha-methyl functionalized amino
      acid"
<220> FEATURE:
<221> NAME/KEY: VARIANT
<222> LOCATION: (11)..(11)
<223> OTHER INFORMATION: /replace="any alpha-methyl functionalized amino
      acid"
<220> FEATURE:
<221> NAME/KEY: VARIANT
<222> LOCATION: (12)..(12)
<223> OTHER INFORMATION: /replace="any lipid modified Lys"
<220> FEATURE:
<221> NAME/KEY: VARIANT
<222> LOCATION: (13)..(13)
<223> OTHER INFORMATION: /replace="any alpha-methyl functionalized amino
      acid"
<220> FEATURE:
<221> NAME/KEY: VARIANT
<222> LOCATION: (20)..(20)
<223> OTHER INFORMATION: /replace="any lipid modified Lys" or "any
      alpha-methyl functionalized amino acid"
<220> FEATURE:
<221> NAME/KEY: VARIANT
<222> LOCATION: (22)..(22)
<223> OTHER INFORMATION: /replace="any alpha-methyl functionalized amino
      acid"
<220> FEATURE:
<221> NAME/KEY: VARIANT
<222> LOCATION: (24)..(24)
<223> OTHER INFORMATION: /replace="any lipid modified Lys"
<220> FEATURE:
<221> NAME/KEY: VARIANT
<222> LOCATION: (25)..(25)
<223> OTHER INFORMATION: /replace="alpha-methyl functionalized amino
      acid"
<220> FEATURE:
<221> NAME/KEY: VARIANT
<222> LOCATION: (28)..(28)
<223> OTHER INFORMATION: /replace="Glu" or "any alpha-methyl
      functionalized amino acid"
<220> FEATURE:
<221> NAME/KEY: misc_feature
<222> LOCATION: (1)..(30)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"
```

```
<400> SEQUENCE: 2

His Ala Glu Gly Ser Phe Thr Ser Asp Val Ser Ser Tyr Leu Glu Gly
1               5                   10                  15

Glu Ala Ala Lys Glu Phe Ile Ala Trp Val Val Lys Gly Gly
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: VARIANT
<222> LOCATION: (12)..(12)
<223> OTHER INFORMATION: /replace="any lipid modified Lys"
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: VARIANT
<222> LOCATION: (24)..(24)
<223> OTHER INFORMATION: /replace="any lipid modified Lys"
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: misc_feature
<222> LOCATION: (1)..(30)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 3

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 4
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (2)..(2)
<223> OTHER INFORMATION: /replace="Aib"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (6)..(6)
<223> OTHER INFORMATION: /replace="any alpha-methyl functionalized amino
      acid"
<220> FEATURE:
<221> NAME/KEY: VARIANT
<222> LOCATION: (10)..(10)
<223> OTHER INFORMATION: /replace="any lipid modified Lys"
<220> FEATURE:
<221> NAME/KEY: VARIANT
<222> LOCATION: (11)..(11)
<223> OTHER INFORMATION: /replace="any alpha-methyl functionalized amino
      acid"
<220> FEATURE:
<221> NAME/KEY: VARIANT
<222> LOCATION: (12)..(12)
<223> OTHER INFORMATION: /replace="any lipid modified Lys"
<220> FEATURE:
<221> NAME/KEY: VARIANT
<222> LOCATION: (13)..(13)
<223> OTHER INFORMATION: /replace="Phe" or "any lipid modified Lys"
<220> FEATURE:
<221> NAME/KEY: VARIANT
<222> LOCATION: (14)..(14)
<223> OTHER INFORMATION: /replace="any lipid modified Lys"
<220> FEATURE:
<221> NAME/KEY: VARIANT
<222> LOCATION: (17)..(17)
<223> OTHER INFORMATION: /replace="Glu"
<220> FEATURE:
<221> NAME/KEY: VARIANT
<222> LOCATION: (20)..(20)
<223> OTHER INFORMATION: /replace="Glu" or "any alpha-methyl
      functionalized amino acid"
<220> FEATURE:
<221> NAME/KEY: VARIANT
<222> LOCATION: (22)..(22)
<223> OTHER INFORMATION: /replace="norleucine" or "tyrosine methyl
      ester" or "any alpha-methyl functionalized amino acid"
<220> FEATURE:
<221> NAME/KEY: VARIANT
<222> LOCATION: (24)..(24)
<223> OTHER INFORMATION: /replace="any lipid modified Lys"
<220> FEATURE:
<221> NAME/KEY: VARIANT
<222> LOCATION: (25)..(25)
<223> OTHER INFORMATION: /replace="Phe" or "any lipid modified Lys"
<220> FEATURE:
<221> NAME/KEY: VARIANT
<222> LOCATION: (26)..(26)
<223> OTHER INFORMATION: /replace="Val" or "any lipid modified Lys"
<220> FEATURE:
<221> NAME/KEY: VARIANT
<222> LOCATION: (28)..(28)
<223> OTHER INFORMATION: /replace="Glu"
<220> FEATURE:
<221> NAME/KEY: VARIANT
<222> LOCATION: (30)..(30)
<223> OTHER INFORMATION: /replace="Gly"
<220> FEATURE:
<221> NAME/KEY: misc_feature
<222> LOCATION: (1)..(30)
<223> OTHER INFORMATION: /note="Variant residues given in the sequence
      have no preference with respect to those in the annotations
      for variant positions"
<220> FEATURE:
```

```
<221> NAME/KEY: source
<223> OTHER INFORMATION: /note="See specification as filed for detailed
      description of substitutions and preferred embodiments"

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (31)..(31)
<223> OTHER INFORMATION: Lys(Epsilon-gammaGlu-Palmitoyl)

<400> SEQUENCE: 5

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (31)..(31)
<223> OTHER INFORMATION: Lys(Epsilon-(PEG)2-(PEG)2-gammaGlu-Stearate)

<400> SEQUENCE: 6

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
```

```
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 7

His Xaa Glu Gly Ser Phe Thr Ser Glu Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 8

His Xaa Glu Gly Ser Phe Ser Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 9
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 9

His Xaa Glu Gly Ser Phe Ser Ser Glu Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 10

His Xaa Glu Gly Ser Phe Thr Ser Asp Val Ser Ser Phe Val Glu Gly
```

```
1               5                   10                  15
Glu Ala Ala Lys Glu Phe Ile Ala Phe Val Val Lys Gly Gly
            20                  25                  30
```

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 11

```
His Xaa Glu Gly Ser Phe Thr Ser Asp Val Ser Ser Phe Leu Glu Gly
1               5                   10                  15

Glu Ala Ala Lys Glu Phe Val Ala Phe Val Val Lys Gly Gly
            20                  25                  30
```

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:

```
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 12

His Xaa Glu Gly Ser Phe Ser Ser Glu Val Ser Ser Phe Val Glu Gly
1               5                   10                  15

Glu Ala Ala Lys Glu Phe Val Ala Phe Val Val Lys Gly Gly
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(gammaGlu-Palmitoyl)
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 13

His Xaa Gln Gly Ser Phe Thr Ser Asp Lys Ser Glu Phe Leu Asp Ser
1               5                   10                  15

Glu Arg Ala Arg Asp Phe Val Ala Phe Leu Glu Ala Gly Gly
            20                  25                  30

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: alpha-Me-Phe
<220> FEATURE:
<221> NAME/KEY: MOD_RES
<222> LOCATION: (13)..(13)
```

-continued

```
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 14

His Xaa Gln Gly Ser Phe Thr Ser Asp Phe Ser Lys Phe Leu Asp Ser
1               5                   10                  15

Arg Arg Ala Gln Asp Phe Val Gln Phe Leu Met Asn Thr
            20                  25

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 15

Tyr Xaa Glu Gly Ser Phe Ile Ser Asp Phe Ser Ile Ala Met Asp Lys
1               5                   10                  15

Ile His Gln Gln Asp Phe Val Asn Phe Leu Leu Ala Gln Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (8)..(8)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
```

<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 16

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 17

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 18
<211> LENGTH: 30
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (8)..(8)
<223> OTHER INFORMATION: alpha-Me-Ser
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 18

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (8)..(8)
<223> OTHER INFORMATION: alpha-Me-Ser

<400> SEQUENCE: 19

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 20
<211> LENGTH: 30
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (8)..(8)
<223> OTHER INFORMATION: Aib

<400> SEQUENCE: 20

His Xaa Glu Gly Thr Phe Thr Xaa Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (11)..(11)
<223> OTHER INFORMATION: alpha-Me-Ser

<400> SEQUENCE: 21

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (11)..(11)
<223> OTHER INFORMATION: Aib

<400> SEQUENCE: 22

His Xaa Glu Gly Thr Phe Thr Ser Asp Val Xaa Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES -continued

```
<222> LOCATION: (2)..(2)
<223> OTHER INFORMATION: Aib
<220> FEATURE:
<221> NAME/KEY: MOD_RES
<222> LOCATION: (8)..(8)
<223> OTHER INFORMATION: alpha-Me-Ser
<220> FEATURE:
<221> NAME/KEY: MOD_RES
<222> LOCATION: (11)..(11)
<223> OTHER INFORMATION: alpha-Me-Ser

<400> SEQUENCE: 23

His Xaa Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (11)..(11)
<223> OTHER INFORMATION: Aib

<400> SEQUENCE: 24

His Xaa Glu Gly Thr Phe Thr Xaa Asp Val Xaa Ser Tyr Leu Glu Gly
1               5                   10                  15
Gln Ala Ala Lys Glu Phe Ile Ala Trp Leu Val Lys Gly Arg
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
```

-continued

```
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 25

His Xaa Glu Gly Ser Phe Thr Gly Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 26

His Xaa Glu Gly Ser Phe Thr Ala Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 27

His Xaa Glu Gly Ser Phe Thr Asp Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 28
```

His Xaa Glu Gly Ser Phe Thr Glu Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 29

His Xaa Glu Gly Ser Phe Thr Thr Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)

```
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 30

His Xaa Glu Gly Ser Phe Thr Val Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-epsilon-gammaGlu-
      Stearate)

<400> SEQUENCE: 31

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30
```

```
<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-Palmitoyl)

<400> SEQUENCE: 32

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
```

```
<221> NAME/KEY: MOD_RES
<222> LOCATION: (20)..(20)
<223> OTHER INFORMATION: Lys(Epsilon-(PEG)2-(PEG)2-epsilon-gammaGlu-
      Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 33

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Palmitoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 34

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 35
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-Palmitoyl)

<400> SEQUENCE: 35

His Xaa Glu Gly Ser Phe Thr Asp Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-epsilon-gammaGlu-
      Stearate)
<220> FEATURE:
<221> NAME/KEY: MOD_RES
```

```
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 36

His Xaa Glu Gly Ser Phe Thr Asp Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Palmitoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 37

His Xaa Glu Gly Ser Phe Thr Asp Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (31)..(31)
<223> OTHER INFORMATION: Lys(Epsilon-(PEG)2-(PEG)2-epsilon-gammaGlu-
      Stearate)

<400> SEQUENCE: 38

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (31)..(31)
<223> OTHER INFORMATION: Lys(Epsilon-gammaGlu-Palmitoyl)

<400> SEQUENCE: 39

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
```

-continued

```
            polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-epsilon-gammaGlu-
      Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 40

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Palmitoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 41

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 42
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 42

His Xaa Glu Gly Ser Phe Thr Ser Asp Val Ser Ser Phe Leu Glu Gly
1               5                   10                  15

Glu Ala Ala Glu Glu Phe Ile Ala Phe Val Val Lys Gly Gly
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
```

```
<400> SEQUENCE: 43

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Glu Gly Gly
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 44

His Xaa Glu Gly Ser Phe Thr Ser Asp Val Ser Ser Phe Leu Glu Gly
1               5                   10                  15

Glu Ala Ala Glu Glu Phe Ile Ala Phe Val Val Glu Gly Gly
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
```

```
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 45

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 46

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
```

```
<223> OTHER INFORMATION: alpha-Me-Ser
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 47

His Xaa Glu Gly Ser Phe Thr Ser Asp Val Ser Ser Tyr Leu Glu Gly
 1               5                  10                  15

Glu Ala Ala Lys Glu Phe Ile Ala Phe Val Val Lys Gly Gly
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 48

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 49

His Xaa Glu Gly Ser Phe Thr Ser Asp Val Ser Ser Phe Leu Glu Gly
1               5                   10                  15

Glu Ala Ala Lys Glu Phe Ile Ala Trp Val Val Lys Gly Gly
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 50

His Xaa Glu Gly Ser Phe Thr Ser Asp Val Ser Ser Phe Leu Glu Gly
1               5                   10                  15
```

Glu Ala Ala Lys Glu Phe Ile Ala Phe Val Val Lys Gly Gly
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 51

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)

-continued

<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 52

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 53

His Xaa Glu Gly Ser Phe Thr Ser Asp Val Ser Ser Tyr Leu Glu Gly
1               5                   10                  15

Glu Ala Ala Lys Glu Phe Ile Ala Phe Val Val Lys Gly Gly
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser

```
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 54

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 55

His Xaa Glu Gly Ser Phe Thr Ser Asp Val Ser Ser Phe Leu Glu Gly
1               5                   10                  15

Glu Ala Ala Lys Glu Phe Ile Ala Trp Val Val Lys Gly Gly
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 56

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 57

His Xaa Glu Gly Ser Phe Thr Ser Asp Val Ser Lys Tyr Leu Glu Gly
 1               5                  10                  15

Glu Ala Ala Lys Glu Phe Ile Ala Phe Val Val Glu Gly Gly
            20                  25                  30

<210> SEQ ID NO 58
<211> LENGTH: 30
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 58

His Xaa Glu Gly Ser Phe Thr Ser Asp Val Ser Lys Tyr Leu Glu Gly
1               5                   10                  15

Glu Ala Ala Glu Glu Phe Ile Ala Phe Val Val Glu Gly Gly
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 59

His Xaa Glu Gly Ser Phe Thr Ser Asp Val Ser Lys Tyr Leu Glu Gly
1               5                   10                  15

Glu Ala Ala Xaa Glu Phe Ile Ala Phe Val Val Glu Gly Gly
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequence: Synthetic

```
          polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 60

His Xaa Glu Gly Ser Phe Thr Ser Asp Val Ser Lys Tyr Leu Glu Gly
1               5                   10                  15

Glu Ala Ala Lys Glu Phe Ile Ala Phe Val Val Glu Gly Gly
            20                  25                  30

<210> SEQ ID NO 61
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 61

His Xaa Glu Gly Ser Phe Thr Ser Asp Val Ser Lys Tyr Leu Glu Gly
1               5                   10                  15

Glu Ala Ala Lys Glu Phe Ile Ala Phe Val Val Glu Gly Gly
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 62

His Xaa Glu Gly Ser Phe Thr Ser Asp Val Ser Lys Tyr Leu Glu Gly
1               5                   10                  15

Glu Ala Ala Glu Glu Phe Ile Ala Phe Val Val Glu Gly Gly
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 63

His Xaa Glu Gly Ser Phe Thr Ser Asp Val Ser Lys Tyr Leu Glu Gly
1               5                   10                  15

Glu Ala Ala Xaa Glu Phe Ile Ala Phe Val Val Glu Gly Gly
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe

<400> SEQUENCE: 64

His Xaa Glu Gly Ser Phe Thr Ser Asp Val Ser Lys Tyr Leu Glu Gly
1               5                   10                  15

Glu Ala Ala Lys Glu Phe Ile Ala Phe Val Val Glu Gly Gly
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 65

His Xaa Glu Gly Ser Phe Thr Ser Asp Val Ser Ser Phe Leu Glu Gly
1               5                   10                  15

Glu Ala Ala Lys Glu Phe Ile Lys Trp Val Val Glu Gly Gly
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

-continued

```
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 66

His Xaa Glu Gly Ser Phe Thr Ser Asp Val Ser Ser Phe Leu Glu Gly
1               5                   10                  15

Glu Ala Ala Glu Glu Phe Ile Lys Trp Val Val Glu Gly Gly
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 67

His Xaa Glu Gly Ser Phe Thr Ser Asp Val Ser Ser Phe Leu Glu Gly
1               5                   10                  15

Glu Ala Ala Xaa Glu Phe Ile Lys Trp Val Val Glu Gly Gly
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 68

His Xaa Glu Gly Ser Phe Thr Ser Asp Val Ser Ser Phe Leu Glu Gly
1               5                   10                  15

Glu Ala Ala Lys Glu Phe Ile Lys Trp Val Val Glu Gly Gly
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 69

His Xaa Glu Gly Ser Phe Thr Ser Asp Val Ser Ser Phe Leu Glu Gly
1               5                   10                  15

Glu Ala Ala Ala Glu Phe Ile Lys Trp Val Val Glu Gly Gly
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (30)..(30)
<223> OTHER INFORMATION: Lys(Epsilon-gammaGlu-Palmitoyl)

<400> SEQUENCE: 70

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Lys
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
```

```
<222> LOCATION: (28)..(28)
<223> OTHER INFORMATION: alpha-Me-Lys
<220> FEATURE:
<221> NAME/KEY: MOD_RES
<222> LOCATION: (29)..(29)
<223> OTHER INFORMATION: Lys(Epsilon-gammaGlu-Palmitoyl)

<400> SEQUENCE: 71

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Lys Gly
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-Palmitoyl)

<400> SEQUENCE: 72

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
```

```
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (27)..(27)
<223> OTHER INFORMATION: Lys(Epsilon-gammaGlu-Palmitoyl)
<220> FEATURE:
<221> NAME/KEY: MOD_RES
<222> LOCATION: (28)..(28)
<223> OTHER INFORMATION: alpha-Me-Lys

<400> SEQUENCE: 73

His Xaa Glu Gly Ser Phe Thr Ser Asp Val Ser Ser Phe Leu Glu Gly
1               5                   10                  15

Glu Ala Ala Lys Glu Phe Ile Ala Phe Val Lys Lys Gly Gly
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (26)..(26)
<223> OTHER INFORMATION: Lys(Epsilon-gammaGlu-Palmitoyl)
<220> FEATURE:
```

```
<221> NAME/KEY: MOD_RES
<222> LOCATION: (28)..(28)
<223> OTHER INFORMATION: alpha-Me-Lys

<400> SEQUENCE: 74

His Xaa Glu Gly Ser Phe Thr Ser Asp Val Ser Ser Phe Leu Glu Gly
1               5                   10                  15

Glu Ala Ala Lys Glu Phe Ile Ala Phe Lys Val Lys Gly Gly
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Palmitoyl)
<220> FEATURE:
<221> NAME/KEY: MOD_RES
<222> LOCATION: (28)..(28)
<223> OTHER INFORMATION: alpha-Me-Lys

<400> SEQUENCE: 75

His Xaa Glu Gly Ser Phe Thr Ser Asp Val Ser Ser Phe Leu Glu Gly
1               5                   10                  15

Glu Ala Ala Lys Glu Phe Ile Ala Lys Val Val Lys Gly Gly
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
```

-continued

```
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (24)..(24)
<223> OTHER INFORMATION: Lys(Epsilon-gammaGlu-Palmitoyl)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 76

His Xaa Glu Gly Ser Phe Thr Ser Asp Val Ser Ser Phe Leu Glu Gly
1               5                   10                  15

Glu Ala Ala Lys Glu Phe Ile Lys Phe Val Val Lys Gly Gly
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (23)..(23)
<223> OTHER INFORMATION: Lys(Epsilon-gammaGlu-Palmitoyl)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
```

<400> SEQUENCE: 77

His Xaa Glu Gly Ser Phe Thr Ser Asp Val Ser Ser Phe Leu Glu Gly
1               5                   10                  15

Glu Ala Ala Lys Glu Phe Lys Ala Phe Val Val Lys Gly Gly
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: Lys(Epsilon-gammaGlu-Palmitoyl)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 78

His Xaa Glu Gly Ser Phe Thr Ser Asp Val Ser Ser Phe Leu Glu Gly
1               5                   10                  15

Glu Ala Ala Lys Glu Lys Ile Ala Phe Val Val Lys Gly Gly
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:

```
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-gammaGlu-Palmitoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 79

His Xaa Glu Gly Ser Phe Thr Ser Asp Val Ser Ser Phe Leu Glu Gly
1               5                   10                  15

Glu Ala Ala Lys Lys Phe Ile Ala Phe Val Val Lys Gly Gly
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Palmitoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 80

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
```

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (19)..(19)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 81

His Xaa Glu Gly Ser Phe Thr Ser Asp Val Ser Ser Phe Leu Glu Gly
1               5                   10                  15
Glu Ala Lys Lys Glu Phe Ile Ala Phe Val Val Lys Gly Gly
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe

```
<220> FEATURE:
<221> NAME/KEY: MOD_RES
<222> LOCATION: (18)..(18)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 82

His Xaa Glu Gly Ser Phe Thr Ser Asp Val Ser Ser Phe Leu Glu Gly
 1               5                  10                  15

Glu Lys Ala Lys Glu Phe Ile Ala Phe Val Val Lys Gly Gly
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (17)..(17)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 83

His Xaa Glu Gly Ser Phe Thr Ser Asp Val Ser Ser Phe Leu Glu Gly
 1               5                  10                  15
```

Lys Ala Ala Lys Glu Phe Ile Ala Phe Val Val Lys Gly Gly
                20              25              30

<210> SEQ ID NO 84
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (16)..(16)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 84

His Xaa Glu Gly Ser Phe Thr Ser Asp Val Ser Ser Phe Leu Glu Lys
1               5                   10                  15

Glu Ala Ala Lys Glu Phe Ile Ala Phe Val Val Lys Gly Gly
                20              25              30

<210> SEQ ID NO 85
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)

```
<223> OTHER INFORMATION: alpha-Me-Phe
<220> FEATURE:
<221> NAME/KEY: MOD_RES
<222> LOCATION: (15)..(15)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 85

His Xaa Glu Gly Ser Phe Thr Ser Asp Val Ser Ser Phe Leu Lys Gly
1               5                   10                  15

Glu Ala Ala Lys Glu Phe Ile Ala Phe Val Val Lys Gly Gly
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (14)..(14)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 86

His Xaa Glu Gly Ser Phe Thr Ser Asp Val Ser Ser Phe Lys Glu Gly
1               5                   10                  15
```

```
Glu Ala Ala Lys Glu Phe Ile Ala Phe Val Val Lys Gly Gly
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 87

His Xaa Glu Gly Ser Phe Thr Ser Asp Val Ser Ser Lys Leu Glu Gly
1               5                   10                  15

Glu Ala Ala Lys Glu Phe Ile Ala Phe Val Val Lys Gly Gly
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (12)..(12)
<223> OTHER INFORMATION: Lys(Epsilon-gammaGlu-Palmitoyl)
<220> FEATURE:
<221> NAME/KEY: MOD_RES
```

```
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 88

His Xaa Glu Gly Ser Phe Thr Ser Asp Val Ser Lys Phe Leu Glu Gly
1               5                   10                  15

Glu Ala Ala Lys Glu Phe Ile Ala Phe Val Val Lys Gly Gly
            20                  25                  30

<210> SEQ ID NO 89
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: Lys(Epsilon-gammaGlu-Palmitoyl)
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 89

His Xaa Glu Gly Ser Phe Thr Ser Asp Val Lys Ser Phe Leu Glu Gly
1               5                   10                  15

Glu Ala Ala Lys Glu Phe Ile Ala Phe Val Val Lys Gly Gly
            20                  25                  30

<210> SEQ ID NO 90
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-gammaGlu-Palmitoyl)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 90

His Xaa Glu Gly Ser Phe Thr Ser Asp Lys Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (9)..(9)
<223> OTHER INFORMATION: Lys(Epsilon-gammaGlu-Palmitoyl)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
```

```
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 91

His Xaa Glu Gly Ser Phe Thr Ser Lys Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (8)..(8)
<223> OTHER INFORMATION: Lys(Epsilon-gammaGlu-Palmitoyl)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 92

His Xaa Glu Gly Ser Phe Thr Lys Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 93
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (7)..(7)
<223> OTHER INFORMATION: Lys(Epsilon-gammaGlu-Palmitoyl)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 93

His Xaa Glu Gly Ser Phe Lys Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: Lys(Epsilon-gammaGlu-Palmitoyl)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
```

<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 94

His Xaa Glu Gly Ser Lys Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (5)..(5)
<223> OTHER INFORMATION: Lys(Epsilon-gammaGlu-Palmitoyl)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 95

His Xaa Glu Gly Lys Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 96
<211> LENGTH: 30
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Lys(Epsilon-gammaGlu-Palmitoyl)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 96

His Xaa Glu Lys Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: Lys(Epsilon-gammaGlu-Palmitoyl)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
```

```
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 97

His Xaa Lys Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys(Epsilon-gammaGlu-Palmitoyl)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 98

His Lys Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 99
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (30)..(30)
<223> OTHER INFORMATION: Lys(Epsilon-(PEG)2-(PEG)2-gammaGlu-Stearate)

<400> SEQUENCE: 99

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Lys
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
```

-continued

```
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (29)..(29)
<223> OTHER INFORMATION: Lys(Epsilon-(PEG)2-(PEG)2-gammaGlu-Stearate)

<400> SEQUENCE: 100

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Lys Gly
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-gammaGlu-Stearate)

<400> SEQUENCE: 101

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 102
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (27)..(27)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (28)..(28)
<223> OTHER INFORMATION: alpha-Me-Lys

<400> SEQUENCE: 102

His Xaa Glu Gly Ser Phe Thr Ser Asp Val Ser Ser Phe Leu Glu Gly
1               5                   10                  15

Glu Ala Ala Lys Glu Phe Ile Ala Phe Val Lys Lys Gly Gly
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
```

-continued

```
<221> NAME/KEY: MOD_RES
<222> LOCATION: (26)..(26)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (28)..(28)
<223> OTHER INFORMATION: alpha-Me-Lys

<400> SEQUENCE: 103

His Xaa Glu Gly Ser Phe Thr Ser Asp Val Ser Ser Phe Leu Glu Gly
 1               5                  10                  15

Glu Ala Ala Lys Glu Phe Ile Ala Phe Lys Val Lys Gly Gly
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (28)..(28)
<223> OTHER INFORMATION: alpha-Me-Lys

<400> SEQUENCE: 104

His Xaa Glu Gly Ser Phe Thr Ser Asp Val Ser Ser Phe Leu Glu Gly
 1               5                  10                  15

Glu Ala Ala Lys Glu Phe Ile Ala Lys Val Val Lys Gly Gly
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 105

His Xaa Glu Gly Ser Phe Thr Ser Asp Val Ser Ser Phe Leu Glu Gly
1               5                   10                  15
Glu Ala Ala Lys Glu Phe Ile Lys Phe Val Val Lys Gly Gly
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (23)..(23)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: alpha-Me-Phe
```

```
<220> FEATURE:
<221> NAME/KEY: MOD_RES
<222> LOCATION: (28)..(28)
<223> OTHER INFORMATION: alpha-Me-Lys

<400> SEQUENCE: 106

His Xaa Glu Gly Ser Phe Thr Ser Asp Val Ser Ser Phe Leu Glu Gly
1               5                   10                  15

Glu Ala Ala Lys Glu Phe Lys Ala Phe Val Val Lys Gly Gly
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 107

His Xaa Glu Gly Ser Phe Thr Ser Asp Val Ser Ser Phe Leu Glu Gly
1               5                   10                  15

Glu Ala Ala Lys Glu Lys Ile Ala Phe Val Val Lys Gly Gly
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
```

```
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 108

His Xaa Glu Gly Ser Phe Thr Ser Asp Val Ser Ser Phe Leu Glu Gly
 1               5                  10                  15

Glu Ala Ala Lys Lys Phe Ile Ala Phe Val Val Lys Gly Gly
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 109
```

```
His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30
```

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (19)..(19)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 110

```
His Xaa Glu Gly Ser Phe Thr Ser Asp Val Ser Ser Phe Leu Glu Gly
1               5                   10                  15

Glu Ala Lys Lys Glu Phe Ile Ala Phe Val Val Lys Gly Gly
            20                  25                  30
```

<210> SEQ ID NO 111
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser

```
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 111

His Xaa Glu Gly Ser Phe Thr Ser Asp Val Ser Ser Phe Leu Glu Gly
 1               5                  10                  15

Glu Lys Ala Lys Glu Phe Ile Ala Phe Val Val Lys Gly Gly
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 112
```

```
His Xaa Glu Gly Ser Phe Thr Ser Asp Val Ser Ser Phe Leu Glu Gly
1               5                   10                  15

Lys Ala Ala Lys Glu Phe Ile Ala Phe Val Val Lys Gly Gly
            20                  25                  30
```

<210> SEQ ID NO 113
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 113

```
His Xaa Glu Gly Ser Phe Thr Ser Asp Val Ser Ser Phe Leu Glu Lys
1               5                   10                  15

Glu Ala Ala Lys Glu Phe Ile Ala Phe Val Val Lys Gly Gly
            20                  25                  30
```

<210> SEQ ID NO 114
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)

```
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (15)..(15)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 114

His Xaa Glu Gly Ser Phe Thr Ser Asp Val Ser Ser Phe Leu Lys Gly
1               5                   10                  15

Glu Ala Ala Lys Glu Phe Ile Ala Phe Val Val Lys Gly Gly
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
```

```
<400> SEQUENCE: 115

His Xaa Glu Gly Ser Phe Thr Ser Asp Val Ser Ser Phe Lys Glu Gly
1               5                   10                  15

Glu Ala Ala Lys Glu Phe Ile Ala Phe Val Val Lys Gly Gly
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 116

His Xaa Glu Gly Ser Phe Thr Ser Asp Val Ser Ser Lys Leu Glu Gly
1               5                   10                  15

Glu Ala Ala Lys Glu Phe Ile Ala Phe Val Val Lys Gly Gly
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
```

```
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 117

His Xaa Glu Gly Ser Phe Thr Ser Asp Val Ser Lys Phe Leu Glu Gly
1               5                   10                  15

Glu Ala Ala Lys Glu Phe Ile Ala Phe Val Val Lys Gly Gly
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 118

His Xaa Glu Gly Ser Phe Thr Ser Asp Val Lys Ser Phe Leu Glu Gly
1               5                   10                  15

Glu Ala Ala Lys Glu Phe Ile Ala Phe Val Val Lys Gly Gly
            20                  25                  30
```

<210> SEQ ID NO 119
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 119

His Xaa Glu Gly Ser Phe Thr Ser Asp Lys Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (9)..(9)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (11)..(11)
<223> OTHER INFORMATION: alpha-Me-Ser
<220> FEATURE:

```
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 120

His Xaa Glu Gly Ser Phe Thr Ser Lys Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (8)..(8)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 121

His Xaa Glu Gly Ser Phe Thr Lys Asp Val Ser Ser Phe Leu Glu Gly
1               5                   10                  15

Glu Ala Ala Lys Glu Phe Ile Ala Phe Val Val Lys Gly Gly
```

<210> SEQ ID NO 122
<211> LENGTH: 30
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (7)..(7)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 122

His Xaa Glu Gly Ser Phe Lys Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe

```
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 123

His Xaa Glu Gly Ser Lys Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (5)..(5)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 124

His Xaa Glu Gly Lys Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30
```

```
<210> SEQ ID NO 125
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (4)..(4)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 125

His Xaa Glu Lys Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (3)..(3)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
```

```
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 126

His Xaa Lys Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
             20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 127

His Lys Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
             20                  25                  30

<210> SEQ ID NO 128
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 128

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
                20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
```

```
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 129

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-gammaGlu-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 130

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
```

<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 131

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 132

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-Ahx-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 133

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES

```
<222> LOCATION: (20)..(20)
<223> OTHER INFORMATION: Lys(Epsilon-(PEG)2-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 134

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 135

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
                polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Lauroyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 136

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
```

```
<220> FEATURE:
<221> NAME/KEY: MOD_RES
<222> LOCATION: (28)..(28)
<223> OTHER INFORMATION: alpha-Me-Lys

<400> SEQUENCE: 137

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 138

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
```

```
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-gammaGlu-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 139

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 140

His Xaa Glu Gly Ser Phe Thr Ser Asp Val Ser Ser Phe Leu Glu Gly
```

```
1               5                   10                  15
Glu Ala Ala Lys Glu Phe Ile Ala Phe Val Val Lys Gly Gly
                20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 141

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
                20                  25                  30

<210> SEQ ID NO 142
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
```

```
<220> FEATURE:
<221> NAME/KEY: MOD_RES
<222> LOCATION: (20)..(20)
<223> OTHER INFORMATION: Lys(Epsilon-Ahx-Ahx-Ahx-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 142

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
             20                  25                  30

<210> SEQ ID NO 143
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 143

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
             20                  25                  30

<210> SEQ ID NO 144
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-12-(4-
      carboxyphenoxy)dodecanoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 144

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 145
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-12-(4-
      carboxyphenoxy)dodecanoyl)
<220> FEATURE:
<221> NAME/KEY: MOD_RES
<222> LOCATION: (22)..(22)
```

```
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 145

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 146

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 147

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 148
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-gammaGlu-
      Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
```

```
<400> SEQUENCE: 148

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 149

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
```

<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 150

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 151
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-Ahx-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 151

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 152
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 152

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
```

```
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 153

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearoyl)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 154

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 155

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 156

His Xaa Glu Gly Ser Phe Thr Ser Asp Val Ser Ser Phe Leu Glu Gly
```

```
            1               5                  10                  15
Glu Ala Ala Lys Glu Phe Ile Ala Phe Val Val Lys Gly Gly
            20                  25                  30
```

<210> SEQ ID NO 157
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-gammaGlu-gammaGlu-gammaGlu-
      Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 157

```
His Xaa Glu Gly Ser Phe Thr Ser Asp Val Ser Phe Leu Glu Gly
1               5                   10                  15

Glu Ala Ala Lys Glu Phe Ile Ala Phe Val Val Lys Gly Gly
            20                  25                  30
```

<210> SEQ ID NO 158
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe

```
<220> FEATURE:
<221> NAME/KEY: MOD_RES
<222> LOCATION: (20)..(20)
<223> OTHER INFORMATION: Lys(Epsilon-Ahx-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 158

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 159

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 160
<211> LENGTH: 30
<212> TYPE: PRT
<213> ORGANISM: Artificial Sequence
```

-continued

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-Ahx-Ahx-Ahx-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 160

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 161
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
```

```
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 161

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 162
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 162

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 163
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
```

```
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: Lys(Epsilon-(PEG)2-(PEG)2-(PEG)2-Stearate)
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys

<400> SEQUENCE: 163

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-Lauroyl)

<400> SEQUENCE: 164

His Xaa Glu Gly Ser Phe Thr Ser Asp Val Ser Ser Phe Leu Glu Gly
1               5                   10                  15
```

Glu Ala Ala Lys Glu Phe Ile Ala Phe Val Val Lys Gly Gly
            20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-Lauroyl)

<400> SEQUENCE: 165

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)

```
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-gammaGlu-Lauroyl)

<400> SEQUENCE: 166

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Lauroyl)

<400> SEQUENCE: 167

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Lauroyl)

<400> SEQUENCE: 168

His Xaa Glu Gly Ser Phe Thr Ser Asp Val Ser Ser Phe Leu Glu Gly
1               5                   10                  15
Glu Ala Ala Lys Glu Phe Ile Ala Phe Val Val Lys Gly Gly
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
```

```
<222> LOCATION: (28)..(28)
<223> OTHER INFORMATION: Lys(Epsilon-Ahx-Ahx-Ahx-Lauroyl)

<400> SEQUENCE: 169

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 170
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-Lauroyl)

<400> SEQUENCE: 170

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 171
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
```

<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-Lauroyl)

<400> SEQUENCE: 171

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 172
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-(PEG)2-Lauroyl)

<400> SEQUENCE: 172

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

```
<210> SEQ ID NO 173
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-Dodecylbenzoate)

<400> SEQUENCE: 173

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
```

```
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-Dodecylbenzoate)

<400> SEQUENCE: 174

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-gammaGlu-
      Dodecylbenzoate)

<400> SEQUENCE: 175

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 176
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Dodecylbenzoate)

<400> SEQUENCE: 176

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 177
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Dodecylbenzoate)
```

<400> SEQUENCE: 177

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Ahx-Dodecylbenzoate)

<400> SEQUENCE: 178

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:

<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-Dodecylbenzoate)

<400> SEQUENCE: 179

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-Dodecylbenzoate)

<400> SEQUENCE: 180

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 181

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-(PEG)2-
      Dodecylbenzoate)

<400> SEQUENCE: 181

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 182
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
```

<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-Stearoyl)

<400> SEQUENCE: 182

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
             20                  25                  30

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-Stearoyl)

<400> SEQUENCE: 183

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
             20                  25                  30

<210> SEQ ID NO 184
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-gammaGlu-
      Stearoyl)

<400> SEQUENCE: 184

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 185
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Stearoyl)
```

<400> SEQUENCE: 185

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Stearoyl)

<400> SEQUENCE: 186

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES

```
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Ahx-Stearoyl)

<400> SEQUENCE: 187

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-Stearoyl)

<400> SEQUENCE: 188

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 189
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-Stearoyl)

<400> SEQUENCE: 189

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
```

```
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-(PEG)2-Stearoyl)

<400> SEQUENCE: 190

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-Stearate)

<400> SEQUENCE: 191

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-Stearate)

<400> SEQUENCE: 192

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly
                20                  25                  30

<210> SEQ ID NO 193
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-gammaGlu-gammaGlu-gammaGlu-
      Stearate)

<400> SEQUENCE: 193
```

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Stearate)

<400> SEQUENCE: 194

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe

```
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Stearate)

<400> SEQUENCE: 195

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-Ahx-Ahx-Ahx-Stearate)

<400> SEQUENCE: 196

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 197
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-Stearate)

<400> SEQUENCE: 197

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
```

```
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-Stearate)

<400> SEQUENCE: 198

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 199
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: Lys(Epsilon-(PEG)2-(PEG)2-(PEG)2-Stearate)

<400> SEQUENCE: 199

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly
            20                  25                  30

<210> SEQ ID NO 200
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
```

```
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-Lauroyl)

<400> SEQUENCE: 200

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly Lys
                20                  25                  30

<210> SEQ ID NO 201
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
```

<222> LOCATION: (31)..(31)
<223> OTHER INFORMATION: Lys(Epsilon-gammaGlu-gammaGlu-Lauroyl)

<400> SEQUENCE: 201

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 202
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-Glu-Lauroyl)

<400> SEQUENCE: 202

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 203
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)

```
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Lauroyl)

<400> SEQUENCE: 203

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 204
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
```

<221> NAME/KEY: MOD_RES
<222> LOCATION: (31)..(31)
<223> OTHER INFORMATION: Lys(Epsilon-Ahx-Ahx-Lauroyl)

<400> SEQUENCE: 204

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 205
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-Ahx-Lauroyl)

<400> SEQUENCE: 205

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 206
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES

```
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-Lauroyl)

<400> SEQUENCE: 206

His Xaa Glu Gly Ser Phe Thr Ser Asp Val Ser Ser Phe Leu Glu Gly
1               5                   10                  15
Glu Ala Ala Lys Glu Phe Ile Ala Phe Val Val Lys Gly Gly Lys
            20                  25                  30

<210> SEQ ID NO 207
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
```

```
<220> FEATURE:
<221> NAME/KEY: MOD_RES
<222> LOCATION: (31)..(31)
<223> OTHER INFORMATION: Lys(Epsilon-(PEG)2-(PEG)2-Lauroyl)

<400> SEQUENCE: 207

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 208
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-(PEG)2-Lauroyl)

<400> SEQUENCE: 208

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 209
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
```

```
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-12-(4-
      carboxyphenoxy)dodecanoyl)

<400> SEQUENCE: 209

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 210
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
```

```
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-12-(4-
      carboxyphenoxy)dodecanoyl)

<400> SEQUENCE: 210

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 211
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-gammaGlu-12-(4-
      carboxyphenoxy)dodecanoyl)

<400> SEQUENCE: 211

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 212
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-12-(4-
      carboxyphenoxy)dodecanoyl)

<400> SEQUENCE: 212

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 213
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
```

```
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-12-(4-
      carboxyphenoxy)dodecanoyl)

<400> SEQUENCE: 213

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
                20                  25                  30

<210> SEQ ID NO 214
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-Ahx-12-(4-
      carboxyphenoxy)dodecanoyl)

<400> SEQUENCE: 214

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
                20                  25                  30

<210> SEQ ID NO 215
<211> LENGTH: 31
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-12-(4-
      carboxyphenoxy)dodecanoyl)

<400> SEQUENCE: 215

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
```

```
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-12-(4-
      carboxyphenoxy)dodecanoyl)

<400> SEQUENCE: 216

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 217
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-(PEG)2-12-(4-
      carboxyphenoxy)dodecanoyl)

<400> SEQUENCE: 217

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30
```

```
<210> SEQ ID NO 218
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-Stearoyl)

<400> SEQUENCE: 218

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 219
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
```

```
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-Stearoyl)

<400> SEQUENCE: 219

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly Lys
             20                  25                  30

<210> SEQ ID NO 220
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-gammaGlu-
      Stearoyl)

<400> SEQUENCE: 220

His Xaa Glu Gly Ser Phe Thr Ser Asp Val Ser Ser Phe Leu Glu Gly
 1               5                  10                  15

Glu Ala Ala Lys Glu Phe Ile Ala Phe Val Val Lys Gly Gly Lys
             20                  25                  30
```

```
<210> SEQ ID NO 221
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Stearoyl)

<400> SEQUENCE: 221

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
                20                  25                  30

<210> SEQ ID NO 222
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
```

```
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-Stearoyl)

<400> SEQUENCE: 222

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 223
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-Stearoyl)

<400> SEQUENCE: 223

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
```

<210> SEQ ID NO 224
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-Stearoyl)

<400> SEQUENCE: 224

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 225
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe

```
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-Stearoyl)

<400> SEQUENCE: 225

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 226
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-(PEG)2-Stearoyl)

<400> SEQUENCE: 226

His Xaa Glu Gly Ser Phe Thr Ser Asp Val Ser Ser Phe Leu Glu Gly
1               5                   10                  15
```

Glu Ala Ala Lys Glu Phe Ile Ala Phe Val Val Lys Gly Gly Lys
            20                  25                  30

<210> SEQ ID NO 227
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-Stearate)

<400> SEQUENCE: 227

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 228
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)

<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-Stearate)

<400> SEQUENCE: 228

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 229
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-gammaGlu-gammaGlu-gammaGlu-
      Stearate)

<400> SEQUENCE: 229

His Xaa Glu Gly Ser Phe Thr Ser Asp Val Ser Ser Phe Leu Glu Gly

```
                1               5                  10                 15
            Glu Ala Ala Lys Glu Phe Ile Ala Phe Val Val Lys Gly Gly Lys
                         20                  25                 30
```

<210> SEQ ID NO 230
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Stearate)

<400> SEQUENCE: 230

```
            His Xaa Glu Gly Ser Phe Thr Ser Asp Val Ser Ser Phe Leu Glu Gly
            1               5                  10                 15
            Glu Ala Ala Lys Glu Phe Ile Ala Phe Val Val Lys Gly Gly Lys
                         20                  25                 30
```

<210> SEQ ID NO 231
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:

```
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-Stearate)

<400> SEQUENCE: 231

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Ahx-Ahx-Ahx-Stearate)

<400> SEQUENCE: 232
```

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 233
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-Stearate)

<400> SEQUENCE: 233

His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30

<210> SEQ ID NO 234
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser

```
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-Stearate)

<400> SEQUENCE: 234

His Xaa Glu Gly Ser Phe Thr Ser Asp Val Ser Ser Phe Leu Glu Gly
1               5                   10                  15
Glu Ala Ala Lys Glu Phe Ile Ala Phe Val Val Lys Gly Gly Lys
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-(PEG)2-(PEG)2-(PEG)2-Stearate)

<400> SEQUENCE: 235
```

```
His Xaa Glu Gly Ser Phe Thr Ser Asp Val Ser Ser Phe Leu Glu Gly
1               5                   10                  15

Glu Ala Ala Lys Glu Phe Ile Ala Phe Val Val Lys Gly Gly Lys
            20                  25                  30
```

<210> SEQ ID NO 236  
<211> LENGTH: 30  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<221> NAME/KEY: MOD_RES  
<222> LOCATION: (2)..(2)  
<223> OTHER INFORMATION: Aib  
<220> FEATURE:  
<221> NAME/KEY: MOD_RES  
<222> LOCATION: (12)..(12)  
<223> OTHER INFORMATION: Lys(Epsilon-(PEG)2-(PEG)2-gammaGlu-Lauroyl)  
<220> FEATURE:  
<221> NAME/KEY: MOD_RES  
<222> LOCATION: (24)..(24)  
<223> OTHER INFORMATION: Lys(Epsilon-(PEG)2-(PEG)2-gammaGlu-Lauroyl)

<400> SEQUENCE: 236

```
His Xaa Glu Gly Thr Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30
```

<210> SEQ ID NO 237  
<211> LENGTH: 30  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<221> NAME/KEY: MOD_RES  
<222> LOCATION: (2)..(2)  
<223> OTHER INFORMATION: Aib  
<220> FEATURE:  
<221> NAME/KEY: MOD_RES  
<222> LOCATION: (12)..(12)  
<223> OTHER INFORMATION: Lys(Epsilon-(PEG)2-(PEG)2-gammaGlu-Lauroyl)  
<220> FEATURE:  
<221> NAME/KEY: MOD_RES  
<222> LOCATION: (24)..(24)  
<223> OTHER INFORMATION: Lys(Epsilon-(PEG)2-(PEG)2-gammaGlu-Lauroyl)

<400> SEQUENCE: 237

```
His Xaa Glu Gly Thr Phe Thr Ser Asp Val Ser Lys Phe Leu Glu Gly
1               5                   10                  15

Glu Ala Ala Glu Glu Phe Ile Lys Trp Val Val Glu Gly Gly
            20                  25                  30
```

<210> SEQ ID NO 238  
<211> LENGTH: 30  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<221> NAME/KEY: MOD_RES  
<222> LOCATION: (2)..(2)  
<223> OTHER INFORMATION: Aib  
<220> FEATURE:  
<221> NAME/KEY: MOD_RES

```
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 238

His Xaa Glu Gly Thr Phe Thr Ser Asp Val Ser Lys Tyr Leu Glu Gly
1               5                   10                  15

Glu Ala Ala Glu Glu Phe Ile Lys Phe Val Val Glu Gly Gly
            20                  25                  30

<210> SEQ ID NO 239
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 239

His Xaa Glu Gly Thr Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 240
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 240

His Xaa Glu Gly Ser Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30

<210> SEQ ID NO 241
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 241

His Xaa Glu Gly Ser Phe Thr Ser Asp Val Ser Lys Phe Leu Glu Gly
1               5                   10                  15
Glu Ala Ala Glu Glu Phe Ile Lys Phe Val Val Glu Gly Gly
            20                  25                  30

<210> SEQ ID NO 242
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 242

His Xaa Glu Gly Thr Phe Thr Ser Asp Val Ser Lys Tyr Leu Glu Gly
1               5                   10                  15
Glu Ala Ala Glu Glu Phe Ile Lys Trp Val Val Glu Gly Gly
            20                  25                  30

<210> SEQ ID NO 243
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
```

<223> OTHER INFORMATION: Lys(Epsilon-(PEG)2-(PEG)2-gammaGlu-Palmitate)

<400> SEQUENCE: 243

His Xaa Glu Gly Thr Phe Thr Ser Asp Val Ser Lys Phe Leu Glu Gly
1               5                   10                  15

Glu Ala Ala Glu Glu Phe Ile Lys Trp Val Val Glu Gly Gly
            20                  25                  30

<210> SEQ ID NO 244
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 244

His Xaa Glu Gly Thr Phe Thr Ser Asp Val Ser Lys Tyr Leu Glu Gly
1               5                   10                  15

Glu Ala Ala Glu Glu Phe Ile Lys Phe Val Val Glu Gly Gly
            20                  25                  30

<210> SEQ ID NO 245
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 245

His Xaa Glu Gly Thr Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 246

His Xaa Glu Gly Ser Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30

<210> SEQ ID NO 247
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 247

His Xaa Glu Gly Ser Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 248
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
```

```
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 248

His Xaa Glu Gly Ser Phe Thr Ser Asp Val Ser Lys Phe Leu Glu Gly
1               5                   10                  15

Glu Ala Ala Lys Glu Phe Ile Lys Phe Val Val Glu Gly Gly
            20                  25                  30

<210> SEQ ID NO 249
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 249

His Xaa Glu Gly Ser Phe Thr Ser Asp Val Ser Lys Tyr Leu Glu Gly
1               5                   10                  15

Glu Ala Ala Lys Glu Phe Ile Lys Trp Val Val Glu Gly Gly
            20                  25                  30

<210> SEQ ID NO 250
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)
```

-continued

<400> SEQUENCE: 250

His Xaa Glu Gly Ser Phe Thr Ser Asp Val Ser Lys Phe Leu Glu Gly
1               5                   10                  15

Glu Ala Ala Lys Glu Phe Ile Lys Phe Val Val Glu Gly Gly
            20                  25                  30

<210> SEQ ID NO 251
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 251

His Xaa Glu Gly Ser Phe Thr Ser Asp Val Ser Lys Tyr Leu Glu Gly
1               5                   10                  15

Glu Ala Ala Lys Glu Phe Ile Lys Trp Val Val Glu Gly Gly
            20                  25                  30

<210> SEQ ID NO 252
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 252

His Xaa Glu Gly Ser Phe Thr Ser Asp Val Ser Lys Tyr Leu Glu Gly
1               5                   10                  15

Glu Ala Ala Lys Glu Phe Ile Ala Lys Val Val Glu Gly Gly
            20                  25                  30

<210> SEQ ID NO 253
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 253

His Xaa Glu Gly Ser Phe Thr Ser Asp Val Ser Lys Tyr Leu Glu Gly
1               5                   10                  15

Glu Ala Ala Lys Glu Phe Ile Ala Trp Lys Val Glu Gly Gly
            20                  25                  30

<210> SEQ ID NO 254
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 254

His Xaa Glu Gly Ser Phe Thr Ser Asp Val Ser Lys Tyr Leu Glu Gly
1               5                   10                  15

Glu Ala Ala Lys Glu Phe Ile Ala Lys Val Val Glu Gly Gly
            20                  25                  30

<210> SEQ ID NO 255

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 255

His Xaa Glu Gly Ser Phe Thr Ser Asp Val Ser Lys Tyr Leu Glu Gly
1               5                   10                  15
Glu Ala Ala Lys Glu Phe Ile Ala Trp Lys Val Glu Gly Gly
            20                  25                  30

<210> SEQ ID NO 256
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 256

His Xaa Glu Gly Ser Phe Thr Ser Asp Lys Ser Tyr Leu Glu Gly
1               5                   10                  15
Glu Ala Ala Lys Glu Phe Ile Lys Trp Val Val Glu Gly Gly
            20                  25                  30

<210> SEQ ID NO 257
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
         polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 257

His Xaa Glu Gly Ser Phe Thr Ser Asp Lys Ser Ser Tyr Leu Glu Gly
1               5                   10                  15

Glu Ala Ala Lys Glu Phe Ile Ala Lys Val Val Glu Gly Gly
            20                  25                  30

<210> SEQ ID NO 258
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 258

His Xaa Glu Gly Ser Phe Thr Ser Asp Lys Ser Ser Tyr Leu Glu Gly
1               5                   10                  15

Glu Ala Ala Lys Glu Phe Ile Ala Trp Lys Val Glu Gly Gly
            20                  25                  30

<210> SEQ ID NO 259
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 259

His Xaa Glu Gly Ser Phe Thr Ser Asp Lys Ser Ser Tyr Leu Glu Gly
1               5                   10                  15

Glu Ala Ala Lys Glu Phe Ile Lys Trp Val Val Glu Gly Gly
            20                  25                  30

<210> SEQ ID NO 260
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 260

His Xaa Glu Gly Ser Phe Thr Ser Asp Lys Ser Ser Tyr Leu Glu Gly
1               5                   10                  15

Glu Ala Ala Lys Glu Phe Ile Ala Lys Val Val Glu Gly Gly
            20                  25                  30

<210> SEQ ID NO 261
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
```

```
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 261

His Xaa Glu Gly Ser Phe Thr Ser Asp Lys Ser Ser Tyr Leu Glu Gly
1               5                   10                  15

Glu Ala Ala Lys Glu Phe Ile Ala Trp Lys Val Glu Gly Gly
            20                  25                  30

<210> SEQ ID NO 262
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 262

His Xaa Glu Gly Ser Phe Thr Ser Asp Val Ser Ser Lys Leu Glu Gly
1               5                   10                  15

Glu Ala Ala Lys Glu Phe Ile Lys Trp Val Val Glu Gly Gly
            20                  25                  30

<210> SEQ ID NO 263
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
```

```
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 263

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 264

His Xaa Glu Gly Ser Phe Thr Ser Asp Val Ser Ser Lys Leu Glu Gly
1               5                   10                  15

Glu Ala Ala Lys Glu Phe Ile Ala Trp Lys Val Glu Gly Gly
            20                  25                  30

<210> SEQ ID NO 265
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
```

```
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 265

His Xaa Glu Gly Ser Phe Thr Ser Asp Val Ser Ser Lys Leu Glu Gly
 1               5                  10                  15
Glu Ala Ala Lys Glu Phe Ile Lys Trp Val Val Glu Gly Gly
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 266

His Xaa Glu Gly Ser Phe Thr Ser Asp Val Ser Ser Lys Leu Glu Gly
 1               5                  10                  15
Glu Ala Ala Lys Glu Phe Ile Ala Lys Val Val Glu Gly Gly
            20                  25                  30

<210> SEQ ID NO 267
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 267

His Xaa Glu Gly Ser Phe Thr Ser Asp Val Ser Ser Lys Leu Glu Gly
1               5                   10                  15
Glu Ala Ala Lys Glu Phe Ile Ala Trp Lys Val Glu Gly Gly
            20                  25                  30

<210> SEQ ID NO 268
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 268

His Xaa Glu Gly Ser Phe Thr Ser Asp Val Ser Ser Tyr Lys Glu Gly
1               5                   10                  15
Glu Ala Ala Lys Glu Phe Ile Lys Trp Val Val Glu Gly Gly
            20                  25                  30

<210> SEQ ID NO 269
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 269

His Xaa Glu Gly Ser Phe Thr Ser Asp Val Ser Ser Tyr Lys Glu Gly
1               5                   10                  15
Glu Ala Ala Lys Glu Phe Ile Ala Lys Val Val Glu Gly Gly
            20                  25                  30

<210> SEQ ID NO 270
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 270

His Xaa Glu Gly Ser Phe Thr Ser Asp Val Ser Ser Tyr Lys Glu Gly
1               5                   10                  15
Glu Ala Ala Lys Glu Phe Ile Ala Trp Lys Val Glu Gly Gly
            20                  25                  30

<210> SEQ ID NO 271
<211> LENGTH: 30
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 271

His Xaa Glu Gly Ser Phe Thr Ser Asp Val Ser Ser Tyr Lys Glu Gly
1               5                   10                  15

Glu Ala Ala Lys Glu Phe Ile Lys Trp Val Val Glu Gly Gly
            20                  25                  30

<210> SEQ ID NO 272
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 272

His Xaa Glu Gly Ser Phe Thr Ser Asp Val Ser Ser Tyr Lys Glu Gly
1               5                   10                  15

Glu Ala Ala Lys Glu Phe Ile Ala Lys Val Val Glu Gly Gly
            20                  25                  30

<210> SEQ ID NO 273
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 273

His Xaa Glu Gly Ser Phe Thr Ser Asp Val Ser Ser Tyr Lys Glu Gly
1               5                   10                  15

Glu Ala Ala Lys Glu Phe Ile Ala Trp Lys Val Glu Gly Gly
            20                  25                  30

<210> SEQ ID NO 274
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 274

His Xaa Glu Gly Ser Phe Thr Ser Asp Val Ser Lys Tyr Leu Glu Gly
1               5                   10                  15

Glu Ala Ala Glu Glu Phe Ile Ala Lys Val Val Glu Gly Gly
            20                  25                  30

<210> SEQ ID NO 275
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 275

His Xaa Glu Gly Ser Phe Thr Ser Asp Val Ser Lys Tyr Leu Glu Gly
 1               5                  10                  15

Glu Ala Ala Glu Glu Phe Ile Ala Trp Lys Val Glu Gly Gly
            20                  25                  30

<210> SEQ ID NO 276
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 276

His Xaa Glu Gly Ser Phe Thr Ser Asp Val Ser Lys Tyr Leu Glu Gly
 1               5                  10                  15

Glu Ala Ala Glu Glu Phe Ile Ala Lys Val Val Glu Gly Gly
            20                  25                  30

<210> SEQ ID NO 277
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
```

```
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 277

His Xaa Glu Gly Ser Phe Thr Ser Asp Val Ser Lys Tyr Leu Glu Gly
1               5                   10                  15

Glu Ala Ala Glu Glu Phe Ile Ala Trp Lys Val Glu Gly Gly
            20                  25                  30

<210> SEQ ID NO 278
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 278

His Xaa Glu Gly Ser Phe Thr Ser Asp Lys Ser Tyr Leu Glu Gly
1               5                   10                  15

Glu Ala Ala Glu Glu Phe Ile Lys Trp Val Val Glu Gly Gly
            20                  25                  30

<210> SEQ ID NO 279
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 279

His Xaa Glu Gly Ser Phe Thr Ser Asp Lys Ser Ser Tyr Leu Glu Gly
1               5                   10                  15

Glu Ala Ala Glu Glu Phe Ile Ala Lys Val Val Glu Gly Gly
            20                  25                  30
```

```
<210> SEQ ID NO 280
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 280

His Xaa Glu Gly Ser Phe Thr Ser Asp Lys Ser Ser Tyr Leu Glu Gly
1               5                  10                  15

Glu Ala Ala Glu Glu Phe Ile Ala Trp Lys Val Glu Gly Gly
            20                  25                  30

<210> SEQ ID NO 281
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 281

His Xaa Glu Gly Ser Phe Thr Ser Asp Lys Ser Ser Tyr Leu Glu Gly
1               5                  10                  15

Glu Ala Ala Glu Glu Phe Ile Lys Trp Val Val Glu Gly Gly
            20                  25                  30

<210> SEQ ID NO 282
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 282

His Xaa Glu Gly Ser Phe Thr Ser Asp Lys Ser Ser Tyr Leu Glu Gly
 1               5                  10                  15

Glu Ala Ala Glu Glu Phe Ile Ala Lys Val Val Glu Gly Gly
            20                  25                  30

<210> SEQ ID NO 283
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 283

His Xaa Glu Gly Ser Phe Thr Ser Asp Lys Ser Ser Tyr Leu Glu Gly
 1               5                  10                  15

Glu Ala Ala Glu Glu Phe Ile Ala Trp Lys Val Glu Gly Gly
            20                  25                  30

<210> SEQ ID NO 284
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
```

```
<223> OTHER INFORMATION: Lys(Epsilon-(PEG)2-(PEG)2-gammaGlu-Lauroyl)

<400> SEQUENCE: 284

His Xaa Glu Gly Ser Phe Thr Ser Asp Val Ser Ser Lys Leu Glu Gly
1               5                   10                  15

Glu Ala Ala Glu Glu Phe Ile Lys Trp Val Val Glu Gly Gly
            20                  25                  30

<210> SEQ ID NO 285
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 285

His Xaa Glu Gly Ser Phe Thr Ser Asp Val Ser Ser Lys Leu Glu Gly
1               5                   10                  15

Glu Ala Ala Glu Glu Phe Ile Ala Lys Val Val Glu Gly Gly
            20                  25                  30

<210> SEQ ID NO 286
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 286

His Xaa Glu Gly Ser Phe Thr Ser Asp Val Ser Ser Lys Leu Glu Gly
```

```
                1               5                  10                  15
Glu Ala Ala Glu Glu Phe Ile Ala Trp Lys Val Glu Gly Gly
            20                  25                  30

<210> SEQ ID NO 287
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 287

His Xaa Glu Gly Ser Phe Thr Ser Asp Val Ser Ser Lys Leu Glu Gly
1               5                   10                  15

Glu Ala Ala Glu Glu Phe Ile Lys Trp Val Val Glu Gly Gly
            20                  25                  30

<210> SEQ ID NO 288
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 288

His Xaa Glu Gly Ser Phe Thr Ser Asp Val Ser Ser Lys Leu Glu Gly
1               5                   10                  15

Glu Ala Ala Glu Glu Phe Ile Ala Lys Val Val Glu Gly Gly
            20                  25                  30
```

```
<210> SEQ ID NO 289
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 289

His Xaa Glu Gly Ser Phe Thr Ser Asp Val Ser Ser Lys Leu Glu Gly
1               5                   10                  15

Glu Ala Ala Glu Glu Phe Ile Ala Trp Lys Val Glu Gly Gly
            20                  25                  30

<210> SEQ ID NO 290
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 290

His Xaa Glu Gly Ser Phe Thr Ser Asp Val Ser Ser Tyr Lys Glu Gly
1               5                   10                  15

Glu Ala Ala Glu Glu Phe Ile Lys Trp Val Val Glu Gly Gly
            20                  25                  30

<210> SEQ ID NO 291
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 291

His Xaa Glu Gly Ser Phe Thr Ser Asp Val Ser Ser Tyr Lys Glu Gly
1               5                   10                  15
Glu Ala Ala Glu Glu Phe Ile Ala Lys Val Val Glu Gly Gly
            20                  25                  30

<210> SEQ ID NO 292
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 292

His Xaa Glu Gly Ser Phe Thr Ser Asp Val Ser Ser Tyr Lys Glu Gly
1               5                   10                  15
Glu Ala Ala Glu Glu Phe Ile Ala Trp Lys Val Glu Gly Gly
            20                  25                  30

<210> SEQ ID NO 293
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 293

His Xaa Glu Gly Ser Phe Thr Ser Asp Val Ser Ser Tyr Lys Glu Gly
1               5                   10                  15

Glu Ala Ala Glu Glu Phe Ile Lys Trp Val Val Glu Gly Gly
            20                  25                  30

<210> SEQ ID NO 294
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 294

His Xaa Glu Gly Ser Phe Thr Ser Asp Val Ser Ser Tyr Lys Glu Gly
1               5                   10                  15

Glu Ala Ala Glu Glu Phe Ile Ala Lys Val Val Glu Gly Gly
            20                  25                  30

<210> SEQ ID NO 295
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
```

```
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 295

His Xaa Glu Gly Ser Phe Thr Ser Asp Val Ser Ser Tyr Lys Glu Gly
1               5                   10                  15

Glu Ala Ala Glu Glu Phe Ile Ala Trp Lys Val Glu Gly Gly
            20                  25                  30

<210> SEQ ID NO 296
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Myristoyl)

<400> SEQUENCE: 296

His Xaa Glu Gly Ser Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30

<210> SEQ ID NO 297
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitoyl)
```

<400> SEQUENCE: 297

His Xaa Glu Gly Ser Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30

<210> SEQ ID NO 298
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearoyl)

<400> SEQUENCE: 298

His Xaa Glu Gly Ser Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30

<210> SEQ ID NO 299
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 299

His Xaa Glu Gly Ser Phe Thr Ser Asp Val Ser Lys Tyr Leu Glu Gly
1               5                   10                  15

Glu Ala Ala Glu Glu Phe Ile Lys Trp Val Val Glu Gly Gly
            20                  25                  30

<210> SEQ ID NO 300
<211> LENGTH: 30
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Myristoyl)

<400> SEQUENCE: 300

His Xaa Glu Gly Ser Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 301
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitoyl)

<400> SEQUENCE: 301

His Xaa Glu Gly Ser Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 302
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
```

```
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearoyl)

<400> SEQUENCE: 302

His Xaa Glu Gly Ser Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 303
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 303

His Xaa Glu Gly Ser Phe Thr Ser Asp Val Ser Lys Phe Leu Glu Gly
1               5                   10                  15

Glu Ala Ala Glu Glu Phe Ile Lys Phe Val Val Glu Gly Gly
            20                  25                  30

<210> SEQ ID NO 304
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Myristoyl)

<400> SEQUENCE: 304
```

-continued

His Xaa Glu Gly Ser Phe Thr Ser Asp Val Ser Lys Tyr Leu Glu Gly
1               5                   10                  15

Glu Ala Ala Lys Glu Phe Ile Lys Trp Val Val Glu Gly Gly
            20                  25                  30

<210> SEQ ID NO 305
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitoyl)

<400> SEQUENCE: 305

His Xaa Glu Gly Ser Phe Thr Ser Asp Val Ser Lys Tyr Leu Glu Gly
1               5                   10                  15

Glu Ala Ala Lys Glu Phe Ile Lys Trp Val Val Glu Gly Gly
            20                  25                  30

<210> SEQ ID NO 306
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearoyl)

<400> SEQUENCE: 306

His Xaa Glu Gly Ser Phe Thr Ser Asp Val Ser Lys Tyr Leu Glu Gly
1               5                   10                  15

Glu Ala Ala Lys Glu Phe Ile Lys Trp Val Val Glu Gly Gly

<210> SEQ ID NO 307
<211> LENGTH: 30
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 307

His Xaa Glu Gly Ser Phe Thr Ser Asp Val Ser Lys Tyr Leu Glu Gly
1               5                   10                  15

Glu Ala Ala Lys Glu Phe Ile Lys Trp Val Val Glu Gly Gly
            20                  25                  30

<210> SEQ ID NO 308
<211> LENGTH: 30
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Myristoyl)

<400> SEQUENCE: 308

His Xaa Glu Gly Ser Phe Thr Ser Asp Val Ser Lys Phe Leu Glu Gly
1               5                   10                  15

Glu Ala Ala Lys Glu Phe Ile Lys Phe Val Val Glu Gly Gly
            20                  25                  30

<210> SEQ ID NO 309
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitoyl)

<400> SEQUENCE: 309

His Xaa Glu Gly Ser Phe Thr Ser Asp Val Ser Lys Phe Leu Glu Gly
1               5                   10                  15

Glu Ala Ala Lys Glu Phe Ile Lys Phe Val Val Glu Gly Gly
            20                  25                  30

<210> SEQ ID NO 310
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearoyl)

<400> SEQUENCE: 310

His Xaa Glu Gly Ser Phe Thr Ser Asp Val Ser Lys Phe Leu Glu Gly
1               5                   10                  15

Glu Ala Ala Lys Glu Phe Ile Lys Phe Val Val Glu Gly Gly
            20                  25                  30

<210> SEQ ID NO 311
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 311

His Xaa Glu Gly Ser Phe Thr Ser Asp Val Ser Lys Phe Leu Glu Gly
1               5                   10                  15

Glu Ala Ala Lys Glu Phe Ile Lys Phe Val Val Glu Gly Gly
            20                  25                  30

<210> SEQ ID NO 312
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 312

His Xaa Glu Gly Ser Phe Thr Ser Asp Val Ser Lys Phe Leu Glu Gly
1               5                   10                  15

Glu Ala Ala Xaa Glu Phe Ile Lys Phe Val Val Glu Gly Gly
            20                  25                  30

<210> SEQ ID NO 313
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
```

```
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 313

His Xaa Glu Gly Ser Phe Thr Ser Asp Val Ser Lys Tyr Leu Glu Gly
1               5                   10                  15

Glu Ala Ala Xaa Glu Phe Ile Lys Trp Val Val Glu Gly Gly
            20                  25                  30

<210> SEQ ID NO 314
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 314

His Xaa Glu Gly Ser Phe Thr Ser Asp Val Ser Lys Phe Leu Glu Gly
1               5                   10                  15

Glu Ala Ala Xaa Glu Phe Ile Lys Phe Val Val Glu Gly Gly
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
```

-continued

```
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 315

His Xaa Glu Gly Ser Phe Thr Ser Asp Val Ser Lys Tyr Leu Glu Gly
1               5                   10                  15

Glu Ala Ala Xaa Glu Phe Ile Lys Trp Val Val Glu Gly Gly
            20                  25                  30

<210> SEQ ID NO 316
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 316

His Xaa Glu Gly Ser Phe Thr Ser Asp Val Ser Lys Tyr Leu Glu Gly
1               5                   10                  15

Glu Ala Ala Xaa Glu Phe Ile Ala Lys Val Val Glu Gly Gly
            20                  25                  30

<210> SEQ ID NO 317
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
```

<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 317

His Xaa Glu Gly Ser Phe Thr Ser Asp Val Ser Lys Tyr Leu Glu Gly
1               5                   10                  15

Glu Ala Ala Xaa Glu Phe Ile Ala Trp Lys Val Glu Gly Gly
            20                  25                  30

<210> SEQ ID NO 318
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 318

His Xaa Glu Gly Ser Phe Thr Ser Asp Val Ser Lys Tyr Leu Glu Gly
1               5                   10                  15

Glu Ala Ala Xaa Glu Phe Ile Ala Lys Val Val Glu Gly Gly
            20                  25                  30

<210> SEQ ID NO 319
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 319

His Xaa Glu Gly Ser Phe Thr Ser Asp Val Ser Lys Tyr Leu Glu Gly
1               5                   10                  15

Glu Ala Ala Xaa Glu Phe Ile Ala Trp Lys Val Glu Gly Gly
            20                  25                  30

<210> SEQ ID NO 320
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 320

His Xaa Glu Gly Ser Phe Thr Ser Asp Lys Ser Ser Tyr Leu Glu Gly
1               5                   10                  15

Glu Ala Ala Xaa Glu Phe Ile Lys Trp Val Val Glu Gly Gly
            20                  25                  30

<210> SEQ ID NO 321
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 321

His Xaa Glu Gly Ser Phe Thr Ser Asp Lys Ser Ser Tyr Leu Glu Gly
1               5                   10                  15

```
Glu Ala Ala Xaa Glu Phe Ile Ala Lys Val Val Glu Gly Gly
            20                  25              30
```

<210> SEQ ID NO 322
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 322

```
His Xaa Glu Gly Ser Phe Thr Ser Asp Lys Ser Ser Tyr Leu Glu Gly
1               5                   10                  15

Glu Ala Ala Xaa Glu Phe Ile Ala Trp Lys Val Glu Gly Gly
            20                  25              30
```

<210> SEQ ID NO 323
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 323

```
His Xaa Glu Gly Ser Phe Thr Ser Asp Lys Ser Ser Tyr Leu Glu Gly
1               5                   10                  15

Glu Ala Ala Xaa Glu Phe Ile Lys Trp Val Val Glu Gly Gly
            20                  25              30
```

```
<210> SEQ ID NO 324
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 324

His Xaa Glu Gly Ser Phe Thr Ser Asp Lys Ser Ser Tyr Leu Glu Gly
1               5                   10                  15

Glu Ala Ala Xaa Glu Phe Ile Ala Lys Val Val Glu Gly Gly
            20                  25                  30

<210> SEQ ID NO 325
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 325

His Xaa Glu Gly Ser Phe Thr Ser Asp Lys Ser Ser Tyr Leu Glu Gly
1               5                   10                  15

Glu Ala Ala Xaa Glu Phe Ile Ala Trp Lys Val Glu Gly Gly
            20                  25                  30

<210> SEQ ID NO 326
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 326

His Xaa Glu Gly Ser Phe Thr Ser Asp Val Ser Ser Lys Leu Glu Gly
1               5                   10                  15

Glu Ala Ala Xaa Glu Phe Ile Lys Trp Val Val Glu Gly Gly
            20                  25                  30

<210> SEQ ID NO 327
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 327

His Xaa Glu Gly Ser Phe Thr Ser Asp Val Ser Ser Lys Leu Glu Gly
1               5                   10                  15

Glu Ala Ala Xaa Glu Phe Ile Ala Lys Val Val Glu Gly Gly
            20                  25                  30

<210> SEQ ID NO 328
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 328

His Xaa Glu Gly Ser Phe Thr Ser Asp Val Ser Ser Lys Leu Glu Gly
1               5                   10                  15

Glu Ala Ala Xaa Glu Phe Ile Ala Trp Lys Val Glu Gly Gly
            20                  25                  30

<210> SEQ ID NO 329
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 329

His Xaa Glu Gly Ser Phe Thr Ser Asp Val Ser Ser Lys Leu Glu Gly
1               5                   10                  15

Glu Ala Ala Xaa Glu Phe Ile Lys Trp Val Val Glu Gly Gly
            20                  25                  30
```

```
<210> SEQ ID NO 330
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 330

His Xaa Glu Gly Ser Phe Thr Ser Asp Val Ser Ser Lys Leu Glu Gly
1               5                   10                  15

Glu Ala Ala Xaa Glu Phe Ile Ala Lys Val Val Glu Gly Gly
            20                  25                  30

<210> SEQ ID NO 331
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 331

His Xaa Glu Gly Ser Phe Thr Ser Asp Val Ser Ser Lys Leu Glu Gly
1               5                   10                  15
```

Glu Ala Ala Xaa Glu Phe Ile Ala Trp Lys Val Glu Gly Gly
            20                  25                  30

<210> SEQ ID NO 332
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 332

His Xaa Glu Gly Ser Phe Thr Ser Asp Val Ser Ser Tyr Lys Glu Gly
1               5                   10                  15

Glu Ala Ala Xaa Glu Phe Ile Lys Trp Val Val Glu Gly Gly
            20                  25                  30

<210> SEQ ID NO 333
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 333

His Xaa Glu Gly Ser Phe Thr Ser Asp Val Ser Ser Tyr Lys Glu Gly
1               5                   10                  15

Glu Ala Ala Xaa Glu Phe Ile Ala Lys Val Val Glu Gly Gly
            20                  25                  30

<210> SEQ ID NO 334
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 334

His Xaa Glu Gly Ser Phe Thr Ser Asp Val Ser Ser Tyr Lys Glu Gly
1               5                   10                  15

Glu Ala Ala Xaa Glu Phe Ile Ala Trp Lys Val Glu Gly Gly
            20                  25                  30

<210> SEQ ID NO 335
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitate)

<400> SEQUENCE: 335

His Xaa Glu Gly Ser Phe Thr Ser Asp Val Ser Ser Tyr Lys Glu Gly
1               5                   10                  15

Glu Ala Ala Xaa Glu Phe Ile Lys Trp Val Val Glu Gly Gly
            20                  25                  30

<210> SEQ ID NO 336
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 336

His Xaa Glu Gly Ser Phe Thr Ser Asp Val Ser Ser Tyr Lys Glu Gly
1               5                   10                  15

Glu Ala Ala Xaa Glu Phe Ile Ala Lys Val Val Glu Gly Gly
            20                  25                  30

<210> SEQ ID NO 337
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: Aib
<220> FEATURE:

-continued

```
<221> NAME/KEY: MOD_RES
<222> LOCATION: (26)..(26)
<223> OTHER INFORMATION: Lys(Epsilon-(PEG)2-(PEG)2-gammaGlu-Palmitate)

<400> SEQUENCE: 337
```

His Xaa Glu Gly Ser Phe Thr Ser Asp Val Ser Ser Tyr Lys Glu Gly
1               5                   10                  15

Glu Ala Ala Xaa Glu Phe Ile Ala Trp Lys Val Glu Gly Gly
            20                  25                  30

```
<210> SEQ ID NO 338
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Myristoyl)

<400> SEQUENCE: 338
```

His Xaa Glu Gly Ser Phe Thr Ser Asp Val Ser Lys Tyr Leu Glu Gly
1               5                   10                  15

Glu Ala Ala Xaa Glu Phe Ile Lys Trp Val Val Glu Gly Gly
            20                  25                  30

```
<210> SEQ ID NO 339
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitoyl)

<400> SEQUENCE: 339
```

-continued

```
His Xaa Glu Gly Ser Phe Thr Ser Asp Val Ser Lys Tyr Leu Glu Gly
1               5                   10                  15

Glu Ala Ala Xaa Glu Phe Ile Lys Trp Val Val Glu Gly Gly
            20                  25                  30

<210> SEQ ID NO 340
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearoyl)

<400> SEQUENCE: 340

His Xaa Glu Gly Ser Phe Thr Ser Asp Val Ser Lys Tyr Leu Glu Gly
1               5                   10                  15

Glu Ala Ala Xaa Glu Phe Ile Lys Trp Val Val Glu Gly Gly
            20                  25                  30

<210> SEQ ID NO 341
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 341

His Xaa Glu Gly Ser Phe Thr Ser Asp Val Ser Lys Tyr Leu Glu Gly
1               5                   10                  15

Glu Ala Ala Xaa Glu Phe Ile Lys Trp Val Val Glu Gly Gly
```

```
                    20                  25                  30
```

<210> SEQ ID NO 342
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Myristoyl)

<400> SEQUENCE: 342

```
His Xaa Glu Gly Ser Phe Thr Ser Asp Val Ser Lys Phe Leu Glu Gly
1               5                   10                  15

Glu Ala Ala Xaa Glu Phe Ile Lys Phe Val Val Glu Gly Gly
            20                  25                  30
```

<210> SEQ ID NO 343
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Palmitoyl)

<400> SEQUENCE: 343

```
His Xaa Glu Gly Ser Phe Thr Ser Asp Val Ser Lys Phe Leu Glu Gly
1               5                   10                  15

Glu Ala Ala Xaa Glu Phe Ile Lys Phe Val Val Glu Gly Gly
            20                  25                  30
```

<210> SEQ ID NO 344
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearoyl)

<400> SEQUENCE: 344

His Xaa Glu Gly Ser Phe Thr Ser Asp Val Ser Lys Phe Leu Glu Gly
1               5                   10                  15

Glu Ala Ala Xaa Glu Phe Ile Lys Phe Val Val Glu Gly Gly
            20                  25                  30

<210> SEQ ID NO 345
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Stearate)

<400> SEQUENCE: 345

His Xaa Glu Gly Ser Phe Thr Ser Asp Val Ser Lys Phe Leu Glu Gly
1               5                   10                  15

Glu Ala Ala Xaa Glu Phe Ile Lys Phe Val Val Glu Gly Gly
            20                  25                  30

<210> SEQ ID NO 346
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 346

His Xaa Glu Gly Ser Phe Thr Ser Asp Val Ser Lys Tyr Leu Glu Gly
 1               5                  10                  15

Glu Ala Ala Glu Glu Phe Ile Ala Lys Val Val Glu Gly Gly
            20                  25                  30

<210> SEQ ID NO 347
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 347

His Xaa Glu Gly Ser Phe Thr Ser Asp Val Ser Lys Tyr Leu Glu Gly
 1               5                  10                  15

Glu Ala Ala Glu Glu Phe Ile Ala Lys Val Val Glu Gly Gly
            20                  25                  30

<210> SEQ ID NO 348
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
```

```
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 348

His Xaa Glu Gly Ser Phe Thr Ser Asp Val Ser Lys Tyr Leu Glu Gly
1               5                   10                  15

Glu Ala Ala Glu Glu Phe Ile Ala Lys Val Val Glu Gly Gly
            20                  25                  30

<210> SEQ ID NO 349
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 349

His Xaa Glu Gly Ser Phe Thr Ser Asp Val Ser Lys Tyr Leu Glu Gly
1               5                   10                  15

Glu Ala Ala Glu Glu Phe Ile Ala Lys Val Val Glu Gly Gly
            20                  25                  30

<210> SEQ ID NO 350
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 350

His Xaa Glu Gly Ser Phe Thr Ser Asp Val Ser Lys Phe Leu Glu Gly
1               5                   10                  15

Glu Ala Ala Glu Glu Phe Ile Ala Lys Val Val Glu Gly Gly
            20                  25                  30
```

```
<210> SEQ ID NO 351
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 351

His Xaa Glu Gly Ser Phe Thr Ser Asp Val Ser Lys Phe Leu Glu Gly
1               5                   10                  15
Glu Ala Ala Glu Glu Phe Ile Ala Lys Val Val Glu Gly Gly
            20                  25                  30

<210> SEQ ID NO 352
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 352

His Xaa Glu Gly Ser Phe Thr Ser Asp Val Ser Lys Phe Leu Glu Gly
1               5                   10                  15
Glu Ala Ala Glu Glu Phe Ile Ala Lys Val Val Glu Gly Gly
            20                  25                  30

<210> SEQ ID NO 353
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 353

His Xaa Glu Gly Ser Phe Thr Ser Asp Val Ser Lys Phe Leu Glu Gly
 1               5                  10                  15

Glu Ala Ala Glu Glu Phe Ile Ala Lys Val Val Glu Gly Gly
             20                  25                  30

<210> SEQ ID NO 354
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 354

His Xaa Glu Gly Ser Phe Thr Ser Asp Val Ser Lys Tyr Leu Glu Gly
 1               5                  10                  15

Glu Ala Ala Lys Glu Phe Ile Ala Lys Val Val Glu Gly Gly
             20                  25                  30

<210> SEQ ID NO 355
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
```

```
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 355

His Xaa Glu Gly Ser Phe Thr Ser Asp Val Ser Lys Tyr Leu Glu Gly
1               5                   10                  15

Glu Ala Ala Lys Glu Phe Ile Ala Lys Val Val Glu Gly Gly
            20                  25                  30

<210> SEQ ID NO 356
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 356

His Xaa Glu Gly Ser Phe Thr Ser Asp Val Ser Lys Tyr Leu Glu Gly
1               5                   10                  15

Glu Ala Ala Lys Glu Phe Ile Ala Lys Val Val Glu Gly Gly
            20                  25                  30

<210> SEQ ID NO 357
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)
```

```
<400> SEQUENCE: 357

His Xaa Glu Gly Ser Phe Thr Ser Asp Val Ser Lys Tyr Leu Glu Gly
1               5                   10                  15

Glu Ala Ala Lys Glu Phe Ile Ala Lys Val Val Glu Gly Gly
            20                  25                  30

<210> SEQ ID NO 358
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 358

His Xaa Glu Gly Ser Phe Thr Ser Asp Val Ser Lys Phe Leu Glu Gly
1               5                   10                  15

Glu Ala Ala Lys Glu Phe Ile Ala Lys Val Val Glu Gly Gly
            20                  25                  30

<210> SEQ ID NO 359
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 359

His Xaa Glu Gly Ser Phe Thr Ser Asp Val Ser Lys Phe Leu Glu Gly
1               5                   10                  15
```

Glu Ala Ala Lys Glu Phe Ile Ala Lys Val Val Glu Gly Gly
            20                  25                  30

<210> SEQ ID NO 360
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 360

His Xaa Glu Gly Ser Phe Thr Ser Asp Val Ser Lys Phe Leu Glu Gly
1               5                   10                  15

Glu Ala Ala Lys Glu Phe Ile Ala Lys Val Val Glu Gly Gly
            20                  25                  30

<210> SEQ ID NO 361
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 361

His Xaa Glu Gly Ser Phe Thr Ser Asp Val Ser Lys Phe Leu Glu Gly
1               5                   10                  15

Glu Ala Ala Lys Glu Phe Ile Ala Lys Val Val Glu Gly Gly
            20                  25                  30

```
<210> SEQ ID NO 362
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 362

His Xaa Glu Gly Ser Phe Thr Ser Asp Val Ser Lys Tyr Leu Glu Gly
1               5                   10                  15

Glu Ala Ala Xaa Glu Phe Ile Ala Lys Val Val Glu Gly Gly
            20                  25                  30

<210> SEQ ID NO 363
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 363

His Xaa Glu Gly Ser Phe Thr Ser Asp Val Ser Lys Tyr Leu Glu Gly
1               5                   10                  15

Glu Ala Ala Xaa Glu Phe Ile Ala Lys Val Val Glu Gly Gly
            20                  25                  30

<210> SEQ ID NO 364
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 364

His Xaa Glu Gly Ser Phe Thr Ser Asp Val Ser Lys Tyr Leu Glu Gly
1               5                   10                  15
Glu Ala Ala Xaa Glu Phe Ile Ala Lys Val Val Glu Gly Gly
            20                  25                  30

<210> SEQ ID NO 365
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 365

His Xaa Glu Gly Ser Phe Thr Ser Asp Val Ser Lys Tyr Leu Glu Gly
1               5                   10                  15
Glu Ala Ala Xaa Glu Phe Ile Ala Lys Val Val Glu Gly Gly
            20                  25                  30

<210> SEQ ID NO 366
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 366

His Xaa Glu Gly Ser Phe Thr Ser Asp Val Ser Lys Phe Leu Glu Gly
1               5                   10                  15

Glu Ala Ala Xaa Glu Phe Ile Ala Lys Val Val Glu Gly Gly
            20                  25                  30

<210> SEQ ID NO 367
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 367

His Xaa Glu Gly Ser Phe Thr Ser Asp Val Ser Lys Phe Leu Glu Gly
1               5                   10                  15

Glu Ala Ala Xaa Glu Phe Ile Ala Lys Val Val Glu Gly Gly
            20                  25                  30

<210> SEQ ID NO 368
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
```

```
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 368

His Xaa Glu Gly Ser Phe Thr Ser Asp Val Ser Lys Phe Leu Glu Gly
1               5                   10                  15

Glu Ala Ala Xaa Glu Phe Ile Ala Lys Val Val Glu Gly Gly
            20                  25                  30

<210> SEQ ID NO 369
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 369

His Xaa Glu Gly Ser Phe Thr Ser Asp Val Ser Lys Phe Leu Glu Gly
1               5                   10                  15

Glu Ala Ala Xaa Glu Phe Ile Ala Lys Val Val Glu Gly Gly
            20                  25                  30

<210> SEQ ID NO 370
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
```

```
<221> NAME/KEY: MOD_RES
<222> LOCATION: (13)..(13)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 370

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 371
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 371

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 372
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
```

```
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 372

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 373
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Laurate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Laurate)

<400> SEQUENCE: 373

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 374
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
```

```
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 374

His Xaa Glu Gly Ser Phe Thr Ser Asp Val Ser Ser Lys Leu Glu Gly
 1               5                  10                  15

Glu Ala Ala Lys Glu Phe Ile Ala Lys Val Val Glu Gly Gly
            20                  25                  30

<210> SEQ ID NO 375
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 375

His Xaa Glu Gly Ser Phe Thr Ser Asp Val Ser Ser Lys Leu Glu Gly
 1               5                  10                  15

Glu Ala Ala Glu Glu Phe Ile Ala Lys Val Val Glu Gly Gly
            20                  25                  30

<210> SEQ ID NO 376
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
```

```
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 376

His Xaa Glu Gly Ser Phe Thr Ser Asp Val Ser Ser Lys Leu Glu Gly
1               5                   10                  15

Glu Ala Ala Glu Glu Phe Ile Ala Lys Val Val Glu Gly Gly
            20                  25                  30

<210> SEQ ID NO 377
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 377

His Xaa Glu Gly Ser Phe Thr Ser Asp Val Ser Ser Lys Leu Glu Gly
1               5                   10                  15

Glu Ala Ala Glu Glu Phe Ile Ala Lys Val Val Glu Gly Gly
            20                  25                  30

<210> SEQ ID NO 378
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
```

```
<221> NAME/KEY: MOD_RES
<222> LOCATION: (13)..(13)
<223> OTHER INFORMATION: Lys(Epsilon-(PEG)2-(PEG)2-gammaGlu-Laurate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Laurate)

<400> SEQUENCE: 378

His Xaa Glu Gly Ser Phe Thr Ser Asp Val Ser Ser Lys Leu Glu Gly
1               5                   10                  15

Glu Ala Ala Glu Glu Phe Ile Ala Lys Val Val Glu Gly Gly
            20                  25                  30

<210> SEQ ID NO 379
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 379

His Xaa Glu Gly Ser Phe Thr Ser Asp Val Ser Ser Lys Leu Glu Gly
1               5                   10                  15

Glu Ala Ala Glu Glu Phe Ile Ala Lys Val Val Glu Gly Gly
            20                  25                  30

<210> SEQ ID NO 380
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Myristoyl)
<220> FEATURE:
<221> NAME/KEY: MOD_RES
```

```
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 380

His Xaa Glu Gly Ser Phe Thr Ser Asp Val Ser Ser Lys Leu Glu Gly
1               5                   10                  15
Glu Ala Ala Xaa Glu Phe Ile Ala Lys Val Val Glu Gly Gly
            20                  25                  30

<210> SEQ ID NO 381
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 381

His Xaa Glu Gly Ser Phe Thr Ser Asp Val Ser Ser Lys Leu Glu Gly
1               5                   10                  15
Glu Ala Ala Xaa Glu Phe Ile Ala Lys Val Val Glu Gly Gly
            20                  25                  30

<210> SEQ ID NO 382
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
```

```
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 382

His Xaa Glu Gly Ser Phe Thr Ser Asp Val Ser Ser Lys Leu Glu Gly
1               5                   10                  15
Glu Ala Ala Xaa Glu Phe Ile Ala Lys Val Val Glu Gly Gly
            20                  25                  30

<210> SEQ ID NO 383
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Laurate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Laurate)

<400> SEQUENCE: 383

His Xaa Glu Gly Ser Phe Thr Ser Asp Val Ser Ser Lys Leu Glu Gly
1               5                   10                  15
Glu Ala Ala Xaa Glu Phe Ile Ala Lys Val Val Glu Gly Gly
            20                  25                  30

<210> SEQ ID NO 384
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
```

-continued

```
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: Aib
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 384

His Xaa Glu Gly Ser Phe Thr Ser Asp Val Ser Ser Lys Leu Glu Gly
 1               5                  10                  15

Glu Ala Ala Xaa Glu Phe Ile Ala Lys Val Val Glu Gly Gly
            20                  25                  30

<210> SEQ ID NO 385
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Lauroyl)

<400> SEQUENCE: 385

His Xaa Glu Gly Ser Phe Thr Ser Asp Val Ser Ser Lys Leu Glu Gly
 1               5                  10                  15

Glu Ala Ala Lys Glu Phe Ile Ala Lys Val Val Glu Gly Gly
            20                  25                  30

<210> SEQ ID NO 386
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
```

```
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Myristoyl)

<400> SEQUENCE: 386

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 387
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Palmitoyl)

<400> SEQUENCE: 387

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 388
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Stearoyl)

<400> SEQUENCE: 388

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 389
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Lauroyl)

<400> SEQUENCE: 389

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 390
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Myristoyl)

<400> SEQUENCE: 390

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 391
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Palmitoyl)

<400> SEQUENCE: 391

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 392
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Stearoyl)

<400> SEQUENCE: 392

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 393
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Lauroyl)

<400> SEQUENCE: 393

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 394
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Myristoyl)

<400> SEQUENCE: 394

His Xaa Glu Gly Ser Phe Thr Ser Asp Val Ser Ser Lys Leu Glu Gly
1               5                   10                  15
Glu Ala Ala Lys Glu Phe Ile Ala Lys Val Val Glu Gly Gly
            20                  25                  30

<210> SEQ ID NO 395
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Palmitoyl)

<400> SEQUENCE: 395

His Xaa Glu Gly Ser Phe Thr Ser Asp Val Ser Ser Lys Leu Glu Gly
1               5                   10                  15
Glu Ala Ala Lys Glu Phe Ile Ala Lys Val Val Glu Gly Gly
            20                  25                  30

<210> SEQ ID NO 396
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES

```
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-gammaGlu-Stearoyl)

<400> SEQUENCE: 396

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 397
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Lauroyl)

<400> SEQUENCE: 397

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 398
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
```

<223> OTHER INFORMATION: Lys(Epsilon-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Myristoyl)

<400> SEQUENCE: 398

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 399
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-gammaGlu-Palmitoyl)

<400> SEQUENCE: 399

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 400
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys -continued

```
<220> FEATURE:
<221> NAME/KEY: MOD_RES
<222> LOCATION: (25)..(25)
<223> OTHER INFORMATION: Lys(Epsilon-(PEG)2-gammaGlu-Stearoyl)

<400> SEQUENCE: 400

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 401
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 401

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 402
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)
```

```
<400> SEQUENCE: 402

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 403
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 403

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 404
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 404

His Xaa Glu Gly Ser Phe Thr Ser Asp Val Ser Ser Lys Leu Glu Gly
1               5                   10                  15
```

Glu Ala Ala Lys Glu Phe Ile Ala Lys Val Val Glu Gly Gly
            20                  25                  30

<210> SEQ ID NO 405
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 405

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 406
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)

```
<223> OTHER INFORMATION: Tyr(OMe)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 406

His Xaa Glu Gly Ser Phe Thr Ser Asp Val Ser Ser Lys Leu Glu Gly
1               5                   10                  15

Glu Ala Ala Lys Glu Tyr Ile Ala Lys Val Val Glu Gly Gly
            20                  25                  30

<210> SEQ ID NO 407
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: Nle
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 407

His Xaa Glu Gly Ser Phe Thr Ser Asp Val Ser Ser Lys Leu Glu Gly
1               5                   10                  15

Glu Ala Ala Lys Glu Xaa Ile Ala Lys Val Val Glu Gly Gly
            20                  25                  30

<210> SEQ ID NO 408
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
```

-continued

```
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristoyl)

<400> SEQUENCE: 408

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 409
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitoyl)

<400> SEQUENCE: 409

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 410
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearoyl)

<400> SEQUENCE: 410

His Xaa Glu Gly Ser Phe Thr Ser Asp Val Ser Ser Lys Leu Glu Gly
1               5                   10                  15
Glu Ala Ala Lys Glu Phe Ile Ala Lys Val Val Glu Gly Gly
            20                  25                  30

<210> SEQ ID NO 411
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Laurate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Laurate)

<400> SEQUENCE: 411

His Xaa Glu Gly Ser Phe Thr Ser Asp Val Ser Ser Lys Leu Glu Gly
1               5                   10                  15
Glu Ala Ala Lys Glu Phe Ile Ala Lys Val Val Glu Gly Gly
```

<210> SEQ ID NO 412
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Myristate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Myristate)

<400> SEQUENCE: 412

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 413
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe

```
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Palmitate)

<400> SEQUENCE: 413

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 414
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Stearate)

<400> SEQUENCE: 414

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 415
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
```

```
<221> NAME/KEY: MOD_RES
<222> LOCATION: (13)..(13)
<223> OTHER INFORMATION: Lys(Epsilon-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Lauroyl)

<400> SEQUENCE: 415

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 416
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Myristoyl)

<400> SEQUENCE: 416

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 417
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Palmitoyl)

<400> SEQUENCE: 417

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 418
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Stearoyl)

<400> SEQUENCE: 418

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30
```

```
<210> SEQ ID NO 419
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Laurate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Laurate)

<400> SEQUENCE: 419

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 420
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Myristate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
```

```
<221> NAME/KEY: MOD_RES
<222> LOCATION: (25)..(25)
<223> OTHER INFORMATION: Lys(Epsilon-(PEG)2-gammaGlu-Myristate)

<400> SEQUENCE: 420

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 421
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Palmitate)

<400> SEQUENCE: 421

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 422
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
```

<222> LOCATION: (13)..(13)
<223> OTHER INFORMATION: Lys(Epsilon-(PEG)2-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-(PEG)2-gammaGlu-Stearate)

<400> SEQUENCE: 422

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 423
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Lauroyl)

<400> SEQUENCE: 423

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 424
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Myristoyl)

<400> SEQUENCE: 424

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 425
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Palmitoyl)

<400> SEQUENCE: 425

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30
```

```
<210> SEQ ID NO 426
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Stearoyl)

<400> SEQUENCE: 426

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 427
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Laurate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
```

<222> LOCATION: (25)..(25)
<223> OTHER INFORMATION: Lys(Epsilon-gammaGlu-Laurate)

<400> SEQUENCE: 427

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 428
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Myristate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Myristate)

<400> SEQUENCE: 428

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 429
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)

```
<223> OTHER INFORMATION: Lys(Epsilon-gammaGlu-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Palmitate)

<400> SEQUENCE: 429

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 430
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-gammaGlu-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-gammaGlu-Stearate)

<400> SEQUENCE: 430

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 431
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
```

```
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Lauroyl)

<400> SEQUENCE: 431

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 432
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Myristoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Myristoyl)

<400> SEQUENCE: 432

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30
```

```
<210> SEQ ID NO 433
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Palmitoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Palmitoyl)

<400> SEQUENCE: 433

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 434
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Stearoyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
```

```
<223> OTHER INFORMATION: Lys(Epsilon-Stearoyl)

<400> SEQUENCE: 434

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 435
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Laurate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Laurate)

<400> SEQUENCE: 435

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 436
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Myristate)
```

```
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Myristate)

<400> SEQUENCE: 436

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 437
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Palmitate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Palmitate)

<400> SEQUENCE: 437

His Xaa Glu Gly Ser Phe Thr Ser Asp Val Ser Ser Lys Leu Glu Gly
1               5                   10                  15

Glu Ala Ala Lys Glu Phe Ile Ala Lys Val Val Glu Gly Gly
            20                  25                  30

<210> SEQ ID NO 438
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
```

```
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-Stearate)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: Lys(Epsilon-Stearate)

<400> SEQUENCE: 438

His Xaa Glu Gly Ser Phe Thr Ser Asp Val Ser Ser Lys Leu Glu Gly
1               5                   10                  15
Glu Ala Ala Lys Glu Phe Ile Ala Lys Val Val Glu Gly Gly
            20                  25                  30

<210> SEQ ID NO 439
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 439

His Xaa Glu Gly Ser Phe Thr Ser Asp Lys Ser Ser Tyr Leu Glu Lys
1               5                   10                  15
Glu Ala Ala Lys Glu Phe Ile Lys Phe Val Val Glu Gly Gly
            20                  25                  30

<210> SEQ ID NO 440
<211> LENGTH: 30
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 440

His Xaa Glu Gly Ser Phe Thr Ser Asp Lys Ser Ser Tyr Leu Glu Gly
1               5                   10                  15

Lys Ala Ala Lys Glu Phe Ile Lys Phe Val Val Glu Gly Gly
            20                  25                  30

<210> SEQ ID NO 441
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 441

His Xaa Glu Gly Ser Phe Thr Ser Asp Lys Ser Ser Tyr Leu Glu Gly
1               5                   10                  15

Glu Lys Ala Lys Glu Phe Ile Lys Phe Val Val Glu Gly Gly
            20                  25                  30

<210> SEQ ID NO 442
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 442

His Xaa Glu Gly Ser Phe Thr Ser Asp Lys Ser Ser Tyr Leu Glu Gly
1               5                   10                  15

Glu Ala Ala Lys Lys Phe Ile Lys Phe Val Val Glu Gly Gly
            20                  25                  30

<210> SEQ ID NO 443
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 443

His Xaa Glu Gly Ser Phe Thr Ser Asp Val Ser Lys Tyr Leu Glu Lys
1               5                   10                  15

Glu Ala Ala Lys Glu Phe Ile Lys Phe Val Val Glu Gly Gly
            20                  25                  30
```

```
<210> SEQ ID NO 444
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 444

His Xaa Glu Gly Ser Phe Thr Ser Asp Val Ser Lys Tyr Leu Glu Gly
1               5                   10                  15

Lys Ala Ala Lys Glu Phe Ile Lys Phe Val Val Glu Gly Gly
            20                  25                  30

<210> SEQ ID NO 445
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 445

His Xaa Glu Gly Ser Phe Thr Ser Asp Val Ser Lys Tyr Leu Glu Gly
1               5                   10                  15
```

Glu Lys Ala Lys Glu Phe Ile Lys Phe Val Val Glu Gly Gly
            20                  25                  30

<210> SEQ ID NO 446
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 446

His Xaa Glu Gly Ser Phe Thr Ser Asp Val Ser Lys Tyr Leu Glu Gly
1               5                   10                  15

Glu Ala Ala Lys Lys Phe Ile Lys Phe Val Val Glu Gly Gly
            20                  25                  30

<210> SEQ ID NO 447
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)

<223> OTHER INFORMATION: Lys(Epsilon-(PEG)2-(PEG)2-gammaGlu-Lauroyl)

<400> SEQUENCE: 447

His Xaa Glu Gly Ser Phe Thr Ser Asp Val Ser Ser Lys Leu Glu Lys
1               5                   10                  15
Glu Ala Ala Lys Glu Phe Ile Lys Phe Val Val Glu Gly Gly
            20                  25                  30

<210> SEQ ID NO 448
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 448

His Xaa Glu Gly Ser Phe Thr Ser Asp Val Ser Ser Lys Leu Glu Gly
1               5                   10                  15
Lys Ala Ala Lys Glu Phe Ile Lys Phe Val Val Glu Gly Gly
            20                  25                  30

<210> SEQ ID NO 449
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)

```
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 449

His Xaa Glu Gly Ser Phe Thr Ser Asp Val Ser Ser Lys Leu Glu Gly
1               5                   10                  15

Glu Lys Ala Lys Glu Phe Ile Lys Phe Val Val Glu Gly Gly
            20                  25                  30

<210> SEQ ID NO 450
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 450

His Xaa Glu Gly Ser Phe Thr Ser Asp Val Ser Ser Lys Leu Glu Gly
1               5                   10                  15

Glu Ala Ala Lys Lys Phe Ile Lys Phe Val Val Glu Gly Gly
            20                  25                  30

<210> SEQ ID NO 451
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
```

```
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 451

His Xaa Glu Gly Ser Phe Thr Ser Asp Val Ser Ser Tyr Lys Glu Lys
1               5                   10                  15

Glu Ala Ala Lys Glu Phe Ile Lys Phe Val Val Glu Gly Gly
            20                  25                  30

<210> SEQ ID NO 452
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 452

His Xaa Glu Gly Ser Phe Thr Ser Asp Val Ser Ser Tyr Lys Glu Gly
1               5                   10                  15

Lys Ala Ala Lys Glu Phe Ile Lys Phe Val Val Glu Gly Gly
            20                  25                  30

<210> SEQ ID NO 453
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)

<400> SEQUENCE: 453

His Xaa Glu Gly Ser Phe Thr Ser Asp Val Ser Ser Tyr Lys Glu Gly
1               5                   10                  15

Glu Lys Ala Lys Glu Phe Ile Lys Phe Val Val Glu Gly Gly
            20                  25                  30

<210> SEQ ID NO 454
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (24)..(24)
<223> OTHER INFORMATION: Lys(Epsilon-(PEG)2-(PEG)2-gammaGlu-Lauroyl)
```

<400> SEQUENCE: 454

His Xaa Glu Gly Ser Phe Thr Ser Asp Val Ser Ser Tyr Lys Glu Gly
1               5                   10                  15

Glu Ala Ala Lys Lys Phe Ile Lys Phe Val Val Glu Gly Gly
            20                  25                  30

<210> SEQ ID NO 455
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 455

His Xaa Glu Gly Ser Phe Thr Ser Asp Lys Ser Ser Tyr Leu Glu Lys
1               5                   10                  15

Glu Ala Ala Lys Glu Phe Ile Ala Lys Val Val Glu Gly Gly
            20                  25                  30

<210> SEQ ID NO 456
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:

```
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 456

His Xaa Glu Gly Ser Phe Thr Ser Asp Lys Ser Ser Tyr Leu Glu Gly
1               5                   10                  15

Lys Ala Ala Lys Glu Phe Ile Ala Lys Val Val Glu Gly Gly
            20                  25                  30

<210> SEQ ID NO 457
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 457

His Xaa Glu Gly Ser Phe Thr Ser Asp Lys Ser Ser Tyr Leu Glu Gly
1               5                   10                  15

Glu Lys Ala Lys Glu Phe Ile Ala Lys Val Val Glu Gly Gly
            20                  25                  30

<210> SEQ ID NO 458
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
```

<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 458

His Xaa Glu Gly Ser Phe Thr Ser Asp Lys Ser Ser Tyr Leu Glu Gly
1               5                   10                  15
Glu Ala Ala Lys Lys Phe Ile Ala Lys Val Val Glu Gly Gly
            20                  25                  30

<210> SEQ ID NO 459
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 459

His Xaa Glu Gly Ser Phe Thr Ser Asp Val Ser Lys Tyr Leu Glu Lys
1               5                   10                  15
Glu Ala Ala Lys Glu Phe Ile Ala Lys Val Val Glu Gly Gly
            20                  25                  30

<210> SEQ ID NO 460
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)

```
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 460

His Xaa Glu Gly Ser Phe Thr Ser Asp Val Ser Lys Tyr Leu Glu Gly
1               5                   10                  15

Lys Ala Ala Lys Glu Phe Ile Ala Lys Val Val Glu Gly Gly
            20                  25                  30

<210> SEQ ID NO 461
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 461

His Xaa Glu Gly Ser Phe Thr Ser Asp Val Ser Lys Tyr Leu Glu Gly
1               5                   10                  15

Glu Lys Ala Lys Glu Phe Ile Ala Lys Val Val Glu Gly Gly
            20                  25                  30

<210> SEQ ID NO 462
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
```

```
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 462

His Xaa Glu Gly Ser Phe Thr Ser Asp Val Ser Lys Tyr Leu Glu Gly
1               5                   10                  15

Glu Ala Ala Lys Lys Phe Ile Ala Lys Val Val Glu Gly Gly
            20                  25                  30

<210> SEQ ID NO 463
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 463

His Xaa Glu Gly Ser Phe Thr Ser Asp Val Ser Ser Lys Leu Glu Lys
1               5                   10                  15

Glu Ala Ala Lys Glu Phe Ile Ala Lys Val Val Glu Gly Gly
            20                  25                  30

<210> SEQ ID NO 464
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
```

```
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 464

His Xaa Glu Gly Ser Phe Thr Ser Asp Val Ser Ser Lys Leu Glu Gly
1               5                   10                  15
Lys Ala Ala Lys Glu Phe Ile Ala Lys Val Val Glu Gly Gly
            20                  25                  30

<210> SEQ ID NO 465
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 465

His Xaa Glu Gly Ser Phe Thr Ser Asp Val Ser Ser Lys Leu Glu Gly
1               5                   10                  15
Glu Lys Ala Lys Glu Phe Ile Ala Lys Val Val Glu Gly Gly
            20                  25                  30

<210> SEQ ID NO 466
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 466

His Xaa Glu Gly Ser Phe Thr Ser Asp Val Ser Lys Leu Glu Gly
1               5                   10                  15

Glu Ala Ala Lys Lys Phe Ile Ala Lys Val Val Glu Gly Gly
                20                  25                  30

<210> SEQ ID NO 467
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)
```

```
<400> SEQUENCE: 467

His Xaa Glu Gly Ser Phe Thr Ser Asp Val Ser Ser Tyr Lys Glu Lys
1               5                   10                  15

Glu Ala Ala Lys Glu Phe Ile Ala Lys Val Val Glu Gly Gly
            20                  25                  30

<210> SEQ ID NO 468
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 468

His Xaa Glu Gly Ser Phe Thr Ser Asp Val Ser Ser Tyr Lys Glu Gly
1               5                   10                  15

Lys Ala Ala Lys Glu Phe Ile Ala Lys Val Val Glu Gly Gly
            20                  25                  30

<210> SEQ ID NO 469
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
```

<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 469

His Xaa Glu Gly Ser Phe Thr Ser Asp Val Ser Ser Tyr Lys Glu Gly
 1               5                  10                  15

Glu Lys Ala Lys Glu Phe Ile Ala Lys Val Val Glu Gly Gly
            20                  25                  30

<210> SEQ ID NO 470
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (25)..(25)
<223> OTHER INFORMATION: Lys(Epsilon-(PEG)2-(PEG)2-gammaGlu-Lauroyl)

<400> SEQUENCE: 470

His Xaa Glu Gly Ser Phe Thr Ser Asp Val Ser Ser Tyr Lys Glu Gly
 1               5                  10                  15

Glu Ala Ala Lys Lys Phe Ile Ala Lys Val Val Glu Gly Gly
            20                  25                  30

<210> SEQ ID NO 471
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 471

His Xaa Glu Gly Ser Phe Thr Ser Asp Lys Ser Ser Tyr Leu Glu Lys
1               5                   10                  15

Glu Ala Ala Lys Glu Phe Ile Ala Phe Lys Val Glu Gly Gly
            20                  25                  30

<210> SEQ ID NO 472
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 472

His Xaa Glu Gly Ser Phe Thr Ser Asp Lys Ser Ser Tyr Leu Glu Gly
1               5                   10                  15

Lys Ala Ala Lys Glu Phe Ile Ala Phe Lys Val Glu Gly Gly
            20                  25                  30

<210> SEQ ID NO 473
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)

-continued

```
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 473

His Xaa Glu Gly Ser Phe Thr Ser Asp Lys Ser Ser Tyr Leu Glu Gly
1               5                   10                  15

Glu Lys Ala Lys Glu Phe Ile Ala Phe Lys Val Glu Gly Gly
            20                  25                  30

<210> SEQ ID NO 474
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (10)..(10)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 474

His Xaa Glu Gly Ser Phe Thr Ser Asp Lys Ser Ser Tyr Leu Glu Gly
1               5                   10                  15

Glu Ala Ala Lys Lys Phe Ile Ala Phe Lys Val Glu Gly Gly
            20                  25                  30

<210> SEQ ID NO 475
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 475

His Xaa Glu Gly Ser Phe Thr Ser Asp Val Ser Lys Tyr Leu Glu Lys
1               5                   10                  15

Glu Ala Ala Lys Glu Phe Ile Ala Phe Lys Val Glu Gly Gly
            20                  25                  30

<210> SEQ ID NO 476
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 476

His Xaa Glu Gly Ser Phe Thr Ser Asp Val Ser Lys Tyr Leu Glu Gly
1               5                   10                  15

Lys Ala Ala Lys Glu Phe Ile Ala Phe Lys Val Glu Gly Gly
            20                  25                  30

<210> SEQ ID NO 477
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 477

His Xaa Glu Gly Ser Phe Thr Ser Asp Val Ser Lys Tyr Leu Glu Gly
1               5                   10                  15

Glu Lys Ala Lys Glu Phe Ile Ala Phe Lys Val Glu Gly Gly
            20                  25                  30

<210> SEQ ID NO 478
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (12)..(12)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 478

His Xaa Glu Gly Ser Phe Thr Ser Asp Val Ser Lys Tyr Leu Glu Gly
1               5                   10                  15

Glu Ala Ala Lys Lys Phe Ile Ala Phe Lys Val Glu Gly Gly
            20                  25                  30

<210> SEQ ID NO 479
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 479

His Xaa Glu Gly Ser Phe Thr Ser Asp Val Ser Ser Lys Leu Glu Lys
1               5                   10                  15

Glu Ala Ala Lys Glu Phe Ile Ala Phe Lys Val Glu Gly Gly
            20                  25                  30

<210> SEQ ID NO 480
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)
```

<400> SEQUENCE: 480

His Xaa Glu Gly Ser Phe Thr Ser Asp Val Ser Ser Lys Leu Glu Gly
1               5                   10                  15

Lys Ala Ala Lys Glu Phe Ile Ala Phe Lys Val Glu Gly Gly
            20                  25                  30

<210> SEQ ID NO 481
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 481

His Xaa Glu Gly Ser Phe Thr Ser Asp Val Ser Ser Lys Leu Glu Gly
1               5                   10                  15

Glu Lys Ala Lys Glu Phe Ile Ala Phe Lys Val Glu Gly Gly
            20                  25                  30

<210> SEQ ID NO 482
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (13)..(13)
<223> OTHER INFORMATION: Lys(Epsilon-(PEG)2-(PEG)2-gammaGlu-Lauroyl)
<220> FEATURE:

```
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 482

His Xaa Glu Gly Ser Phe Thr Ser Asp Val Ser Ser Lys Leu Glu Gly
1               5                   10                  15
Glu Ala Ala Lys Lys Phe Ile Ala Phe Lys Val Glu Gly Gly
                20                  25                  30

<210> SEQ ID NO 483
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (16)..(16)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 483

His Xaa Glu Gly Ser Phe Thr Ser Asp Val Ser Ser Tyr Lys Glu Lys
1               5                   10                  15
Glu Ala Ala Lys Glu Phe Ile Ala Phe Lys Val Glu Gly Gly
                20                  25                  30

<210> SEQ ID NO 484
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
```

```
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (17)..(17)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 484

His Xaa Glu Gly Ser Phe Thr Ser Asp Val Ser Ser Tyr Lys Glu Gly
1               5                   10                  15

Lys Ala Ala Lys Glu Phe Ile Ala Phe Lys Val Glu Gly Gly
            20                  25                  30

<210> SEQ ID NO 485
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (18)..(18)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 485

His Xaa Glu Gly Ser Phe Thr Ser Asp Val Ser Ser Tyr Lys Glu Gly
1               5                   10                  15

Glu Lys Ala Lys Glu Phe Ile Ala Phe Lys Val Glu Gly Gly
            20                  25                  30

<210> SEQ ID NO 486
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: MOD_RES
<222> LOCATION: (11)..(11)
<223> OTHER INFORMATION: alpha-Me-Ser
<220> FEATURE:
<221> NAME/KEY: MOD_RES
<222> LOCATION: (14)..(14)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (21)..(21)
<223> OTHER INFORMATION: Lys(Epsilon-(PEG)2-(PEG)2-gammaGlu-Lauroyl)
<220> FEATURE:
<221> NAME/KEY: MOD_RES
<222> LOCATION: (26)..(26)
<223> OTHER INFORMATION: Lys(Epsilon-(PEG)2-(PEG)2-gammaGlu-Lauroyl)

<400> SEQUENCE: 486

His Xaa Glu Gly Ser Phe Thr Ser Asp Val Ser Ser Tyr Lys Glu Gly
1               5                   10                  15

Glu Ala Ala Lys Lys Phe Ile Ala Phe Lys Val Glu Gly Gly
            20                  25                  30

<210> SEQ ID NO 487
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
<221> NAME/KEY: VARIANT
<222> LOCATION: (10)..(10)
<223> OTHER INFORMATION: /replace="lipid modified Lys"
<220> FEATURE:
<221> NAME/KEY: VARIANT
<222> LOCATION: (11)..(11)
<223> OTHER INFORMATION: /replace="alpha-methyl functionalized amino
      acid"
<220> FEATURE:
<221> NAME/KEY: VARIANT
<222> LOCATION: (12)..(12)
<223> OTHER INFORMATION: /replace="lipid modified Lys"
<220> FEATURE:
<221> NAME/KEY: VARIANT
<222> LOCATION: (13)..(13)
<223> OTHER INFORMATION: /replace="lipid modified Lys"
<220> FEATURE:
<221> NAME/KEY: VARIANT
<222> LOCATION: (14)..(14)
<223> OTHER INFORMATION: /replace="lipid modified Lys"
```

```
<220> FEATURE:
<221> NAME/KEY: VARIANT
<222> LOCATION: (16)..(16)
<223> OTHER INFORMATION: /replace="lipid modified Lys"
<220> FEATURE:
<221> NAME/KEY: VARIANT
<222> LOCATION: (17)..(17)
<223> OTHER INFORMATION: /replace="lipid modified Lys"
<220> FEATURE:
<221> NAME/KEY: VARIANT
<222> LOCATION: (18)..(18)
<223> OTHER INFORMATION: /replace="lipid modified Lys"
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: VARIANT
<222> LOCATION: (21)..(21)
<223> OTHER INFORMATION: /replace="lipid modified Lys"
<220> FEATURE:
<221> NAME/KEY: VARIANT
<222> LOCATION: (24)..(24)
<223> OTHER INFORMATION: /replace="lipid modified Lys"
<220> FEATURE:
<221> NAME/KEY: VARIANT
<222> LOCATION: (25)..(25)
<223> OTHER INFORMATION: /replace="lipid modified Lys"
<220> FEATURE:
<221> NAME/KEY: VARIANT
<222> LOCATION: (26)..(26)
<223> OTHER INFORMATION: /replace="lipid modified Lys"

<400> SEQUENCE: 487

His Xaa Glu Gly Ser Phe Thr Ser Asp Val Ser Ser Tyr Leu Glu Gly
1               5                   10                  15

Glu Ala Ala Lys Glu Phe Ile Ala Phe Val Val Glu Gly Gly
            20                  25                  30

<210> SEQ ID NO 488
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 488

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 489
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (6)..(6)
<223> OTHER INFORMATION: alpha-Me-Phe
<220> FEATURE:
```

```
<221> NAME/KEY: MOD_RES
<222> LOCATION: (13)..(13)
<223> OTHER INFORMATION: alpha-Me-Phe
<220> FEATURE:
<221> NAME/KEY: MOD_RES
<222> LOCATION: (20)..(20)
<223> OTHER INFORMATION: alpha-Me-Lys
<220> FEATURE:
<221> NAME/KEY: MOD_RES
<222> LOCATION: (22)..(22)
<223> OTHER INFORMATION: alpha-Me-Phe
<220> FEATURE:
<221> NAME/KEY: MOD_RES
<222> LOCATION: (25)..(25)
<223> OTHER INFORMATION: alpha-Me-Phe
<220> FEATURE:
<221> NAME/KEY: MOD_RES
<222> LOCATION: (28)..(28)
<223> OTHER INFORMATION: alpha-Me-Lys
<220> FEATURE:
<221> NAME/KEY: MOD_RES
<222> LOCATION: (31)..(31)
<223> OTHER INFORMATION: Lys(Epsilon-Palmitoyl)

<400> SEQUENCE: 489

His Xaa Glu Gly Ser Phe Thr Ser Asp Val Ser Ser Phe Leu Glu Gly
 1               5                  10                  15

Gln Ala Ala Lys Glu Phe Ile Ala Phe Val Val Lys Gly Gly Lys
            20                  25                  30

<210> SEQ ID NO 490
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys(Epsilon-gammaGlu-palmitoyl)

<400> SEQUENCE: 490

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg Gly
            20                  25                  30

<210> SEQ ID NO 491
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Lys(Epsilon-(PEG)2-(PEG)2-gammaGlu-stearate)

<400> SEQUENCE: 491

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg Gly
            20                  25                  30
```

```
<210> SEQ ID NO 492
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (2)..(2)
<223> OTHER INFORMATION: /replace="Aib"
<220> FEATURE:
<221> NAME/KEY: VARIANT
<222> LOCATION: (6)..(6)
<223> OTHER INFORMATION: /replace="any alpha-methyl functionalized amino
      acid"
<220> FEATURE:
<221> NAME/KEY: VARIANT
<222> LOCATION: (11)..(11)
<223> OTHER INFORMATION: /replace="any alpha-methyl functionalized amino
      acid"
<220> FEATURE:
<221> NAME/KEY: VARIANT
<222> LOCATION: (12)..(12)
<223> OTHER INFORMATION: /replace="any lipid modified Lys" or "any lipid
      modified Cys"
<220> FEATURE:
<221> NAME/KEY: VARIANT
<222> LOCATION: (13)..(13)
<223> OTHER INFORMATION: /replace="any alpha-methyl functionalized amino
      acid"
<220> FEATURE:
<221> NAME/KEY: VARIANT
<222> LOCATION: (20)..(20)
<223> OTHER INFORMATION: /replace="any lipid modified Lys" or "any lipid
      modified Cys" or "any alpha-methyl functionalized amino acid"
<220> FEATURE:
<221> NAME/KEY: VARIANT
<222> LOCATION: (22)..(22)
<223> OTHER INFORMATION: /replace="any alpha-methyl functionalized amino
      acid"
<220> FEATURE:
<221> NAME/KEY: VARIANT
<222> LOCATION: (24)..(24)
<223> OTHER INFORMATION: /replace="any lipid modified Lys" or "any lipid
      modified Cys"
<220> FEATURE:
<221> NAME/KEY: VARIANT
<222> LOCATION: (25)..(25)
<223> OTHER INFORMATION: /replace="alpha-methyl functionalized amino
      acid"
<220> FEATURE:
<221> NAME/KEY: VARIANT
<222> LOCATION: (28)..(28)
<223> OTHER INFORMATION: /replace="Glu" or "any alpha-methyl
      functionalized amino acid"
<220> FEATURE:
<221> NAME/KEY: misc_feature
<222> LOCATION: (1)..(30)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 492

His Ala Glu Gly Ser Phe Thr Ser Asp Val Ser Ser Tyr Leu Glu Gly
1               5                   10                  15

Glu Ala Ala Lys Glu Phe Ile Ala Trp Val Val Lys Gly Gly
            20                  25                  30
```